United States Patent
Boss et al.

(10) Patent No.: US 11,427,586 B2
(45) Date of Patent: Aug. 30, 2022

(54) 1,2,4-OXADIAZOLE DERIVATIVES AS LIVER X RECEPTOR AGONISTS

(71) Applicant: NOVARTIS AG, Basel (CH)

(72) Inventors: Kelly D. Boss, Cambridge, MA (US); Yi Fan, San Diego, CA (US); Alec Nathanson Flyer, Boston, MA (US); Declan Hardy, Cambridge, MA (US); Zhihong Huang, San Diego, CA (US); Kathryn Taylor Linkens, Brookline, MA (US); Jon Christopher Loren, San Diego, CA (US); Fupeng Ma, Melrose, MA (US); Valentina Molteni, San Diego, CA (US); Duncan Shaw, Sharon, MA (US); Jeffrey Smith, San Diego, CA (US); Catherine Fooks Solovay, Arlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/101,510

(22) Filed: Nov. 23, 2020

(65) Prior Publication Data
US 2022/0064164 A1 Mar. 3, 2022

Related U.S. Application Data

(60) Provisional application No. 62/940,061, filed on Nov. 25, 2019, provisional application No. 63/106,293, filed on Oct. 27, 2020.

(51) Int. Cl.
| | |
|---|---|
| *C07D 471/10* | (2006.01) |
| *C07D 413/14* | (2006.01) |
| *C07D 491/107* | (2006.01) |
| *C07D 413/06* | (2006.01) |
| *A61P 27/04* | (2006.01) |

(52) U.S. Cl.
CPC ............ *C07D 471/10* (2013.01); *A61P 27/04* (2018.01); *C07D 413/06* (2013.01); *C07D 413/14* (2013.01); *C07D 491/107* (2013.01); *C07B 2200/13* (2013.01)

(58) Field of Classification Search
CPC .............. C07D 491/107; C07D 471/10; C07D 413/06; C07D 413/14; A61P 27/04
See application file for complete search history.

(56) References Cited

U.S. PATENT DOCUMENTS

2020/0188297 A1 6/2020 Kaja et al.

FOREIGN PATENT DOCUMENTS

| WO | 2011/071570 A1 | 6/2011 |
| WO | 2013/131018 A1 | 9/2013 |
| WO | 2015/187840 A2 | 12/2015 |

OTHER PUBLICATIONS

Schultz, J. R. et al.: "Role of LXRs in control of lipogenesis", Genes & Development, Cold Spring Harbor, Laboratory Press, vol. 14, No. 22, Nov. 15, 2000, pp. 2831-2838.
Yasar, D. et al.: "Synthesis and crystal structure of new heterocycles containing 1,2,4-oxadiazole, 1,2,4-oxadiazoline (thione), hydantoin, and mercaptobenzimidazole units", Molecular Diversity, Aug. 1, 2014, vol. 18, No. 3, pp. 545-558.
Notification of Transmittal of the International Search Report and the Written Opinion of the International Searching Authority, or the Declaration, dated Feb. 4, 2021, issued in International Patent Application No. PCT/IB2020/061053, filed Nov. 23, 2020.
Tice, C. M. et al.: "The Medicinal Chemistry of Liver X Receptor (LXR) Modulators", Journal of Medicinal Chemistry, (2014), vol. 57, pp. 7182-7205.

*Primary Examiner* — Rebecca L Anderson
(74) *Attorney, Agent, or Firm* — Asha K. Nadipuram

(57) ABSTRACT

Provided herein are compounds and pharmaceutical compositions useful for treating meibomian gland dysfunction (MGD), comprising administering to a subject in need thereof a therapeutically effective amount of a compound of Formula (I) or a compound of Formula (I'), or pharmaceutical composition described herein.

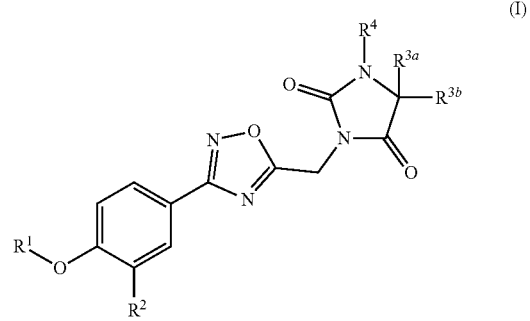

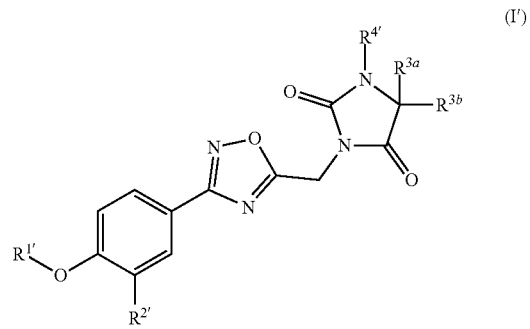

21 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 1

Gly Ser Ser Gly Gly Ser Ser Gly
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 2

Val Ser Gly Trp Arg Leu Phe Lys Lys Ile Ser
1               5                   10

<210> SEQ ID NO 3
<211> LENGTH: 20
<212> TYPE: DNA
<213> ORGANISM: Homo sapiens

<400> SEQUENCE: 3
actacaagag tggctgagtt                                              20

<210> SEQ ID NO 4
<211> LENGTH: 200
<212> TYPE: DNA
<213> ORGANISM: Homo sapiens
```

```
<400> SEQUENCE: 4
gaagaaagtc tccaaggccg ccatcttggc caggattaaa agaaccggag atggaaacta      60
caagagtggc ggtagtagtg gtggtagtag tggtgtgagc ggctggcggc tgttcaagaa     120
gattagctga gtttggggtc cctcaggttc cttttttcaaa aaccagccag gcagaggttt    180
taatgtctgt ttattaacta                                                  200

<210> SEQ ID NO 5
<211> LENGTH: 1137
<212> TYPE: DNA
<213> ORGANISM: Homo sapiens

<400> SEQUENCE: 5
atgccggccc acttgctgca ggacgatatc tctagctcct ataccaccac caccaccatt      60
acagcgcctc cctccagggt cctgcagaat ggaggagata agttggagac gatgcccctc    120
tacttggaag acgacattcg ccctgatata aaagatgata tatatgaccc cacctacaag    180
gataaggaag gcccaagccc caaggttgaa tatgtctgga gaaacatcat ccttatgtct    240
ctgctacact tgggagccct gtatgggatc actttgattc ctacctgcaa gttctacacc    300
tggctttggg gggtattcta ctattttgtc agtgccctgg gcataacagc aggagctcat    360
cgtctgtgga gccaccgctc ttacaaagct cggctgcccc tacggctctt tctgatcatt    420
gccaacacaa tggcattcca gaatgatgtc tatgaatggg ctcgtgacca ccgtgcccac    480
cacaagtttt cagaaacaca tgctgatcct cataattccc gacgtggctt tttcttctct    540
cacgtgggtt ggctgcttgt gcgcaaacac ccagctgtca aagagaaggg gagtacgcta    600
gacttgtctg acctagaagc tgagaaactg gtgatgttcc agaggaggta ctacaaacct    660
ggcttgctga tgatgtgctt catcctgccc acgcttgtgc cctggtattt ctggggtgaa    720
acttttcaaa acagtgtgtt cgttgccact ttcttgcgat atgctgtggt gcttaatgcc    780
acctggctgg tgaacagtgc tgcccacctc ttcggatatc gtccttatga caagaacatt    840
agcccccggg agaatatcct ggtttcactt ggagctgtgg gtgagggctt ccacaactac    900
caccactcct ttcccatga ctactctgcc agtgagtacc gctggcacat caacttcacc    960
acattcttca ttgattgcat ggccgccctc ggtctggcct atgaccggaa gaaagtctcc   1020
aaggccgcca tcttggccag gattaaaaga accggagatg gaaactacaa gagtggcggt   1080
agtagtggtg gtagtagtgg tgtgagcggc tggcggctgt tcaagaagat tagctga      1137
```

1,2,4-OXADIAZOLE DERIVATIVES AS LIVER X RECEPTOR AGONISTS

CROSS REFERENCE TO RELATED APPLICATIONS

This application is claims the benefit of priority to U.S. Provisional Application Nos. 62/940,061 and 63/106,293 filed Nov. 25, 2019 and Oct. 27, 2020, respectively, the disclosure of which is incorporated by reference herein in its entirety.

SEQUENCE LISTING

The instant application contains a Sequence Listing, which has been submitted electronically in ASCII format and is hereby incorporated by reference in its entirety. The ASCII copy, created on Apr. 7, 2021, is named "PAT058697-US-NP_SL" and is 2,813 bytes in size.

FIELD OF THE INVENTION

Provided herein are novel 1,2,4-oxadiazole derivatives that act as liver X receptor agonists, as well as pharmaceutical compositions thereof, uses for the treatment of meibomian gland dysfunction.

BACKGROUND OF THE INVENTION

Human tear film is comprised of three layers. The mucus layer coats the cornea forming a foundation so the tear film can adhere to the eye. The middle aqueous layer provides moisture and supplies oxygen and other important nutrients to the cornea. The outer lipid layer is an oily film that seals the tear film on the eye and helps to prevent evaporation of the layers beneath.

A large part of the lipids that contribute to the tear film are made in the meibomian gland, which is a holocrine type of exocrine gland, at the rim of the eyelid inside the tarsal plate. Meibomian glands are primarily responsible for lipid generation, and abnormal lipid secretions from in these glands can affect the various functions required of the tear film. For instance, the lipid layer of tear film prevents evaporation, lowers surface tension of tears thereby preventing spillover of tears from the lid margin and tear film lipids also play a role in the ability of the tear film to spread on the ocular surface and thereby influences the interaction between the lid and ocular surface to prevent damage to either surface. All these properties of the tear film are influenced by the lipids provided by the meibomian gland to the ocular surface to be incorporated into the tear film, Dysfunction of the meibomian glands can lead to lipid insufficiency that destabilizes the tear film and causes decreases in tear film break-up time and evaporative dry eye (see, e.g., Sullivan et al., Ann. NY Acad. Sci., 966, 211-222, 2002). Meibomian gland dysfunction (MGD), also known as meibomitis, posterior blepharitis or inflammation of the meibomian glands, is a chronic, diffuse abnormality of the meibomian glands, commonly characterized by terminal duct obstruction and/or qualitative/quantitative changes in the glandular secretion (Nelson J D, et al., Invest Ophthalmol Vis Sci 2011; 52:1930-7). MGD is further characterized by meibum with higher viscosity and melting temperature, as well as a suboptimal tear lipid layer that cannot prevent the evaporation of tears. It may result in alteration of the tear film, symptoms of eye irritation, clinically apparent inflammation, and ocular surface disease. MGD often causes dry eye, and may contribute to blepharitis. There is high unmet medical need with symptomatic MGD in ~3.5% of population presenting in up to ~70% of evaporative dry eye disease patients.

MGD may also be characterized by increased melting point of the lipids, causing solidification of the lipids and obstruction of the meibomian gland secretion. This can result in cysts, infections and decreased lipid content in the tears.

Commonly used methods to treat meibomian gland dysfunction include warm compresses to eyelid margins or mechanical treatments that apply heat and pressure to express the glands (eg, LipiFlow) or even mechanical probing of meibomian ducts. Other treatments include infrared devices to provide intense pulsed light (IPL) treatments or chemicals to eyelid margins to induce tear lipid melting and secretion. For inflammation, glucocorticoids may be used and antibiotics like penicillin, doxycycline, and tetracyclines may be used, although neither glucocorticoids nor antibiotics have been approved for this use by the FDA. Additionally, these therapies are not suitable for long term use, either for side-effects or for a lack of demonstrated efficacy. There is a long-felt and unmet need for safe, effective treatments for the treatment of meibomian gland dysfunction that can improve lipid quality and tear film.

The liver X receptors (LXRs) are ligand-activated transcription factors of the nuclear receptor superfamily and were first described by Willy, P. J., et al., "LXR, a nuclear receptor that defines a distinct retinoid response pathway," Genes & Development 9:1033-1045 (Cold Spring Harbor Laboratory Press). LXRs comprise two isoforms (LXR alpha and LXR beta) which are highly expressed in the epidermis. LXR transcriptionally regulates a number of processes involved in lipid homeostasis including cholesterol transport and fatty acid synthesis. For example, it has been reported that stearoyl-coenzyme A desaturase 1 (SCD1), the enzyme necessary for the biosynthesis of mono-unsaturated fatty acids, is a direct transcriptional target of LXR. See Shultz et al., Genes & Dev. 2000. 14: 2831-2838. Other biological pathways that are regulated by these actions of LXR include the stimulation of epidermal lipid synthesis, which can increase lamellar body formation, secretion and processing in the stratum corneum, which leads to formation of lamellar membranes that regulate the permeability of the corneal barrier. LXR also has a complex interaction with inflammatory pathways. While LXR can transcriptionally downregulate a number of inflammatory cytokines, it can also be itself downregulated by inflammatory pathways. The ability of LXR to reduce inflammation has been the explored in indications such as atherosclerosis in which macrophages play a role in the pathology.

Overall, the current treatments for meibomian gland dysfunction do not adequately address pharmacologically the cause or pathology of disease and there remains a need for new treatments or therapies.

SUMMARY OF THE INVENTION

The present invention provides compounds of Formula (I), pharmaceutically acceptable salts thereof, pharmaceutical compositions thereof and combinations thereof, wherein the compounds of the invention are LXR agonists that upregulate stearoyl-CoA desaturase-1 (SCD-1) in cutaneous cells and surprisingly decreased the melting point of secretions of the meibomian gland in vivo, thereby potentially relieving meibomian gland dysfunction. Further provided herein are methods of treating, preventing, or ameliorating meibomian gland dysfunction, comprising administering to a subject in need thereof an effective amount of a compound of Formula (I) or a pharmaceutically acceptable salt, solvate, co-crystal, polymorph or stereoisomer thereof. Also provided herein are the uses of a compound of Formula (I) or a pharmaceutically acceptable salt, solvate, co-crystal, polymorph or stereoisomer thereof, for treating, preventing, or ameliorating meibomian gland dysfunction. Further provided herein are methods of treating, preventing, or ameliorating evaporative dry eye disease, comprising administering to a subject in need thereof an effective amount of a compound of Formula (I) or a pharmaceutically acceptable salt, solvate, co-crystal, polymorph or stereoisomer thereof. Also provided herein are the uses of a compound of Formula (I) or a pharmaceutically acceptable salt, solvate, co-crystal, polymorph or stereoisomer thereof, for treating, preventing, or ameliorating evaporative dry eye disease.

Further provided herein are methods of treating, preventing, or ameliorating meibomian gland dysfunction, comprising administering to a subject in need thereof an effective amount of a compound of Formula (I') or a pharmaceutically acceptable salt, solvate, co-crystal, polymorph or stereoisomer thereof. Also provided herein are the uses of a compound of Formula (I') or a pharmaceutically acceptable salt, solvate, co-crystal, polymorph or stereoisomer thereof, for treating, preventing, or ameliorating meibomian gland dysfunction.

Further provided herein are methods of treating, preventing, or ameliorating evaporative dry eye disease, comprising administering to a subject in need thereof an effective amount of a compound of Formula (I') or a pharmaceutically acceptable salt, solvate, co-crystal, polymorph or stereoisomer thereof. Also provided herein are the uses of a compound of Formula (I') or a pharmaceutically acceptable salt, solvate, co-crystal, polymorph or stereoisomer thereof, for treating, preventing, or ameliorating evaporative dry eye disease.

In one aspect, the invention provides compounds of Formula (i):

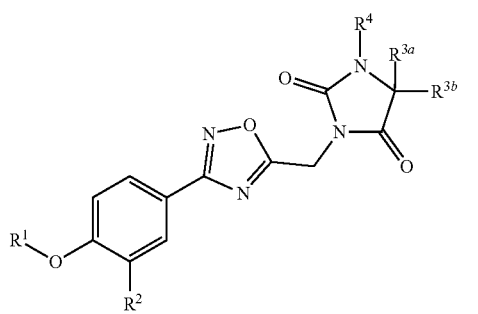

(I)

or a pharmaceutically acceptable salt, solvate, co-crystal, polymorph, or stereoisomer thereof, wherein:
$R^1$ is

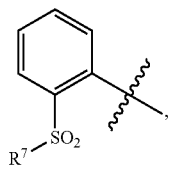

, $C_1$-$C_6$alkyl,
phenyl, or
5-6 membered heteroaryl having 1 to 3 heteroatoms independently selected from the heteroatoms N, O and S as ring members,
wherein the phenyl and heteroaryl are optionally substituted with one $R^{10}$, and the $C_1$-$C_6$alkyl is substituted with one or two —$CF_3$;
$R^2$ is —$CF_3$ or Cl;
$R^{3a}$ is
H, or
$C_1$-$C_6$alkyl optionally substituted with one, two, or three substituents independently selected from the group consisting of —OH and —N($R^{12}$)$_2$;
$R^{3b}$ is
H, or
$C_1$-$C_6$alkyl optionally substituted with one, two, or three substituents independently selected from the group consisting of —OH and —N($R^{12}$)$_2$;
or $R^{3a}$ and $R^{3b}$ together with the carbon atom they are attached to may combine to form a $C_3$-$C_8$cycloalkyl, wherein the cycloalkyl is optionally substituted with one $R^5$;
or $R^{3a}$ and $R^{3b}$ together with the carbon atom they are attached to may combine to form a 4-6 membered heterocycloalkyl having 1 to 2 ring members independently selected from N, NH, $NR^{12}$, O or S, wherein the heterocycloalkyl is optionally substituted with one $R^5$;
$R^4$ is $C_1$-$C_6$alkyl substituted with one or two groups independently selected from:
$R^6$,
4-6 membered heterocycloalkyl having 1 to 2 ring members independently selected from N, NH, $NR^{12}$, O or S,
5-6 membered heteroaryl having 1 to 3 heteroatoms independently selected from the heteroatoms N, O and S as ring members, and
$C_3$-$C_8$cycloalkyl,
wherein the heterocycloalkyl is optionally substituted with one or two substituents independently selected from —OH and $C_1$-$C_3$alkyl;
each $R^5$ is independently selected from:
—C(=O)$R^8$,
$C_1$-$C_3$alkyl,
$C_3$-$C_8$cycloalkyl, and
4-6 membered heterocycloalkyl having 1 to 2 ring members independently selected from N, NH, $NR^{12}$, O or S,
wherein the $C_1$-$C_3$alkyl is optionally substituted with one $R^9$, and the heterocycloalkyl is optionally substituted with one $C_1$-$C_3$alkyl or —C(=O)$R^8$;
each $R^6$ is independently selected from —OH and $C_1$-$C_3$alkyl;
$R^7$ is
$C_1$-$C_6$alkyl,
—N($R^{12}$)$_2$,
$C_3$-$C_8$cycloalkyl, or
4-6 membered heterocycloalkyl having 1 to 2 ring members independently selected from N, NH, $NR^{12}$, O or S,
wherein the $C_1$-$C_6$alkyl is optionally substituted with one or more $R^{11}$, and the $C_3$-$C_8$cycloalkyl is optionally substituted with one or more —OH;
$R^8$ is
$C_1$-$C_6$alkyl,
5-6 membered heteroaryl having 1 to 3 heteroatoms independently selected from the heteroatoms N, O and S as ring members, or
4-6 membered heterocycloalkyl having 1 to 2 ring members independently selected from N, NH, $NR^{12}$, O or S, wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12})_2$, and $C_3$-$C_8$cycloalkyl;

$R^9$ is phenyl, $C_3$-$C_8$cycloalkyl, 4-6 membered heterocycloalkyl having 1 to 2 ring members independently selected from N, NH, $NR^{12}$, O or S, or 5-6 membered heteroaryl having 1 to 3 heteroatoms independently selected from the heteroatoms N, O and S as ring members, wherein the heteroaryl is optionally substituted with —OH, the heterocycloalkyl is optionally substituted with $C_1$-$C_6$alkyl, and the phenyl is optionally substituted with one or two —OH;

$R^{10}$ is $C_1$-$C_6$alkyl or $C_1$-$C_6$haloalkyl;

each $R^{11}$ is independently selected from halogen, $C_1$-$C_6$haloalkyl, $C_1$-$C_6$alkoxy,

—$N(R^{13})_2$,

—OH, and 4-6 membered heterocycloalkyl having 1 to 2 ring members independently selected from N, NH, $NR^{12}$, O or S;

each $R^{12}$ is independently selected from H and $C_1$-$C_6$alkyl, and each $R^{13}$ is independently selected from H, and $C_1$-$C_6$alkyl, wherein the alkyl is optionally substituted with —OH or $C_1$-$C_6$alkoxy.

In an embodiment the compound of Formula (I) is a compound of Formula (Ia):

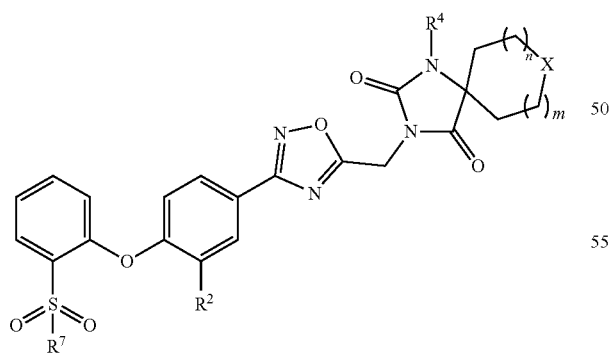

(Ia)

or a pharmaceutically acceptable salt, solvate, co-crystal, polymorph or stereoisomer thereof, where X is $NR^5$, O or $CH_2$, n is 0 or 1 and m is 0 or 1, and where $R^2$, $R^4$, $R^5$ and $R^7$ are as defined herein.

In an embodiment the compound of Formula (I) is a compound of Formula (Ib):

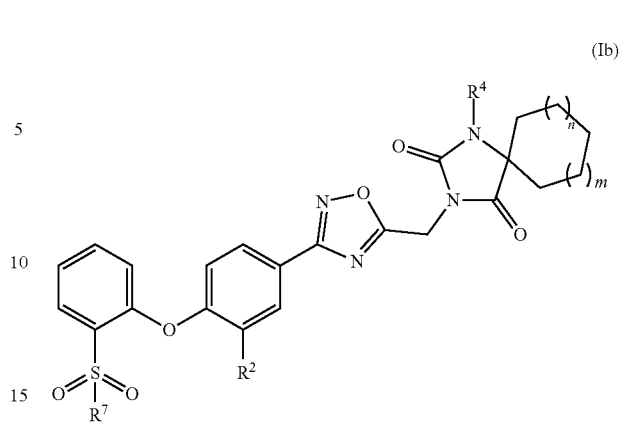

(Ib)

or a pharmaceutically acceptable salt, solvate, co-crystal, polymorph or stereoisomer thereof, where n is 0 or 1 and m is 0 or 1, and where $R^2$, $R^4$ and $R^7$ are as defined herein.

In an embodiment the compound of Formula (I) is a compound of Formula (Ic):

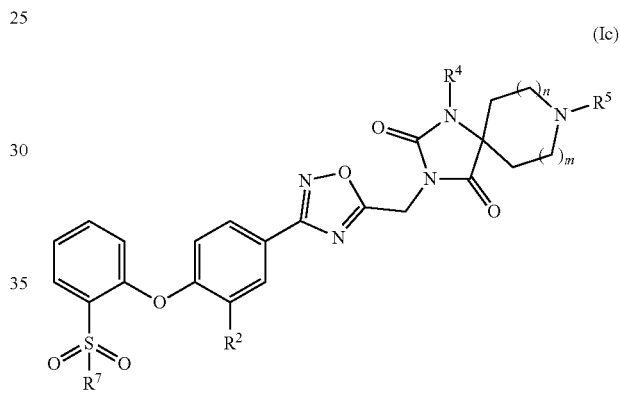

(Ic)

or a pharmaceutically acceptable salt, solvate, co-crystal, polymorph or stereoisomer thereof, where n is 0 or 1 and m is 0 or 1, and where $R^2$, $R^4$, $R^5$ and $R^7$ are as defined herein.

In an embodiment the compound of Formula (I) is a compound of Formula (Id):

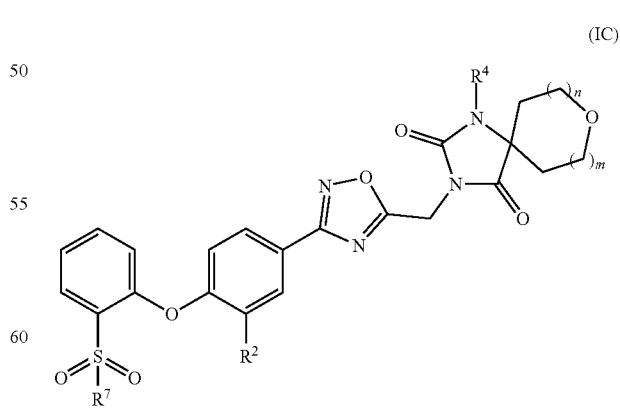

(IC)

or a pharmaceutically acceptable salt, solvate, co-crystal, polymorph or stereoisomer thereof, where n is 0 or 1 and m is 0 or 1, and where $R^2$, $R^4$ and $R^7$ are as defined herein.

In another embodiment, the compound of Formula (I) is a compound of Formula (Ie):

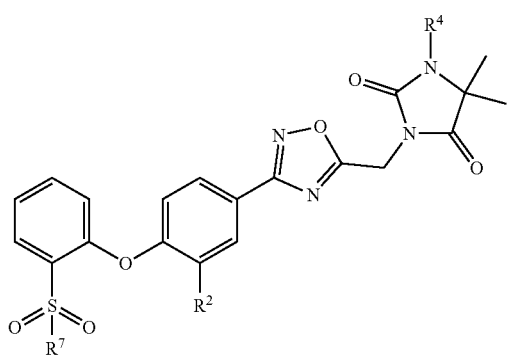

(Ie)

or a pharmaceutically acceptable salt, solvate, co-crystal, polymorph or stereoisomer thereof, where $R^2$, $R^4$ and $R^7$ are as defined herein.

In another embodiment the compound of Formula (I) is a compound of Formula (If):

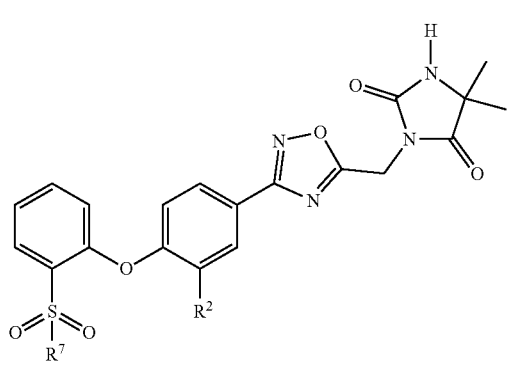

(If)

or a pharmaceutically acceptable salt, solvate, co-crystal, polymorph or stereoisomer thereof, wherein $R^2$ and $R^7$ are as defined herein.

In another embodiment, the compound of Formula (I) is a compound of Formula (Ig):

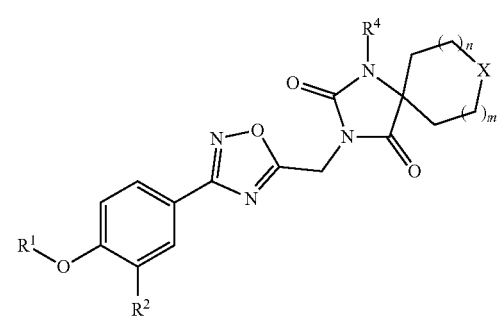

(Ig)

or a pharmaceutically acceptable salt, solvate, co-crystal, polymorph or stereoisomer thereof, wherein:
$R^1$ is $C_1$-$C_6$alkyl, wherein the $C_1$-$C_6$alkyl is optionally substituted with one or two —$CF_3$;

X is $NR^5$, $CH_2$, or O;
n is 0 or 1,
m is 0 or 1, and
wherein all other substituents are as defined herein.

In another aspect, the invention provides pharmaceutical compositions comprising a compounds of Formula (I), or a pharmaceutically acceptable salt, solvate, co-crystal, polymorph, or stereoisomer thereof, and one or more pharmaceutically acceptable carriers.

In another aspect, the invention provides compounds of Formula (I'):

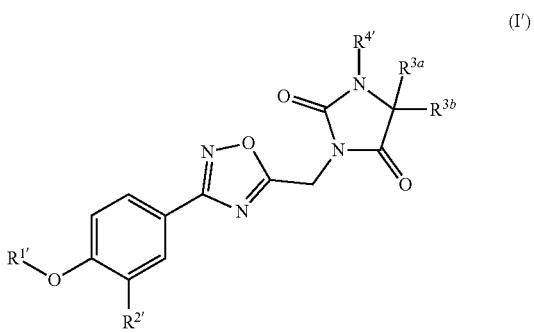

(I')

or a pharmaceutically acceptable salt, solvate, co-crystal, polymorph, or stereoisomer thereof, wherein:
$R^{1''}$ is

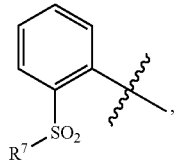

$C_1$-$C_6$alkyl,
phenyl or
5-6 membered heteroaryl having 1 to 3 heteroatoms independently selected from the heteroatoms N, O and S as ring members,
wherein the phenyl and heteroaryl are optionally substituted with one $R^{10'}$, and the $C_1$-$C_6$alkyl is optionally substituted with one or two —$CF_3$;
$R^{2'}$ is $C_1$-$C_6$haloalkyl or halo;
$R^{4'}$ is
hydrogen, or
$C_1$-$C_6$alkyl optionally substituted with one or two groups independently selected from:
$R^6$,
4-6 membered heterocycloalkyl having 1 to 2 ring members independently selected from N, NH, $NR^{12'}$, O and S,
5-6 membered heteroaryl having 1 to 3 heteroatoms independently selected from the heteroatoms N, O and S as ring members, and
$C_3$-$C_8$cycloalkyl,
wherein the heterocycloalkyl is optionally substituted with one or two substituents independently selected from —OH and $C_1$-$C_3$alkyl;
$R^{8'}$ is
$C_1$-$C_6$alkyl,
$C_1$-$C_6$alkyl-COOH, 5-6 membered heteroaryl having 1 to 3 heteroatoms independently selected from the heteroatoms N, O and S as ring members, or 4-6 membered heterocycloalkyl having 1 to 2 ring members independently selected from N, NH, NR$^{12'}$, O and S, wherein the heterocycloalkyl is optionally substituted with one C$_1$-C$_6$alkyl, and the C$_1$-C$_6$alkyl is optionally substituted with one or more substituents selected from the group consisting of —C(═O)OH, N(R$^{12'}$)$_2$, and C$_3$-C$_8$cycloalkyl;

R$^{10'}$ is C$_1$-C$_6$alkyl, C$_1$-C$_6$haloalkyl, or S—CF$_3$;

each R$^{12'}$ is independently selected from
hydrogen,
C$_1$-C$_6$alkyl, and
—C(═O)R$^8$; and wherein all other substituents are as defined above herein.

In an embodiment, the compound of Formula (I') is a compound of Formula (Ia'):

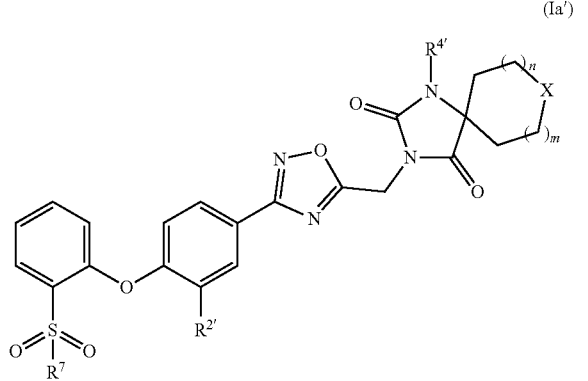

(Ia')

or a pharmaceutically acceptable salt, solvate, co-crystal, polymorph or stereoisomer thereof, wherein X is NR$^5$, O or CH$_2$, n is 0 or 1 and m is 0 or 1, and wherein R$^{2'}$, R$^{4'}$, R$^5$ and R$^7$ are as defined herein.

In an embodiment, the compound of Formula (I') is a compound of Formula (Ib'):

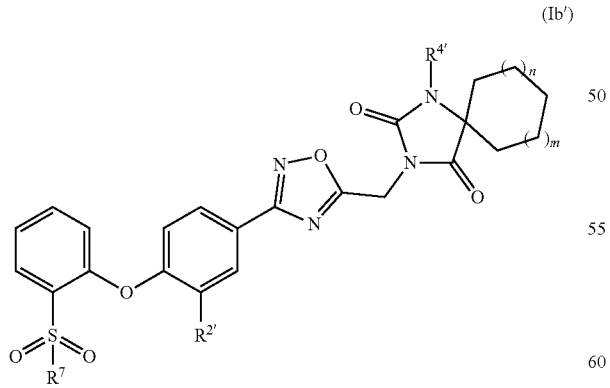

(Ib')

or a pharmaceutically acceptable salt, solvate, co-crystal, polymorph or stereoisomer thereof, wherein n is 0 or 1 and m is 0 or 1, and wherein R$^{2'}$, R$^{4'}$ and R$^7$ are as defined herein.

In an embodiment, the compound of Formula (I') is a compound of Formula (Ic'):

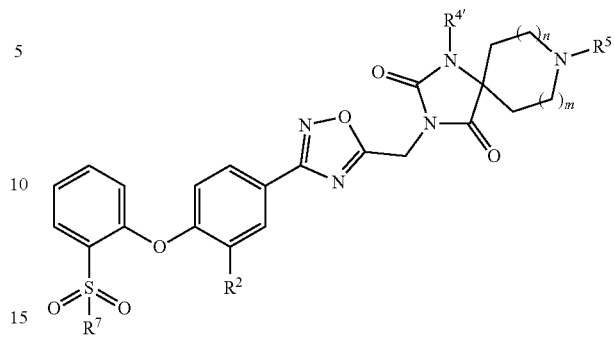

(Ic')

or a pharmaceutically acceptable salt, solvate, co-crystal, polymorph or stereoisomer thereof, wherein n is 0 or 1 and m is 0 or 1, and wherein R$^{2'}$, R$^{4'}$, R$^5$ and R$^7$ are as defined herein.

In an embodiment, the compound of Formula (I') is a compound of Formula (Id'):

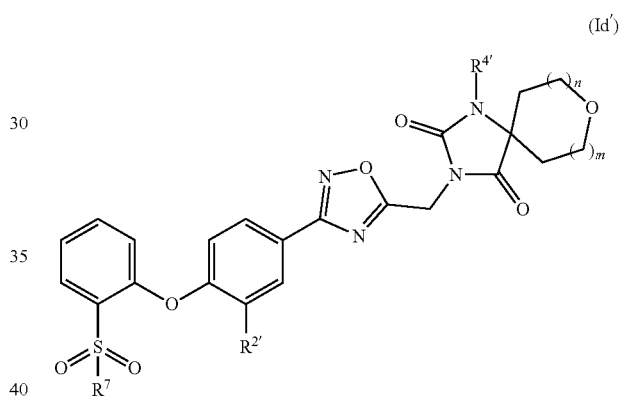

(Id')

or a pharmaceutically acceptable salt, solvate, co-crystal, polymorph or stereoisomer thereof, wherein n is 0 or 1 and m is 0 or 1, and wherein R$^{2'}$, R$^{4'}$ and R$^7$ are as defined herein.

In another embodiment the compound of Formula (I') is a compound of Formula (Ie'):

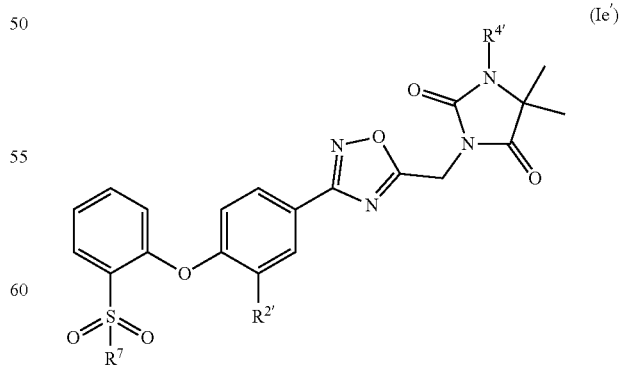

(Ie')

or a pharmaceutically acceptable salt, solvate, co-crystal, polymorph or stereoisomer thereof, wherein R$^{2'}$, R$^{4'}$ and R$^7$ are as defined herein.

In another embodiment the compound of Formula (I') is a compound of Formula (If'):

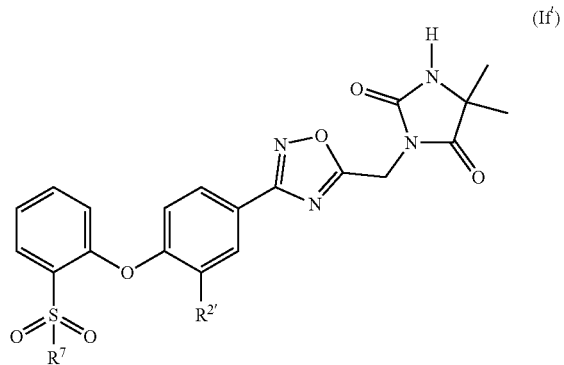

(If')

or a pharmaceutically acceptable salt, solvate, co-crystal, polymorph or stereoisomer thereof, wherein $R^{2'}$ and $R^7$ are as defined herein.

In another embodiment, the compound of Formula (I') is a compound of Formula (Ig'):

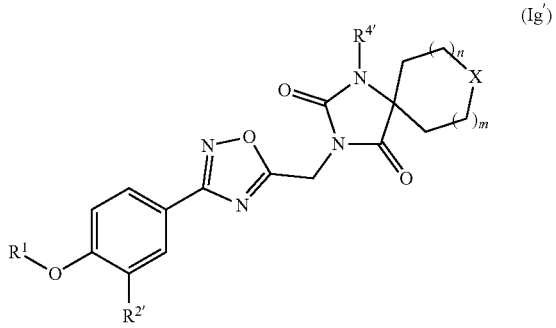

(Ig')

or a pharmaceutically acceptable salt, solvate, co-crystal, polymorph or stereoisomer thereof, wherein:
$R^{1'}$ is $C_1$-$C_6$alkyl, wherein the $C_1$-$C_6$alkyl is optionally substituted with one or two —$CF_3$;
X is $NR^5$, $CH_2$, or O;
n is 0 or 1, and
m is 0 or 1,
wherein all other substituents are as defined herein.

In another aspect, the invention provides pharmaceutical compositions comprising a compound of Formula (I'), or a pharmaceutically acceptable salt, solvate, co-crystal, polymorph, or stereoisomer thereof, and one or more pharmaceutically acceptable carriers.

In another aspect, the invention provides a method for the treatment of meibomian gland dysfunction comprising administration to a patient in need thereof a therapeutically effective amount of a compound of the invention, or a pharmaceutically acceptable salt, solvate, co-crystal, polymorph or stereoisomer thereof.

In another aspect, the invention provides a method for the treatment of meibomian gland dysfunction comprising administration of a compound of the invention, or a pharmaceutically acceptable salt, solvate, co-crystal, polymorph or stereoisomer thereof, to a patient in need of such treatment.

In another aspect, the invention provides the use of a compound of the invention, or a pharmaceutically acceptable salt, solvate, co-crystal, polymorph or stereoisomer thereof, in the manufacture of a medicament for the treatment of meibomian gland dysfunction.

In another aspect, the invention provides the use of a compound of the invention, or a pharmaceutically acceptable salt, solvate, co-crystal, polymorph or stereoisomer thereof, for the treatment of meibomian gland dysfunction.

In another aspect, the invention provides a compound of the invention, or a pharmaceutically acceptable salt, solvate, co-crystal, polymorph or stereoisomer thereof, for use in the treatment of meibomian gland dysfunction.

In another aspect, the invention provides a method for the treatment of evaporative dry eye disease comprising administration to a patient in need thereof a therapeutically effective amount of a compound of the invention, or a pharmaceutically acceptable salt, solvate, co-crystal, polymorph or stereoisomer thereof.

In another aspect, the invention provides a method for the treatment of evaporative dry eye disease comprising administration of a compound of the invention, or a pharmaceutically acceptable salt, solvate, co-crystal, polymorph or stereoisomer thereof, to a patient in need of such treatment.

In another aspect, the invention provides the use of a compound of the invention, or a pharmaceutically acceptable salt, solvate, co-crystal, polymorph or stereoisomer thereof, in the manufacture of a medicament for the treatment of evaporative dry eye disease.

In another aspect, the invention provides the use of a compound of the invention, or a pharmaceutically acceptable salt, solvate, co-crystal, polymorph or stereoisomer thereof, for the treatment of evaporative dry eye disease.

In another aspect, the invention provides a compound of the invention, or a pharmaceutically acceptable salt, solvate, co-crystal, polymorph or stereoisomer thereof, for use in the treatment of evaporative dry eye disease.

In another aspect, the invention provides a crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione characterized by an X-ray powder diffraction comprising one or more peaks at 2-Theta angles selected from 7.2±0.2, 7.8±0.2, 8.2±0.2, 10.7±0.2, 11.6±0.2, 12.5±0.2, 13.8±0.2, 14.5±0.2, 15.0±0.2, 15.8±0.2, 17.7±0.2, 18.9±0.2, 20.7±0.2, 21.3±0.2, 21.8±0.2, 22.1±0.2, and 23.1±0.2.

imidazolidine-2,4-dione, designated herein as Form A. The TGA profile graphs the percent loss of weight of the sample as a function of temperature, the temperature rate change being about 10 K/min.

Figure 4:
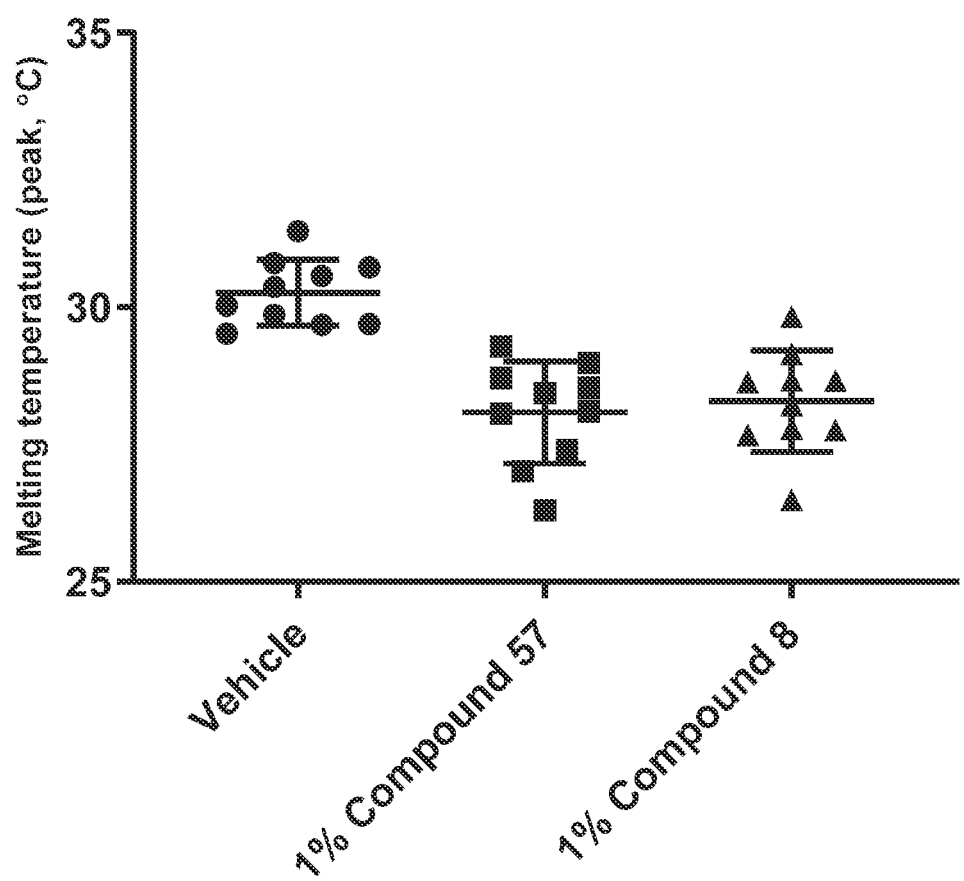

FIG. 4 demonstrates the decrease in meibum melting temperature measured upon administration of exemplary compounds (compound 57 and compound 8) to rat eyes at a concentration of 1%.

DETAILED DESCRIPTION

Various enumerated embodiments of the present invention are described herein. It will be recognized that features specified in each embodiment may be combined with other specified features to provide further embodiments of the present invention.

Definitions

The term "alkyl," as used herein, refers to a fully saturated branched or straight chain hydrocarbon. In certain embodiments an alkyl group is a "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" or "$C_1$-$C_{10}$alkyl", wherein the terms "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" and "$C_1$-$C_{10}$alkyl", as used herein, refer to an alkyl group containing at least 1, and at most 2, 3, 4, 5, 6, 7, 8, 9 or 10 carbon atoms, respectively. Non-limiting examples of alkyl groups include methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl.

The term "alkoxy", as used herein, refers to —O-alkyl or -alkyl-O—, wherein the "alkyl" group is as defined herein. In certain embodiments an alkoxy group is a "$C_1$-$C_2$alkoxy", "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" or "$C_1$-$C_{10}$alkoxy", wherein the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" and "$C_1$-$C_{10}$alkoxy", as used herein refer to —O—$C_1$-$C_2$alkyl, —O—$C_1$-$C_3$alkyl, —O—$C_1$-$C_4$alkyl, —O—$C_1$-$C_5$alkyl, —O—$C_1$-$C_6$alkyl, —O—$C_1$-$C_7$alkyl, —O—$C_1$-$C_8$alkyl, —O—$C_1$-$C_9$alkyl or —O—$C_1$-$C_{10}$alkyl, respectively. Non-limiting examples of "alkoxy" groups include methoxy, ethoxy, n-propoxy, isopropoxy, n-butoxy, isobutoxy, sec-butoxy, tert-butoxy, n-pentoxy, isopentoxy, hexoxy, heptoxy, octoxy, nonoxy, decoxy and the like.

The term "$C_3$-$C_8$cycloalkyl" as used herein, refers to a fully saturated, monocyclic hydrocarbon ring system having 3 to 8 carbon atoms as ring members. Non-limiting examples of such "$C_3$-$C_8$cycloalkyl" groups include cyclopropyl, cyclobutyl, cyclopentyl, cyclohexyl, cycloheptyl and cyclooctyl groups.

The term "haloalkyl" as used herein, refers to an alkyl as defined herein, wherein at least one of the hydrogen atoms of the alkyl is replaced by a halo group as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g., trifluoromethyl. Representative haloalkyl groups, unless specified otherwise, include methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CH(CF_3)$— or $CF_3CF_2CF_2CF_2$—.

The term "$C_1$-$C_6$haloalkyl" as used herein, refers to the respective "$C_1$-$C_6$alkyl", as defined herein, wherein at least one of the hydrogen atoms of the "$C_1$-$C_6$alkyl" is replaced by a halo atom. The $C_1$-$C_6$haloalkyl groups can be mono$C_1$-$C_6$haloalkyl, wherein such $C_1$-$C_6$haloalkyl groups have one iodo, one bromo, one chloro or one fluoro. Additionally, the $C_1$-$C_6$haloalkyl groups can be di$C_1$-$C_6$haloalkyl wherein such $C_1$-$C_6$haloalkyl groups can have two halo atoms independently selected from iodo, bromo, chloro or fluoro. Furthermore, the $C_1$-$C_6$haloalkyl groups can be poly$C_1$-$C_6$haloalkyl wherein such $C_1$-$C_6$haloalkyl groups can have two or more of the same halo atoms or a combination of two or more different halo atoms. Such poly$C_1$-$C_6$haloalkyl can be perhalo$C_1$-$C_6$haloalkyl where all the hydrogen atoms of the respective $C_1$-$C_6$alkyl have been replaced with halo atoms and the halo atoms can be the same or a combination of different halo atoms. Non-limiting examples of "$C_1$-$C_6$haloalkyl" groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, fluoroethyl, difluoroethyl, trifluoroethyl, difluoropropyl, dichloroethyl and dichloropropyl.

The terms "halo" or "halogen" as used herein, refer to fluoro (F), chloro (Cl), bromo (Br) or iodo (I).

The term "heteroaryl," as used herein, refers to an aromatic ring system containing one or more heteroatoms. Heteroaryl groups containing more than one heteroatom may contain different heteroatoms. Heteroaryl groups may be optionally substituted with one or more substituents as defined in Formula (I) and Formula (I'). Heteroaryl groups may be monocyclic ring systems or fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Non-limiting examples of heteroaryl groups, as used herein, include benzofuranyl, benzo[c]thiophenyl, benzothiophenyl, benzoxazolyl, benzthiazolyl, benzimidazolyl, cinnolinyl, furazanyl, furyl, imidazolyl, indolyl, indolizinyl, indazolyl, isoindolyl, isoquinolinyl, isoxazolyl, isothiazolyl, oxazolyl, oxaindolyl, oxadiazolyl (including 1,3,4-oxadiazolyl and 1,2,4-oxadiazolyl), purinyl, pyrazolyl, pyrrolyl, phthalazinyl, pyridinyl (including 2-, 3-, and 4-pyridinyl), pyridazinyl, pyrazinyl, pyrimidinyl, quinoxalinyl, quinolinyl, quinazolinyl, tetrazinyl, tetrazolyl, tetrazolo[1,5-a]pyridinyl, thiazolyl, thiadiazolyl (including 1,3,4-thiadiazolyl), thienyl, triazinyl, and triazolyl.

The term "5-6 membered heteroaryl having 1 to 3 heteroatoms independently selected from the heteroatoms N, O and S as ring members", refers to an aromatic, 5-6 membered monocyclic ring system having 1 to 3 heteroatoms independently selected from the heteroatoms N, O and S as ring members.

The term "heteroatom", as used herein, refers to a nitrogen, oxygen, or sulfur atom.

The term "heterocycloalkyl," as used herein refers to a cycloalkyl group as defined herein having one to two carbon atoms in the ring structure being replaced with one to two groups independently selected from N, NH, $N^{12}, N^{12'}$, O or S, wherein $R^{12}$ is H or $C_1$-$C_6$alkyl and $R^{12'}$ is H, $C_1$-$C_6$alkyl, or —C(=O)$R^{8'}$. The term "4 to 6 membered heterocycloalkyl having one to two ring members independently selected from N, NH, $NR^{12}$, $NR^{12'}$, O or S", as used herein refers to a 4 to 6 ring membered heterocycloalkyl which is a fully saturated, monocyclic hydrocarbon ring structure having 4 to 6 ring members, wherein one to two of the ring members are independently selected from N, NH, $NR^{12}$, $NR^{12'}$, O or —S—, wherein $R^{12}$ is H or $C_1$-$C_6$alkyl and $R^{12'}$ is H, $C_1$-$C_6$alkyl, or —C(=O)$R^{8'}$. Non-limiting examples of heterocycloalkyl groups, as used herein, include azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrazolidinyl, pyrazolidin-1-yl, pyrazolidin-2-yl, pyrazolidin-3-yl, pyrazolidin-4-yl and pyrazolidin-5-yl.

The term "optionally substituted", as used herein indicates that a group, such as an alkyl, heteroaryl and heterocycloalkyl, may be unsubstituted or the group may be substituted with one or more substituents as defined in Formula (I) and Formula (I').

The term "amorphous", as used herein refers to a solid form of a molecule, atom, and/or ions that is not crystalline. An amorphous solid does not display a definitive X-ray diffraction pattern.

The term "substantially the same", as used herein with reference to X-ray diffraction peak positions means that typical peak position and intensity variability are taken into account. For example, one skilled in the art will appreciate that the peak positions (° 2θ) will show some inter-apparatus variability, typically as much as ±0.2° 2θ. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The term "substantially pure", as used herein, when used in reference to a form, such as Form A, means a compound having a purity greater than 90 weight %, including greater than 90, 91, 92, 93, 94, 95, 96, 97, 98, and 99 weight %, and also including equal to about 100 weight % of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione, based on the weight of the compound. The remaining material comprises other form(s) of the compound, and/or reaction impurities and/or processing impurities arising from its preparation. For example, a crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione may be deemed substantially pure in that it has a purity greater than 90 weight %, as measured by means that are at this time known and generally accepted in the art, where the remaining less than 10 weight % of material comprises other form(s) of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione and/or reaction impurities and/or processing impurities.

The term "polymorph", as used herein, refers to crystalline forms having the same chemical composition but different spatial arrangements of the molecules, atoms, and/or ions forming the crystal.

The term "ophthalmically compatible", as used herein refers to formulations, polymers and other materials and/or dosage forms which are suitable for use in contact with the ocular tissues of subject, including human beings and animals, without excessive toxicity, irritation, allergic response, or other problem or complication, commensurate with a reasonable benefit/risk ratio.

The term "ocular surface", as used herein refers to the outer surface of the eye, which anatomically comprises the cornea (with epithelium, bowman layer, stroma, descement membrane, endothelium), conjunctiva, and the corneoscleral junction, i.e., the limbus.

The term "administration" and "administering" and "administer" as used herein refer to the manner in which a compound provided herein (e.g., a compound according to Formula (I) or a compound accordingly to Formula (I')) is presented to a subject.

The term "subject" or "patient" as used herein refers to a living organism suffering from one or more of the diseases or disorders described here that can be treated by administration of a pharmaceutical composition described herein. Examples of subjects include mammals (e.g., humans and animals such as dogs, cows, horses, monkeys, pigs, guinea pigs, sheep, goats, cats, mice, rabbits, rats, and transgenic non-human animals). In certain embodiments, the subject is a primate. In certain embodiments, the subject is a human, e.g., a human suffering from, at risk of suffering from, or potentially capable of suffering from a disease described herein. In particular embodiments, the subject is an adult human at least about 18 years of age. In particular embodiments, the subject is an adult human from about 18 to about 75 years of age. In some embodiments, the subject is a human child up to about 18 years of age.

The terms "treat", "treating" or "treatment" of any disease or disorder, as used herein, refers to relieve, alleviate, delay, reduce, reverse, or improve at least one symptom or sign of a condition in a subject. In one embodiment, the term "treating" refers to relieving, alleviating, delaying, reducing, reversing, or improving at least one symptom or sign selected from abnormal meibomian gland secretions, meibomian gland dysfunction, dry eye, meibomian gland secretions, redness of the eyelid margins, burning and/or itching in a subject's eye, ocular discomfort, corneal epithelial erosion, ocular and conjunctival staining, and reducing blurred and/or fuzzy vision. The term "treating" may also mean to arrest, delay the onset (i.e., the period prior to clinical manifestation of a disease) and/or reduce the risk of developing or worsening a condition.

The term "prevent", "preventing" or "prevention" of any disease or disorder as used herein refers to the prophylactic treatment of the disease or disorder; or delaying the onset or progression of the disease or disorder The term "pharmaceutical composition", as used herein refers to a compound provided herein, or a pharmaceutically acceptable salt, solvate, co-crystal, polymorph or stereoisomer thereof, together with at least one pharmaceutically acceptable carrier, in a form suitable for pharmaceutical use. A composition suitable for pharmaceutical use may be sterile, homogeneous and/or isotonic. Pharmaceutical compositions may be prepared in certain embodiments in an aqueous form, for example in a pre-filled syringe or other single- or multi-dose container. In certain embodiments, the pharmaceutical composition provided herein is ophthalmically compatible and suitable for ophthalmic administration to a human subject by, for example, topical or local application (to the eye or eyelid) or other known methods of drug delivery.

The term "pharmaceutically acceptable carrier", as used herein, refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

The term "placebo", as used herein, refers to an ophthalmic formulation that includes all of the components of the administered pharmaceutical composition without a compound provided herein.

The term "therapeutically effective amount", as used herein refers to an amount of a compound of the invention that will elicit the biological or medical response of a subject, for example, increase enzyme or a protein activity, or ameliorate symptoms, alleviate conditions, slow or delay disease progression, or prevent a disease, etc. In one embodiment, the term "a therapeutically effective amount" refers to the amount of the compound of the invention that, when administered to a subject, is effective to agonize LXR and thereby at least partially alleviate, prevent and/or ameliorate meibomian gland dysfunction. In another embodiment, the term "a therapeutically effective amount" refers to the amount of the compound provided herein that, when administered to a cell, or a tissue, or a non-cellular biological material, or a medium, is effective to increase the activity of LXR.

The terms "inhibit", "inhibition" or "inhibiting", as used herein, refers to the reduction or suppression of a given condition, symptom, or disorder, or disease, or a significant decrease in the baseline activity of a biological activity or process.

The term "Liver X receptor" or "LXR" as used herein refers to a nuclear receptor implicated in cholesterol biosynthesis. As used herein, the term LXR refers to both LXRα and LXRβ isoforms of the protein found in mammals and fragments thereof.

The term "a subject is in need of a treatment" refers to if such subject would benefit biologically, medically or in quality of life from such treatment.

Unless specified otherwise, "a compound provided herein" or "compounds provided herein" refers to compounds of Formula (I) and subformulae thereof, including Formula (Ia), (Ib), (Ic), (Id), (Ie), (If), and (Ig), compounds of Formula (I') and subformulae thereof, including Formula (Ia'), (Ib'), (Ic'), (Id'), (Ie'), (If'), and (Ig'), and any exemplified compounds and salts thereof, as well as all stereoisomers (including diastereoisomers and enantiomers), rotamers, tautomers and isotopically labeled compounds (including deuterium substitutions), as well as inherently formed moieties. In some embodiments, a compound provided herein is in polymorphic Form A. In some embodiments, Form A is characterized by an XRPD pattern comprising one or more peaks selected from 7.2, 8.2, 10.7, 14.5, 15.0, 20.7, 21.8±0.2° 2θ. In some embodiments, Form A is characterized by an XRPD pattern comprising two, three, or four representative peaks selected from 7.2, 8.2, 10.7, 14.5, 15.0, 20.7, 21.8±0.2° 2θ. In other embodiments, Form A is characterized by an XRPD pattern comprising one or more peaks selected from FIG. 1, as shown in Table 1.

"A," "an," "the" and similar terms as used herein (especially in the context of the claims) are to be construed to cover both the singular and plural unless otherwise indicated herein or clearly contradicted by the context.

Compounds of the Invention

The invention provides compounds having the structure of Formula (I), or a pharmaceutically acceptable salt, solvate, co-crystal, polymorph, or stereoisomer thereof,

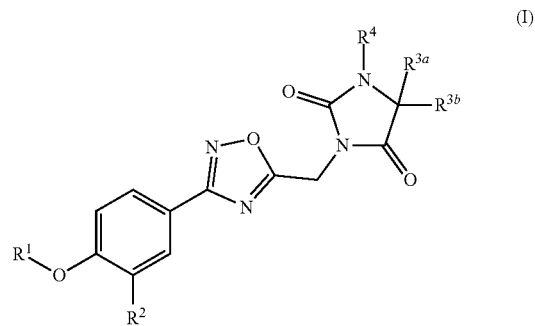

wherein:
R$^1$ is

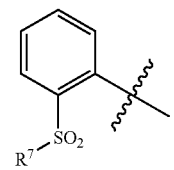

C$_1$-C$_6$alkyl,
phenyl, or
5-6 membered heteroaryl having 1 to 3 heteroatoms independently selected from the heteroatoms N, O and S as ring members,
wherein the phenyl and heteroaryl are optionally substituted with one R$^{10}$, and the C$_1$-C$_6$alkyl is substituted with one or two —CF$_3$;

$R^2$ is —$CF_3$ or Cl;
$R^{3a}$ is
H, or
$C_1$-$C_6$alkyl optionally substituted with one, two, or three substituents independently selected from the group consisting of —OH and —N($R^{12}$)$_2$;
$R^{3b}$ is
H, or
$C_1$-$C_6$alkyl optionally substituted with one, two, or three substituents independently selected from the group consisting of —OH and —N($R^{12}$)$_2$;
or $R^{3a}$ and $R^{3b}$ together with the carbon atom they are attached to may combine to form a $C_3$-$C_8$cycloalkyl, wherein the cycloalkyl is optionally substituted with one $R^5$;
or $R^{3a}$ and $R^{3b}$ together with the carbon atom they are attached to may combine to form a 4-6 membered heterocycloalkyl having 1 to 2 ring members independently selected from N, NH, $NR^{12}$, O or S, wherein the heterocycloalkyl is optionally substituted with one $R^5$;
$R^4$ is $C_1$-$C_6$alkyl substituted with one or two groups independently selected from
$R^6$,
4-6 membered heterocycloalkyl having 1 to 2 ring members independently selected from N, NH, $NR^{12}$, O or S,
5-6 membered heteroaryl having 1 to 3 heteroatoms independently selected from the heteroatoms N, O and S as ring members, and
$C_3$-$C_8$cycloalkyl,
wherein the heterocycloalkyl is optionally substituted with one or two substituents independently selected from —OH and $C_1$-$C_3$alkyl;
each $R^5$ is independently selected from
—C(=O)$R^8$,
$C_1$-$C_3$alkyl,
$C_3$-$C_8$cycloalkyl, and
4-6 membered heterocycloalkyl having 1 to 2 ring members independently selected from N, NH, $NR^{12}$, O or S,
wherein the $C_1$-$C_3$alkyl is optionally substituted with one $R^9$, and the heterocycloalkyl is optionally substituted with one $C_1$-$C_3$alkyl or —C(=O)$R^8$;
each $R^6$ is independently selected from —OH and $C_1$-$C_3$alkyl;
$R^7$ is
$C_1$-$C_6$alkyl,
—N($R^{12}$)$_2$,
$C_3$-$C_8$cycloalkyl, or
4-6 membered heterocycloalkyl having 1 to 2 ring members independently selected from N, NH, $NR^{12}$, O or S,
wherein the $C_1$-$C_6$alkyl is optionally substituted with one or more $R^{11}$, and the $C_3$-$C_8$cycloalkyl is optionally substituted with one or more —OH;
$R^8$ is
$C_1$-$C_6$alkyl,
5-6 membered heteroaryl having 1 to 3 heteroatoms independently selected from the heteroatoms N, O and S as ring members, or
4-6 membered heterocycloalkyl having 1 to 2 ring members independently selected from N, NH, $NR^{12}$, O or S,
wherein the heterocycloalkyl is optionally substituted with one $C_1$-$C_6$alkyl, and the $C_1$-$C_6$alkyl is optionally substituted with one or more substituents selected from the group consisting of —C(=O)OH, N($R^{12}$)$_2$, and $C_3$-$C_8$cycloalkyl;

$R^9$ is
phenyl,
$C_3$-$C_8$cycloalkyl,
4-6 membered heterocycloalkyl having 1 to 2 ring members independently selected from N, NH, $NR^{12}$, O or S, or
5-6 membered heteroaryl having 1 to 3 heteroatoms independently selected from the heteroatoms N, O and S as ring members,
wherein the heteroaryl is optionally substituted with —OH, the heterocycloalkyl is optionally substituted with $C_1$-$C_6$alkyl, and the phenyl is optionally substituted with one or two —OH;
$R^{10}$ is $C_1$-$C_6$alkyl or $C_1$-$C_6$haloalkyl;
each $R^{11}$ is independently selected from
halogen,
$C_1$-$C_6$haloalkyl,
$C_1$-$C_6$alkoxy,
—N($R^{13}$)$_2$,
—OH, and
4-6 membered heterocycloalkyl having 1 to 2 ring members independently selected from N, NH, $NR^{12}$, O or S;
each $R^{12}$ is independently selected from H and $C_1$-$C_6$alkyl, and
each $R^{13}$ is independently selected from
H, and
$C_1$-$C_6$alkyl,
wherein the alkyl is optionally substituted with —OH or $C_1$-$C_6$alkoxy.

In another aspect, the invention provides compounds of Formula (I'):

(I')

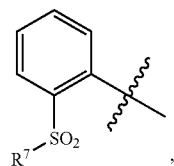

or a pharmaceutically acceptable salt, solvate, co-crystal, polymorph, or stereoisomer thereof, wherein:
$R^{1'}$ is $C_1$-$C_6$alkyl,
phenyl or
5-6 membered heteroaryl having 1 to 3 heteroatoms independently selected from the heteroatoms N, O and S as ring members,
wherein the phenyl and heteroaryl are optionally substituted with one $R^{10'}$, and the $C_1$-$C_6$alkyl is optionally substituted with one or two —$CF_3$;

$R^{2'}$ is $C_1$-$C_6$haloalkyl or halo;
$R^{4'}$ is
  hydrogen, or
  $C_1$-$C_6$alkyl optionally substituted with one or two groups independently selected from:
    $R^6$,
    4-6 membered heterocycloalkyl having 1 to 2 ring members independently selected from N, NH, $NR^{12'}$, O and S,
    5-6 membered heteroaryl having 1 to 3 heteroatoms independently selected from the heteroatoms N, O and S as ring members, and
    $C_3$-$C_8$cycloalkyl,
    wherein the heterocycloalkyl is optionally substituted with one or two substituents independently selected from —OH and $C_1$-$C_3$alkyl;
$R^{8'}$ is
  $C_1$-$C_6$alkyl,
  $C_1$-$C_6$alkyl-COOH,
  5-6 membered heteroaryl having 1 to 3 heteroatoms independently selected from the heteroatoms N, O and S as ring members, or
  4-6 membered heterocycloalkyl having 1 to 2 ring members independently selected from N, NH, $NR^{12'}$, O and S,
  wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12'})_2$, and $C_3$-$C_8$cycloalkyl;
$R^{10'}$ is $C_1$-$C_6$alkyl, $C_1$-$C_6$haloalkyl, or S—$CF_3$;
each $R^{12'}$ is independently selected from
  hydrogen,
  $C_1$-$C_6$alkyl, and
  —C(=O)$R^8$; and
wherein all other substituents are as defined above herein.

Various embodiments of the compounds of the invention are described herein. It will be recognized that features specified in each embodiment may be combined with other specified features to provide further embodiments. The following enumerated embodiments are representative of the compounds of Formula (I) and compounds of Formula (I') of the invention:

Embodiment 1. The compound of Formula (I), or a pharmaceutically acceptable salt, solvate, co-crystal, polymorph, or stereoisomer thereof, wherein,
  $R^1$ is

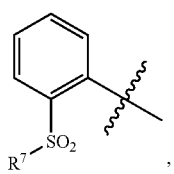

$C_1$-$C_6$alkyl, phenyl or 5-6 membered heteroaryl having 1 to 3 heteroatoms independently selected from the heteroatoms N, O and S as ring members, wherein the phenyl and heteroaryl are optionally substituted with one $R^{10}$, and the $C_1$-$C_6$alkyl is substituted with one or two —$CF_3$.

Embodiment 2. The compound of Formula (I), or a pharmaceutically acceptable salt, solvate, co-crystal, polymorph, or stereoisomer thereof, wherein,
  $R^1$ is

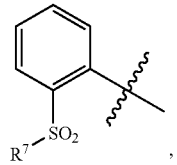

$C_1$-$C_6$alkyl or phenyl, wherein the phenyl is optionally substituted with one $R^{10}$, and the $C_1$-$C_6$alkyl is substituted with one or two —$CF_3$.

Embodiment 3. The compound of Formula (I), or a pharmaceutically acceptable salt, solvate, co-crystal, polymorph, or stereoisomer thereof, wherein $R^1$ is

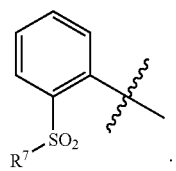

Embodiment 4. The compound of Formula (I), or a pharmaceutically acceptable salt, solvate, co-crystal, polymorph, or stereoisomer thereof, wherein $R^1$ is $C_1$-$C_6$alkyl substituted with one or two —$CF_3$.

Embodiment 5. The compound of Formula (I), or a pharmaceutically acceptable salt, solvate, co-crystal, polymorph, or stereoisomer thereof, wherein $R^1$ is phenyl substituted with one $R^{10}$.

Embodiment 6. The compound of Formula (I), or a pharmaceutically acceptable salt, solvate, co-crystal, polymorph, or stereoisomer thereof, wherein $R^1$ is selected from the group consisting of:

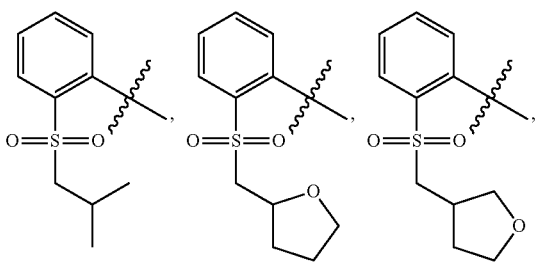

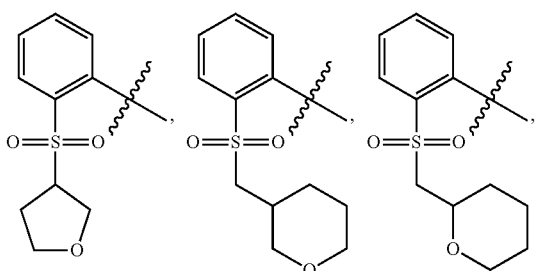

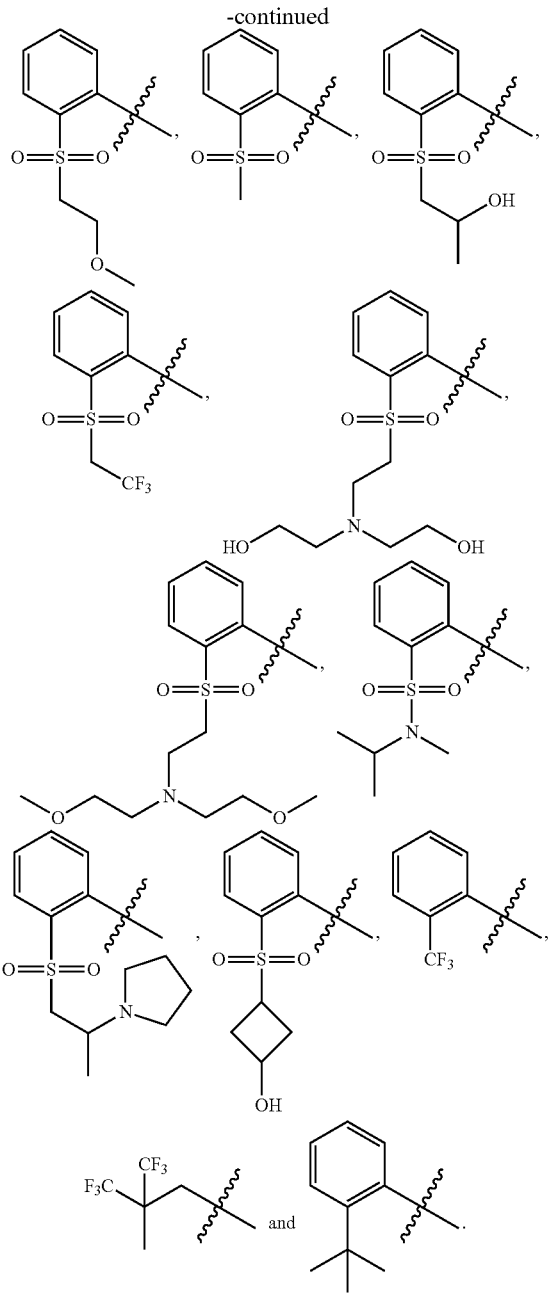

Embodiment 7. The compound of Formula (I), or a pharmaceutically acceptable salt, solvate, co-crystal, polymorph, or stereoisomer thereof, or any one of Embodiments 1 to 6, wherein:
  $R^{3a}$ is H or $C_1$-$C_6$alkyl optionally substituted with —OH or —N($R^{12}$)$_2$; and
  $R^{3b}$ is H or $C_1$-$C_6$alkyl optionally substituted with —OH or —N($R^{12}$)$_2$.

Embodiment 8. The compound of Formula (I), or a pharmaceutically acceptable salt, solvate, co-crystal, polymorph, or stereoisomer thereof, or any one of Embodiments 1 to 6, wherein:
  $R^{3a}$ is H or $C_1$-$C_6$alkyl substituted with —OH or —N($R^{12}$)$_2$; and
  $R^{3b}$ is H or $C_1$-$C_6$alkyl substituted with —OH or —N($R^{12}$)$_2$.

Embodiment 9. The compound of Formula (I), or a pharmaceutically acceptable salt, solvate, co-crystal, polymorph, or stereoisomer thereof, or any one of Embodiments 1 to 6, wherein:
  $R^{3a}$ is $C_1$-$C_6$alkyl optionally substituted with —OH or —N($R^{12}$)$_2$; and
  $R^{3b}$ is $C_1$-$C_6$alkyl optionally substituted with —OH or —N($R^{12}$)$_2$.

Embodiment 10. The compound of Formula (I), or a pharmaceutically acceptable salt, solvate, co-crystal, polymorph, or stereoisomer thereof, or any one of Embodiments 1 to 6, wherein:
  $R^{3a}$ is H or $C_1$-$C_6$alkyl; and
  $R^{3b}$ is H or $C_1$-$C_6$alkyl.

Embodiment 11. The compound of Formula (I), or a pharmaceutically acceptable salt, solvate, co-crystal, polymorph, or stereoisomer thereof, or any one of Embodiments 1 to 6, wherein $R^{3a}$ is $C_1$-$C_6$alkyl and $R^{3b}$ is $C_1$-$C_6$alkyl.

Embodiment 12. The compound of Formula (I), or a pharmaceutically acceptable salt, solvate, co-crystal, polymorph, or stereoisomer thereof, or any one of Embodiments 1 to 6, wherein $R^{3a}$ is H, $CH_3$, —$(CH_2)_2CH_3$, —$CH_2OH$ or

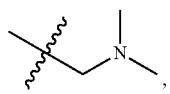

and $R^{3b}$ is H, $CH_3$, —$(CH_2)_2CH_3$, —$CH_2OH$, or

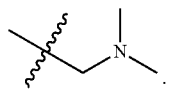 [SMILES: *CN(C)C]

Embodiment 13. The compound of Formula (I), or a pharmaceutically acceptable salt, solvate, co-crystal, polymorph, or stereoisomer thereof, or any one of Embodiments 1 to 6, wherein $R^{3a}$ and $R^{3b}$ together with the carbon atom they are attached to combine to form a $C_3$-$C_8$cycloalkyl, wherein the cycloalkyl is optionally substituted with one $R^5$.

Embodiment 14. The compound of Formula (I), or a pharmaceutically acceptable salt, solvate, co-crystal, polymorph, or stereoisomer thereof, or any one of Embodiments 1 to 6, wherein $R^{3a}$ and $R^{3b}$ together with the carbon atom they are attached to combine to form a 4-6 membered heterocycloalkyl having 1 to 2 ring members independently selected from N, NH, $NR^{12}$, O or S, wherein the heterocycloalkyl is optionally substituted with one $R^5$.

Embodiment 15. The compound of Formula (I), or a pharmaceutically acceptable salt, solvate, co-crystal, polymorph, or stereoisomer thereof, or any one of Embodiments 1 to 6, wherein:
  $R^{3a}$ and $R^{3b}$ together combine to form a group selected from:

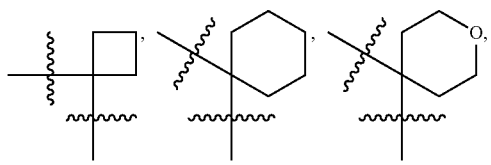

-continued
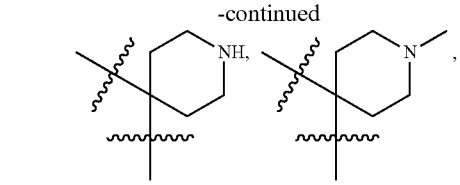
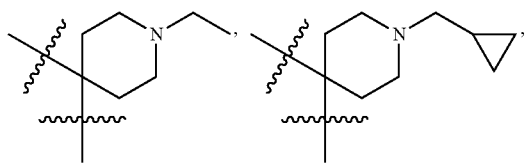
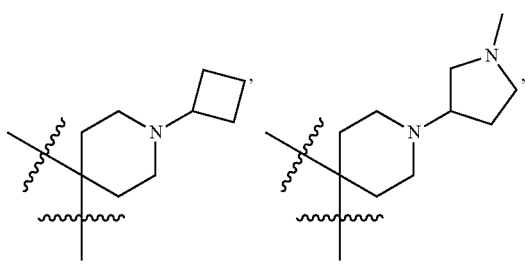
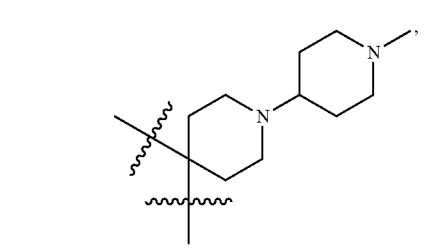
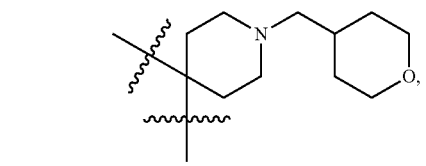
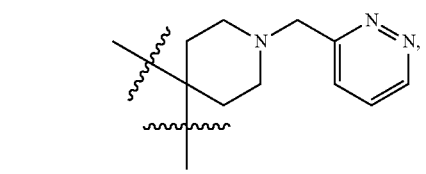
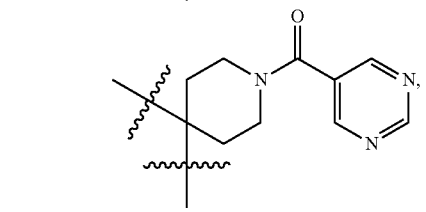
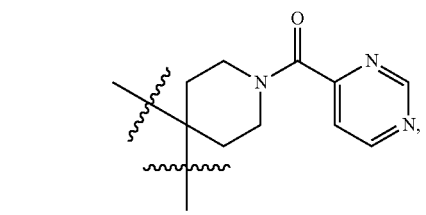
-continued
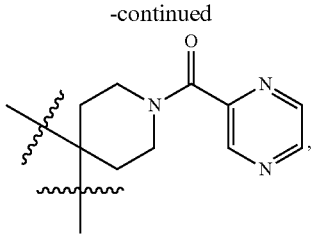
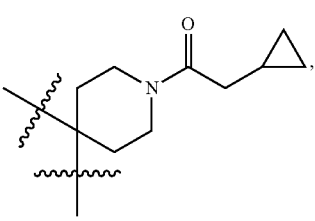
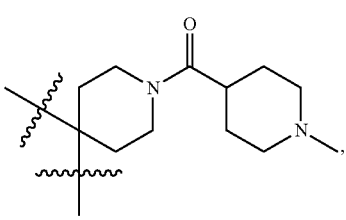
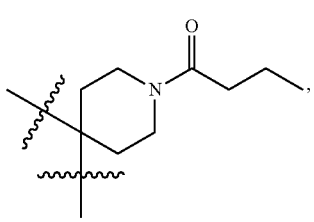
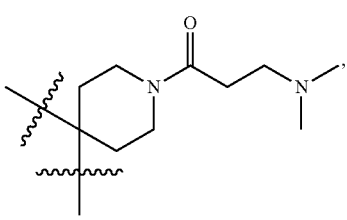
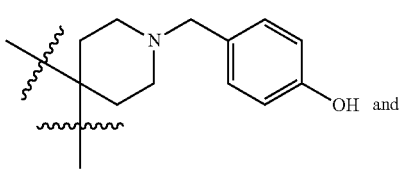
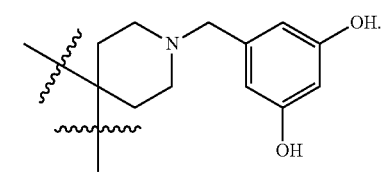
Embodiment 16. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Ia):

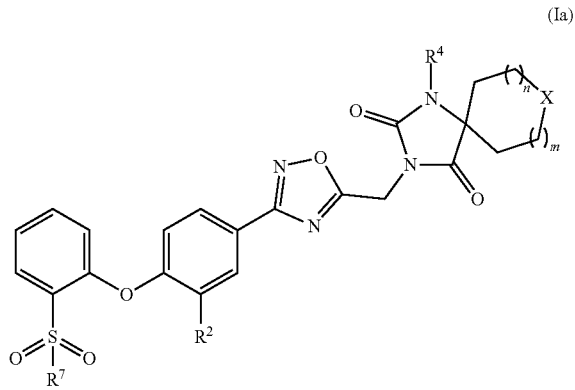

(Ia)

or a pharmaceutically acceptable salt, solvate, co-crystal, polymorph or stereoisomer thereof, wherein:
X is $NR^5$, $CH_2$, or O;
n is 0 or 1, and
m is 0 or 1.

Embodiment 17. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Ib):

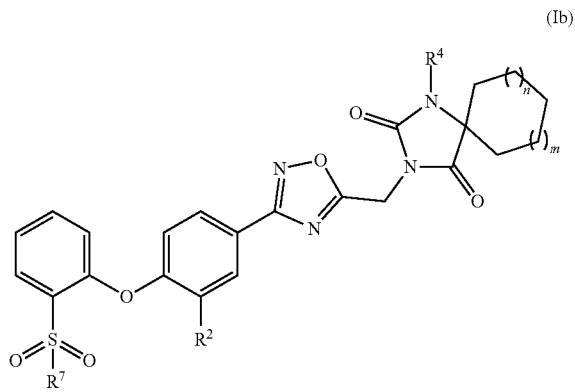

(Ib)

or a pharmaceutically acceptable salt, solvate, co-crystal, polymorph or stereoisomer thereof, wherein:
n is 0 or 1, and
m is 0 or 1.

Embodiment 18. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Ic):

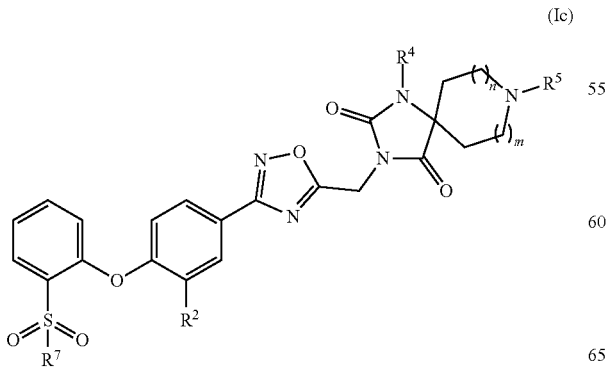

(Ic)

or a pharmaceutically acceptable salt, solvate, co-crystal, polymorph or stereoisomer thereof, wherein:
n is 0 or 1, and
m is 0 or 1.

Embodiment 19. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Id):

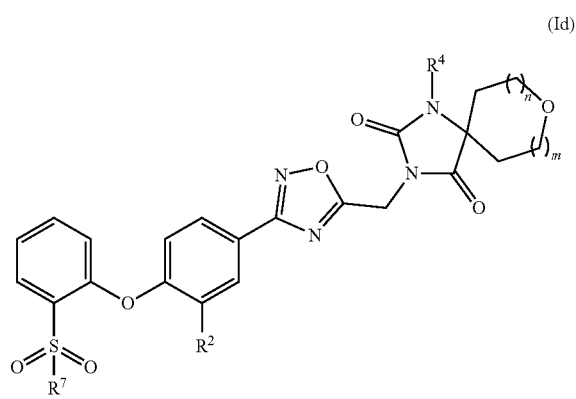

(Id)

or a pharmaceutically acceptable salt, solvate, co-crystal, polymorph or stereoisomer thereof, wherein:
n is 0 or 1, and
m is 0 or 1.

Embodiment 20. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (If):

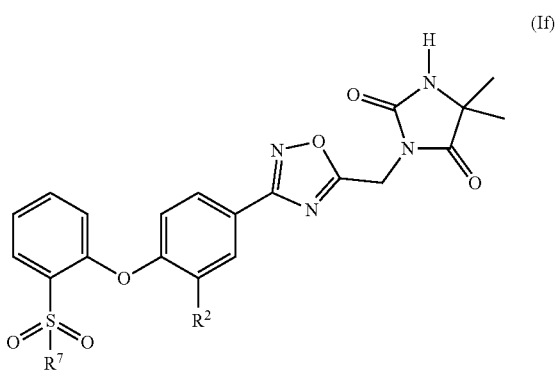

(If)

or a pharmaceutically acceptable salt, solvate, co-crystal, polymorph or stereoisomer thereof, wherein $R^2$ and $R^7$ are as defined herein.

Embodiment 21. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Ig):

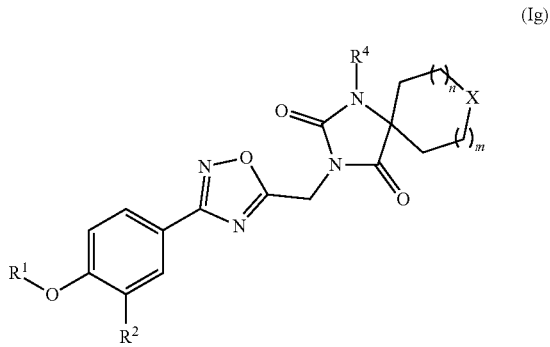

(Ig)

or a pharmaceutically acceptable salt, solvate, co-crystal, polymorph or stereoisomer thereof, wherein:
$R^1$ is $C_1$-$C_6$alkyl, wherein the $C_1$-$C_6$alkyl is optionally substituted with one or two —$CF_3$;
X is $NR^5$, $CH_2$, or O;
n is 0 or 1, and
m is 0 or 1,
wherein all other substituents are as defined herein.

Embodiment 22. The compound of Formula (Ia), or a pharmaceutically acceptable salt, solvate, co-crystal, polymorph, or stereoisomer thereof, or Embodiment 16, wherein X is $CH_2$.

Embodiment 23. The compound of Formula (Ia), or a pharmaceutically acceptable salt, solvate, co-crystal, polymorph, or stereoisomer thereof, or Embodiment 16, wherein X is O.

Embodiment 24. The compound of Formula (Ia), or a pharmaceutically acceptable salt, solvate, co-crystal, polymorph, or stereoisomer thereof, or Embodiment 16, wherein X is $NR^5$.

Embodiment 25. The compound of Formula (I), or a pharmaceutically acceptable salt, solvate, co-crystal, polymorph, or stereoisomer thereof, or any one of Embodiments 1-24, wherein each $R^5$ is independently selected from —C(=O)$R^8$, $C_1$-$C_3$alkyl, $C_3$-$C_8$cycloalkyl and 4-6 membered heterocycloalkyl having 1 to 2 ring members independently selected from N, NH, $NR^{12}$, O or S, wherein the $C_1$-$C_3$alkyl is optionally substituted with one $R^9$, and the heterocycloalkyl is optionally substituted with one $C_1$-$C_3$alkyl or —C(=O)$R^8$,
and wherein $R^8$ is $C_1$-$C_6$alkyl, 5-6 membered heteroaryl having 1 to 3 heteroatoms independently selected from the heteroatoms N, O and S as ring members, or 4-6 membered heterocycloalkyl having 1 to 2 ring members independently selected from N, NH, $NR^{12}$, O or S, wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12})_2$, and $C_3$-$C_8$cycloalkyl.

Embodiment 26. The compound of Formula (I), or a pharmaceutically acceptable salt, solvate, co-crystal, polymorph, or stereoisomer thereof, or any one of Embodiments 1-24, wherein $R^9$ is phenyl, $C_3$-$C_8$cycloalkyl, 4-6 membered heterocycloalkyl having 1 to 2 ring members independently selected from N, NH, $NR^{12}$, O or S, or 5-6 membered heteroaryl having 1 to 3 heteroatoms independently selected from the heteroatoms N, O and S as ring members, wherein the heteroaryl is optionally substituted with —OH, the heterocycloalkyl is optionally substituted with $C_1$-$C_6$alkyl, and the phenyl is optionally substituted with one or two —OH.

Embodiment 27. The compound of Formula (I), or a pharmaceutically acceptable salt, solvate, co-crystal, polymorph, or stereoisomer thereof, or any one of Embodiments 1-24, wherein each $R^5$ is independently selected from —C(=O)$R^8$, $C_1$-$C_3$alkyl and $C_3$-$C_8$cycloalkyl, wherein the $C_1$-$C_3$alkyl is optionally substituted with one $R^9$, wherein $R^9$ is phenyl, $C_3$-$C_8$cycloalkyl, 4-6 membered heterocycloalkyl having 1 to 2 ring members independently selected from N, NH, $NR^{12}$, O or S, or 5-6 membered heteroaryl having 1 to 3 heteroatoms independently selected from the heteroatoms N, O and S as ring members, wherein the heteroaryl is optionally substituted with —OH, the heterocycloalkyl is optionally substituted with $C_1$-$C_6$alkyl, and the phenyl is optionally substituted with one or two —OH.

Embodiment 28. The compound of Formula (I), or a pharmaceutically acceptable salt, solvate, co-crystal, polymorph, or stereoisomer thereof, or any one of Embodiments 1-24, wherein $R^5$ is —C(=O)$R^8$, wherein $R^8$ is $C_1$-$C_6$alkyl, 5-6 membered heteroaryl having 1 to 3 heteroatoms independently selected from the heteroatoms N, O and S as ring members, or 4-6 membered heterocycloalkyl having 1 to 2 ring members independently selected from N, NH, $NR^{12}$, O or S, wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12})_2$, and $C_3$-$C_8$cycloalkyl.

Embodiment 29. The compound of Formula (I), or a pharmaceutically acceptable salt, solvate, co-crystal, polymorph, or stereoisomer thereof, or any one of Embodiments 1-24, wherein each $R^5$ is $C_1$-$C_3$alkyl optionally substituted with one $R^9$, wherein $R^9$ is phenyl, $C_3$-$C_8$cycloalkyl, 4-6 membered heterocycloalkyl having 1 to 2 ring members independently selected from N, NH, $NR^{12}$, O or S, or 5-6 membered heteroaryl having 1 to 3 heteroatoms independently selected from the heteroatoms N, O and S as ring members, wherein the heteroaryl is optionally substituted with —OH, the heterocycloalkyl is optionally substituted with $C_1$-$C_6$alkyl, and the phenyl is optionally substituted with one or two —OH.

Embodiment 30. The compound of Formula (I), or a pharmaceutically acceptable salt, solvate, co-crystal, polymorph, or stereoisomer thereof, or any one of Embodiments 1-24, wherein each $R^5$ is $C_3$-$C_8$cycloalkyl.

Embodiment 31. The compound of Formula (I), or a pharmaceutically acceptable salt, solvate, co-crystal, polymorph, or stereoisomer thereof, or any one of Embodiments 1-24, wherein each $R^5$ is independently selected from $CH_3$, —$CH_2CH_3$,

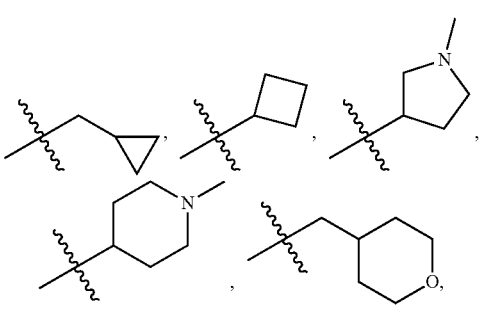

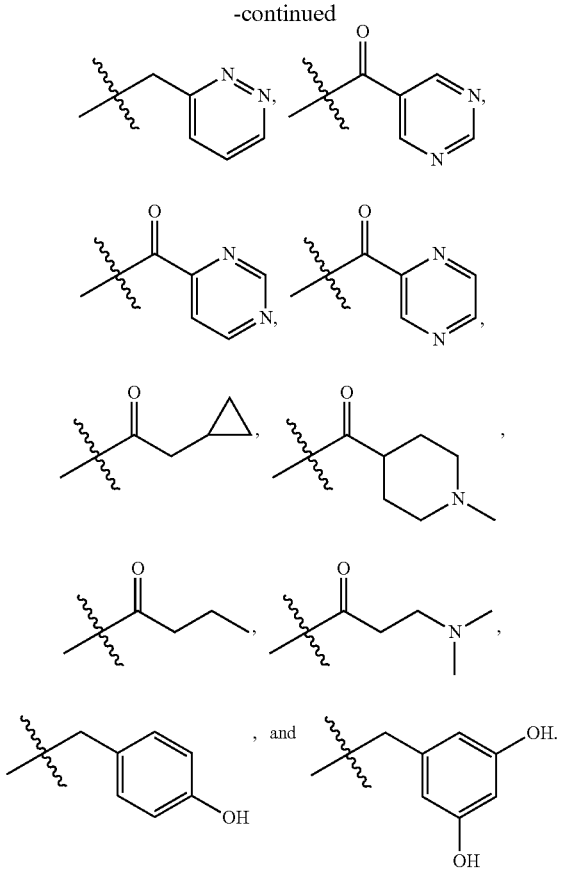

Embodiment 32. The compound of Formula (I), or a pharmaceutically acceptable salt, solvate, co-crystal, polymorph, or stereoisomer thereof, or any one of Embodiments 16-31, wherein n is 0 or 1.

Embodiment 33. The compound of Formula (I), or a pharmaceutically acceptable salt, solvate, co-crystal, polymorph, or stereoisomer thereof, or any one of Embodiments 16-31, wherein n is 0.

Embodiment 34. The compound of Formula (I), or a pharmaceutically acceptable salt, solvate, co-crystal, polymorph, or stereoisomer thereof, or any one of Embodiments 16-31, wherein n is 1.

Embodiment 35. The compound of Formula (I), or a pharmaceutically acceptable salt, solvate, co-crystal, polymorph, or stereoisomer thereof, or any one of Embodiments 16-34, wherein m is 0 or 1.

Embodiment 36. The compound of Formula (I), or a pharmaceutically acceptable salt, solvate, co-crystal, polymorph, or stereoisomer thereof, or any one of Embodiments 16-34, wherein m is 0.

Embodiment 37. The compound of Formula (I), or a pharmaceutically acceptable salt, solvate, co-crystal, polymorph, or stereoisomer thereof, or any one of Embodiments 16-34, wherein m is 1.

Embodiment 38. The compound of Formula (I), or a pharmaceutically acceptable salt, solvate, co-crystal, polymorph, or stereoisomer thereof, or any one of Embodiments 1 to 6, wherein the compound of Formula (I) is a compound of Formula (Ie):

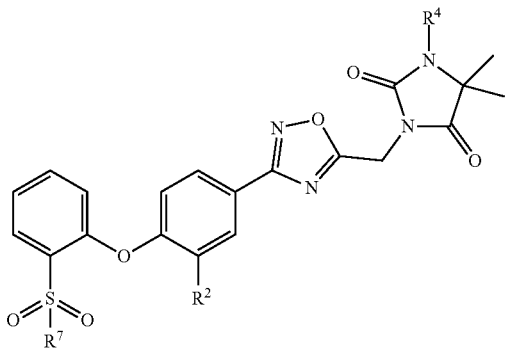

or a pharmaceutically acceptable salt, solvate, co-crystal, polymorph or stereoisomer thereof.

Embodiment 39. The compound of Formula (I), or a pharmaceutically acceptable salt, solvate, co-crystal, polymorph, or stereoisomer thereof, or any one of Embodiments 1 to 38, wherein:

$R^7$ is $C_1$-$C_6$alkyl, —$N(R^{12})_2$, $C_3$-$C_8$cycloalkyl, or 4-6 membered heterocycloalkyl having 1 to 2 ring members independently selected from N, NH, $NR^{12}$, O or S, wherein the $C_1$-$C_6$alkyl is optionally substituted with one or more $R^{11}$; and the $C_3$-$C_8$cycloalkyl is optionally substituted with one or more —OH.

Embodiment 40. The compound of Formula (I), or a pharmaceutically acceptable salt, solvate, co-crystal, polymorph, or stereoisomer thereof, or any one of Embodiments 1 to 38, wherein:

$R^7$ is $C_1$-$C_6$alkyl, —$N(R^{12})_2$ or $C_3$-$C_8$cycloalkyl, wherein the $C_1$-$C_6$alkyl is optionally substituted with one or more $R^{11}$; and the $C_3$-$C_8$cycloalkyl is optionally substituted with one or more —OH.

Embodiment 41. The compound of Formula (I), or a pharmaceutically acceptable salt, solvate, co-crystal, polymorph, or stereoisomer thereof, or any one of Embodiments 1 to 38, wherein $R^7$ is $C_1$-$C_6$alkyl optionally substituted with one or more $R^{11}$, where each $R^{11}$ is independently selected from halogen, $C_1$-$C_6$haloalkyl, $C_1$-$C_6$alkoxy, —$N(R^{13})_2$, —OH, and 4-6 membered heterocycloalkyl having 1 to 2 ring members independently selected from N, NH, $NR^{12}$, O or S.

Embodiment 42. The compound of Formula (I), or a pharmaceutically acceptable salt, solvate, co-crystal, polymorph, or stereoisomer thereof, or any one of Embodiments 1 to 38, wherein $R^7$ is C—$N(R^{12})_2$, where each $R^{12}$ is independently selected from H and $C_1$-$C_6$alkyl.

Embodiment 43. The compound of Formula (I), or a pharmaceutically acceptable salt, solvate, co-crystal, polymorph, or stereoisomer thereof, or any one of Embodiments 1 to 38, wherein $R^7$ is $C_3$-$C_8$cycloalkyl optionally substituted with one or more —OH.

Embodiment 44. The compound of Formula (I), or a pharmaceutically acceptable salt, solvate, co-crystal, polymorph, or stereoisomer thereof, or any one of Embodiments 1 to 38,

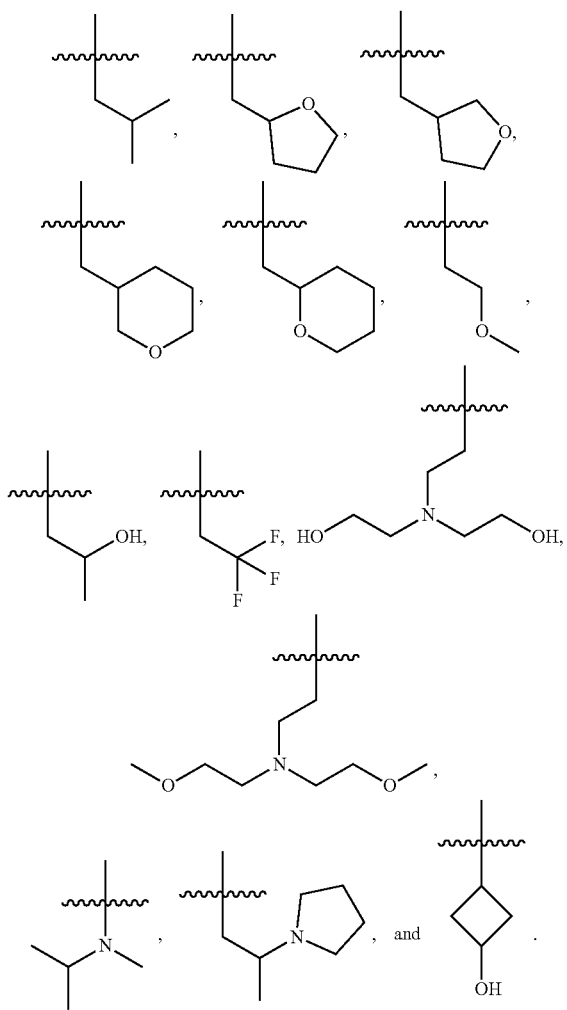

wherein R⁷ is selected from —CH₃,

Embodiment 45. The compound of Formula (I), or a pharmaceutically acceptable salt, solvate, co-crystal, polymorph, or stereoisomer thereof, or any one of Embodiments 1 to 44, wherein $R^2$ is halo or $C_1$-$C_6$haloalkyl.

Embodiment 46. The compound of Formula (I), or a pharmaceutically acceptable salt, solvate, co-crystal, polymorph, or stereoisomer thereof, or any one of Embodiments 1 to 44, wherein $R^2$ is halo.

Embodiment 47. The compound of Formula (I), or a pharmaceutically acceptable salt, solvate, co-crystal, polymorph, or stereoisomer thereof, or any one of Embodiments 1 to 44, wherein $R^2$ is $C_1$-$C_6$haloalkyl.

Embodiment 48. The compound of Formula (I), or a pharmaceutically acceptable salt, solvate, co-crystal, polymorph, or stereoisomer thereof, or any one of Embodiments 1 to 44, wherein $R^2$ is —CF₃.

Embodiment 49. The compound of Formula (I), or a pharmaceutically acceptable salt, solvate, co-crystal, polymorph, or stereoisomer thereof, or any one of Embodiments 1 to 44, wherein $R^2$ is —Cl.

Embodiment 50. The compound of Formula (I), or a pharmaceutically acceptable salt, solvate, co-crystal, polymorph, or stereoisomer thereof, or any one of Embodiments 1 to 49, wherein
$R^4$ is $C_1$-$C_6$alkyl substituted with one or two groups independently selected from $R^6$, 4-6 membered heterocycloalkyl having 1 to 2 ring members independently selected from N, NH, $NR^{12}$, O or S, 5-6 membered heteroaryl having 1 to 3 heteroatoms independently selected from the heteroatoms N, O and S as ring members, and $C_3$-$C_8$cycloalkyl, wherein the heterocycloalkyl is optionally substituted with one or two substituents independently selected from —OH and $C_1$-$C_3$alkyl.

Embodiment 51. The compound of Formula (I), or a pharmaceutically acceptable salt, solvate, co-crystal, polymorph, or stereoisomer thereof, or any one of Embodiments 1 to 49, wherein
$R^4$ is $C_1$-$C_6$alkyl optionally substituted with one or two groups independently selected from $R^6$, 4-6 membered heterocycloalkyl having 1 to 2 ring members independently selected from N, NH, $NR^{12}$, O or S, 5-6 membered heteroaryl having 1 to 3 heteroatoms independently selected from the heteroatoms N, O and S as ring members, and $C_3$-$C_8$cycloalkyl, wherein the heterocycloalkyl is optionally substituted with one or two substituents independently selected from —OH and $C_1$-$C_3$alkyl, and wherein each $R^6$ is independently selected from —OH and $C_1$-$C_3$alkyl.

Embodiment 52. The compound of Formula (I), or a pharmaceutically acceptable salt, solvate, co-crystal, polymorph, or stereoisomer thereof, or any one of Embodiments 1 to 49, wherein
$R^4$ is $C_1$-$C_6$alkyl substituted with one or two groups independently selected from $R^6$, 4-6 membered heterocycloalkyl having 1 to 2 ring members independently selected from N, NH, $NR^{12}$, O or S, 5-6 membered heteroaryl having 1 to 3 heteroatoms independently selected from the heteroatoms N, O and S as ring members, and $C_3$-$C_8$cycloalkyl, and wherein each $R^6$ is independently selected from —OH and $C_1$-$C_3$alky.

Embodiment 53. The compound of Formula (I), or a pharmaceutically acceptable salt, solvate, co-crystal, polymorph, or stereoisomer thereof, or any one of Embodiments 1 to 49, wherein $R^4$ is $C_1$-$C_6$alkyl substituted with 4-6 membered heterocycloalkyl having 1 to 2 ring members independently selected from N, NH, $NR^{12}$, O or S.

Embodiment 54. The compound of Formula (I), or a pharmaceutically acceptable salt, solvate, co-crystal, polymorph, or stereoisomer thereof, or any one of Embodiments 1 to 49, wherein $R^4$ is $C_1$-$C_6$alkyl substituted with 5-6 membered heteroaryl having 1 to 3 heteroatoms independently selected from the heteroatoms N, O and S as ring members.

Embodiment 55. The compound of Formula (I), or a pharmaceutically acceptable salt, solvate, co-crystal, polymorph, or stereoisomer thereof, or any one of Embodiments 1 to 49, wherein $R^4$ is $C_1$-$C_6$alkyl substituted with $C_3$-$C_8$cycloalkyl.

Embodiment 56. The compound of Formula (I), or a pharmaceutically acceptable salt, solvate, co-crystal, polymorph, or stereoisomer thereof, or any one of Embodiments 1 to 49, wherein $R^4$ is selected from

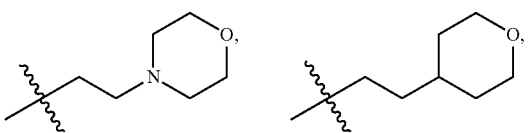

-continued

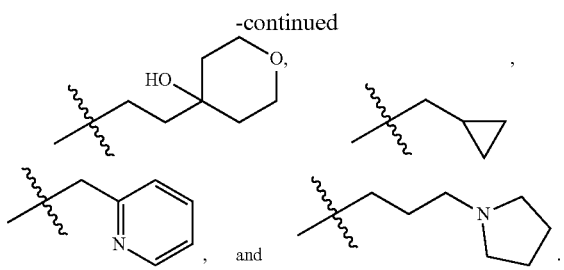

Embodiment 57. The compound of Formula (I'), or a pharmaceutically acceptable salt, solvate, co-crystal, polymorph, or stereoisomer thereof, wherein, $R^{1'}$ is

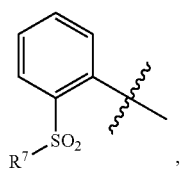

$C_1$-$C_6$alkyl, phenyl or 5-6 membered heteroaryl having 1 to 3 heteroatoms independently selected from the heteroatoms N, O and S as ring members, wherein the phenyl and heteroaryl are optionally substituted with one $R^{10'}$, and the $C_1$-$C_6$alkyl is optionally substituted with one or two —$CF_3$.

Embodiment 58. The compound of Formula (I'), or a pharmaceutically acceptable salt, solvate, co-crystal, polymorph, or stereoisomer thereof, wherein, $R^{1'}$ is

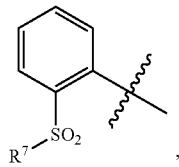

$C_1$-$C_6$alkyl or phenyl, wherein the phenyl is optionally substituted with one
$R^{10'}$, and the $C_1$-$C_6$alkyl is substituted with one or two —$CF_3$.

Embodiment 59. The compound of Formula (I'), or a pharmaceutically acceptable salt, solvate, co-crystal, polymorph, or stereoisomer thereof, wherein $R^{1'}$ is

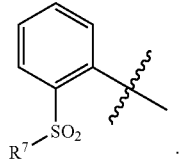

Embodiment 60. The compound of Formula (I'), or a pharmaceutically acceptable salt, solvate, co-crystal, polymorph, or stereoisomer thereof, wherein $R^{1'}$ is $C_1$-$C_6$alkyl substituted with one or two —$CF_3$.

Embodiment 61. The compound of Formula (I'), or a pharmaceutically acceptable salt, solvate, co-crystal, polymorph, or stereoisomer thereof, wherein $R^{1'}$ is phenyl substituted with one $R^{10'}$.

Embodiment 62. The compound of Formula (I'), or a pharmaceutically acceptable salt, solvate, co-crystal, polymorph, or stereoisomer thereof, wherein $R^{1'}$ is 5-6 membered heteroaryl having 1 to 3 heteroatoms independently selected from the heteroatoms N, O and S as ring members, wherein said heteroaryl is substituted with one $R^{10'}$.

Embodiment 63. The compound of Formula (I'), or a pharmaceutically acceptable salt, solvate, co-crystal, polymorph, or stereoisomer thereof, wherein $R^{1'}$ is selected from the group consisting of:

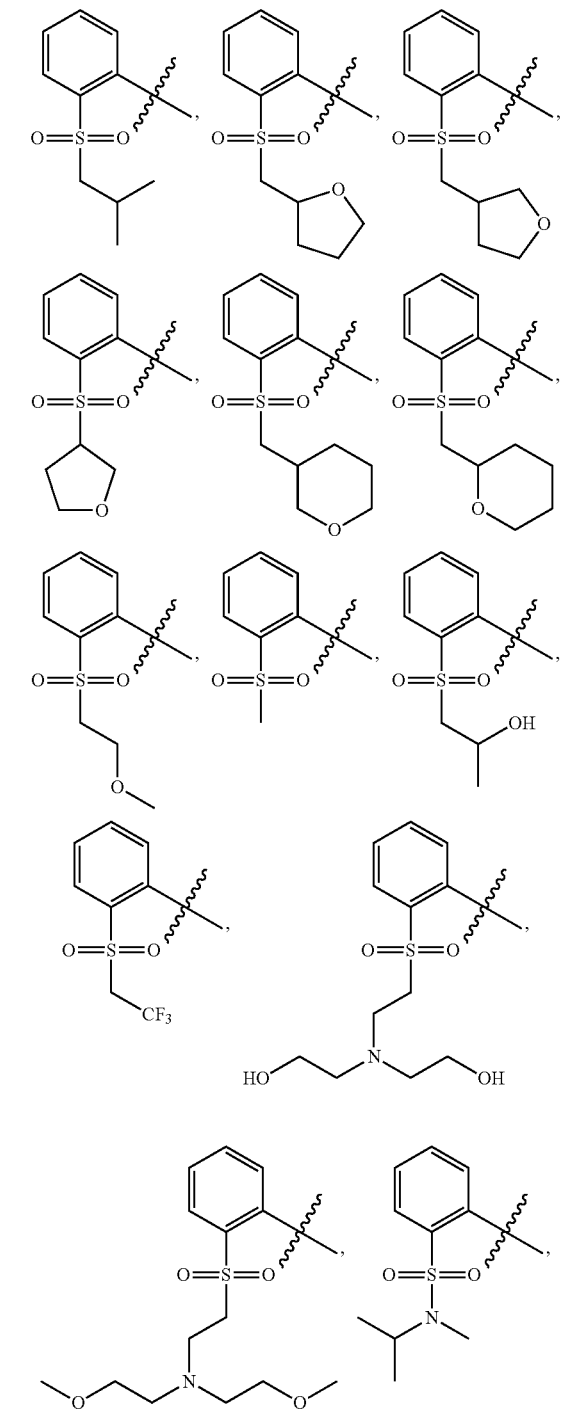

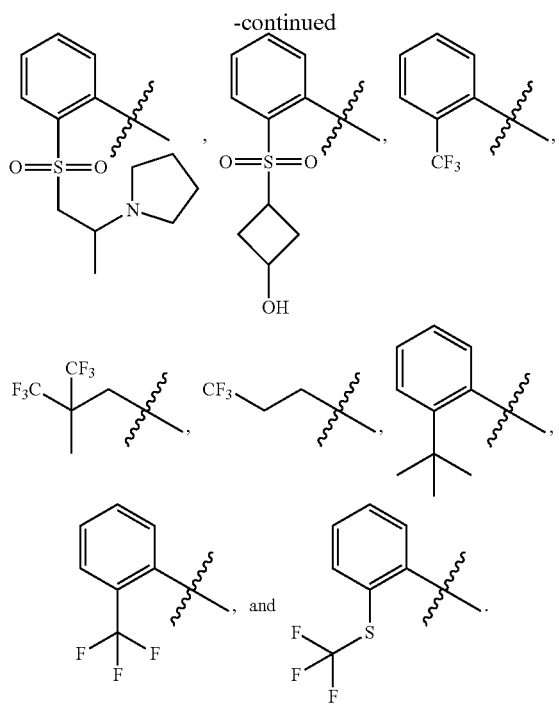

Embodiment 64. The compound of Formula (I'), or a pharmaceutically acceptable salt, solvate, co-crystal, polymorph, or stereoisomer thereof, or any one of Embodiments 57 to 63, wherein:
$R^{3a}$ is hydrogen or $C_1$-$C_6$alkyl optionally substituted with —OH or —N($R^{12'}$)$_2$; and
$R^{3b}$ is hydrogen or $C_1$-$C_6$alkyl optionally substituted with —OH or —N($R^{12'}$)$_2$.

Embodiment 65. The compound of Formula (I'), or a pharmaceutically acceptable salt, solvate, co-crystal, polymorph, or stereoisomer thereof, or any one of Embodiments 57 to 63, wherein:
$R^{3a}$ is hydrogen or $C_1$-$C_6$alkyl substituted with —OH or —N($R^{12'}$)$_2$; and
$R^{3b}$ is hydrogen or $C_1$-$C_6$alkyl substituted with —OH or —N($R^{12'}$)$_2$.

Embodiment 66. The compound of Formula (I'), or a pharmaceutically acceptable salt, solvate, co-crystal, polymorph, or stereoisomer thereof, or any one of Embodiments 57 to 63, wherein:
$R^{3a}$ is $C_1$-$C_6$alkyl optionally substituted with —OH or —N($R^{12'}$)$_2$; and
$R^{3b}$ is $C_1$-$C_6$alkyl optionally substituted with —OH or —N($R^{12'}$)$_2$.

Embodiment 67. The compound of Formula (I'), or a pharmaceutically acceptable salt, solvate, co-crystal, polymorph, or stereoisomer thereof, or any one of Embodiments 57 to 63, wherein:
$R^{3a}$ is hydrogen or $C_1$-$C_6$alkyl, and
$R^{3b}$ is hydrogen or $C_1$-$C_6$alkyl.

Embodiment 68. The compound of Formula (I'), or a pharmaceutically acceptable salt, solvate, co-crystal, polymorph, or stereoisomer thereof, or any one of Embodiments 57 to 63, wherein $R^{3a}$ is $C_1$-$C_6$alkyl and $R^{3b}$ is $C_1$-$C_6$alkyl.

Embodiment 69. The compound of Formula (I'), or a pharmaceutically acceptable salt, solvate, co-crystal, polymorph, or stereoisomer thereof, or any one of Embodiments 57 to 63, wherein $R^{3a}$ is hydrogen and $R^{3b}$ is hydrogen.

Embodiment 70. The compound of Formula (I'), or a pharmaceutically acceptable salt, solvate, co-crystal, polymorph, or stereoisomer thereof, or any one of Embodiments 57 to 63, wherein $R^{3a}$ is hydrogen, $CH_3$, —($CH_2$)$_2$$CH_3$, —$CH_2$OH or

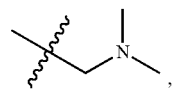 [SMILES: *CN(C)C]

and $R^{3b}$ is hydrogen, $CH_3$, —($CH_2$)$_2$$CH_3$, —$CH_2$OH, or

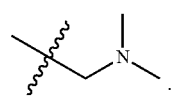 [SMILES: *CN(C)C]

Embodiment 71. The compound of Formula (I'), or a pharmaceutically acceptable salt, solvate, co-crystal, polymorph, or stereoisomer thereof, or any one of Embodiments 57 to 63, wherein $R^{3a}$ and $R^{3b}$ together with the carbon atom they are attached to combine to form a $C_3$-$C_8$cycloalkyl, wherein the cycloalkyl is optionally substituted with one $R^5$.

Embodiment 72. The compound of Formula (I'), or a pharmaceutically acceptable salt, solvate, co-crystal, polymorph, or stereoisomer thereof, or any one of Embodiments 57 to 63, wherein $R^{3a}$ and $R^{3b}$ together with the carbon atom they are attached to combine to form a 4-6 membered heterocycloalkyl having 1 to 2 ring members independently selected from N, NH, $NR^{12'}$, O or S, wherein the heterocycloalkyl is optionally substituted with one $R^5$.

Embodiment 73. The compound of Formula (I'), or a pharmaceutically acceptable salt, solvate, co-crystal, polymorph, or stereoisomer thereof, or any one of Embodiments 57 to 63, wherein:
$R^{3a}$ and $R^{3b}$ together combine to form a group selected from:

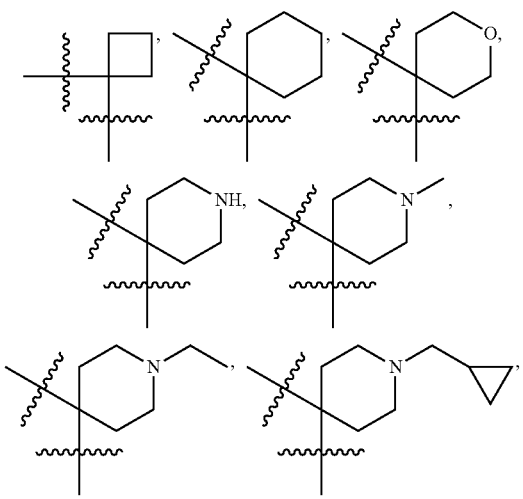

-continued
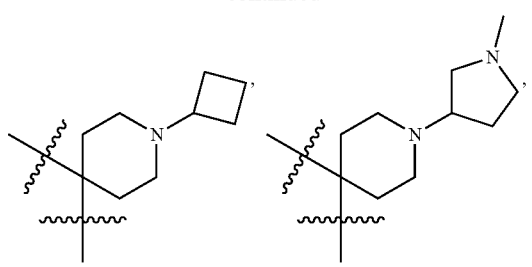
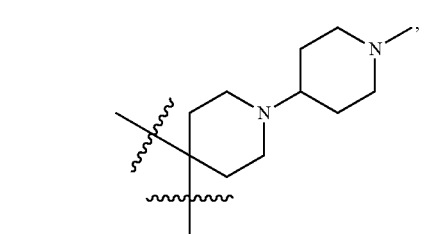
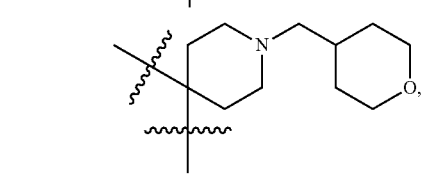
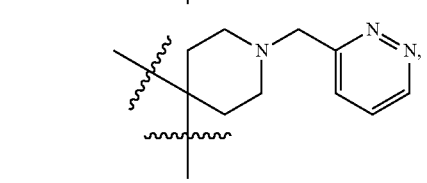
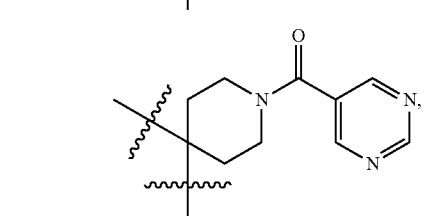
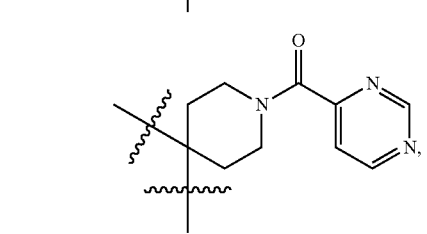
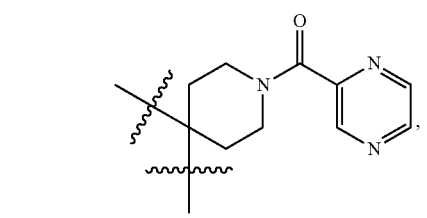
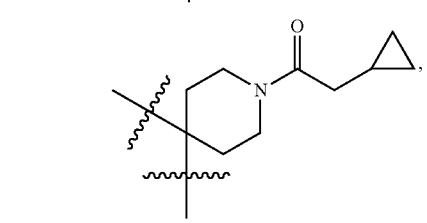
-continued
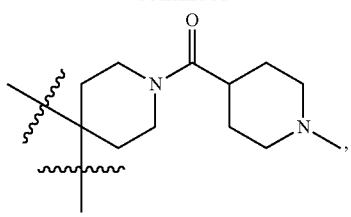
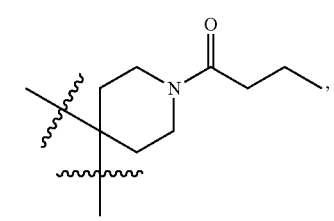
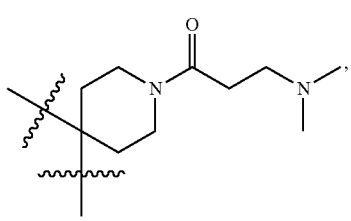
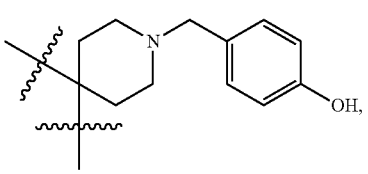
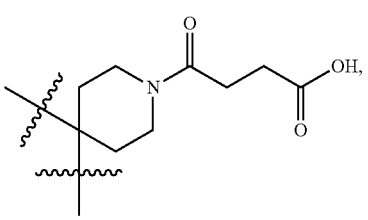
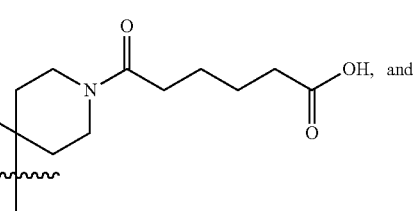
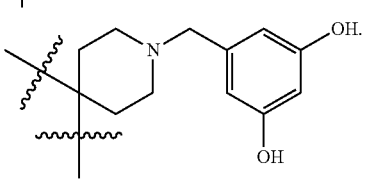
Embodiment 74. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (Ia'):

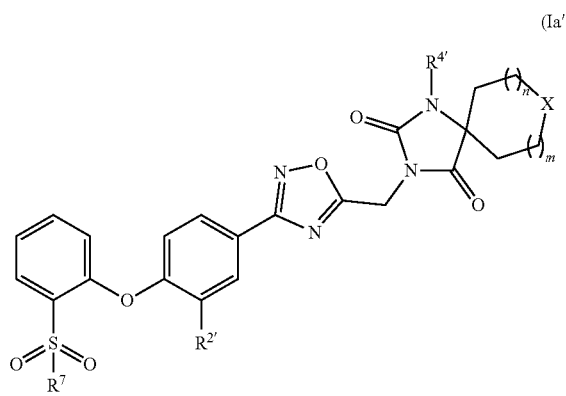

(Ia')

or a pharmaceutically acceptable salt, solvate, co-crystal, polymorph or stereoisomer thereof, wherein:

X is $NR^5$, $CH_2$, or O;

n is 0 or 1, and m is 0 or 1.

Embodiment 75. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (Ib'):

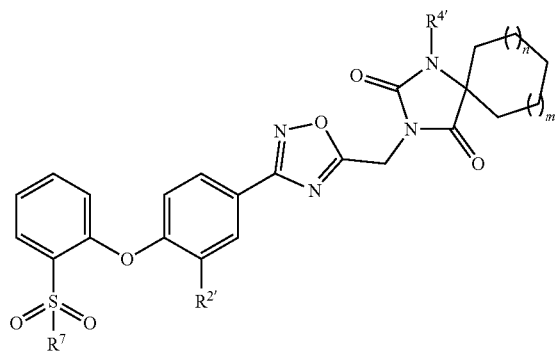

(Ib')

or a pharmaceutically acceptable salt, solvate, co-crystal, polymorph or stereoisomer thereof, wherein:

n is 0 or 1, and m is 0 or 1.

Embodiment 76. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (Ic'):

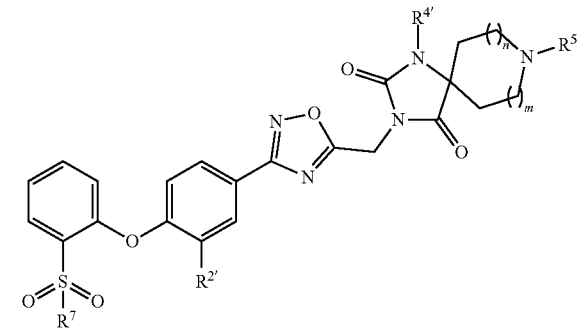

(Ic')

or a pharmaceutically acceptable salt, solvate, co-crystal, polymorph or stereoisomer thereof, wherein:

n is 0 or 1, and m is 0 or 1.

Embodiment 77. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (Id'):

(Id')

or a pharmaceutically acceptable salt, solvate, co-crystal, polymorph or stereoisomer thereof, wherein:

n is 0 or 1, and m is 0 or 1.

Embodiment 78. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (If'):

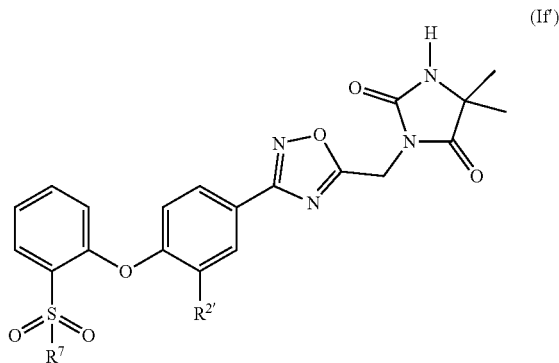

(If')

or a pharmaceutically acceptable salt, solvate, co-crystal, polymorph or stereoisomer thereof.

Embodiment 79. The compound of Formula (I'), or a pharmaceutically acceptable salt, solvate, co-crystal, polymorph, or stereoisomer thereof, or any one of Embodiments 57 to 63, wherein the compound of Formula (I') is a compound of Formula (Ig'):

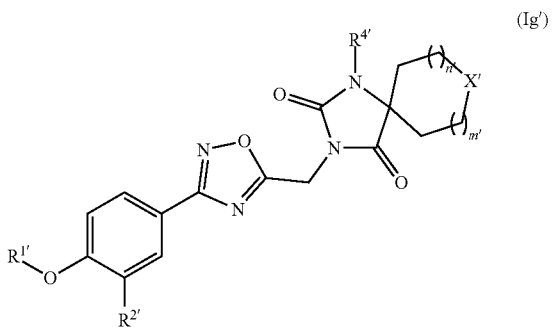

(Ig')

or a pharmaceutically acceptable salt, solvate, co-crystal, polymorph or stereoisomer thereof, wherein:
$R^{1'}$ is $C_1$-$C_6$alkyl, wherein the $C_1$-$C_6$alkyl is optionally substituted with one or two —$CF_3$;
X is $NR^5$, $CH_2$, or O;
n is 0 or 1, and
m is 0 or 1.

Embodiment 80. The compound of Formula (Ia'), or a pharmaceutically acceptable salt, solvate, co-crystal, polymorph, or stereoisomer thereof, or Embodiment 74, wherein X is $CH_2$.

Embodiment 81. The compound of Formula (Ia'), or a pharmaceutically acceptable salt, solvate, co-crystal, polymorph, or stereoisomer thereof, or Embodiment 74, wherein X is O.

Embodiment 82. The compound of Formula (Ia'), or a pharmaceutically acceptable salt, solvate, co-crystal, polymorph, or stereoisomer thereof, or Embodiment 74, wherein X is $NR^5$.

Embodiment 83. The compound of Formula (I'), or a pharmaceutically acceptable salt, solvate, co-crystal, polymorph, or stereoisomer thereof, or any one of Embodiments 57-82, wherein each $R^5$ is independently selected from —C(=O)$R^{8'}$, $C_1$-$C_3$alkyl, $C_3$-$C_8$cycloalkyl and 4-6 membered heterocycloalkyl having 1 to 2 ring members independently selected from N, NH, $NR^{12'}$, O or S, wherein the $C_1$-$C_3$alkyl is optionally substituted with one $R^9$, and the heterocycloalkyl is optionally substituted with one $C_1$-$C_3$alkyl or —C(=O)$R^{8'}$, and wherein $R^{8'}$ is $C_1$-$C_6$alkyl, $C_1$-$C_6$alkyl-COOH, 5-6 membered heteroaryl having 1 to 3 heteroatoms independently selected from the heteroatoms N, O and S as ring members, or 4-6 membered heterocycloalkyl having 1 to 2 ring members independently selected from N, NH, $NR^{12'}$, O or S, and
wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12'})_2$, and $C_3$-$C_8$cycloalkyl.

Embodiment 84. The compound of Formula (I'), or a pharmaceutically acceptable salt, solvate, co-crystal, polymorph, or stereoisomer thereof, or any one of Embodiments 57-82,
wherein $R^9$ is phenyl, $C_3$-$C_8$cycloalkyl, 4-6 membered heterocycloalkyl having 1 to 2 ring members independently selected from N, NH, $NR^{12'}$, O or S, or 5-6 membered heteroaryl having 1 to 3 heteroatoms independently selected from the heteroatoms N, O and S as ring members,
wherein the heteroaryl is optionally substituted with —OH, the heterocycloalkyl is optionally substituted with $C_1$-$C_6$alkyl, and the phenyl is optionally substituted with one or two —OH.

Embodiment 85. The compound of Formula (I'), or a pharmaceutically acceptable salt, solvate, co-crystal, polymorph, or stereoisomer thereof, or any one of Embodiments 57-82,
wherein each $R^5$ is independently selected from —C(=O)$R^{8'}$, $C_1$-$C_3$alkyl and $C_3$-$C_8$cycloalkyl,
wherein the $C_1$-$C_3$alkyl is optionally substituted with one $R^9$,
wherein $R^9$ is phenyl, $C_3$-$C_8$cycloalkyl, 4-6 membered heterocycloalkyl having 1 to 2 ring members independently selected from N, NH, $NR^{12'}$, O or S, or 5-6 membered heteroaryl having 1 to 3 heteroatoms independently selected from the heteroatoms N, O and S as ring members, and
wherein the heteroaryl is optionally substituted with —OH, the heterocycloalkyl is optionally substituted with $C_1$-$C_6$alkyl, and the phenyl is optionally substituted with one or two —OH.

Embodiment 86. The compound of Formula (I'), or a pharmaceutically acceptable salt, solvate, co-crystal, polymorph, or stereoisomer thereof, or any one of Embodiments 57-82,
wherein $R^5$ is —C(=O)$R^{8'}$,
wherein $R^{8'}$ is $C_1$-$C_6$alkyl, 5-6 membered heteroaryl having 1 to 3 heteroatoms independently selected from the heteroatoms N, O and S as ring members, or 4-6 membered heterocycloalkyl having 1 to 2 ring members independently selected from N, NH, $NR^{12'}$, O or S, and
wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12'})_2$, and $C_3$-$C_8$cycloalkyl.

Embodiment 87. The compound of Formula (I'), or a pharmaceutically acceptable salt, solvate, co-crystal, polymorph, or stereoisomer thereof, or any one of Embodiments 57-82,
wherein each $R^5$ is $C_1$-$C_3$alkyl optionally substituted with one $R^9$,
wherein $R^9$ is phenyl, $C_3$-$C_8$cycloalkyl, 4-6 membered heterocycloalkyl having 1 to 2 ring members independently selected from N, NH, NR$^{12'}$, O or S, or 5-6 membered heteroaryl having 1 to 3 heteroatoms independently selected from the heteroatoms N, O and S as ring members, and wherein the heteroaryl is optionally substituted with —OH, the heterocycloalkyl is optionally substituted with $C_1$-$C_6$alkyl, and the phenyl is optionally substituted with one or two —OH.

Embodiment 88. The compound of Formula (I'), or a pharmaceutically acceptable salt, solvate, co-crystal, polymorph, or stereoisomer thereof, or any one of Embodiments 57-82, wherein each $R^5$ is $C_3$-$C_8$cycloalkyl.

Embodiment 89. The compound of Formula (I'), or a pharmaceutically acceptable salt, solvate, co-crystal, polymorph, or stereoisomer thereof, or any one of Embodiments 57-82, wherein each $R^5$ is independently selected from $CH_3$, —$CH_2CH_3$,

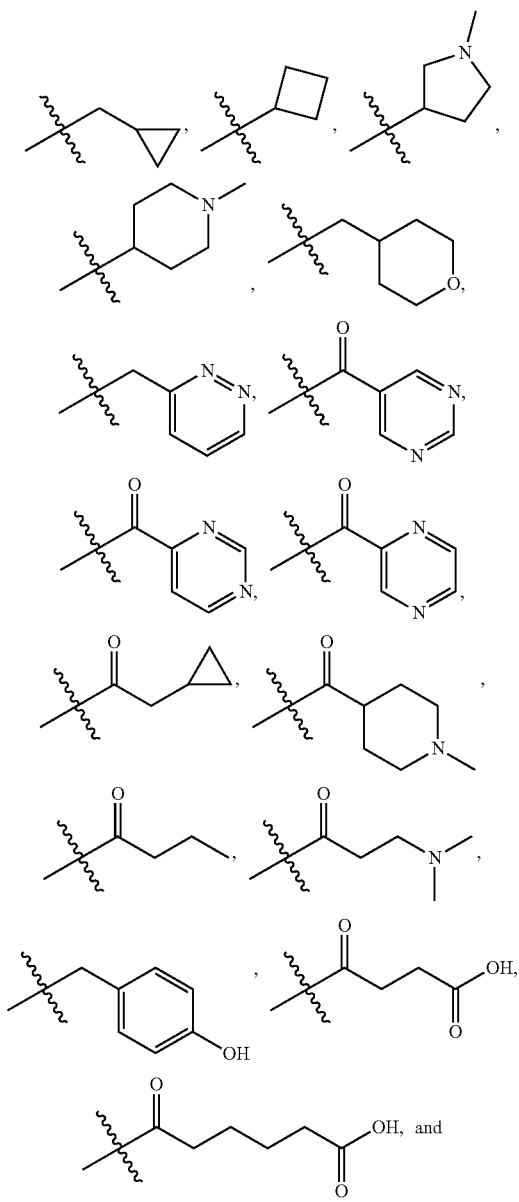

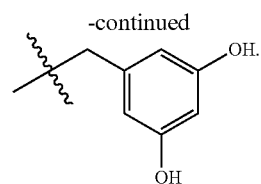

Embodiment 90. The compound of Formula (I'), or a pharmaceutically acceptable salt, solvate, co-crystal, polymorph, or stereoisomer thereof, or any one of Embodiments 74-89, wherein n is 0 or 1.

Embodiment 91. The compound of Formula (I'), or a pharmaceutically acceptable salt, solvate, co-crystal, polymorph, or stereoisomer thereof, or any one of Embodiments 74-89, wherein n is 0.

Embodiment 92. The compound of Formula (I'), or a pharmaceutically acceptable salt, solvate, co-crystal, polymorph, or stereoisomer thereof, or any one of Embodiments 74-89, wherein n is 1.

Embodiment 93. The compound of Formula (I'), or a pharmaceutically acceptable salt, solvate, co-crystal, polymorph, or stereoisomer thereof, or any one of Embodiments 74-89, wherein m is 0 or 1.

Embodiment 94. The compound of Formula (I'), or a pharmaceutically acceptable salt, solvate, co-crystal, polymorph, or stereoisomer thereof, or any one of Embodiments 74-89, wherein m is 0.

Embodiment 95. The compound of Formula (I'), or a pharmaceutically acceptable salt, solvate, co-crystal, polymorph, or stereoisomer thereof, or any one of Embodiments 74-89, wherein m is 1.

Embodiment 96. The compound of Formula (I'), or a pharmaceutically acceptable salt, solvate, co-crystal, polymorph, or stereoisomer thereof, or any one of Embodiments 57-95, wherein the compound of Formula (I') is a compound of Formula (Ie'):

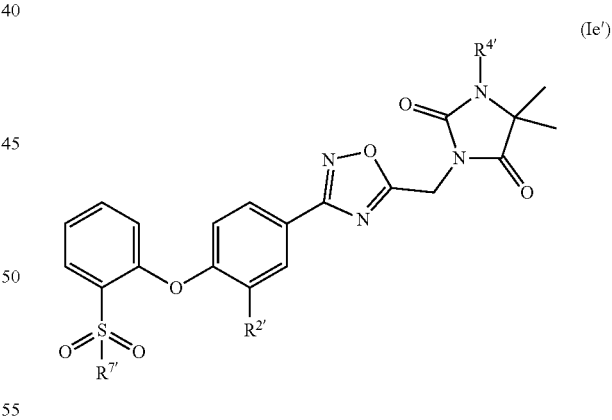

(Ie')

or a pharmaceutically acceptable salt, solvate, co-crystal, polymorph or stereoisomer thereof.

Embodiment 97. The compound of Formula (I'), or a pharmaceutically acceptable salt, solvate, co-crystal, polymorph, or stereoisomer thereof, or any one of Embodiments 57-96, wherein:

$R^7$ is $C_1$-$C_6$alkyl, —N($R^{12'}$)$_2$, $C_3$-$C_8$cycloalkyl, or 4-6 membered heterocycloalkyl having 1 to 2 ring members independently selected from N, NH, NR$^{12'}$, O or S, wherein the $C_1$-$C_6$alkyl is optionally substituted with one or more $R^{11}$, and the $C_3$-$C_8$cycloalkyl is optionally substituted with one or more —OH.

Embodiment 98. The compound of Formula (I'), or a pharmaceutically acceptable salt, solvate, co-crystal, polymorph, or stereoisomer thereof, or any one of Embodiments 57 to 96, wherein:
$R^7$ is $C_1$-$C_6$alkyl, —$N(R^{12'})_2$ or $C_3$-$C_8$cycloalkyl,
wherein the $C_1$-$C_6$alkyl is optionally substituted with one or more $R^{11}$, and the $C_3$-$C_8$cycloalkyl is optionally substituted with one or more —OH.

Embodiment 99. The compound of Formula (I'), or a pharmaceutically acceptable salt, solvate, co-crystal, polymorph, or stereoisomer thereof, or any one of Embodiments 57 to 96, wherein:
$R^7$ is $C_1$-$C_6$alkyl optionally substituted with one or more $R^{11}$,
wherein each $R^{11}$ is independently selected from halogen, $C_1$-$C_6$haloalkyl, $C_1$-$C_3$alkoxy, —$N(R^{13})_2$, —OH, and 4-6 membered heterocycloalkyl having 1 to 2 ring members independently selected from N, NH, $NR^{12'}$, O or S.

Embodiment 100. The compound of Formula (I'), or a pharmaceutically acceptable salt, solvate, co-crystal, polymorph, or stereoisomer thereof, or any one of Embodiments 57 to 96, wherein $R^7$ is C—$N(R^{12'})_2$, wherein each $R^{12'}$ is independently selected from hydrogen, $C_1$-$C_6$alkyl, and —C(=O)$R^{8'}$.

Embodiment 101. The compound of Formula (I'), or a pharmaceutically acceptable salt, solvate, co-crystal, polymorph, or stereoisomer thereof, or any one of Embodiments 57 to 96, wherein $R^7$ is $C_3$-$C_8$cycloalkyl optionally substituted with one or more —OH.

Embodiment 102. The compound of Formula (I'), or a pharmaceutically acceptable salt, solvate, co-crystal, polymorph, or stereoisomer thereof, or any one of Embodiments 57 to 96, wherein $R^7$ is selected from —$CH_3$,

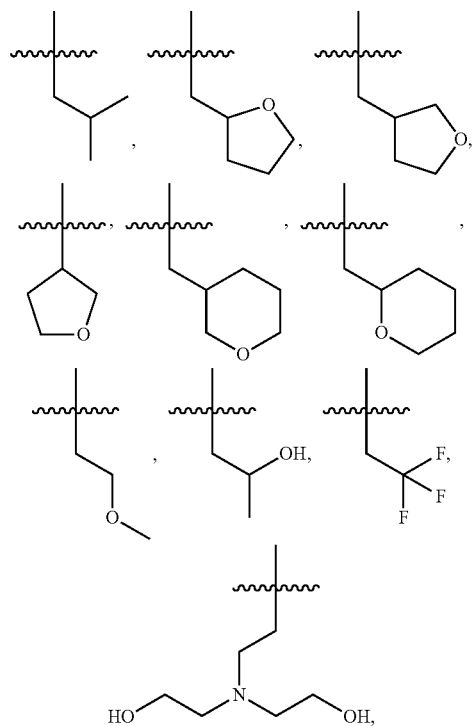

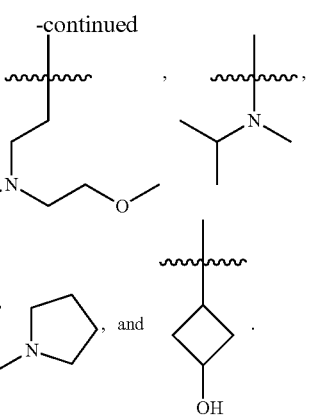

Embodiment 103. The compound of Formula (I'), or a pharmaceutically acceptable salt, solvate, co-crystal, polymorph, or stereoisomer thereof, or any one of Embodiments 57 to 102, wherein $R^{2'}$ is halo or $C_1$-$C_6$haloalkyl.

Embodiment 104. The compound of Formula (I'), or a pharmaceutically acceptable salt, solvate, co-crystal, polymorph, or stereoisomer thereof, or any one of Embodiments 57 to 102, wherein $R^{2'}$ is halo.

Embodiment 105. The compound of Formula (I'), or a pharmaceutically acceptable salt, solvate, co-crystal, polymorph, or stereoisomer thereof, or any one of Embodiments 57 to 102, wherein $R^{2'}$ is $C_1$-$C_6$haloalkyl.

Embodiment 106. The compound of Formula (I'), or a pharmaceutically acceptable salt, solvate, co-crystal, polymorph, or stereoisomer thereof, or any one of Embodiments 57 to 102, wherein $R^{2'}$ is —$CF_3$.

Embodiment 107. The compound of Formula (I'), or a pharmaceutically acceptable salt, solvate, co-crystal, polymorph, or stereoisomer thereof, or any one of Embodiments 57 to 102, wherein $R^{2'}$ is —Cl.

Embodiment 108. The compound of Formula (I'), or a pharmaceutically acceptable salt, solvate, co-crystal, polymorph, or stereoisomer thereof, or any one of Embodiments 57 to 107, wherein
$R^{4'}$ is hydrogen, $C_1$-$C_6$alkyl substituted with one or two groups independently selected from $R^6$, 4-6 membered heterocycloalkyl having 1 to 2 ring members independently selected from N, NH, $NR^{12'}$, O or S, 5-6 membered heteroaryl having 1 to 3 heteroatoms independently selected from the heteroatoms N, O and S as ring members, and $C_3$-$C_8$cycloalkyl,
wherein the heterocycloalkyl is optionally substituted with one or two substituents independently selected from —OH and $C_1$-$C_3$alkyl.

Embodiment 109. The compound of Formula (I'), or a pharmaceutically acceptable salt, solvate, co-crystal, polymorph, or stereoisomer thereof, or any one of Embodiments 57 to 107, wherein
$R^{4'}$ is $C_1$-$C_6$alkyl optionally substituted with one or two groups independently selected from $R^6$, 4-6 membered heterocycloalkyl having 1 to 2 ring members independently selected from N, NH, $NR^{12'}$, O or S, 5-6 membered heteroaryl having 1 to 3 heteroatoms independently selected from the heteroatoms N, O and S as ring members, and $C_3$-$C_8$cycloalkyl, wherein the heterocycloalkyl is optionally substituted with one or two substituents independently selected from —OH and $C_1$-$C_3$alkyl, and wherein each $R^6$ is independently selected from —OH and $C_1$-$C_3$alkyl.

Embodiment 110. The compound of Formula (I'), or a pharmaceutically acceptable salt, solvate, co-crystal, polymorph, or stereoisomer thereof, or any one of Embodiments 57 to 107, wherein
R$^{4'}$ is C$_1$-C$_6$alkyl substituted with one or two groups independently selected from R$^6$, 4-6 membered heterocycloalkyl having 1 to 2 ring members independently selected from N, NH, NR$^{12'}$, O or S, 5-6 membered heteroaryl having 1 to 3 heteroatoms independently selected from the heteroatoms N, O and S as ring members, and C$_3$-C$_8$cycloalkyl, and wherein each R$^6$ is independently selected from —OH and C$_1$-C$_3$alky.

Embodiment 111. The compound of Formula (I'), or a pharmaceutically acceptable salt, solvate, co-crystal, polymorph, or stereoisomer thereof, or any one of Embodiments 57 to 107, wherein R$^{4'}$ is C$_1$-C$_6$alkyl substituted with 4-6 membered heterocycloalkyl having 1 to 2 ring members independently selected from N, NH, NR$^{12'}$, O or S.

Embodiment 112. The compound of Formula (I'), or a pharmaceutically acceptable salt, solvate, co-crystal, polymorph, or stereoisomer thereof, or any one of Embodiments 57 to 107, wherein R$^{4'}$ is C$_1$-C$_6$alkyl substituted with 5-6 membered heteroaryl having 1 to 3 heteroatoms independently selected from the heteroatoms N, O and S as ring members.

Embodiment 113. The compound of Formula (I'), or a pharmaceutically acceptable salt, solvate, co-crystal, polymorph, or stereoisomer thereof, or any one of Embodiments 57 to 107, wherein R$^{4'}$ is C$_1$-C$_6$alkyl substituted with C$_3$-C$_8$cycloalkyl.

Embodiment 114. The compound of Formula (I'), or a pharmaceutically acceptable salt, solvate, co-crystal, polymorph, or stereoisomer thereof, or any one of Embodiments 57 to 107, wherein R$^{4'}$ is hydrogen.

Embodiment 115. The compound of Formula (I'), or a pharmaceutically acceptable salt, solvate, co-crystal, polymorph, or stereoisomer thereof, or any one of Embodiments 57 to 107, wherein R$^{4'}$ is selected from hydrogen,

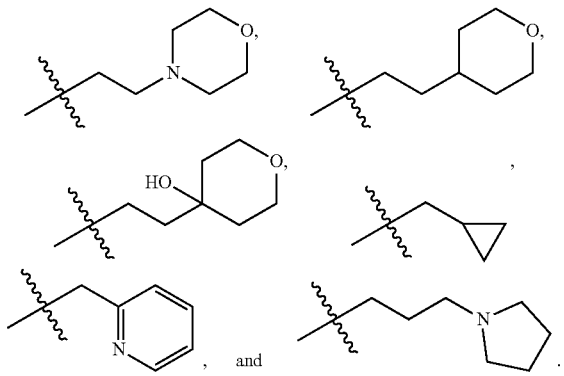

Embodiment 116. A compound selected from the group consisting of:
5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione;
3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)-5-propylimidazolidine-2,4-dione;
3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione;
3-((3-(4-(2-(isobutylsulfonyl)phenoxy)-3-(trifluoromethyl)phenyl)-1,2,4-oxadiazol-5-yl)methyl)-5,5-dimethyl-1-(2-(tetrahydro-2H-pyran-4-yl)ethyl)imidazolidine-2,4-dione;
2-(4-(5-((4,4-dimethyl-2,5-dioxo-3-(2-(tetrahydro-2H-pyran-4-yl)ethyl)imidazolidin-1-yl)methyl)-1,2,4-oxadiazol-3-yl)-2-(trifluoromethyl)phenoxy)-N-isopropyl-N-methylbenzenesulfonamide;
1-(2-(4-hydroxytetrahydro-2H-pyran-4-yl)ethyl)-3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione;
3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione;
8-cyclobutyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;
3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;
3-((3-(4-(2-(isobutylsulfonyl)phenoxy)-3-(trifluoromethyl)phenyl)-1,2,4-oxadiazol-5-yl)methyl)-8-methyl-1-(2-morpholinoethyl)-1,3,8-triazaspiro[4.5]decane-2,4-dione;
2-(4-(5-((8-cyclobutyl-1-(2-morpholinoethyl)-2,4-dioxo-1,3,8-triazaspiro[4.5]decan-3-yl)methyl)-1,2,4-oxadiazol-3-yl)-2-(trifluoromethyl)phenoxy)-N-isopropyl-N-methylbenzenesulfonamide;
8-cyclobutyl-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione;
8-cyclobutyl-1-(2-morpholinoethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione;
8-cyclobutyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;
8-cyclobutyl-3-((3-(4-(2-(methylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;
3-((3-(4-(2-(tert-butyl)phenoxy)-3-(trifluoromethyl)phenyl)-1,2,4-oxadiazol-5-yl)methyl)-8-cyclobutyl-1-(2-morpholinoethyl)-1,3,8-triazaspiro[4.5]decane-2,4-dione;
8-cyclobutyl-1-(2-(tetrahydro-2H-pyran-4-yl)ethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione;
8-cyclobutyl-3-((3-(4-(2-(methylsulfonyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione;
8-cyclobutyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione;
8-cyclobutyl-1-(2-(tetrahydro-2H-pyran-4-yl)ethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione;

8-(4-hydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-(3,5-dihydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(1-methylpiperidin-4-yl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(1-methylpyrrolidin-3-yl)-1-(2-morpholinoethyl)-1,3,8-triazaspiro[4.5]decane-2,4-dione;

8-ethyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyridazin-3-ylmethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-8-((tetrahydro-2H-pyran-4-yl)methyl)-1,3,8-triazaspiro[4.5]decane-2,4-dione;

8-(cyclopropylmethyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-5-carbonyl)-1,3,8-triazaspiro[4.5]decane-2,4-dione;

1-(2-morpholinoethyl)-8-(pyrimidine-5-carbonyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-(pyrimidine-5-carbonyl)-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-(3-(dimethylamino)propanoyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(1-methylpiperidine-4-carbonyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-4-carbonyl)-1,3,8-triazaspiro[4.5]decane-2,4-dione;

8-butyryl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(pyrazine-2-carbonyl)-1-(2-(tetrahydro-2H-pyran-4-yl)ethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(pyrimidine-5-carbonyl)-1-(2-(tetrahydro-2H-pyran-4-yl)ethyl)-1,3,8-triazaspiro[4.5]decane-2,4-dione;

5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione;

3-((3-(4-(2-((3-hydroxycyclobutyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-morpholinoethyl)-3-((3-(4-(2-(((tetrahydro-2H-pyran-3-yl)methyl)sulfonyl)phenoxy)-3-(trifluoromethyl)phenyl)-1,2,4-oxadiazol-5-yl)methyl)imidazolidine-2,4-dione;

5,5-dimethyl-1-(2-morpholinoethyl)-3-((3-(3-(trifluoromethyl)-4-(2-(trifluoromethyl)phenoxy)phenyl)-1,2,4-oxadiazol-5-yl)methyl)imidazolidine-2,4-dione;

5,5-dimethyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione;

5,5-dimethyl-1-(2-morpholinoethyl)-3-((3-(4-(2-((2-(pyrrolidin-1-yl)propyl)sulfonyl)phenoxy)-3-(trifluoromethyl)phenyl)-1,2,4-oxadiazol-5-yl)methyl)imidazolidine-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)imidazolidine-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione;

7-((3-(4-(2-(isobutylsulfonyl)phenoxy)-3-(trifluoromethyl)phenyl)-1,2,4-oxadiazol-5-yl)methyl)-5-(2-morpholinoethyl)-5,7-diazaspiro[3.4]octane-6,8-dione;

5-(hydroxymethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione;

8-cyclobutyl-1-(2-morpholinoethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione;

3-((3-(3-chloro-4-(2-(isobutylsulfonyl)phenoxy)phenyl)-1,2,4-oxadiazol-5-yl)methyl)-5,5-dimethyl-1-(2-morpholinoethyl)imidazolidine-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(pyridin-2-ylmethyl)imidazolidine-2,4-dione;

3-((3-(4-(2-((2-hydroxypropyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-morpholinoethyl)-3-((3-(4-(2-(((tetrahydro-2H-pyran-2-yl)methyl)sulfonyl)phenoxy)-3-(trifluoromethyl)phenyl)-1,2,4-oxadiazol-5-yl)methyl)imidazolidine-2,4-dione;

1-(cyclopropylmethyl)-3-((3-(4-(2-((2-methoxyethyl)sulfonyl)phenoxy)-3-(trifluoromethyl)phenyl)-1,2,4-oxadiazol-5-yl)methyl)-5,5-dimethylimidazolidine-2,4-dione;

5,5-dimethyl-3-((3-(4-(2-(methylsulfonyl)phenoxy)-3-(trifluoromethyl)phenyl)-1,2,4-oxadiazol-5-yl)methyl)-1-(2-morpholinoethyl)imidazolidine-2,4-dione;

1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-8-oxa-1,3-diazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

3-((3-(4-(2-((2-methoxyethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-(tetrahydro-2H-pyran-4-yl)ethyl)-3-((3-(4-(2-(((tetrahydrofuran-3-yl)sulfonyl)phenoxy)-3-(trifluoromethyl)phenyl)-1,2,4-oxadiazol-5-yl)methyl)imidazolidine-2,4-dione;

5-((dimethylamino)methyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione;

3-((3-(4-(2-((2-(bis(2-methoxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

3-((3-(4-(2-((2-(bis(2-hydroxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione;

(R or S) 5,5-dimethyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione, and (R or S) 5,5-dimethyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione, or a pharmaceutically acceptable salt thereof.

Embodiment 117. A compound selected from the group consisting of:

3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

8-cyclobutyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-cyclobutyl-3-((3-(4-(2-(methylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-cyclobutyl-1-(2-(tetrahydro-2H-pyran-4-yl)ethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione;

8-cyclobutyl-3-((3-(4-(2-(methylsulfonyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione;

8-cyclobutyl-1-(2-(tetrahydro-2H-pyran-4-yl)ethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione;

2-(4-(5-((8-cyclobutyl-1-(2-morpholinoethyl)-2,4-dioxo-1,3,8-triazaspiro[4.5]decan-3-yl)methyl)-1,2,4-oxadiazol-3-yl)-2-(trifluoromethyl)phenoxy)-N-isopropyl-N-methylbenzenesulfonamide;

8-cyclobutyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-cyclobutyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

3-((3-(4-(2-(tert-butyl)phenoxy)-3-(trifluoromethyl)phenyl)-1,2,4-oxadiazol-5-yl)methyl)-8-cyclobutyl-1-(2-morpholinoethyl)-1,3,8-triazaspiro[4.5]decane-2,4-dione;

2-(4-(5-((4,4-dimethyl-2,5-dioxo-3-(2-(tetrahydro-2H-pyran-4-yl)ethyl)imidazolidin-1-yl)methyl)-1,2,4-oxadiazol-3-yl)-2-(trifluoromethyl)phenoxy)-N-isopropyl-N-methylbenzenesulfonamide, and 8-cyclobutyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione, or a pharmaceutically acceptable salt thereof.

Embodiment 118. A compound selected from the group consisting of:

3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione, 5,5-dimethyl-1-(2-morpholinoethyl)-3-((3-(3-(trifluoromethyl)-4-((4-(trifluoromethyl)pyridin-3-yl)oxy)phenyl)-1,2,4-oxadiazol-5-yl)methyl)imidazolidine-2,4-dione, 5,5-dimethyl-1-(2-morpholinoethyl)-3-((3-(3-(trifluoromethyl)-4-(3,3,3-trifluoropropoxy)phenyl)-1,2,4-oxadiazol-5-yl)methyl)imidazolidine-2,4-dione, 6-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-6-oxohexanoic acid, 4-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-4-oxobutanoic acid, 6-(1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decan-8-yl)-6-oxohexanoic acid, 5,5-dimethyl-3-((3-(3-(trifluoromethyl)-4-(2-((trifluoromethyl)thio)phenoxy)phenyl)-1,2,4-oxadiazol-5-yl)methyl)imidazolidine-2,4-dione, 5,5-dimethyl-3-((3-(3-(trifluoromethyl)-4-(2-(trifluoromethyl)phenoxy)phenyl)-1,2,4-oxadiazol-5-yl)methyl)imidazolidine-2,4-dione, and 1,5,5-trimethyl-3-((3-(3-(trifluoromethyl)-4-(2-(trifluoromethyl)phenoxy)phenyl)-1,2,4-oxadiazol-5-yl)methyl)imidazolidine-2,4-dione, or a pharmaceutically acceptable salt thereof.

Depending on the choice of the starting materials and procedures, the compounds according to Formula (I) and the compounds according to Formula (I') can be present in the form of one of the possible stereoisomers or as mixtures thereof, for example as pure optical isomers, or as stereoisomer mixtures, such as racemates and diastereoisomer mixtures, depending on the number of asymmetric carbon atoms. The compounds according to Formula (I) and the compounds according to Formula (I') provided herein are meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compounds according to Formula (I) and the compounds according to Formula (I') can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, a compound provided herein can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of the compounds according to Formula (I) or the compounds according to Formula (I') or of intermediates thereof can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds according to Formula (I) or the compounds according to Formula (I') into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds according to Formula (I), the compounds according to Formula (I') or racemic intermediates can also be resolved by chiral chromatography, e.g., high pressure liquid chromatography (HPLC) using a chiral adsorbent.

As used herein, the term "isomers" refers to different compounds according to Formula (I) that have the same molecular formula but differ in arrangement and configuration of the atoms.

As used herein, the term "optical isomer" or "stereoisomer" refers to any of the various stereo isomeric configurations which may exist for a given compound provided herein and includes geometric isomers. It is understood that a substituent may be attached at a chiral center of a carbon atom. Therefore, compounds provided herein include enantiomers, diastereomers or racemates of the compound.

The terms, "salt" or "salts" as used herein refers to an acid addition or base addition salt of a compound provided herein. "Salts" include in particular "pharmaceutically acceptable salts". "Pharmaceutically acceptable salts" as used herein refers to salts that retain the biological effectiveness and properties of the compounds according to Formula (I) or of the compounds according to Formula (I') and, which typically are not biologically or otherwise undesirable. In many cases, the compounds according to Formula (I) and the compounds according to Formula (I') are capable of forming acid and/or base salts by virtue of the presence of amino and/or carboxyl groups or groups similar thereto. The skilled artisan will appreciate that salts, including pharmaceutically acceptable salts, of the compounds according to Formula (I) and of the compounds according to Formula (I') may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases, such as carboxylate, sulfonate and phosphate salts.

In certain embodiments, provided herein are compounds according to Formula (I) and compounds according to Formula (I') in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, formate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form.

In other embodiments, inorganic bases from which salts of compounds according to Formula (I) and compounds according to Formula (I') can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds according to Formula (I) and compounds according to Formula (I') include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound provided herein. The concentration of deuterium may be defined by the isotopic enrichment factor. "Isotopic enrichment factor" as used herein means the ratio between the isotopic abundance and the natural abundance of a specified isotope. If a substituent in a compound provided herein is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

For example, Formula (I) may be deuterated as shown in Formula (Ih):

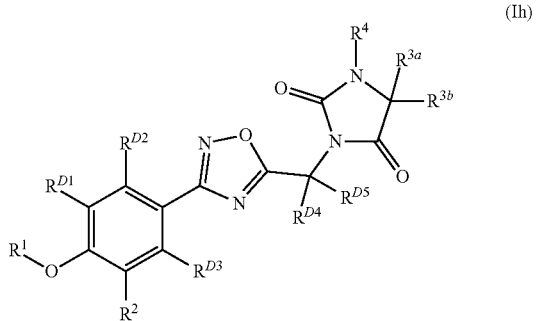

(Ih)

or a pharmaceutically acceptable salt, solvate, co-crystal, polymorph or stereoisomer thereof, wherein $R^1$, $R^2$, $R^{3a}$, $R^{3b}$, and $R^4$ are as defined in Formula (I); each of $R^{D1}$, $R^{D2}$, $R^{D3}$, $R^{D4}$, and $R^{D5}$ is independently D or hydrogen.

For example, Formula (I') may be deuterated as shown in Formula (Ih'):

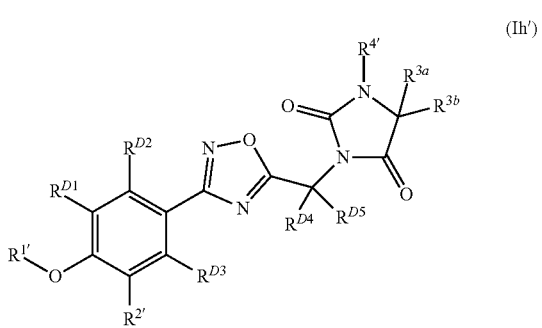

(Ih')

or a pharmaceutically acceptable salt, solvate, co-crystal, polymorph or stereoisomer thereof, wherein $R^1$, $R^{2'}$, $R^{3a}$, $R^{3b}$, and $R^{4'}$ are as defined in Formula (I'); each of $R^{D1}$, $R^{D2}$, $R^{D3}$, $R^{D4}$, and $R^{D5}$ is independently D or hydrogen.

Other examples of isotopes that can be incorporated into compounds according to Formula (I) and compounds according to Formula (I') include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$, $^{35}S$, $^{36}Cl$, $^{123}I$, $^{124}I$, $^{125}I$ respectively. Accordingly it should be understood that compounds according to Formula (I) and compounds according to Formula (I') includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds according to Formula (I) and compounds according to Formula (I') can generally be prepared by conventional techniques known to those skilled in the art or by processes analogous to those described in the accompanying Examples and preparations using an appropriate isotopically-labeled reagents in place of the non-labeled reagent previously employed.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

General Synthetic Procedures

Generally, compounds of Formula (I) and compounds according to Formula (I') can be synthesized by the routes described in the Examples below. The skilled person will appreciate that the general synthetic routes detailed below show common reactions to transform the starting materials as required. The specific reaction conditions are not provided, but these are well known to those skilled in the art and appropriate conditions considered to be within the skilled person's common general knowledge. The starting materials are either commercially available compounds or are known compounds and can be prepared from procedures described in the organic chemistry art.

Compounds of Formula (I) and compounds according to Formula (I') can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of Formula (I) into another compound of Formula (I) or one compound of Formula (I') into another compound of Formula (I'). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are March's Organic Chemistry, 5th Edition, Wiley and Chichester, Eds. (2001); Comprehensive Organic Transformations, Larock, Ed., VCH (1989); Comprehensive Organic Functional Group Transformations, Katritzky et al. (series editors), Pergamon (1995); and Comprehensive Organic Synthesis, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, Protective Groups in Organic Synthesis, Wiley and Sons (1999).

General methods for the synthesis of compounds of Formula (I) and compounds of Formula (I') are provided below in Schemes I-VIII, wherein $R^1$, $R^2$, $R^{3a}$, $R^{3b}$, $R^4$, $R^7$ are as described herein and $X_a$, $X_b$ and X are each independently selected from F, Cl and Br. In addition, $X_a$ and $X_b$ are different when present together on the same structure.

Scheme I below shows a synthetic approach to obtaining compounds of Formula (I) or compounds of Formula (I'). In step 1, a hydantoin moiety is added to intermediate (Ia) to give intermediate (Ib), then in step 2, an $R^1$ group is added to intermediate (Ib) to give intermediate (Ic). In step 3, alkylation of the hydantoin moiety adds an $R^4$ group to intermediate (Ic) thereby giving compounds of Formula (I) or compounds of Formula (I').

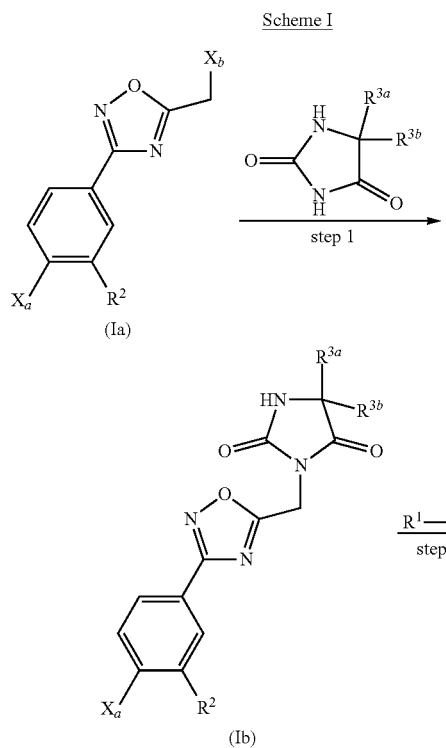

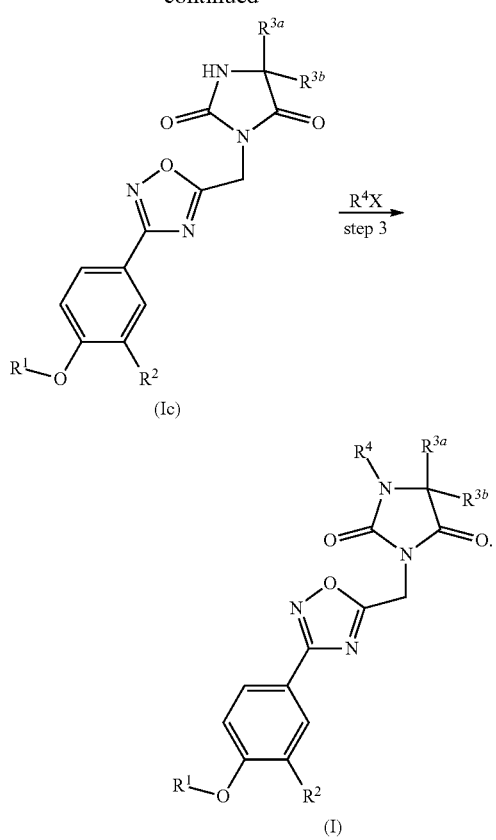

Scheme II below shows another synthetic approach to obtaining compounds of Formula (I) or compounds of Formula (I'), wherein in step 1 an $R^1$ group is added to intermediate (11a) to give intermediate (IIb), followed by step 2 with formation of the oxadiazole moiety by treatment of the nitrile with hydroxylamine then chloroacetyl chloride giving intermediate (IIc). In step 3a a hydantoin moiety is then added to intermediate (IIc) to give intermediate (IId). In step 4, alkylation of the hydantoin moiety adds an $R^4$ group to intermediate (IIc) thereby giving compounds of Formula (I) or compounds of Formula (I'). Alternatively, in step 3a a hydantoin moiety which includes an $R^4$ group is added to intermediate (IIc) to give compounds of Formula (I) or compounds of Formula (I').

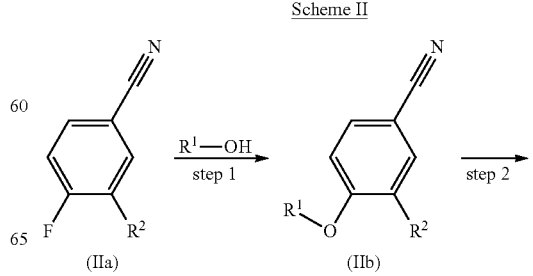

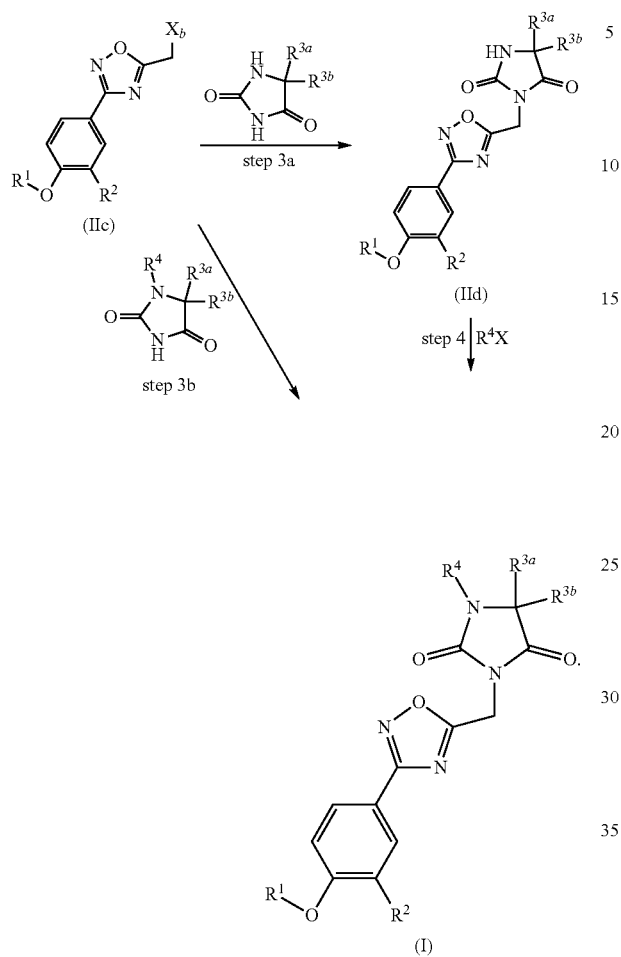

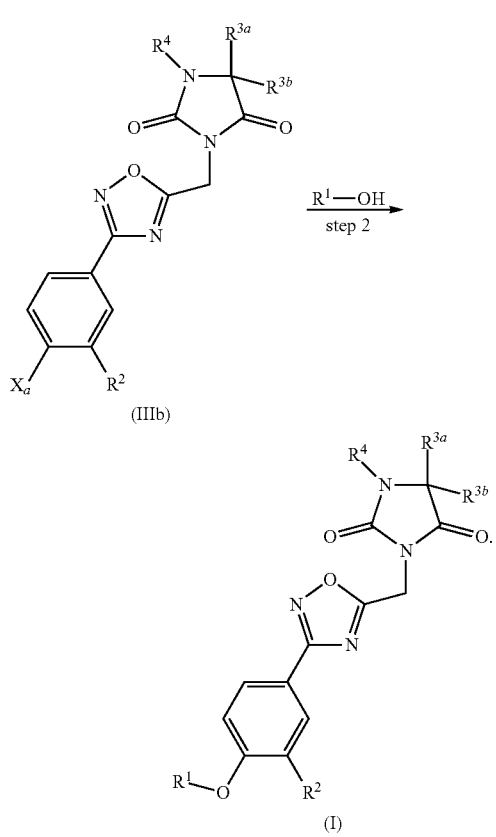

Scheme III below shows another synthetic approach to obtaining compounds of Formula (I) or compounds of Formula (I'). In step 1, a hydantoin moiety which includes an R⁴ group is added to intermediate (IIIa), followed by addition of an R¹ group to intermediate (IIIb) in step 2, thereby giving compounds of Formula (I) or compounds of Formula (I').

Scheme III

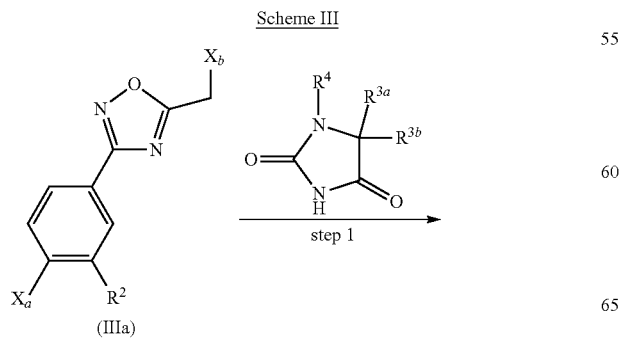

Scheme IV below shows another synthetic approach to obtaining compounds of Formula (I) or compounds of Formula (I'), wherein in step 1 an R¹ group is added to intermediate (IVa) by SnAr coupling to give intermediate (IVb), followed by step 2 with formation of the oxadiazole moiety by treatment of the nitrile with hydroxylamine then chloroacetyl chloride giving intermediate (IVc). In step 3a a hydantoin moiety is then added to intermediate (IVc) to give intermediate (IVd). In step 4, alkylation of the hydantoin moiety adds an R⁴ group to intermediate (IVc) thereby giving compounds of Formula (I) or compounds of Formula (I') where R¹ is

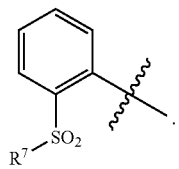

Alternatively, In step 3b a hydantoin moiety which includes an R⁴ group is added to intermediate (IVc) to give compounds of Formula (I) or compounds of Formula (I') where R¹ is

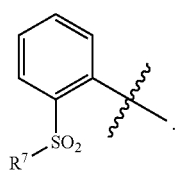

Scheme IV
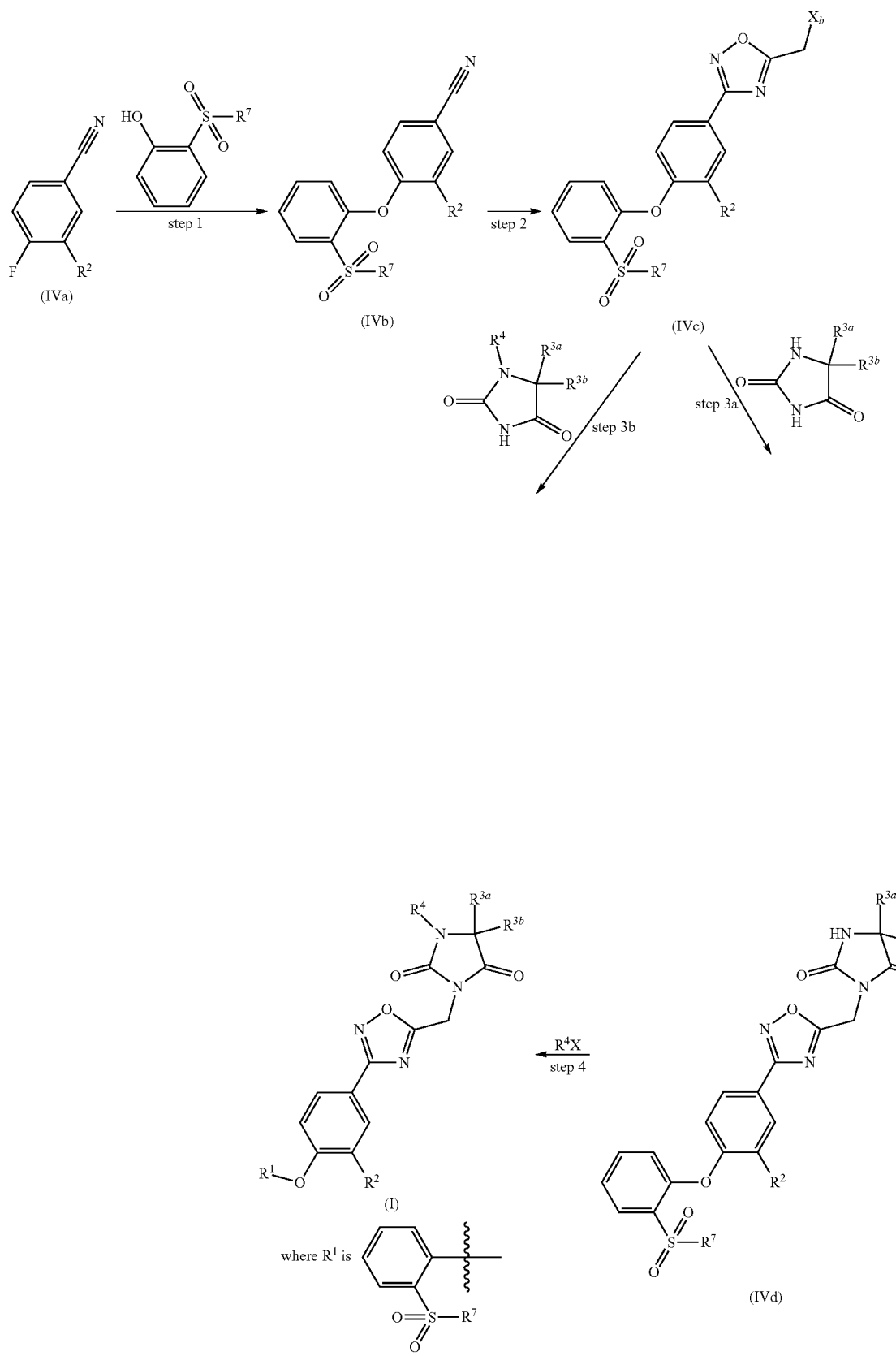

Scheme V below shows another synthetic approach to obtaining compounds of Formula (I) or compounds of Formula (I'), wherein in step 1 an $R^1$ group is added to intermediate (Va) by SnAr coupling to give intermediate (Vb), followed by step 2 with formation of the oxadiazole moiety by treatment of the nitrile with hydroxylamine then chloroacetyl chloride giving intermediate (Vc). Oxidation of the sulfur in intermediate (Vc) in step 3 gives intermediate (Vd), whereby in step 4a a hydantoin moiety is then added to intermediate (Vd) to give intermediate (Ve). In step 5, alkylation of the hydantoin moiety adds an $R^4$ group to intermediate (Ve) thereby giving compounds of Formula (I) or compounds of Formula (I') where $R^1$ is

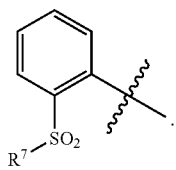

Alternatively, In step 4b a hydantoin moiety which includes an $R^4$ group is added to intermediate (Vd) to give compounds of Formula (I) or compounds of Formula (I') where $R^1$ is

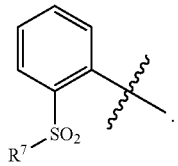

Scheme V

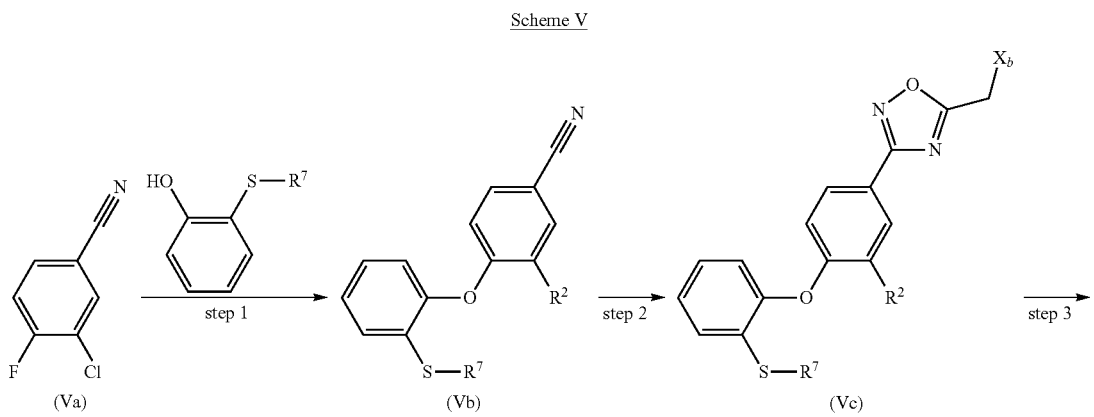

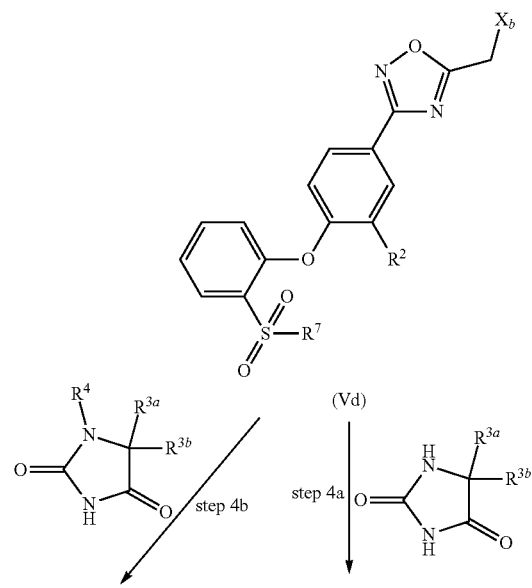

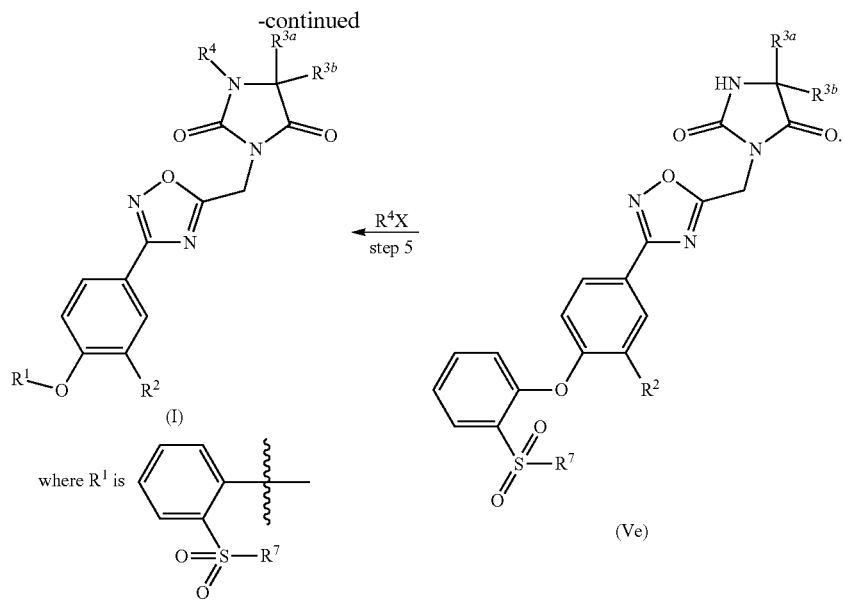

(I)

where R¹ is

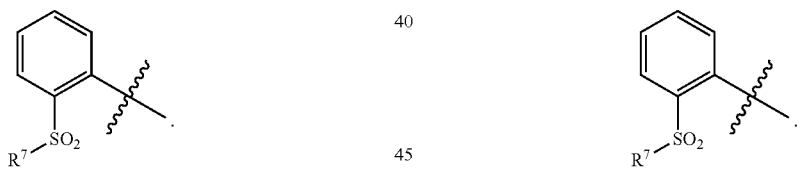

Scheme VI below shows a synthetic approach to obtaining certain compounds of Formula (I) or compounds of Formula (I'). In step 1 addition of a hydantoin moiety to intermediate (VIa) is followed by the addition of R¹ to intermediate (VIb) by SnAr coupling in step 2, giving intermediate (VIc). In step 3, an R⁴ group is added by alkylation of the hydantoin moiety in intermediate (VIc) to give intermediate (VId). Subsequent oxidation of the sulfur group in intermediate (VId) in step 4b gives compounds of Formula (I) or compounds of Formula (I') where R¹ is Alternatively, oxidation of the sulfur in intermediate (VIc) in step 4a, followed by alkylation of the hydantoin moiety in intermediate (VIe) in step 5 to add an R⁴ group, also gives compounds of Formula (I) or compounds of Formula (I') where R¹ is Scheme VI

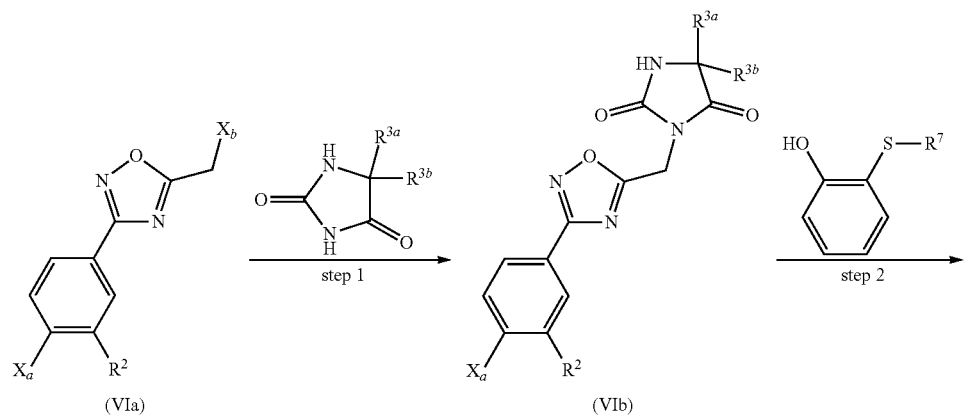

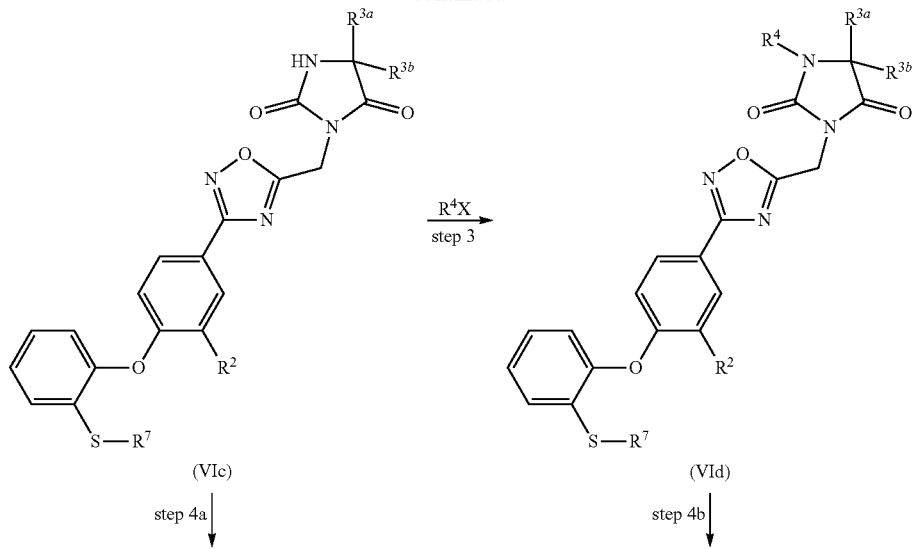
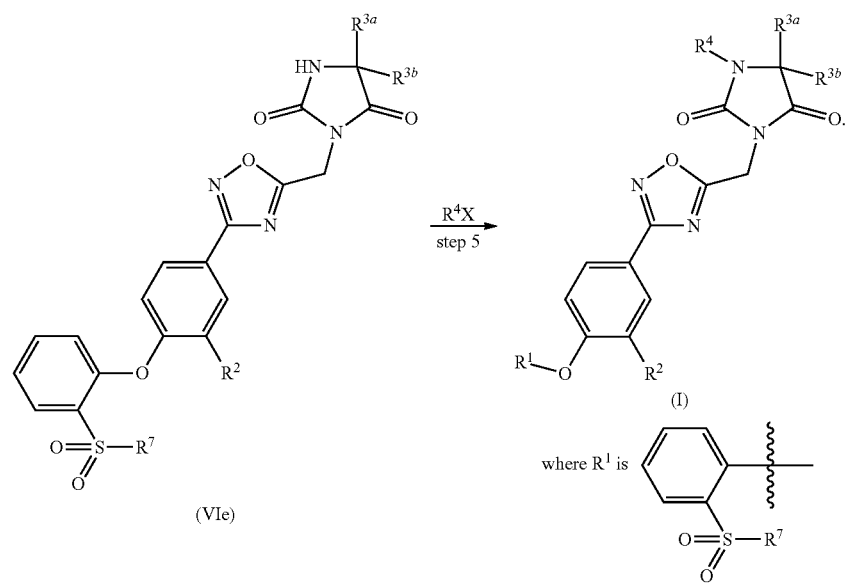

Scheme VII below shows another synthetic approach to obtaining compounds of Formula (I) or compounds of Formula (I'). In step 1, a hydantoin moiety which includes an R⁴ group is added to intermediate (VIIa), followed by addition of an R¹ group to intermediate (VIIb) by SnAr coupling in step 2, to give intermediate (VIIc). Subsequent oxidation of the sulfur group in intermediate (VIIc) in step 3 gives compounds of Formula (I) or compounds of Formula (I') where R¹ is

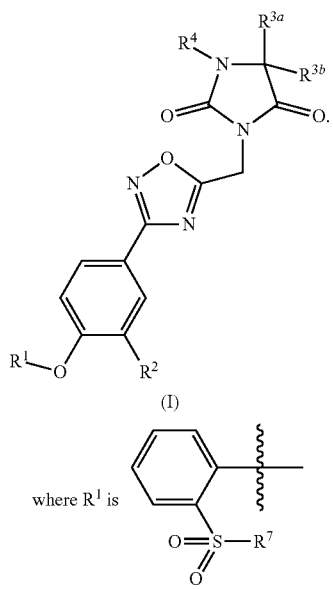

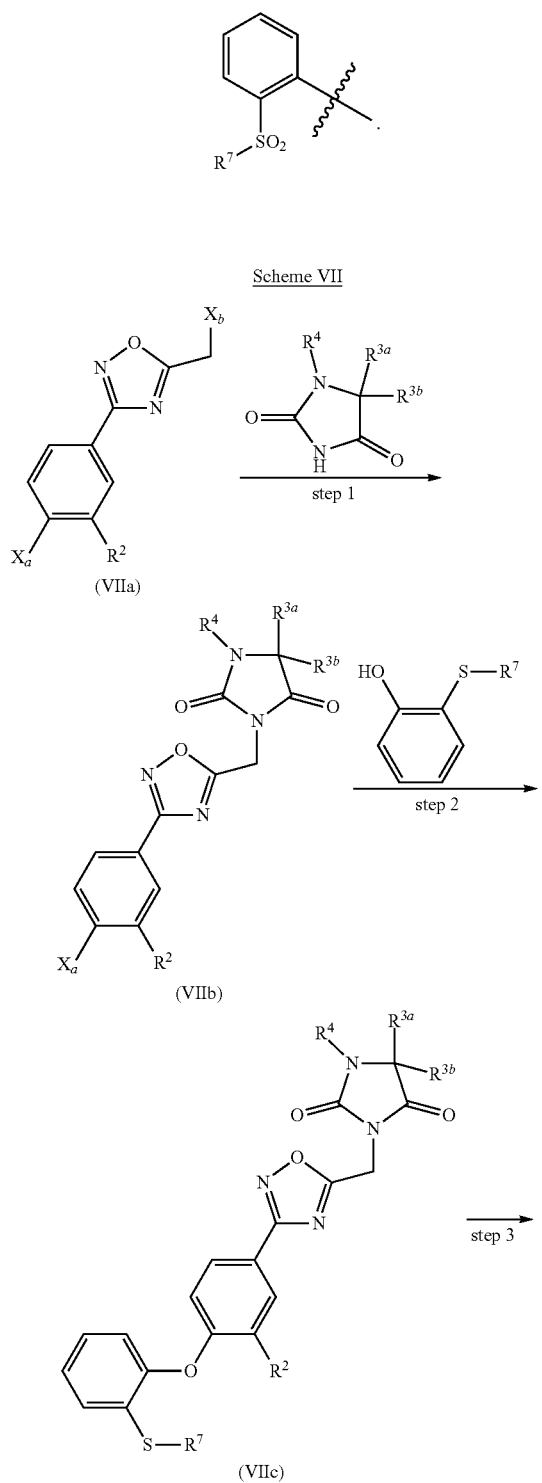

Scheme VIII below shows another synthetic approach to obtaining compounds of Formula (I) or compounds of Formula (I'). In step 1, a hydantoin moiety which includes an R⁴ group is added to intermediate (VIIIa), followed by addition of an R¹ group to intermediate (VIIIb) by SnAr coupling in step 2, to give compounds of Formula (I) or compounds of Formula (I') where R¹ is

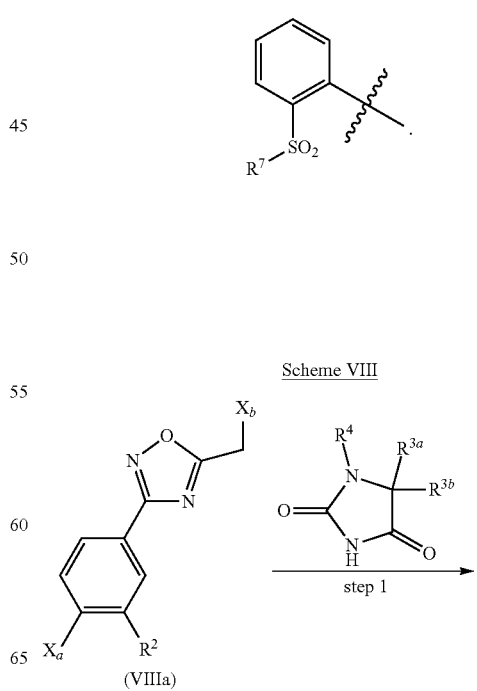

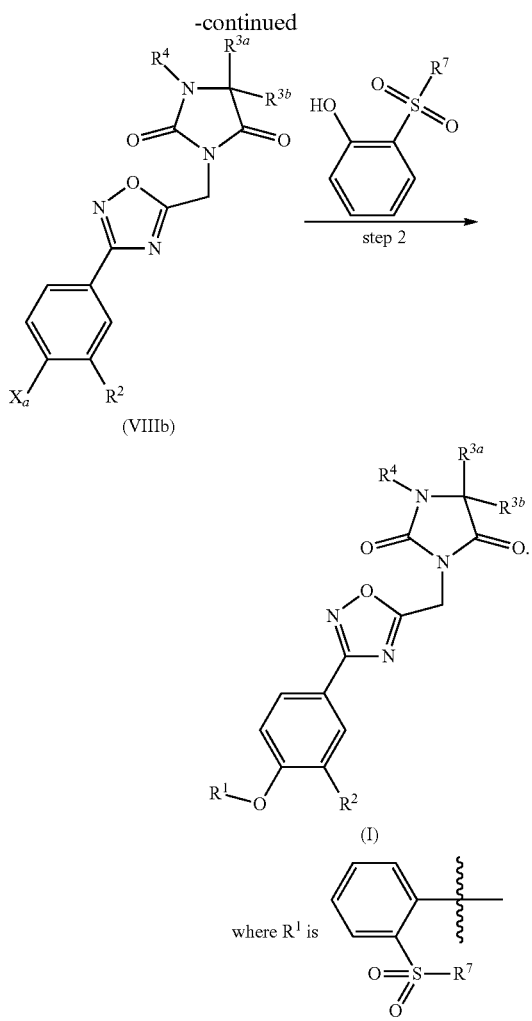

Pharmaceutical Compositions

The compounds of Formula (I), the compounds of Formula (I'), and subformulae thereof, described herein may be administered alone or as an active ingredient of a pharmaceutical composition. Accordingly, provided herein are pharmaceutical compositions comprising a compounds of Formula (I), compounds of Formula (I'), or subformulae thereof, or a pharmaceutically acceptable salt, solvate, co-crystal, polymorph or stereoisomer thereof, and one or more pharmaceutically acceptable carriers.

Methods of preparing various pharmaceutical composition are known to those of skill in the art and may be described in, for example, in the Handbook of Pharmaceutical Excipients, American Pharmaceutical Association (current edition); Pharmaceutical Dosage Forms Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and pharmaceutical composition are closely related to the therapeutic amounts of the compounds or compositions which are desirable and efficacious for the given treatment application. Pharmaceutical compositions provided herein can be formulated for ophthalmic, ocular, topical, and transdermal administration. In particular embodiments, the pharmaceutical compositions provided herein are suitable for ocular administration. To prepare pharmaceutical compositions, the active ingredient may be mixed with one or more pharmaceutically acceptable carrier(s) according to conventional pharmaceutical compounding techniques. The carrier(s) may take a wide variety of forms depending on the form of preparation desired for administration.

In certain embodiments, the pharmaceutical compositions provided herein are formulated as solutions, suspensions, gels, creams, ointments, liposomes, ocular inserts or other pharmaceutical compositions suitable, in particular embodiments, for topical administration to the ocular surface, the cornea, the eyelid, margins of the eye, eyelashes and/or eye lid margin in order to deliver the composition to the meibomian gland. In some embodiments, liquid (aqueous or non-aqeuous) solutions may be used. In certain embodiments the pharmaceutical compositions are formulated as eye drops for topical administration to the ocular surface, the cornea, the eyelid, eye lid margins, eyelashes and/or margins of the eye in order to deliver the composition to the meibomian gland. Application of the pharmaceutical composition may be performed with an applicator, such as the subject's finger, a Week-Cel®, Q-tip®, or other device capable of delivering a formulation to the eyelid, eyelashes and/or eyelid margin in order to deliver the formulation to the meibomian gland. The pharmaceutical compositions provided herein may be viscous or semi-viscous; liquid, solid, or semi-solid; aqueous or non-aqueous, depending on the site of application, dose, solubility of drug, and a variety of other factors that are considered by those of skill in the art.

Any of a variety of carriers may be used in a pharmaceutical composition provided herein. In one embodiment, the pharmaceutically acceptable carrier is a non-aqueous carrier (e.g., oil, or oil mixture) having a viscosity in a range from about 50 cps to about 1000 cps, about 50 cps to about 500 cps, about 50 cps to about 200 cps, or about 60 cps to about 120 cps. In certain embodiments, the non-aqueous carrier comprises an oil, e.g., vegetable oils, silicone oils, mineral oil or any combination thereof. In some embodiments, the carrier may be liquid paraffin, white petrolatum, purified lanolin, gelation hydrocarbon, polyethylene glycol, hydrophilic ointment base, white ointment base, absorptive ointment base, Macrogol ointment base, simple ointment base, and the like. In certain embodiments, the pharmaceutical composition may include a monomeric polyol such as, glycerol, propylene glycol, and ethylene glycol, polymeric polyols such as polyethylene glycol, cellulose esters such hydroxypropylmethyl cellulose, carboxy methylcellulose sodium and hydroxy propylcellulose; dextrans such as dextran 70; water soluble proteins such as gelatin, polymers such as polyvinyl alcohol, polyvinylpyrrolidone, and povidone; carbomers, such as carbomer 934P. carbomer 941, carbomer 940 and carbomer 974P; and gums such as HP-guar.

Additional excipients may optionally be included in the pharmaceutical compositions provided herein. Examples of additional excipients include, for example, tonicity enhancers, preservatives, solubilizers, non-toxic excipients, demulcents, sequestering agents, pH adjusting agents, co-solvents, viscosity building agents, and combinations thereof.

For the adjustment of the pH, e.g., to a physiological pH, buffers may be used. In certain embodiments, the pH of the pharmaceutical composition is maintained within the range of about 4.0 to about 8.0, such as, about 4.0 to about 6.0, for example, about 6.5 to about 7.8. Suitable buffers may be added, such as, e.g., boric acid, sodium borate, potassium citrate, citric acid, sodium bicarbonate, tris(hydroxymethyl)

aminomethane (TRIS), and various mixed phosphate buffers (including combinations of $Na_2HPO_4$, $NaH_2PO_4$ and $KH_2PO_4$) and mixtures thereof. Generally, buffers may be used in amounts ranging from about 0.05 to about 2.5 percent by weight, such as, from about 0.1 to about 1.5 percent by weight.

Tonicity may be adjusted, if needed, by the use of tonicity enhancing agents. Such agents may, for example, be of ionic and/or non-ionic type. Examples of ionic tonicity enhancers include, for example, alkali metal or earth metal halides such as, e.g., $CaCl_2$, KBr, KCl, LiCl, NaI, NaBr or NaCl, $Na_2SO_4$ or boric acid. Non-ionic tonicity enhancing agents include, e.g., urea, glycerol, sorbitol, mannitol, propylene glycol, or dextrose. In one embodiment, the pharmaceutical compositions provided herein may have an osmolality of about 225 to about 400 milliosmoles per kilogram (mOsm/kg). In one embodiment, an osmolality of about 280 to about 320 mOsm is obtained.

In further embodiments, the pharmaceutical compositions provided herein, such as topical compositions, may additionally comprise a preservative. A preservative may typically be selected from a quaternary ammonium compound such as benzalkonium chloride, benzoxonium chloride (e.g., N-benzyl-N—(C8-C18 dimethylammonium chloride) or the like. Examples of preservatives different from quaternary ammonium salts include, e.g., alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenylethanol, guanidine derivatives, such as, for example, chlorohexidine or polyhexamethylene biguanide, sodium perborate, or sorbic acid. Where appropriate, a sufficient amount of preservative may be added to the pharmaceutical composition provided herein to ensure protection against secondary-contaminations during use caused by bacteria and fungi. In certain embodiments the pharmaceutical compositions provided herein, such as topical compositions, may additionally comprise Polyquad®. In another embodiment, the pharmaceutical compositions provided herein do not comprise a preservative.

The pharmaceutical compositions provided herein may additionally comprise a solubilizer. Suitable solubilizers include, but are not limited to, tyloxapol, fatty acid glycerol polyethylene glycol esters, fatty acid polyethylene glycol esters, polyethylene glycols, glycerol ethers, or cyclodextrins.

The pharmaceutical compositions provided herein may further comprise non-toxic excipients, such as emulsifiers, wetting agents or fillers, by way of example, polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight. Other compounds may also be added to the pharmaceutical compositions provided herein to adjust (e.g., increase) the viscosity of the carrier. Examples of viscosity enhancing agents include, but are not limited to, polysaccharides, such as hyaluronic acid and its salts, chondroitin sulfate and its salts, dextrans, various polymers of the cellulose family, vinyl polymers, and acrylic acid polymers.

Dosages of a compound of Formula (I) or a pharmaceutically acceptable salt, solvate, co-crystal, polymorph or stereoisomer thereof and one or more pharmaceutically acceptable carriers will vary depending, e.g., on the particular condition to be treated, the effect desired and the mode of administration. In certain embodiments, a compound of Formula (I) or a pharmaceutically acceptable salt, solvate, co-crystal, polymorph or stereoisomer thereof is present in the pharmaceutical composition for topical administration at a concentration from about 0.1% to about 5.0% w/v. In certain embodiments, a compound of Formula (I) or a pharmaceutically acceptable salt, solvate, co-crystal, polymorph or stereoisomer thereof is present in the pharmaceutical composition for topical administration at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I) or a pharmaceutically acceptable salt, solvate, co-crystal, polymorph or stereoisomer thereof is present in the pharmaceutical composition for topical administration at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I) or a pharmaceutically acceptable salt, solvate, co-crystal, polymorph or stereoisomer thereof is present in the pharmaceutical composition for topical administration at a concentration of no more than about 6.0% w/w, no more than about 4.5% w/w, no more than about 4.0% w/w, no more than about 3.5% w/w, or no more than about 3.0% w/w. In particular embodiments, a compound of Formula (I) or a pharmaceutically acceptable salt, solvate, co-crystal, polymorph or stereoisomer thereof is present in the pharmaceutical composition for topical administration at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

Dosages of a compound of Formula (I') or a pharmaceutically acceptable salt, solvate, co-crystal, polymorph or stereoisomer thereof and one or more pharmaceutically acceptable carriers will vary depending, e.g., on the particular condition to be treated, the effect desired and the mode of administration. In certain embodiments, a compound of Formula (I') or a pharmaceutically acceptable salt, solvate, co-crystal, polymorph or stereoisomer thereof is present in the pharmaceutical composition for topical administration at a concentration from about 0.1% to about 5.0% w/v. In certain embodiments, a compound of Formula (I') or a pharmaceutically acceptable salt, solvate, co-crystal, polymorph or stereoisomer thereof is present in the pharmaceutical composition for topical administration at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I') or a pharmaceutically acceptable salt, solvate, co-crystal, polymorph or stereoisomer thereof is present in the pharmaceutical composition for topical administration at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I') or a pharmaceutically acceptable salt, solvate, co-crystal, polymorph or stereoisomer thereof is present in the pharmaceutical composition for topical administration at a concentration of no more than about 6.0% w/w, no more than about 4.5% w/w, no more than about 4.0% w/w, no more than about 3.5% w/w, or no more than about 3.0% w/w. In particular embodiments, a compound of Formula (I') or a pharmaceutically acceptable salt, solvate, co-crystal, polymorph or stereoisomer thereof is present in the pharmaceutical composition for topical administration at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

In certain embodiments, provided herein are pharmaceutical compositions comprising a compound of Formula (I) or a pharmaceutically acceptable salt, solvate, co-crystal, polymorph or stereoisomer thereof and one or more pharmaceutically acceptable carriers. In other embodiments, provided herein are pharmaceutical compositions comprising a compound of Formula (I') or a pharmaceutically acceptable salt, solvate, co-crystal, polymorph or stereoisomer thereof and one or more pharmaceutically acceptable carriers. In particular embodiments, the pharmaceutical composition provided herein is suitable for ophthalmic administration to a subject. In certain embodiments, the pharmaceutical composition provided herein is suitable for topical administration to the ocular surface, the cornea, the eyelid, eye lid margins, eyelashes and/or margins of the eye in order to deliver the composition to the meibomian gland to a subject. In some embodiments, liquid (aqueous or non-aqeuous) solutions may be used. Application of the pharmaceutical composition may be performed with an applicator, such as the subject's finger, a Weck-Cel(R), Q-tip, or other device capable of delivering a formulation to the eyelid, eyelashes and/or eyelid margin in order to deliver the formulation to the meibomian gland. The pharmaceutical compositions provided herein may be viscous or semi-viscous; liquid, solid, or semi-solid; aqueous or non-aqueous, depending on the site of application, dose, solubility of drug, and a variety of other factors that are considered by those of skill in the art. In certain embodiments, the pharmaceutical composition provided herein is an ophthalmically compatible composition for delivery to the eye of a subject.

In other embodiments, the pharmaceutical compositions provided herein comprise ophthalmologically acceptable preservatives, surfactants, viscosity enhancers, penetration enhancers, buffers, sodium chloride, and water to form an aqueous, sterile ophthalmic suspension or solution.

In certain embodiments, the pharmaceutical compositions provided herein may further comprise an additional therapeutic agent. Further therapeutic agents may include, for instance, other compounds and antibodies useful for treating ocular disorders. A non-limiting list of such agents incudes retinoid X receptor agonists, such as vitamin A, retinoic acid, phytanic acid, lithocholic acid, bexarotene, docosahexaenoic acid, or flurobexarotene. Other additional therapeutic agents include ophthalmic steroids such as, dexamethasone, fluocinolone, loteprednol, difluprednate, fluorometholone, prednisolone, prednisone, medrysone, triamcinolone, betamethasone, rimexolone, or pharmaceutically acceptable salts thereof. In addition, other additional therapeutic agents include those used to target ocular surface disease disorders, such as dry eye disease. Non-limiting example of such additional therapeutic agents include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

In certain preferred embodiments, the subject is a human.

In certain embodiments, the pharmaceutical compositions provided herein are delivered to the surface of the eye or the eyelid one to four times a day, depending on the routine discretion of the skilled clinician. In certain embodiments, the pharmaceutical compositions provided herein are administered, one, two, three, or four times a day. In certain embodiments, the pharmaceutical compositions provided herein may be administered for at least a week, four weeks, or more. In particular embodiments, the pharmaceutical compositions provided herein may be administered for up to about 12 weeks, or greater than about 12 weeks, or chronically.

In some embodiments, compounds of Formula (I), or subformulae thereof, or a pharmaceutically acceptable salt, solvate, co-crystal, polymorph or stereoisomer thereof, or pharmaceutical compositions provided herein are administered to the eye of the subject. In some embodiments, compounds of Formula (I'), or subformulae thereof, or a pharmaceutically acceptable salt, solvate, co-crystal, polymorph or stereoisomer thereof, or pharmaceutical compositions provided herein are administered to the eye of the subject. Administration to the eye includes administration to all parts of the eye including all parts of the ocular surface such as the cornea, conjunctiva, and the corneo-scleral junction, i.e., the limbus. In some embodiments, the pharmaceutical compositions provided herein are administered to the eyelid of the subject. Administration to the eyelid includes administration individually to the upper or lower eyelids, or both.

In certain embodiments, administration of a compound of Formula (I), or subformulae thereof, or a pharmaceutically acceptable salt, solvate, co-crystal, polymorph or stereoisomer thereof, or a pharmaceutical composition provided herein reduces the signs and/or symptoms of meibomian gland dysfunction. Thus, in some embodiments, administration of a compound of Formula (I), or subformulae thereof, or a pharmaceutically acceptable salt, solvate, co-crystal, polymorph or stereoisomer thereof, or a pharmaceutical composition provided herein results in a decrease of at least about 10%, at least about 15%, at least about 20%, or at least about 30% in the symptoms and/or signs of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, or loss of tolerability to contact lens use.

In certain embodiments, administration of a compound of Formula (I'), or subformulae thereof, or a pharmaceutically acceptable salt, solvate, co-crystal, polymorph or stereoisomer thereof, or a pharmaceutical composition provided herein reduces the signs and/or symptoms of meibomian gland dysfunction. Thus, in some embodiments, administration of a compound of Formula (I'), or subformulae thereof, or a pharmaceutically acceptable salt, solvate, co-crystal, polymorph or stereoisomer thereof, or a pharmaceutical composition provided herein results in a decrease of at least about 10%, at least about 15%, at least about 20%, or at least about 30% in the symptoms and/or signs of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, or loss of tolerability to contact lens use.

In certain embodiments, the administration of the pharmaceutical composition provided herein does not result in a change (e.g., of less than 5% difference, less than 4% difference, or less than 3% difference) in one or more of best corrected visual acuity, slit-lamp biomicroscopy, dilated eye exam, or intraocular pressure, when compared to a placebo.

Unless otherwise specified, the weight or dosage referred to herein for compounds of Formula (I) or compounds of Formula (I') provided herein is the weight or dosage of the compound itself, not that of a salt thereof, which can be different to achieve the intended therapeutic effect. For example, the weight or dosage of a corresponding salt of a compound of Formula (I) or a compound of Formula (I') suitable for the methods, compositions, or combinations disclosed herein may be calculated based on the ratio of the molecular weights of the salt and compound itself.

In some embodiments, the pharmaceutical compositions provided herein comprise a crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione.

Embodiments of the crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione provided herein include the form designated as Form A. The names used herein to identify a specific form, e.g. "Form A", etc., should not be considered limiting with respect to any other substance possessing similar or identical physical and chemical characteristics, but rather it should be understood that these designations are mere identifiers that should be interpreted according to the characterization information also presented herein.

Figure 1:
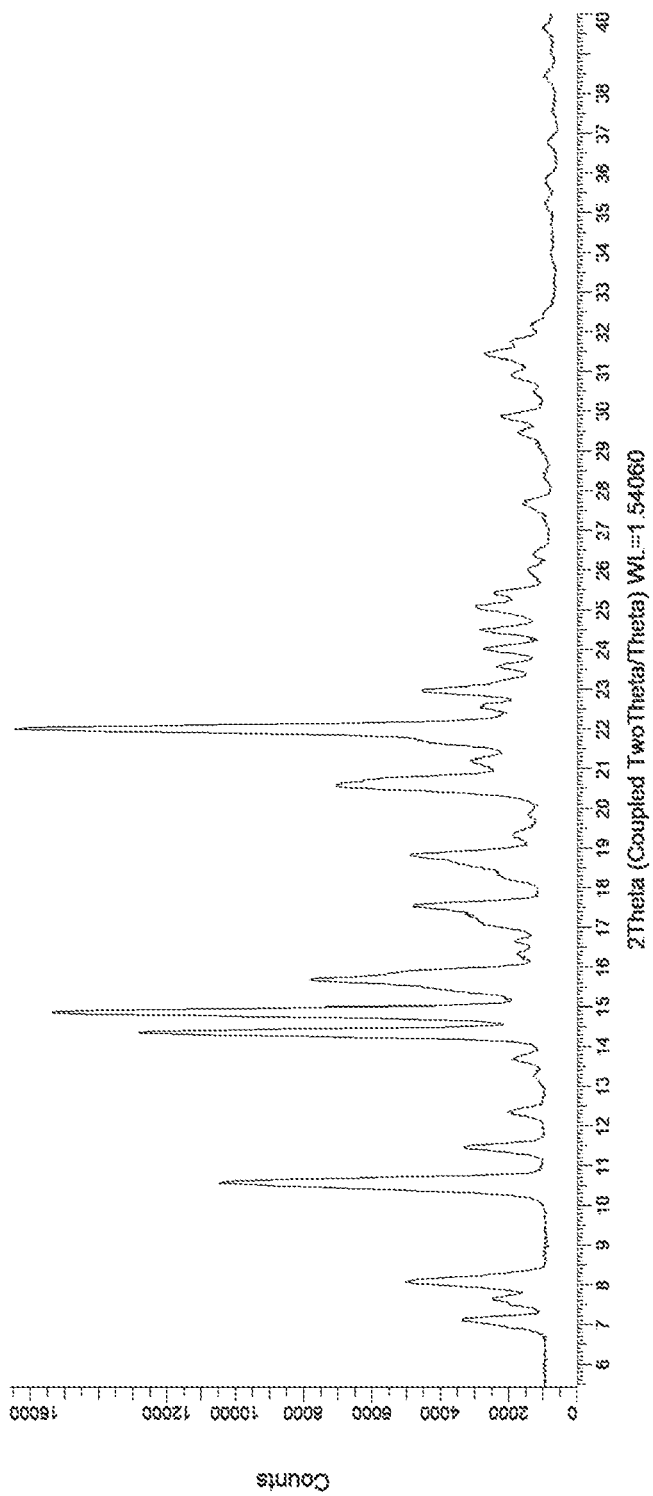
FIG. 1 provides an illustrative X-ray powder diffraction pattern (XRPD) of the crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl) imidazolidine-2,4-dione, designated herein as Form A, showing degrees 2θ (2-theta) on the X-axis and intensity on the Y-axis. More detailed listings of the XRPD peaks for Form A are set forth in Table 1.

In certain embodiment, the pharmaceutical compositions provided herein comprise a Form A having an X-ray powder diffraction (XRPD) spectrum substantially the same as the XRPD shown in FIG. 1. In other embodiments, the pharmaceutical composition comprises Form A characterized by an XRPD pattern comprising one or more peaks selected from 7.2±0.2, 7.8±0.2, 8.2±0.2, 10.7±0.2, 11.6±0.2, 12.5±0.2, 13.8±0.2, 14.5±0.2, 15.0±0.2, 15.8±0.2, 17.7±0.2, 18.9±0.2, 20.7±0.2, 21.3±0.2, 21.8±0.2, 22.1±0.2, and 23.1±0.2. Accordingly, the XRPD pattern for Form A may comprise one, two, three, or four representative peaks. In other embodiments, the pharmaceutical composition comprises Form A characterized by an XRPD pattern comprising one or more peaks selected from FIG. 1, as shown in Table 1.

Figure 2:
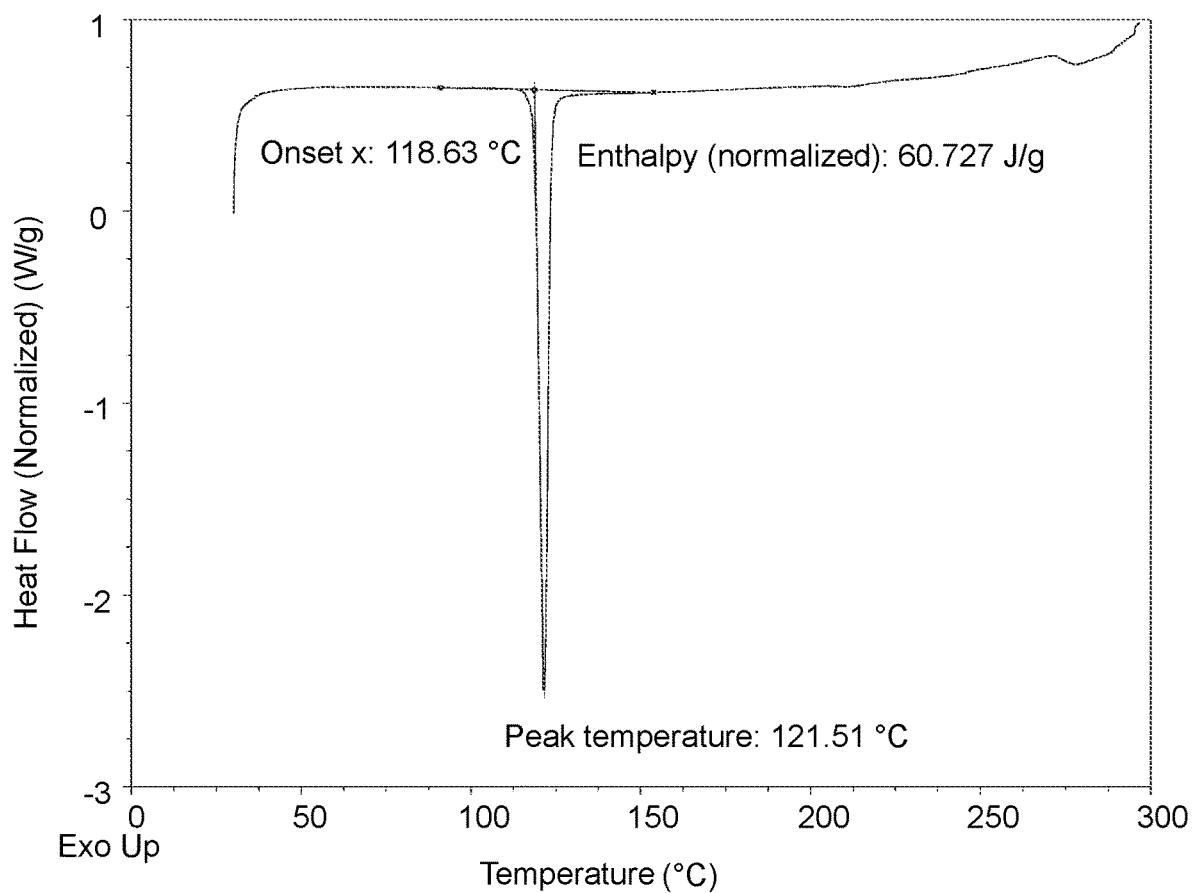
FIG. 2 provides an illustrative differential scanning calorimetry (DSC) profile of the crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione, designated herein as Form A. The DSC graph plots the heat flow as a function of temperature from a sample, the temperature rate change being about 10 K/min.

In another embodiment, the pharmaceutical compositions provided herein comprise Form A having a differential scanning calorimetry (DSC) profile substantially the same as the DSC profile shown in FIG. 2. In certain embodiments, the DSC profile is characterized by a single endothermic event representing the melting of the compound with a melting onset at about 118.6° C. at a heating rate of 10 K/min. In certain embodiments, the DSC profile is characterized by a single endothermic event at about 121.5° C. at a heating rate of 10 K/min which represents the melting of the compound In another embodiment, the pharmaceutical compositions provided herein comprise Form A having a thermo gravimetric analysis (TGA) profile substantially the same as the TGA profile shown in FIG. 3. In certain embodiments, the weight loss represents a loss of about 0.04% of the sample as the temperature is changed from about 30° C. to about 150° C. In certain embodiments, the weight loss represents a loss of less than about 0.5% of the sample as the temperature is changed from about 30° C. to about 150° C.

In other embodiments, the pharmaceutical compositions provided herein comprise an amorphous form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione. In certain embodiments, Form A is substantially pure.

It should be understood that in the XRPD spectra or pattern that there is inherent variability in the values measured in degrees 2theta (° 2θ) as a result of, for example, instrumental variation (including differences between instruments). As such, it should be understood that there is a variability of up to ±0.2° 2θ in XRPD peak measurements and yet such peak values would still be considered to be representative of a particular solid state form of the crystalline materials described herein. It should also be understood that other measured values from XRPD experiments and Karl Fisher analysis, such as relative intensity and water content, can vary as a result of, for example, sample preparation and/or storage and/or environmental conditions, and yet the measured values will still be considered to be representative of a particular solid state form of the crystalline materials described herein.

Pharmacology and Utility

In certain embodiments, provided herein is a method for treating an ocular disease or disorder, wherein the method comprises administering a compound of Formula (I), or subformulae thereof, or a pharmaceutically acceptable salt, solvate, co-crystal, polymorph or stereoisomer thereof, or a pharmaceutical composition provided herein, to a subject in need thereof. In certain other embodiments, provided herein is a method for treating an ocular disease or disorder, wherein the method comprises administering a compound of Formula (I'), or subformulae thereof, or a pharmaceutically acceptable salt, solvate, co-crystal, polymorph or stereoisomer thereof, or a pharmaceutical composition provided herein, to a subject in need thereof. In certain embodiments, the ocular disease or disorder is selected from meibomian gland dysfunction, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, the ocular disease or disorder is selected from the group consisting of lipid deficient dry eye, tear film lipid deficiency, ocular rosacea, chalazion, and hordeola.

In certain embodiments, provided herein is a method for treating meibomian gland dysfunction, wherein the method comprises administering a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating meibomian gland dysfunction, wherein the method comprises administering a compound of Formula (I'), or subformulae thereof, or a pharmaceutically acceptable salt, solvate, co-crystal, polymorph or stereoisomer thereof, or a pharmaceutical composition provided herein, to a subject in need thereof.

In certain embodiments, provided herein is a method for treating the signs and/or symptoms of an ocular disease or disorder, wherein the method comprises administering a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating the signs and/or symptoms of an ocular disease or disorder, wherein the method comprises administering a compound of Formula (I'), or subformulae thereof, or a pharmaceutically acceptable salt, solvate, co-crystal, polymorph or stereoisomer thereof, or a pharmaceutical composition provided herein, to a subject in need thereof. In certain embodiments, the ocular disease or disorder is selected from meibomian gland dysfunction, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, the ocular disease or disorder is selected from the group consisting of lipid deficient dry eye, tear film lipid deficiency, ocular rosacea, chalazion, and hordeola.

In certain embodiments, provided herein is a method for treating the signs and/or symptoms of meibomian gland dysfunction, wherein the method comprises administering a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating the signs and/or symptoms of meibomian gland dysfunction, wherein the method comprises administering a compound of Formula (I'), or subformulae thereof, or a pharmaceutically acceptable salt, solvate, co-crystal, polymorph or stereoisomer thereof, or a pharmaceutical composition provided herein, to a subject in need thereof.

In certain embodiments, provided herein is a method for treating an ocular disease or disorder, wherein the method comprises administering a therapeutically effective amount of a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating an ocular disease or disorder, wherein the method comprises administering a therapeutically effective amount of a compound of Formula (I'), or subformulae thereof, or a pharmaceutically acceptable salt, solvate, co-crystal, polymorph or stereoisomer thereof, or a pharmaceutical composition provided herein, to a subject in need thereof. In certain embodiments, the ocular disease or disorder is selected from meibomian gland dysfunction, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, the ocular disease or disorder is selected from the group consisting of lipid deficient dry eye, tear film lipid deficiency, ocular rosacea, chalazion, and hordeola.

In certain embodiments, provided herein is a method for treating meibomian gland dysfunction, wherein the method comprises administering a therapeutically effective amount of a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating meibomian gland dysfunction, wherein the method comprises administering a therapeutically effective amount of a compound of Formula (I'), or subformulae thereof, or a pharmaceutically acceptable salt, solvate, co-crystal, polymorph or stereoisomer thereof, or a pharmaceutical composition provided herein, to a subject in need thereof.

In certain embodiments, provided herein is a method for treating the signs and/or symptoms of an ocular disease or disorder, wherein the method comprises administering a therapeutically effective amount of a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating the signs and/or symptoms of an ocular disease or disorder, wherein the method comprises administering a therapeutically effective amount of a compound of Formula (I'), or subformulae thereof, or a pharmaceutically acceptable salt, solvate, co-crystal, polymorph or stereoisomer thereof, or a pharmaceutical composition provided herein, to a subject in need thereof. In certain embodiments, the ocular disease or disorder is selected from meibomian gland dysfunction, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, the ocular disease or disorder is selected from the group consisting of lipid deficient dry eye, tear film lipid deficiency, ocular rosacea, chalazion, and hordeola.

In certain embodiments, provided herein is a method for treating the signs and/or symptoms of meibomian gland dysfunction, wherein the method comprises administering a therapeutically effective amount of a compound of Formula (I), or subformulae thereof, or a pharmaceutically acceptable salt, solvate, co-crystal, polymorph or stereoisomer thereof, or a pharmaceutical composition provided herein, to a subject in need thereof. In certain embodiments, provided herein is a method for treating the signs and/or symptoms of meibomian gland dysfunction, wherein the method comprises administering a therapeutically effective amount of a compound of Formula (I'), or subformulae thereof, or a pharmaceutically acceptable salt, solvate, co-crystal, polymorph or stereoisomer thereof, or a pharmaceutical composition provided herein, to a subject in need thereof.

In certain embodiments, provided herein is a use of a compound of Formula (I), or subformulae thereof, or a pharmaceutically acceptable salt, solvate, co-crystal, polymorph or stereoisomer thereof, in the manufacture of a medicament for the treatment of meibomian gland dysfunction. In other embodiments, provided herein is a use of a compound of Formula (I), or subformulae thereof, or a pharmaceutically acceptable salt, solvate, co-crystal, polymorph or stereoisomer thereof, for the treatment of meibomian gland dysfunction. In other embodiments, provided herein is a compound of Formula (I), or subformulae thereof, or a pharmaceutically acceptable salt, solvate, co-crystal, polymorph or stereoisomer thereof, for use in the treatment of meibomian gland dysfunction. In certain embodiments, provided herein is a use of a compound of Formula (I'), or subformulae thereof, or a pharmaceutically acceptable salt, solvate, co-crystal, polymorph or stereoisomer thereof, in the manufacture of a medicament for the treatment of meibomian gland dysfunction. In other embodiments, provided herein is a use of a compound of Formula (I'), or subformulae thereof, or a pharmaceutically acceptable salt, solvate, co-crystal, polymorph or stereoisomer thereof, for the treatment of meibomian gland dysfunction. In other embodiments, provided herein is a compound of Formula (I), or subformulae thereof, or a pharmaceutically acceptable salt, solvate, co-crystal, polymorph or stereoisomer thereof, for use in the treatment of meibomian gland dysfunction.

In certain embodiments, provided herein is a method for treating a subject in need thereof, said method comprising administering a pharmaceutical composition comprising a compound of Formula (I) or subformulae thereof, or a pharmaceutically acceptable salt, solvate, co-crystal, polymorph or stereoisomer thereof, to the subject. In certain embodiments, provided herein is a method for treating meibomian gland dysfunction, said method comprising administering a pharmaceutical composition comprising a compound of Formula (I) or subformulae thereof, or a pharmaceutically acceptable salt, solvate, co-crystal, polymorph or stereoisomer thereof, to a subject in need thereof. In certain preferred embodiments, the subject is a human. In certain embodiments, provided herein is a method for treating a subject in need thereof, said method comprising administering a pharmaceutical composition comprising a compound of Formula (I') or subformulae thereof, or a pharmaceutically acceptable salt, solvate, co-crystal, polymorph or stereoisomer thereof, to the subject. In certain embodiments, provided herein is a method for treating meibomian gland dysfunction, said method comprising administering a pharmaceutical composition comprising a compound of Formula (I') or subformulae thereof, or a pharmaceutically acceptable salt, solvate, co-crystal, polymorph or stereoisomer thereof, to a subject in need thereof. In certain preferred embodiments, the subject is a human.

In some embodiments, a compound of Formula (I), or subformulae thereof, or a pharmaceutically acceptable salt, solvate, co-crystal, polymorph or stereoisomer thereof is administered to the eye of the subject. In some embodiments, a pharmaceutical composition comprising a compound of Formula (I), or subformulae thereof, or a pharmaceutically acceptable salt, solvate, co-crystal, polymorph or stereoisomer thereof is administered to the eye of the subject. In particular embodiments, a compound of Formula (I), or subformulae thereof, or a pharmaceutically acceptable salt, solvate, co-crystal, polymorph or stereoisomer thereof is suitable for ophthalmic administration to a subject. In some embodiments, a compound of Formula (I), or subformulae thereof, or a pharmaceutically acceptable salt, solvate, co-crystal, polymorph or stereoisomer thereof is administered to the eyelid of the subject. In some embodiments, a therapeutically effective amount of a compound of Formula (I), or subformulae thereof, or a pharmaceutically acceptable salt, solvate, co-crystal, polymorph or stereoisomer thereof is administered to the eyelid of the subject. In some embodiments, a pharmaceutical composition comprising a compound of Formula (I), or subformulae thereof, or a pharmaceutically acceptable salt, solvate, co-crystal, polymorph or stereoisomer thereof is administered to the eyelid of the subject. Administration to the eye includes administration to all parts of the eye including all parts of the ocular surface such as the cornea, conjunctiva, and the corneoscleral junction, i.e., the limbus. Administration to the eyelid includes administration individually to the upper or lower eyelids, or both. In some embodiments, a compound of Formula (I'), or subformulae thereof, or a pharmaceutically acceptable salt, solvate, co-crystal, polymorph or stereoisomer thereof is administered to the eye of the subject. In some embodiments, a pharmaceutical composition comprising a compound of Formula (I'), or subformulae thereof, or a pharmaceutically acceptable salt, solvate, co-crystal, polymorph or stereoisomer thereof is administered to the eye of the subject. In particular embodiments, a compound of Formula (I'), or subformulae thereof, or a pharmaceutically acceptable salt, solvate, co-crystal, polymorph or stereoisomer thereof is suitable for ophthalmic administration to a subject. In some embodiments, a compound of Formula (I'), or subformulae thereof, or a pharmaceutically acceptable salt, solvate, co-crystal, polymorph or stereoisomer thereof is administered to the eyelid of the subject. In some embodiments, a therapeutically effective amount of a compound of Formula (I'), or subformulae thereof, or a pharmaceutically acceptable salt, solvate, co-crystal, polymorph or stereoisomer thereof is administered to the eyelid of the subject. In some embodiments, a pharmaceutical composition comprising a compound of Formula (I'), or subformulae thereof, or a pharmaceutically acceptable salt, solvate, co-crystal, polymorph or stereoisomer thereof is administered to the eyelid of the subject. Administration to the eye includes administration to all parts of the eye including all parts of the ocular surface such as the cornea, conjunctiva, and the corneoscleral junction, i.e., the limbus. Administration to the eyelid includes administration individually to the upper or lower eyelids, or both.

In certain embodiments, the methods described herein provide for administration of a compound of Formula (I), or subformulae thereof, or a pharmaceutically acceptable salt, solvate, co-crystal, polymorph or stereoisomer thereof to a subject in need thereof in an ophthalmically compatible pharmaceutical composition, wherein said compound is present at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I), or subformulae thereof, or a pharmaceutically acceptable salt, solvate, co-crystal, polymorph or stereoisomer thereof is present at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I), or subformulae thereof, or a pharmaceutically acceptable salt, solvate, co-crystal, polymorph or stereoisomer thereof is present at a concentration of no more than about 6.0% w/w, no more than about 4.5% w/w, no more than about 4.0% w/w, no more than about 3.5% w/w, or no more than about 3.0% w/w. In particular embodiments, a compound of Formula (I), or subformulae thereof, or a pharmaceutically acceptable salt, solvate, co-crystal, polymorph or stereoisomer thereof is present at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

In certain embodiments, the methods described herein provide for administration of a compound of Formula (I'), or subformulae thereof, or a pharmaceutically acceptable salt, solvate, co-crystal, polymorph or stereoisomer thereof to a subject in need thereof in an ophthalmically compatible pharmaceutical composition, wherein said compound is present at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I'), or subformulae thereof, or a pharmaceutically acceptable salt, solvate, co-crystal, polymorph or stereoisomer thereof is present at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I'), or subformulae thereof, or a pharmaceutically acceptable salt, solvate, co-crystal, polymorph or stereoisomer thereof is present at a concentration of no more than about 6.0% w/w, no more than about 4.5% w/w, no more than about 4.0% w/w, no more than about 3.5% w/w, or no more than about 3.0% w/w. In particular embodiments, a compound of Formula (I'), or subformulae thereof, or a pharmaceutically accept-able salt, solvate, co-crystal, polymorph or stereoisomer thereof is present at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

In certain embodiments, the methods described herein provide for administration of a pharmaceutical composition comprising a compound of Formula (I), or subformulae thereof, or a pharmaceutically acceptable salt, solvate, co-crystal, polymorph or stereoisomer thereof, to a subject in need thereof, wherein said pharmaceutical composition is an ophthalmically compatible composition and wherein said compound is present at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I), or subformulae thereof, or a pharmaceutically acceptable salt, solvate, co-crystal, polymorph or stereoisomer thereof is present in the pharmaceutical composition at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I), or subformulae thereof, or a pharmaceutically acceptable salt, solvate, co-crystal, polymorph or stereoisomer thereof is present in the pharmaceutical composition at a concentration of no more than about 6.0% w/w, no more than about 4.5% w/w, no more than about 4.0% w/w, no more than about 3.5% w/w, or no more than about 3.0% w/w. In particular embodiments, a compound of Formula (I), or subformulae thereof, or a pharmaceutically acceptable salt, solvate, co-crystal, polymorph or stereoisomer thereof is present in the pharmaceutical composition at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

In certain embodiments, the methods described herein provide for administration of a pharmaceutical composition comprising a compound of Formula (I'), or subformulae thereof, or a pharmaceutically acceptable salt, solvate, co-crystal, polymorph or stereoisomer thereof, to a subject in need thereof, wherein said pharmaceutical composition is an ophthalmically compatible composition and wherein said compound is present at a concentration of about 0.01% w/w to about 5% w/w, or about 0.05% to about 3% w/w, or about 0.05% w/w to about 0.5% w/w, or about 0.15% w/w, about 0.1% w/w, about 0.5% w/w, about 1.0% w/w about 1.5% w/w or about 2.0% w/w. In some embodiments, a compound of Formula (I'), or subformulae thereof, or a pharmaceutically acceptable salt, solvate, co-crystal, polymorph or stereoisomer thereof is present in the pharmaceutical composition at a concentration of at least about 0.5% w/w, at least about 1.0% w/w, at least about 1.5% w/w, at least about 2.0% w/w, at least about 2.5% w/w, about 3.0% w/w, about 3.5% w/w, about 4.0% w/w, about 4.5% w/w, about 5.0% w/w, about 5.5% w/w, or about 6.0% w/w. In some embodiments, a compound of Formula (I'), or subformulae thereof, or a pharmaceutically acceptable salt, solvate, co-crystal, polymorph or stereoisomer thereof is present in the pharmaceutical composition at a concentration of no more than about 6.0% w/w, no more than about 4.5% w/w, no more than about 4.0% w/w, no more than about 3.5% w/w, or no more than about 3.0% w/w. In particular embodiments, a compound of Formula (I'), or subformulae thereof, or a pharmaceutically acceptable salt, solvate, co-crystal, polymorph or stereoisomer thereof is present in the pharmaceutical composition at a concentration of about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, or about 6.0% w/w.

In certain embodiments, a compound of Formula (I), or subformulae thereof, or a pharmaceutically acceptable salt, solvate, co-crystal, polymorph or stereoisomer thereof is delivered to the surface of the eye one to six times a day, depending on the routine discretion of the skilled clinician. In certain embodiments, a compound of Formula (I), or subformulae thereof, or a pharmaceutically acceptable salt, solvate, co-crystal, polymorph or stereoisomer thereof is administered, one, two, three, or four times a day. In certain embodiments, a compound of Formula (I), or subformulae thereof, or a pharmaceutically acceptable salt, solvate, co-crystal, polymorph or stereoisomer thereof may be administered for at least a week, four weeks, or more. In particular embodiments, a compound of Formula (I) or a pharmaceutically acceptable salt, solvate, co-crystal, polymorph or stereoisomer thereof may be administered for up to about 12 weeks, or greater than about 12 weeks, or chronically.

In certain embodiments, a compound of Formula (I'), or subformulae thereof, or a pharmaceutically acceptable salt, solvate, co-crystal, polymorph or stereoisomer thereof is delivered to the surface of the eye one to six times a day, depending on the routine discretion of the skilled clinician. In certain embodiments, a compound of Formula (I'), or subformulae thereof, or a pharmaceutically acceptable salt, solvate, co-crystal, polymorph or stereoisomer thereof is administered, one, two, three, or four times a day. In certain embodiments, a compound of Formula (I'), or subformulae thereof, or a pharmaceutically acceptable salt, solvate, co-crystal, polymorph or stereoisomer thereof may be administered for at least a week, four weeks, or more. In particular embodiments, a compound of Formula (I') or a pharmaceutically acceptable salt, solvate, co-crystal, polymorph or stereoisomer thereof may be administered for up to about 12 weeks, or greater than about 12 weeks, or chronically.

In certain embodiments, a pharmaceutical composition comprising a compound of Formula (I), or subformulae thereof, or a pharmaceutically acceptable salt, solvate, co-crystal, polymorph or stereoisomer thereof is delivered to the surface of the eye one to six times a day, depending on the routine discretion of the skilled clinician. In certain embodiments, a pharmaceutical composition comprising a compound of Formula (I), or subformulae thereof, or a pharmaceutically acceptable salt, solvate, co-crystal, polymorph or stereoisomer thereof is administered, one, two, three, or four times a day. In certain embodiments, a pharmaceutical composition comprising a compound of Formula (I), or subformulae thereof, or a pharmaceutically acceptable salt, solvate, co-crystal, polymorph or stereoisomer thereof may be administered for at least a week, four weeks, or more. In particular embodiments, a pharmaceutical composition comprising a compound of Formula (I), or subformulae thereof, or a pharmaceutically acceptable salt, solvate, co-crystal, polymorph or stereoisomer thereof may be administered for up to about 12 weeks, or greater than about 12 weeks.

In certain embodiments, a pharmaceutical composition comprising a compound of Formula (I'), or subformulae thereof, or a pharmaceutically acceptable salt, solvate, co-crystal, polymorph or stereoisomer thereof is delivered to the surface of the eye one to six times a day, depending on the routine discretion of the skilled clinician. In certain embodiments, a pharmaceutical composition comprising a compound of Formula (I'), or subformulae thereof, or a pharmaceutically acceptable salt, solvate, co-crystal, polymorph or stereoisomer thereof is administered, one, two, three, or four times a day. In certain embodiments, a pharmaceutical composition comprising a compound of Formula (I'), or subformulae thereof, or a pharmaceutically acceptable salt, solvate, co-crystal, polymorph or stereoisomer thereof may be administered for at least a week, four weeks, or more. In particular embodiments, a pharmaceutical composition comprising a compound of Formula (I'), or subformulae thereof, or a pharmaceutically acceptable salt, solvate, co-crystal, polymorph or stereoisomer thereof may be administered for up to about 12 weeks, or greater than about 12 weeks.

In certain embodiments, a compound of Formula (I), or subformulae thereof, or a pharmaceutically acceptable salt, solvate, co-crystal, polymorph or stereoisomer thereof may be administered with an additional therapeutic agent. In certain embodiments, a compound of Formula (I'), or subformulae thereof, or a pharmaceutically acceptable salt, solvate, co-crystal, polymorph or stereoisomer thereof may be administered with an additional therapeutic agent. Further therapeutic agents may include, for instance, other compounds and antibodies useful for treating ocular disorders. A non-limiting list of such agents incudes retinoid X receptor agonists, such as vitamin A, retinoic acid, phytanic acid, lithocholic acid, bexarotene, docosahexaenoic acid, or flurobexarotene. Other additional therapeutic agents include ophthalmic steroids such as, dexamethasone, fluocinolone, loteprednol, difluprednate, fluorometholone, prednisolone, prednisone, medrysone, triamcinolone, betamethasone, rimexolone, or pharmaceutically acceptable salts thereof. In addition, other additional therapeutic agents include those used to target ocular surface disease disorders, such as dry eye disease. Non-limiting example of such additional therapeutic agents include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

In certain embodiments of the methods described herein, administration of a compound of Formula (I), or subformulae thereof, or a pharmaceutically acceptable salt, solvate, co-crystal, polymorph or stereoisomer thereof reduces the signs and/or symptoms of meibomian gland dysfunction. In certain embodiments of the methods described herein, administration of a compound of Formula (I'), or subformulae thereof, or a pharmaceutically acceptable salt, solvate, co-crystal, polymorph or stereoisomer thereof reduces the signs and/or symptoms of meibomian gland dysfunction. In certain embodiments, meibomian gland dysfunction is associated with one or more of dry eye disease, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, meibomian gland dysfunction is associated with one or more of lipid deficient dry eye, tear film lipid deficiency, ocular rosacea, chalazion, and hordeola.

Thus, in some embodiments, administration of a compound of Formula (I), or subformulae thereof, or a pharmaceutically acceptable salt, solvate, co-crystal, polymorph or stereoisomer thereof results in a decrease of at least about 10%, at least about 15%, at least about 20%, or at least about 30% in the signs and/or symptoms of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, loss of tolerability to contact lens use. In certain embodiments of the methods described herein, administration of a compound of Formula (I), or subformulae thereof, or a pharmaceutically acceptable salt, solvate, co-crystal, polymorph or stereoisomer thereof does not result in a change (e.g., of less than 5% difference, less than 4% difference, or less than 3% difference) in one or more of best corrected visual acuity, slit-lamp biomicroscopy, dilated eye exam, and intraocular pressure, when compared to a placebo. In some embodiments, administration of a compound of Formula (I'), or subformulae thereof, or a pharmaceutically acceptable salt, solvate, co-crystal, polymorph or stereoisomer thereof results in a decrease of at least about 10%, at least about 15%, at least about 20%, or at least about 30% in the signs and/or symptoms of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, loss of tolerability to contact lens use. In certain embodiments of the methods described herein, administration of a compound of Formula (I'), or subformulae thereof, or a pharmaceutically acceptable salt, solvate, co-crystal, polymorph or stereoisomer thereof does not result in a change (e.g., of less than 5% difference, less than 4% difference, or less than 3% difference) in one or more of best corrected visual acuity, slit-lamp biomicroscopy, dilated eye exam, and intraocular pressure, when compared to a placebo.

In certain embodiments of the methods described herein, administration of a therapeutically effective amount of a compound of Formula (I), or subformulae thereof, or a pharmaceutically acceptable salt, solvate, co-crystal, polymorph or stereoisomer thereof reduces the signs and/or symptoms of meibomian gland dysfunction. In certain embodiments of the methods described herein, administration of a therapeutically effective amount of a compound of Formula (I'), or subformulae thereof, or a pharmaceutically acceptable salt, solvate, co-crystal, polymorph or stereoisomer thereof reduces the signs and/or symptoms of meibomian gland dysfunction. In certain embodiments, meibomian gland dysfunction is associated with one or more of dry eye disease, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), blepharitis (anterior, posterior, Demodex mites), blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In other embodiments, meibomian gland dysfunction is associated with one or more of lipid deficient dry eye, tear film lipid deficiency, ocular rosacea, chalazion, and hordeola.

Thus, in some embodiments, administration of a therapeutically effective amount of a compound of Formula (I), or subformulae thereof, or a pharmaceutically acceptable salt, solvate, co-crystal, polymorph or stereoisomer thereof results in a decrease of at least about 10%, at least about 15%, at least about 20%, or at least about 30% in the signs and/or symptoms of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, or loss of tolerability to contact lens use. In certain embodiments of the methods described herein, administration of a therapeutically effective amount of a compound of Formula (I), or subformulae thereof, or a pharmaceutically acceptable salt, solvate, co-crystal, polymorph or stereoisomer thereof does not result in a change (e.g., of less than 5% difference, less than 4% difference, or less than 3% difference) in one or more of best corrected visual acuity, slit-lamp biomicroscopy, dilated eye exam, and intraocular pressure, when compared to a placebo.

Thus, in some embodiments, administration of a therapeutically effective amount of a compound of Formula (I'), or subformulae thereof, or a pharmaceutically acceptable salt, solvate, co-crystal, polymorph or stereoisomer thereof results in a decrease of at least about 10%, at least about 15%, at least about 20%, or at least about 30% in the signs and/or symptoms of meibomian gland dysfunction, including one or more of ocular dryness, ocular discomfort or pain, eye itchiness, blurry vision, heavy or fatigued eyes, watery eyes, ocular hyperemia, ocular burning or stinging, grittiness or foreign body sensation, or photophobia or light sensitivity, crusty or red or swollen eyelids or eyelid margins, sensitivity to environmental factors such as wind or low humidity, or loss of tolerability to contact lens use. In certain embodiments of the methods described herein, administration of a therapeutically effective amount of a compound of Formula (I'), or subformulae thereof, or a pharmaceutically acceptable salt, solvate, co-crystal, polymorph or stereoisomer thereof does not result in a change (e.g., of less than 5% difference, less than 4% difference, or less than 3% difference) in one or more of best corrected visual acuity, slit-lamp biomicroscopy, dilated eye exam, and intraocular pressure, when compared to a placebo.

In some embodiments, the symptoms of a patient are assessed by asking the patient a series of questions. Questionnaires allow the assessment of a range of symptoms associated with ocular discomfort. In some embodiments, the questionnaire is the SPEED questionnaire. The SPEED questionnaire assesses frequency and severity of a patient's dry eye symptoms. It examines the occurrence of symptoms on the current day, past 72 hours and past three months. A SPEED score is tallied based on the patient's answers to the questions, to give a range of severity of the patient's symptoms. The SPEED questionnaire includes questions such as the following: 1) what dry eye symptoms are you experiencing, and when do they occur? 2) how frequently do you experience dryness, grittiness, or scratchiness in your eyes? 3) how often do you experience soreness or irritation of the eyes? 4) how often do you experience burning or watering of the eyes? 5) how often do you experience eye fatigue? and 6) how severe are the symptoms? In some embodiments, the questionnaire is the IDEEL questionnaire, which is similar to the SPEED questionnaire described above.

Meibomian gland expressibility is optionally determined to assess the meibomian gland function. In normal patients, meibum is a clear to light yellow oil. Meibum is excreted from the glands when digital pressure is placed on the glands. Changes in meibomian gland expressibility are one potential indicator of MGD. In some embodiments, during expression, quantifying the amount of physical force applied during expression is monitored in addition to assessing lipid volume and lipid quantity.

Tear stability break up time (TBUT) is a surrogate marker for tear stability. Tear film instability is a core mechanism in dry eye and MGD. Low TBUT implies a possibility of lipid layer compromise and MGD. TBUT is optionally measured by examining fluorescein breakup time, as defined as the time to initial breakup of the tear film after a blink. Fluorescein is optionally applied by wetting a commercially available fluorescein-impregnated strip with saline, and applied to the inferior fornix or bulbar conjunctiva. The patient is then asked to blink several times and move the eyes. The break up is then analyzed with a slit lamp, a cobalt blue filter, and a beam width of 4 mm. The patient is instructed to blink, and the time from upstroke of the last blink to the first tear film break or dry spot formation is recorded as a measurement.

Other methods for assessing MGD signs and/or symptoms, include but are not limited to, Schirmer test, ocular surface staining, lid morphology analysis, meibography, meibometry, interferometry, evaporimetry, tear lipid composition analysis, fluorophotometry, meiscometry, lipid layer thickness, Meibum desaturation index, meibomian gland loss osmolarity analysis, indices of tear film dynamics, reading speed, evaporation and tear turnover. Analysis of MGD signs and/or symptoms is performed by commonly understood methods known to those of skill in the art.

In some embodiments of the present invention, the administration of a compound of Formula (I), or subformulae thereof, or a pharmaceutically acceptable salt, solvate, co-crystal, polymorph or stereoisomer thereof, results in the increase in the desaturation index of nonpolar lipids generated by human sebaceous gland cell line (SZ95) cells, when measured in vitro as described herein by about 10% to about 200%, by about 10% to about 150%, by about 10% to about 100%. In some embodiments of the present invention, the administration of a compound of Formula (I'), or subformulae thereof, or a pharmaceutically acceptable salt, solvate, co-crystal, polymorph or stereoisomer thereof, results in the increase in the desaturation index of nonpolar lipids generated by human sebaceous gland cell line (SZ95) cells, when measured in vitro as described herein by about 10% to about 200%, by about 10% to about 150%, by about 10% to about 100%. In particular embodiments, the desaturation index is increased by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, or about 200%.

In some embodiments, the administration of a compound of Formula (I), or subformulae thereof, or a pharmaceutically acceptable salt, solvate, co-crystal, polymorph or stereoisomer thereof, results in a decrease in the melting temperature of meibum in the subject. In some embodiments, the administration of a compound of Formula (I'), or subformulae thereof, or a pharmaceutically acceptable salt, solvate, co-crystal, polymorph or stereoisomer thereof, results in a decrease in the melting temperature of meibum in the subject. In particular embodiments, the melting temperature of meibum is decreased by about 5, about 4, about 3, about 2, or about 1 degrees centigrade.

In some embodiments of the present invention, the subject is diagnosed with meibomian gland dysfunction or dry eye disease or ocular surface disease. In some embodiments, the administration decreases the signs and/or symptoms of meibomian gland dysfunction or dry eye disease or ocular surface disease. In particular embodiments, the administration of a compound of Formula (I), or subformulae thereof, or a pharmaceutically acceptable salt, solvate, co-crystal, polymorph or stereoisomer thereof, results in one or more of the following (or similar or equivalent tests):

i) increased tear film break-up time of at least about 2, 3, 4, or 5 seconds;

ii) meibomian gland expression grading improvement by 1 or 2 or 3 grades;

iii) increased tear meniscus of at least about 10%;

iv) decreased corneal fluorescein staining of at least about 10%, or v) increased Schirmer test score of at least about 2 mm.

In some embodiments, the administration decreases the signs and/or symptoms of meibomian gland dysfunction or dry eye disease or ocular surface disease. In particular embodiments, the administration of a compound of Formula (I'), or subformulae thereof, or a pharmaceutically acceptable salt, solvate, co-crystal, polymorph or stereoisomer thereof, results in one or more of the following (or similar or equivalent tests):

vi) increased tear film break-up time of at least about 2, 3, 4, or 5 seconds;

vii) meibomian gland expression grading improvement by 1 or 2 or 3 grades;

viii) increased tear meniscus of at least about 10%;

ix) decreased corneal fluorescein staining of at least about 10%, or x) increased Schirmer test score of at least about 2 mm.

As used herein, "meibomian gland expression grading" refers to a scale for assessing the severity of meibomian gland dysfunction, for example, as described in Tomlinson, Alan, et al. (2011), "The International Workshop on meibomian Gland Dysfunction: Report of the Diagnosis Subcommittee," Investigative Ophthalmology & Visual Science, vol. 52, no. 4, pp. 2006-2049.

INCORPORATION BY REFERENCE

The entire disclosure of each of the patent documents and scientific articles cited herein are incorporated by reference for all purposes.

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, and NMR. Abbreviations used are those conventional in the art. If not defined, the terms have their generally accepted meanings.

Abbreviations

Abbreviations used are those conventional in the art or the following:

aq.: aqueous
br: broad
d: doublet; dd: doublet of doublets;
ddd: doublets of doublet of doublets
DCM: dichloromethane
DMF: dimethylformamide
DMSO: dimethylsulfoxide
EtOAc: ethyl acetate
HPLC: high pressure liquid chromatography
h, hr: hour(s)
Isco, ISCO: Flash chromatography cartridge containing silica gel provided by Teledyne Isco
LC and LCMS: liquid chromatography and liquid chromatography-mass spectrometry
MeOH: methanol
MS: mass
m: multiplet
min(s): minute(s)
mCPBA: m-chloroperoxybenzoic acid
FCC: flash column chromatography
M and mM: molar and millimolar
mg: milligram
m/z: mass to charge ratio
N: equivalent per liter
NMR: nuclear magnetic resonance
NMP: N-methylpyrrolidinone
q: quartet
s: singlet
t: triplet
td: triplet of doublets
tt: triplet of triplets
THF: tetrahydrofuran
TFA: trifluoroacetic acid
wt: weight
μL, mL and L: microliter, milliliter and liter
Rt.: retention time
rt or RT: room temperature
TEA: triethylamine Analytical Methods
LCMS Method 1:
Instrument: Waters AcQuity UPLC; column AcQuity UPLC BEH C18 1.7 μm 2.1×50 mm; 5.2 min run time, 2→98% solvent B:solvent A from 0 to 5.15 min, 98% solvent B from 5.15 to 5.20 min. Solvents: solvent A=5 mM ammonium hydroxide in water, solvent B=5 mM ammonium hydroxide in acetonitrile. UV detection array 210-400; mass detection 120-1250; column at 50° C.; flow rate 1.0 mL/min; pH 10.2.

LCMS Method 2:
Instrument: Waters AcQuity UPLC; column: AcQuity UPLC BEH $C_{18}$ 1.7 μm, 2.1×30 mm; 2 min run time, 2% solvent B from 0 to 0.1 min, 2→98% solvent B:solvent A from 0.1 to 1.8 min, 98% solvent B for 0.2 min. Solvents: solvent A=0.1% formic acid in water (v/v), solvent B=0.1% formic acid in acetonitrile (v/v). UV detection array 210-400; mass detection 120-1250; column at 50° C.; flow rate 1.0 mL/min; pH 2.6.

LCMS Method 3:
Instrument: Waters AcQuity UPLC; column: AcQuity UPLC BEH $C_{18}$ 1.7 μm 2.1×30 mm; 2 min run time, 2% solvent B from 0 to 0.1 min, 2→98% solvent B:solvent A from 0.1 to 1.8 min, 98% solvent B for 0.2 min. Solvents: solvent A=5 mM ammonium hydroxide in water, solvent B=5 mM ammonium hydroxide in acetonitrile. UV detection array 210-400; mass detection 120-1250; column at 50° C.; flow rate 1.0 mL/min; pH 10.2.

LCMS Method 4:
Instrument: Waters AcQuity UPLC; column AcQuity UPLC BEH $C_{18}$ 1.7 μm 2.1×50 mm; 5.2 min run time, 2→98% solvent B:solvent A from 0 to 5.15 min, 98% solvent B from 5.15 to 5.20 min. Solvents: solvent A=0.1% formic acid in water (v/v), solvent B=0.1% formic acid in acetonitrile (v/v). UV detection array 210-400; mass detection 120-1250; column at 50° C.; flow rate 1.0 mL/min; pH 2.6.

LCMS Method 5:
Instrument: Waters AcQuity UPLC; column AcQuity UPLC BEH C18 1.7 μm 2.1×50 mm; 5.2 min run time, 2→98% solvent B:solvent A from 0 to 5.15 min, 98% solvent B from 5.15 to 5.20 min. Solvents: solvent A=5 mM ammonium hydroxide in water, solvent B=5 mM ammonium hydroxide in acetonitrile. UV detection array 210-400; mass detection 120-1600; column at 50° C.; flow rate 1.0 mL/min; pH 10.2.

LCMS Method 6:
Instrument: Waters AcQuity UPLC; column AcQuity UPLC BEH C18 1.7 μm 2.1×50 mm; 5.2 min run time, 2→98% solvent B:solvent A from 0 to 5.15 min, 98% solvent B from 5.15 to 5.20 min. Solvents: solvent A=5 mM ammonium hydroxide in water, solvent B=5 mM ammonium hydroxide in acetonitrile. UV detection array 210-400; mass detection 120-2850; column at 50° C.; flow rate 1.0 mL/min; pH 10.2.

LCMS Method 7:
Instrument: Agilent 1290 Infinity RRLC and Agilent 6120 Mass and Diode Array Detector; column BEH C18 1.7 μm 2.1×50 mm; 8 min run time, 2→95% solvent B:solvent A from 0 to 7 min, 98% solvent A from 7.01 to 8 min. Solvents: solvent A=5 mM ammonium acetate and 0.1% formic acid in water, solvent B=0.1% formic acid in acetonitrile. Column at ambient temperature; flow rate 0.45 mL/min.

LCMS Method 8:
Instrument: Shimadzu Nexera High Pressure UHPLC and LCMS-2020; column X-Bridge C18 3.5 μm 4.6×50 mm; 10 min run time, 5→95% solvent B:solvent A from 0 to 7.2 min, 95% solvent A from 7.21 to 10 min. Solvents: solvent A=5 mM ammonium bicarbonate in water, solvent B=100% acetonitrile. Column at ambient temperature; flow rate 1.0 mL/min.

LCMS Method 9:
Instrument: Waters AcQuity UPLC; column: AcQuity UPLC BEH $C_{18}$ 1.7 μm 2.1×30 mm; 1.15 min run time, 5% solvent B from 0 to 0.1 min, 5→95% solvent B:solvent A from 0.1 to 0.9 min, 95% solvent B for 0.25 min. Solvents:

solvent A=0.05% formic acid in water (v/v), solvent B=0.04% formic acid in methanol (v/v). Column at 55° C.; flow rate 1.0 mL/min.

LCMS Method 10:

Instrument: Shimadzu Nexera High Pressure UHPLC and LCMS-2020; column Synergi 2.5 μm MAX-RP 100A Mercury; 5 min run time, 5% solvent B:solvent A from 0 to 0.5 min, 5→95% solvent B:solvent A from 0.5 to 1.0 min, 95% solvent B:solvent A from 1.0 to 1.5 min, 95→5% solvent B:solvent A from 1.5 to 2.0 min, 5% solvent B:solvent A from 2.0 to 3.0 min. Solvents: solvent A=0.1% formic acid in water, solvent B=100% acetonitrile. Column at 40° C.; flow rate 2.0 mL/min.

LCMS Method 11:

Instrument: Agilent 6120 Quadrupole LCMS; column Kinetex C18 2.6 μm 100A 4.6×30 mm; 5 min run time, 5→90% solvent B:solvent A from 0 to 1.5 min, 90% solvent B:solvent A from 1.5 to 4.0 min, 90→5% solvent B:solvent A from 4.0 to 4.1 min. Solvents: solvent A=0.1% formic acid in water, solvent B=100% acetonitrile. Column at ambient temperature; flow rate 1.0 mL/min.

Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Synthesis of Intermediates

A) Type 1:

Synthesis of 2-(isobutylthio)phenol (int-A1)

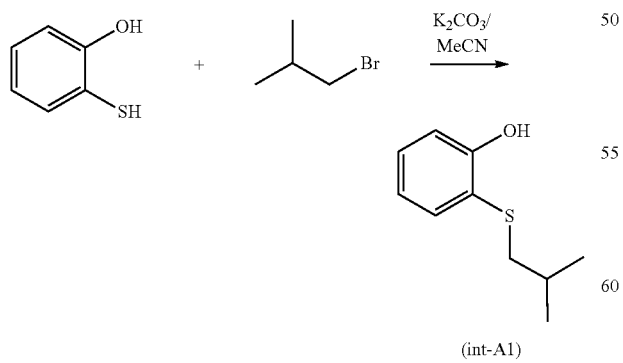

(int-A1)

2-mercaptophenol (8.00 mL, 79 mmol) was added to a stirred suspension of potassium carbonate (21.91 g, 159 mmol) in acetonitrile (200 mL) at room temperature. After 10 min, 1-bromo-2-methylpropane (9.48 mL, 87 mmol) was added. The mixture was then stirred at room temperature overnight. Additional portions of 0.3 eq of 1-bromo-2-methylpropane and 0.5 eq of potassium carbonate were added and the mixture was further stirred for one more day. After concentration in vacuo, the residue was dissolved in DCM and filtered through Celite® to remove solid potassium carbonate. The filtrate was purified by column chromatography (0-20% EtOAc/heptane) to provide 2-(isobutylthio)phenol (int-A1). $^1$H NMR (400 MHz, CD$_2$Cl$_2$) δ ppm 7.50 (dd, J=7.70, 1.59 Hz, 1H) 7.25-7.32 (m, 1H) 6.99 (dd, J=8.13, 1.16 Hz, 1H) 6.90 (td, J=7.52, 1.34 Hz, 1H) 6.76 (s, 1H) 2.64 (d, J=6.97 Hz, 2H) 1.72-1.88 (m, 1H) 1.04 (d, J=6.60 Hz, 6H).

Synthesis of 2-((2-methoxyethyl)thio)phenol (int-A2)

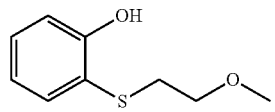

(int-A2)

2-((2-methoxyethyl)thio)phenol (int-A2) was obtained using a procedure similar to the procedure described for the synthesis of 2-(isobutylthio)phenol (int-A1), except bromo-2-methylpropane was replaced with 1-bromo-2-methoxyethane and potassium carbonate was replaced with cesium carbonate. LCMS Method 4: Rt.=0.80 mins; m/z 151.0 [M+H]+.

Synthesis of 2-((tetrahydrofuran-3-yl)thio)phenol (int-A3)

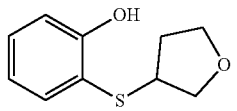

(int-A3)

2-((tetrahydrofuran-3-yl)thio)phenol (int-A3) was obtained using a procedure similar to the procedure described for the synthesis of 2-(isobutylthio)phenol (int-A1), except bromo-2-methylpropane was replaced with 3-bromotetrahydrofuran and potassium carbonate was replaced with cesium carbonate. LCMS Method 3: Rt.=0.74 mins; m/z 196.1 [M+H]+.

Synthesis of 2-(((tetrahydrofuran-3-yl)methyl)thio)phenol (int-A4)

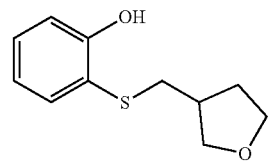

(int-A4)

2-(((tetrahydrofuran-3-yl)methyl)thio)phenol (int-A4) was obtained using a procedure similar to the procedure described for the synthesis of 2-(isobutylthio)phenol (int-A1), except bromo-2-methylpropane was replaced with 3-(bromomethyl)tetrahydrofuran. $^1$H(CDCl$_3$) 7.49-7.44 (1H, m), 7.30-7.25 (1H, m), 7.01 (1H, d), 6.91-6.85 (1H, m), 3.90-3.85 (2H, m), 3.77-3.69 (1H, m), 3.56-3.51 (1H, m), 2.76-2.73 (2H, d), 2.41-2.32 (1H, m), 2.14-2.03 (1H, m), 1.70-1.56 (1H, m).

Synthesis of 2-(((tetrahydro-2H-pyran-3-yl)methyl) thio)phenol (int-A5)

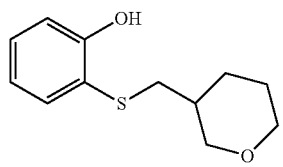

(int-A5)

2-(((tetrahydro-2H-pyran-3-yl)methyl)thio)phenol (int-A5) was obtained using a procedure similar to the procedure described for the synthesis of 2-(isobutylthio)phenol (int-A1), except bromo-2-methylpropane was replaced with 3-(bromomethyl)tetrahydro-2H-pyran. $^1$H(CDCl$_3$) 7.46-7.43 (1H, m), 7.26-7.21 (1H, m), 7.01-6.97 (1H, m), 6.89-6.87 (1H, m), 3.96-3.89 (1H, m), 3.84-3.80 (1H, m), 3.44-3.36 (1H, m), 3.22-3.15 (1H, m), 2.95-2.88 (1H, d), 2.61-2.58 (2H, m), 1.97-1.94 (1H, m), 1.73-1.69 (1H, m), 1.64-1.59 (1H, m), 1.34-1.25 (1H, m).

Synthesis of 2-((2,2,2-trifluoroethyl)thio)phenol (int-A6)

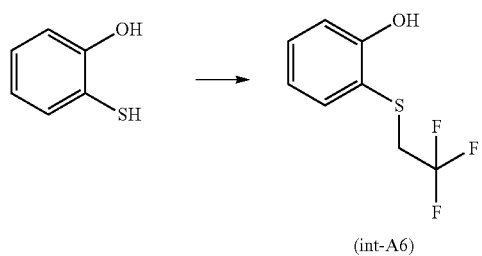 [SMILES: Oc1ccccc1S ; Oc1ccccc1SCC(F)(F)F]

(int-A6)

To a solution of 2-mercaptophenol (3 g, 23.80 mmol) in DMF (30 mL) was added potassium carbonate (8.22 g, 59.52 mmol), followed by 2,2,2-trifluoroethyl 4-methylbenzenesulfonate (6.05 g, 23.08 mmol). The reaction mixture was stirred at 60° C. for 3 hours, then 40° C. for 4 hours and finally 50° C. for 6 hours. The reaction mixture was diluted with water (240 mL) and the pH adjusted to pH 3 with dilute HCl at 20° C. The resulting mixture was extracted with toluene (100 mL). The toluene layer was stirred with 10% KOH solution (50 mL). The aqueous layer was separated and again pH adjusted to pH 2 with concentrated HCl. The resulting mixture was extracted with toluene (100 mL), and the combined organic layers were washed with cold water (3×25 mL), then dried over sodium sulfate, filtered, and concentrated to give 2-((2,2,2-trifluoroethyl)thio)phenol (int-A6). 1H NMR (400 MHz, (CD$_3$)$_2$SO) δ 10.12 (s, 1H), 7.34-7.36 (d, J=7.6 Hz, 1H), 7.11-7.15 (t, J=8.0 Hz, 1H), 6.86-6.88 (d, J=8.0 Hz, 1H), 6.76-6.80 (t, J=7.6 Hz, 1H), 3.78-3.86 (m, 2H).

Synthesis of 2-((3-hydroxycyclobutyl)thio)phenol (int-A7)

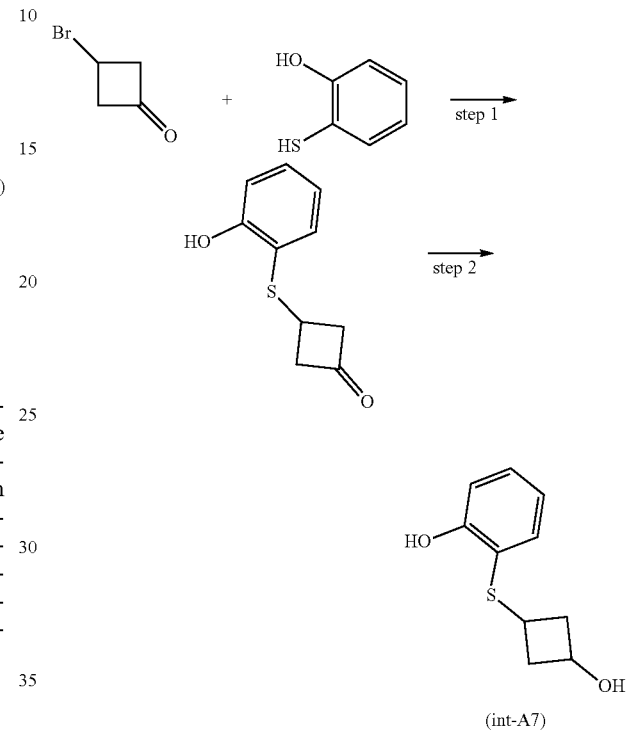

(int-A7)

Step 1: To a solution of 3-bromocyclobutanone (15 g, 61.4 mmol) and 2-mercaptophenol (8.03 mL, 80 mmol) in DMF (25 mL) cooled to 0° C. was added cesium carbonate (50.0 g, 154 mmol), and the reaction mixture stirred at room temperature for 6 hours. Water (250 mL) and ethyl acetate were then added, the layers separated, and the aqueous layer extracted with ethyl acetate (3×). The combined organic layers were dried over magnesium sulfate, filtered through a silica pad washing with ethyl acetate, and evaporated to dryness. The residue was purified by flash column chromatography, eluting with 0-50% EtOAc in heptanes, to provide 3-((2-hydroxyphenyl)thio)cyclobutanone.

Step 2: A solution of 3-((2-hydroxyphenyl)thio)cyclobutanone (2 g, 10.30 mmol) in MeOH (40 mL) was treated with sodium borohydride (0.779 g, 20.59 mmol) at 0° C. and allowed to warm to room temperature over 2 hours. 10% aqueous citric acid (5 mL) was added slowly, and after bubbling ceased the mixture was evaporated to dryness. The residue was extracted with ethyl acetate (3×) and then the combined organic layers were dried over magnesium sulfate, filtered and evaporated to dryness. The residue was purified by flash column chromatography, eluting with 0-50% EtOAc in heptanes, to provide 2-((3-hydroxycyclobutyl)thio)phenol (int-A7). 1H NMR (400 MHz, CD$_2$Cl$_2$) δ 7.52-7.43 (m, 1H), 7.39-7.30 (m, 1H), 7.07-6.88 (m, 2H), 6.74 (s, 1H), 4.06 (tt, J=7.7, 6.7 Hz, 1H), 3.05 (tt, J=9.6, 7.3 Hz, 1H), 2.73-2.61 (m, 2H), 1.93-1.79 (m, 2H).

2Synthesis of 2-((2-(pyrrolidin-1-yl)propyl)thio)phenol (int-A8)

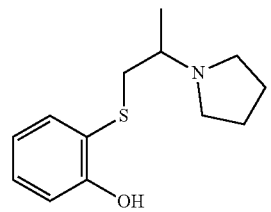

(int-A8)

2-((2-(pyrrolidin-1-yl)propyl)thio)phenol (int-A8) was obtained using a procedure similar to the procedure described for the synthesis of 2-(isobutylthio)phenol (int-A1), except bromo-2-methylpropane was replaced with 1-(1-chloropropan-2-yl)pyrrolidine was replaced with cesium carbonate. LCMS Method 3: Rt.=0.87 mins; m/z 237.9 [M+H]+.

Synthesis of 2-(((1,3-dioxolan-2-yl)methyl)thio)phenol (int-A9)

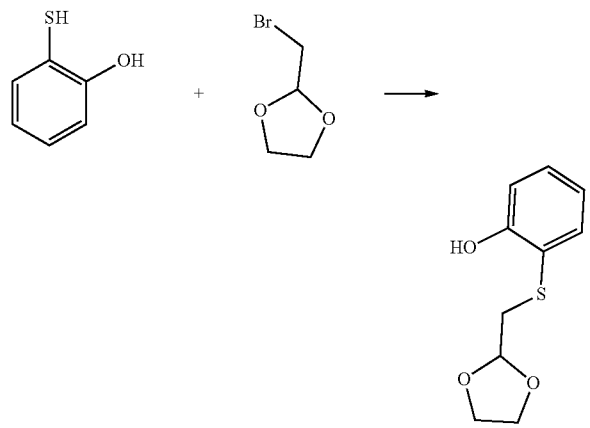

2-hydroxythiophenol (0.862 mL, 7.93 mmol) was dissolved up in DMF (10 mL) then potassium carbonate (2.410 g, 17.44 mmol) was added and stirred at rt for 30 mins, then 2-(bromomethyl)-1,3-dioxolane (0.903 mL, 8.72 mmol) was added and the mixture was heated to 90° C. overnight. The reaction mixture was then purified on an ISCO using eluents heptane: DCM (0-30%) and the product fractions were combined and concentrated under vacuum to give 2-(((1,3-dioxolan-2-yl)methyl)thio)phenol (int-A9). $^1$H NMR (400 MHz, CDCl$_3$) δ 7.54 (dd, J=7.7, 1.7 Hz, 1H), 7.40-7.32 (m, 1H), 7.32-7.23 (m, 1H), 6.99 (dd, J=8.2, 1.3 Hz, 1H), 6.86 (td, J=7.5, 1.4 Hz, 1H), 5.07 (t, J=4.0 Hz, 1H), 4.17-4.04 (m, 2H), 4.04-3.91 (m, 2H), 2.98 (d, J=4.0 Hz, 2H).

B) Type 2:

Synthesis of 2-hydroxy-N-isopropyl-N-methylbenzenesulfonamide (int-B1)

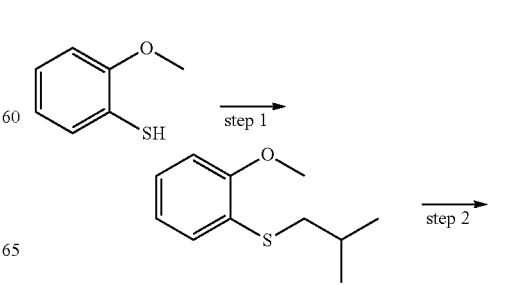

(int-B1)

Step 1: A solution of N-methylpropan-2-amine (0.655 mL, 6.29 mmol) and triethylamine (1.349 mL, 9.68 mmol) in dichloromethane (50 mL) at 0° C. was treated dropwise with a solution of 2-methoxybenzenesulfonyl chloride (1 g, 4.84 mmol) in DCM (5 mL) and the mixture was allowed to warm to room temperature over 3 hours. Water was added and the layers were separated. The organic layer was washed sequentially with 1 N HCl and brine, then dried over magnesium sulfate, filtered and evaporated to dryness to provide N-isopropyl-2-methoxy-N-methylbenzenesulfonamide as an oil.

Step 2: A solution of N-isopropyl-2-methoxy-N-methylbenzenesulfonamide (1.1 g, 4.52 mmol) in dry dichloromethane (30 mL) was treated at room temperature with boron tribromide (1.0M in DCM, 9.04 mL, 9.04 mmol) and stirred for 3 hours. Ice water was added dropwise until the vigorous reaction ceased, then additional water (30 mL) was added. The resulting mixture was stirred for 5 min, the layers separated, and the aqueous layer extracted with dichloromethane. The combined organic layers were dried over magnesium sulfate, filtered and evaporated to dryness to provide 2-hydroxy-N-isopropyl-N-methylbenzenesulfonamide (int-B1). LCMS Method 3: Rt.=0.71 min.; m/z 228.2 [M–H]–.

Synthesis of 2-(isobutylsulfonyl)phenol (int-B2)

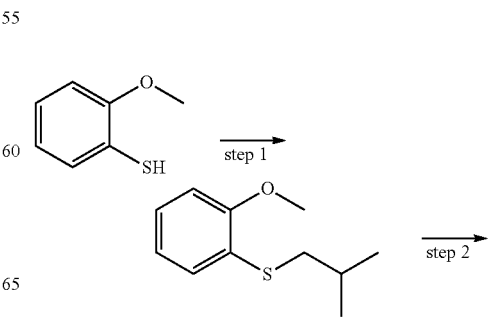

-continued

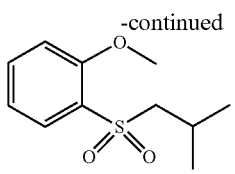

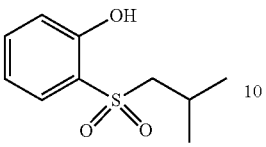

(int-B2)

Step 1: A solution of 2-methoxybenzenethiol (3 mL, 24.61 mmol) in DMF (30 mL) was cooled to 0° C. and then sodium hydride (60% in mineral oil, 1.083 g, 27.1 mmol) was added in portions and the suspension was then stirred at 0° C. for 30 min. After bubbling had ceased, 1-bromo-2-methylpropane (4.01 mL, 36.9 mmol) was added over 20 min. The resulting mixture was stirred at 0° C. for 1 h, then allowed to warm to room temperature and stirred overnight. Saturated aqueous ammonium chloride solution and EtOAc were added and the organic layer was washed three times with water, dried over sodium sulfate and concentrated to provide isobutyl(2-methoxyphenyl)sulfane. The crude material obtained was used in the next step without purification. 1H NMR (400 MHz, CDCl$_3$) d ppm 1.05 (d, J=6.57 Hz, 6H) 1.88 (dt, J=13.39, 6.69 Hz, 1H) 2.77 (d, J=6.82 Hz, 2H) 3.89 (s, 3H) 6.84 (d, J=8.08 Hz, 1H) 6.92 (td, J=7.58, 1.14 Hz, 1H) 7.10-7.20 (m, 1H) 7.20-7.29 (m, 1H).

Step 2: To a solution of isobutyl(2-methoxyphenyl)sulfane (4.76 g, 24.25 mmol) in dichloromethane (100 mL) was added mCPBA (13.59 g, 60.6 mmol) and the resulting suspension was stirred for 2 hours. The solvent was removed under vacuum. 2 N aqueous NaOH solution and EtOAc were added. The layers were separated, and the organic layer was washed with 2 N NaOH solution, dried over sodium sulfate, and concentrated. The residue was purified by flash column chromatography (0-50% EtOAc in heptanes) to provide 1-(isobutylsulfonyl)-2-methoxybenzene. 1H NMR (400 MHz, CDCl$_3$) d ppm 1.02 (dd, J=6.69, 1.52 Hz, 6H) 2.17-2.28 (m, 1H) 3.25 (dd, J=6.51, 1.45 Hz, 2H) 3.97 (d, J=1.52 Hz, 3H) 7.03 (d, J=8.34 Hz, 1H) 7.09 (t, J=7.64 Hz, 1H) 7.51-7.62 (m, 1H) 7.91-8.01 (m, 1H).

Step 3: To a solution of 1-(isobutylsulfonyl)-2-methoxybenzene (4.50 g, 19.71 mmol) in dichloromethane (50 mL) was added boron tribromide (1.0 M in DCM, 23.65 mL, 23.65 mmol) over 20 min and the resulting solution was stirred at room temperature for 2 hours. The reaction mixture was concentrated in vacuo, ice was slowly added, and the aqueous solution extracted twice with EtOAc. The combined organic layers were dried over sodium sulfate and concentrated. The residue was purified by flash column chromatography (0-50% EtOAc in heptanes) to provide 2-(isobutylsulfonyl)phenol (int-B2). 1H NMR (400 MHz, CDCl$_3$) δ ppm 1.07 (d, J=6.69 Hz, 7H) 2.28 (dt, J=13.26, 6.63 Hz, 1H) 3.04 (d, J=6.44 Hz, 2H) 6.95-7.10 (m, 2H) 7.52 (ddd, J=8.53, 7.20, 1.71 Hz, 1H) 7.64 (dd, J=8.15, 1.71 Hz, 1H) 8.97 (s, 1H).

Synthesis of 2-((2-hydroxypropyl)sulfonyl)phenol (int-B3)

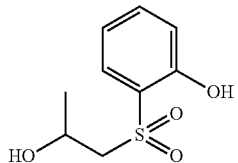

(int-B3)

2-((2-hydroxypropyl)sulfonyl)phenol (int-B3) was obtained using a procedure similar to the procedure described for the synthesis of 2-(isobutylsulfonyl)phenol (int-B2), except in 1-bromo-2-methylpropane was replaced with 1-bromopropan-2-ol. LCMS Method 11: Rt.=1.67 mins; m/z 219.1 [M+H]+.

Synthesis of 2-(((tetrahydro-2H-pyran-2-yl)methyl)sulfonyl)phenol (int-B4)

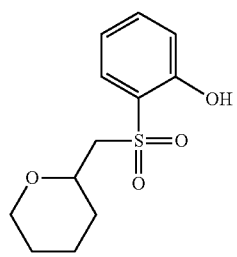

(int-B4)

2-(((tetrahydro-2H-pyran-2-yl)methyl)sulfonyl)phenol (int-B4) was obtained using a procedure similar to the procedure described for the synthesis of 2-(isobutylsulfonyl)phenol (int-B2), except in 1-bromo-2-methylpropane was replaced with 2-(bromomethyl)tetrahydro-2H-pyran. LCMS Method 11: Rt.=1.89 mins; 257.1 m/z [M+H]+.

Synthesis of 2-((2-methoxyethyl)sulfonyl)phenol (int-B5)

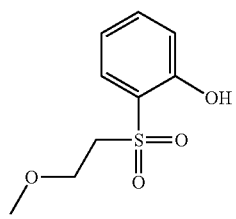

(int-B5)

2-((2-methoxyethyl)sulfonyl)phenol (int-B5) was obtained using a procedure similar to the procedure described for the synthesis of 2-(isobutylsulfonyl)phenol (int-B2), except in 1-bromo-2-methylpropane was replaced with 1-bromo-2-methoxyethane. LCMS Method 11: Rt.=1.66 mins; m/z 217.1 [M+H]+.

Synthesis of 2-(((tetrahydrofuran-2-yl)methyl)sulfonyl)phenol (int-B6)

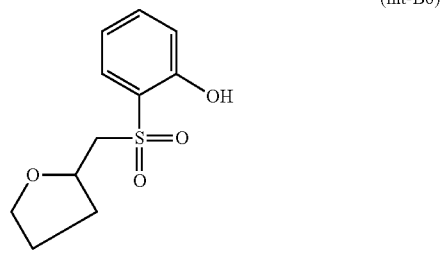

(int-B6)

2-(((tetrahydrofuran-2-yl)methyl)sulfonyl)phenol (int-B6) was obtained using a procedure similar to the procedure described for the synthesis of 2-(isobutylsulfonyl)phenol (int-B2), except in 1-bromo-2-methylpropane was replaced with 2-(bromomethyl)tetrahydrofuran. LCMS Method 2: Rt.=0.69 mins; m/z 243.4 [M+H]+.

C) Type 3:

Synthesis of 5-(chloromethyl)-3-(4-(2-(isobutylthio)phenoxy)-3-(trifluoromethyl)phenyl)-1,2,4-oxadiazole (int-C1)

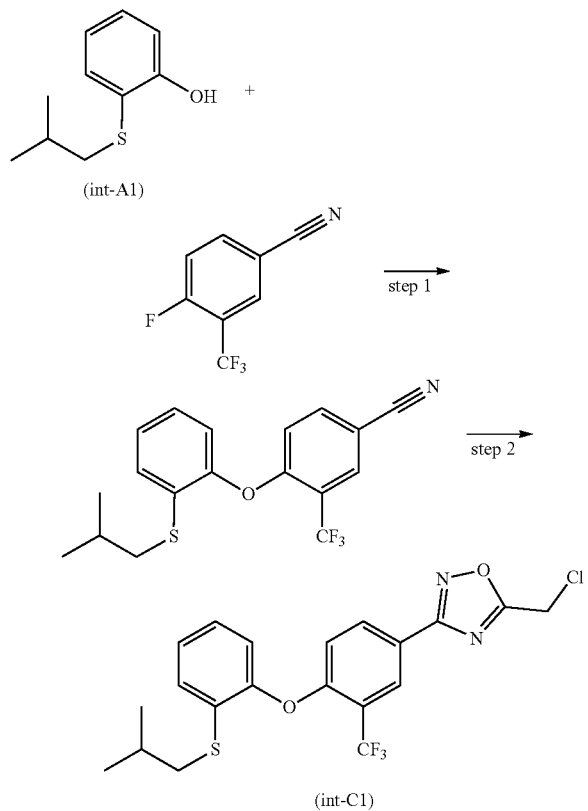

Step 1: To a solution of 2-(isobutylthio)phenol (int-A1) (10.7 g, 38.2 mmol) in DMF (100 mL) was added cesium carbonate (24.86 g, 76 mmol), followed by 4-fluoro-3-(trifluoromethyl)benzonitrile (7.22 g, 38.2 mmol), and the resulting mixture was stirred overnight. Water (300 mL) was then added, and the mixture was extracted twice with ethyl acetate. The combined organic layers were washed with 0.5M LiCl (2×400 mL), then dried over magnesium sulfate, filtered and evaporated to dryness to give 4-(2-(isobutylthio)phenoxy)-3-(trifluoromethyl)benzonitrile which was used directly in the next step.

Step 2: A solution of 4-(2-(isobutylthio)phenoxy)-3-(trifluoromethyl)benzonitrile (12.9 g, 36.7 mmol) in ethanol (130 mL) was treated with hydroxylamine (9.94 mL, 367 mmol), warmed to 45° C. for 2 hours, and then allowed to cool to room temperature overnight. The mixture was evaporated to dryness under high vacuum and the residue was then dissolved in toluene (130 mL) and treated with chloroacetyl chloride (4.41 mL, 55.1 mmol). The reaction mixture was stirred at room temperature, then heated to 110° C. for 24 hours. Additional chloroacetyl chloride (4.41 mL, 55.1 mmol) was added and the mixture was further refluxed for 3 hours. The mixture was then allowed to cool to room temperature and evaporated to dryness. The residue was suspended in ethyl acetate (200 mL), filtered, and the filtrate evaporated to dryness. The residue was purified by flash column chromatography, eluting with 0-20% ethyl acetate in heptanes, to provide 5-(chloromethyl)-3-(4-(2-(isobutylthio)phenoxy)-3-(trifluoromethyl)phenyl)-1,2,4-oxadiazole (int-C1). ¹H NMR (400 MHz, (CD$_3$)$_2$SO) δ 8.29 (d, J=2.1 Hz, 1H), 8.21 (dd, J=8.8, 2.2 Hz, 1H), 7.56 (dd, J=6.9, 2.5 Hz, 1H), 7.34 (ddt, J=10.2, 7.5, 3.8 Hz, 2H), 7.23-7.15 (m, 1H), 6.88 (d, J=8.8 Hz, 1H), 5.20 (s, 2H), 2.83 (d, J=6.8 Hz, 2H), 1.74 (dt, J=13.3, 6.7 Hz, 1H), 0.96-0.82 (m, 6H).

Synthesis of 5-(chloromethyl)-3-(4-(2-(isobutylsulfonyl)phenoxy)-3-(trifluoromethyl)phenyl)-1,2,4-oxadiazole (int-C2)

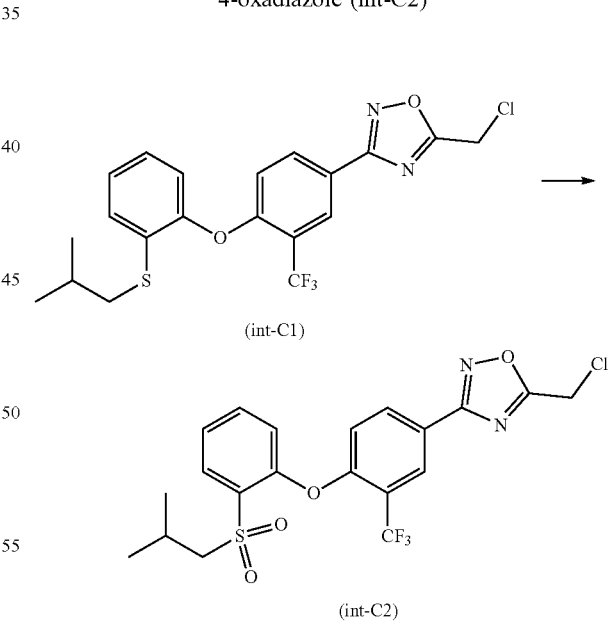

A solution of 5-(chloromethyl)-3-(4-(2-(isobutylthio)phenoxy)-3-(trifluoromethyl)phenyl)-1,2,4-oxadiazole (int-C1) (12.2 g, 27.5 mmol) in dichloromethane (150 mL) was treated at room temperature with mCPBA (18.52 g, 83 mmol) and the reaction mixture was stirred for 2 hours. The reaction mixture was then treated with saturated aqueous sodium thiosulfate and stirred for 1 hour. The layers were separated, and the organic layer was washed with saturated aqueous sodium bicarbonate solution, then dried over magnesium sulfate, filtered, and evaporated to dryness to provide 5-(chloromethyl)-3-(4-(2-(isobutylsulfonyl)phenoxy)-3-(trifluoromethyl)phenyl)-1,2,4-oxadiazole (int-C2). $^1$H NMR (400 MHz, CDCl$_3$) δ 8.42 (d, J=2.2 Hz, 1H), 8.10 (dd, J=8.7, 2.2 Hz, 1H), 7.47-7.40 (m, 1H), 7.27-7.18 (m, 2H), 7.06-6.98 (m, 1H), 6.76 (d, J=8.7 Hz, 1H), 4.75 (s, 2H), 2.78 (d, J=6.9 Hz, 2H), 1.88-1.74 (m, 1H), 0.98 (d, J=6.6 Hz, 6H)

Synthesis of 3-(4-(2-(tert-butyl)phenoxy)-3-(trifluoromethyl)phenyl)-5-(chloromethyl)-1,2,4-oxadiazole (int-C$_3$)

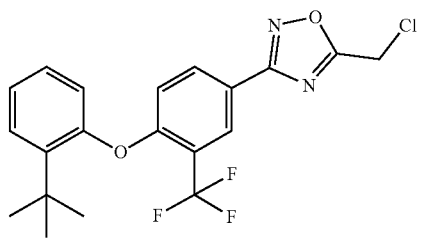

(int-C3)

3-(4-(2-(tert-butyl)phenoxy)-3-(trifluoromethyl)phenyl)-5-(chloromethyl)-1,2,4-oxadiazole (int-C$_3$) was obtained using a procedure similar to the procedure described for the synthesis of 5-(chloromethyl)-3-(4-(2-(isobutylthio)phenoxy)-3-(trifluoromethyl)phenyl)-1,2,4-oxadiazole (int-C1), except 2-(isobutylthio)phenol (int-A1) was replaced with 2-(tert-butyl)phenol. $^1$H NMR (400 MHz, CDCl$_3$) δ 8.44 (s, 1H), 8.13-8.15 (d, J=8.8 Hz, 1H), 7.47-7.49 (d, J=7.2 Hz, 1H), 7.35 (m, 1H), 7.18-7.27 (m, 1H), 6.91-6.93 (d, J=8.4 Hz, 1H), 6.86-6.88 (d, J=7.6 Hz, 1H), 4.77 (s, 2H), 1.41 (s, 9H).

Synthesis of 2-(4-(5-(chloromethyl)-1,2,4-oxadiazol-3-yl)-2-(trifluoromethyl)phenoxy)-N-isopropyl-N-methylbenzenesulfonamide (int-C4)

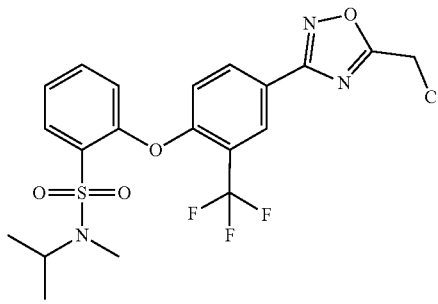

(int-C4)

2-(4-(5-(chloromethyl)-1,2,4-oxadiazol-3-yl)-2-(trifluoromethyl)phenoxy)-N-isopropyl-N-methylbenzenesulfonamide (int-C4) was obtained using a procedure similar to the procedure described in steps 1-2 for the synthesis of 5-(chloromethyl)-3-(4-(2-(isobutylthio)phenoxy)-3-(trifluoromethyl)phenyl)-1,2,4-oxadiazole (int-C1), except 2-(isobutylthio)phenol (int-A1) was replaced with 2-hydroxy-N-isopropyl-N-methylbenzenesulfonamide (int-B1). LCMS Method 3: Rt.=1.35 mins; m/z 490.2 [M+H]+.

Synthesis of 5-(chloromethyl)-3-(3-(trifluoromethyl)-4-(2-(trifluoromethyl)phenoxy)phenyl)-1,2,4-oxadiazole (int-C5)

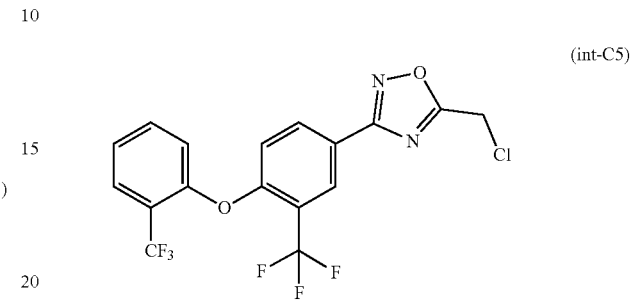

(int-C5)

5-(chloromethyl)-3-(3-(trifluoromethyl)-4-(2-(trifluoromethyl)phenoxy)phenyl)-1,2,4-oxadiazole (int-C5) was obtained using a procedure similar to the procedure described in steps 1-2 for the synthesis of 5-(chloromethyl)-3-(4-(2-(isobutylthio)phenoxy)-3-(trifluoromethyl)phenyl)-1,2,4-oxadiazole (int-C1), except 2-(isobutylthio)phenol (int-A1) was replaced with 2-(trifluoromethyl)phenol. LCMS Method 3: Rt.=1.17 mins; m/z 423.1 [M+H]+.

Synthesis of 5-(chloromethyl)-3-(4-(3,3,3-trifluoro-2-methyl-2-(trifluoromethyl)propoxy)-3-(trifluoromethyl)phenyl)-1,2,4-oxadiazole (int-C6)

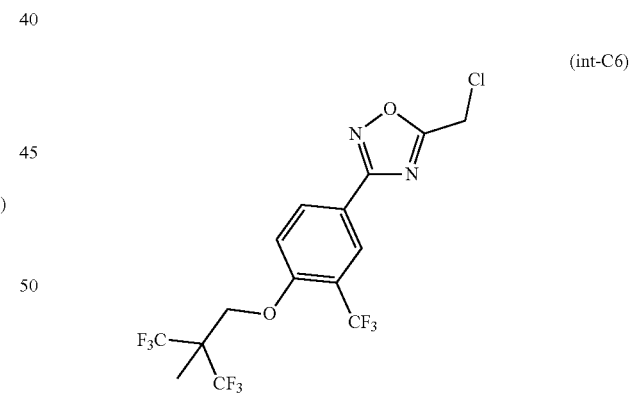

(int-C6)

5-(chloromethyl)-3-(4-(3,3,3-trifluoro-2-methyl-2-(trifluoromethyl)propoxy)-3-(trifluoromethyl)phenyl)-1,2,4-oxadiazole (int-C6) was obtained using a procedure similar to the procedure for the synthesis of 5-(chloromethyl)-3-(4-(2-(isobutylthio)phenoxy)-3-(trifluoromethyl)phenyl)-1,2,4-oxadiazole (int-C1), except 2-(isobutylthio)phenol (int-A1) was replaced with 3,3,3-trifluoro-2-methyl-2-(trifluoromethyl)propan-1-ol. LCMS Method 2: Rt.=1.28 mins; m/z 457.2 [M+H]+

Synthesis of 3-(3-chloro-4-(2-(isobutylthio)phenoxy)phenyl)-5-(chloromethyl)-1,2,4-oxadiazole (int-C7)

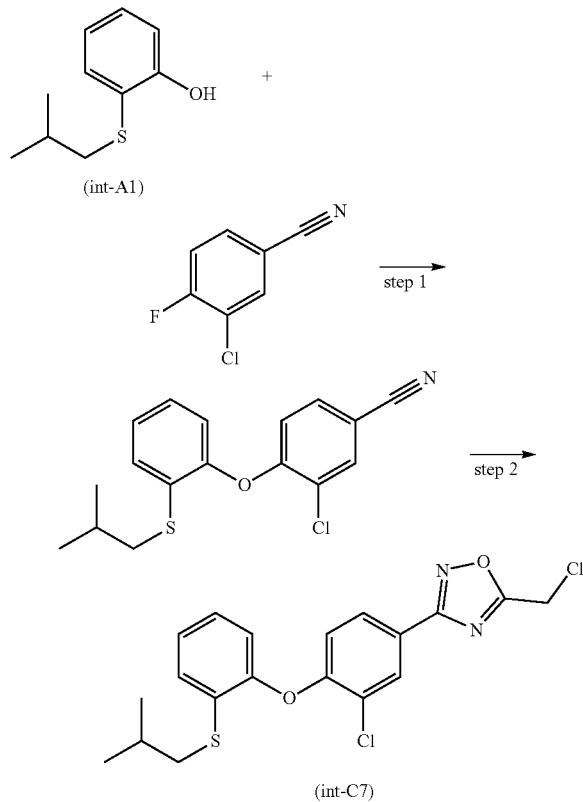

(int-C7)

Step 1: Cesium carbonate (402 mg, 1.23 mmol) was added to a solution of 2-(isobutylthio)phenol (int-A1) (75 mg, 0.411 mmol) and 3-chloro-4-fluorobenzonitrile (64.0 mg, 0.411 mmol) in DMF (4 mL). The resulting suspension was heated to 160° C. under microwave irradiation for 30 min. The reaction was filtered and azeotroped with toluene (3×) to provide 3-chloro-4-(2-(isobutylthio)phenoxy)benzonitrile. The material was used in next step without further purification. LCMS method 5: Rt.=3.29 min.; m/z 318.2 [M+H]+; 1H NMR (400 MHz, CDCl$_3$) δ 7.76 (d, J=2.0 Hz, 1H), 7.45-7.39 (m, 2H), 7.26-7.21 (m, 2H), 7.04-6.99 (m, 1H), 6.65 (d, J=8.6 Hz, 1H), 2.77 (d, J=6.9 Hz, 2H), 1.89-1.75 (m, 1H), 0.98 (d, J=6.6 Hz, 6H).

Step 2: Hydroxylamine (0.121 mL, 4.09 mmol) was added to a solution of 3-chloro-4-(2-(isobutylthio)phenoxy)benzonitrile (130 mg, 0.409 mmol) in EtOH (1.5 mL) and the reaction was heated to 45° C. After 2 hours the reaction was concentrated under reduced pressure. The material was taken up in toluene (1.5 mL). 2-chloroacetyl chloride (0.036 mL, 0.452 mmol) was added and the reaction was heated to 100° C. overnight. The reaction was concentrated under reduced pressure and the crude material was purified via flash column chromatography eluting 0-40% EtOAc in heptane. Product fractions were collected, combined, and concentrated to give 3-(3-chloro-4-(2-(isobutylthio)phenoxy)phenyl)-5-(chloromethyl)-1,2,4-oxadiazole (int-C7). LCMS method 5: Rt.=3.61 min.; m/z 409.1 [M+H]; 1H NMR (400 MHz, CDCl$_3$) δ 8.24 (d, J=2.0 Hz, 1H), 7.89 (dd, J=8.6, 2.1 Hz, 1H), 7.47-7.43 (m, 1H), 7.26-7.18 (m, 2H), 7.00-6.96 (m, 1H), 6.82 (d, J=8.6 Hz, 1H), 4.76 (s, 2H), 2.83 (d, J=6.9 Hz, 2H), 1.92-1.78 (m, 1H), 1.02 (d, J=6.6 Hz, 6H).

Synthesis of 5-(chloromethyl)-3-(4-fluoro-3-(trifluoromethyl)phenyl)-1,2,4-oxadiazole (int-C8)

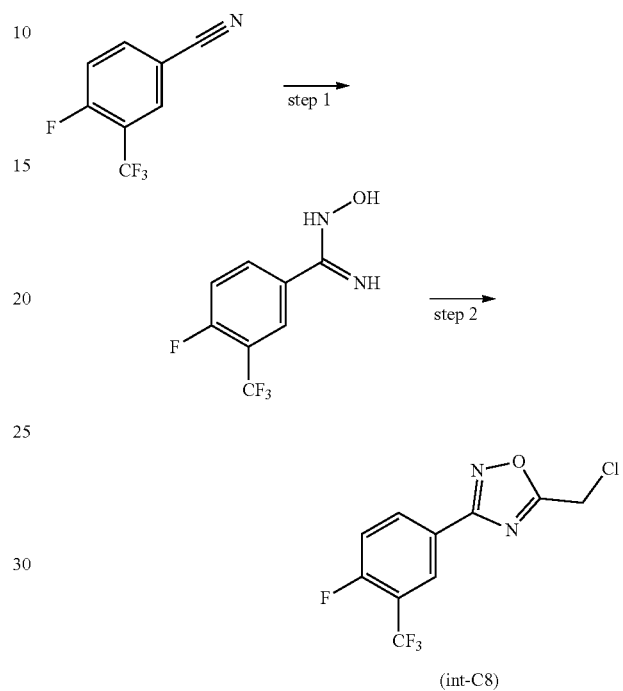

(int-C8)

Step 1: In a 500 mL 3 neck flask, to a solution of 4-fluoro-3-(trifluoromethyl)benzonitrile (15.0 g, 79.32 mmol) in methanol (150 mL) was added a hydroxylamine solution 50 wt. % in water (52.4 mL, 793.2 mmol) dropwise at room temperature. The reaction mixture was stirred at room temperature for 16 hours, then concentrated in vacuo and the residue diluted with water (100 mL). The mixture was extracted with ethyl acetate (3×150 mL) and the combined organic layers dried over sodium sulfate, filtered, and concentrated to provide 4-fluoro-N-hydroxy-3-(trifluoromethyl)benzimidamide. LCMS Method 3: Rt.=0.97 min.; m/z 223.1 [M+H]+; 1H NMR (400 MHz, (CD$_3$)$_2$SO) δ 9.88 (s, 1H), 8.02-8.03 (m, 2H), 7.51-7.56 (m, 1H), 6.06 (s, 2H).

Step 2: In a 500 mL 3 neck flask, to a solution of 4-fluoro-N-hydroxy-3-(trifluoromethyl)benzimidamide (16.0 g, 72.0 mmol) in toluene (160 mL) was added chloroacetyl chloride (17.2 mL, 216.2 mmol) dropwise at 0° C. After completion of addition, the turbid yellow reaction mixture was heated to reflux for 6 hours. The clear reaction solution was then allowed to cool to room temperature and quenched with ice-cold water. The organic layer was washed with saturated sodium bicarbonate solution (100 mL) and brine (100 mL); the dried over sodium sulfate, filtered, and concentrated. The crude product was purified by column chromatography using 3-6% ethyl acetate-hexane to obtain 5-(chloromethyl)-3-(4-fluoro-3-(trifluoromethyl)phenyl)-1,2,4-oxadiazole (int-C8). 1H NMR (400 MHz, (CD$_3$)$_2$SO) δ 8.38-8.39 (m, 1H), 8.25-8.27 (m, 1H), 7.73-7.78 (m, 1H), 5.24 (s, 2H).

Synthesis of 5-(chloromethyl)-3-(4-(2-(((tetrahydrofuran-2-yl)methyl)sulfonyl)phenoxy)-3-(trifluoromethyl)phenyl)-1,2,4-oxadiazole (int-C9)

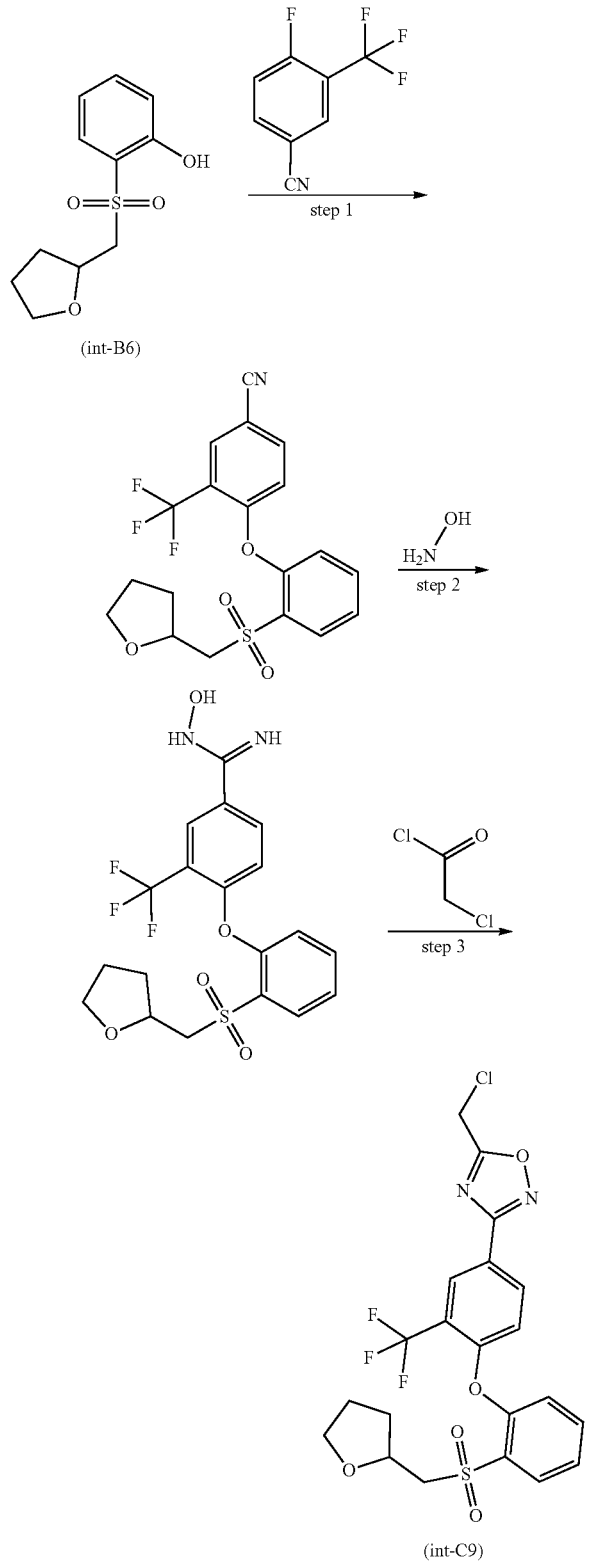

Step 1: 2-(((tetrahydrofuran-2-yl)methyl)sulfonyl)phenol (int-B6) (2.56 g, 10.58 mmol) was dissolved in DMF (21.15 mL), cesium carbonate (6.89 g, 21.15 mmol) was then added and the reaction mixture was cooled to 0° C. 4-fluoro-3-(trifluoromethyl)benzonitrile (2 g, 10.58 mmol) was added and the reaction mixture was allowed to warm to room temperature and then stirred for 72 hours. The reaction mixture was then added to 100 mL water, and extracted with too EtOAc (3×100 mL). The organics were combined and dried over $MgSC_4$ and then purified by flash column chromatography with eluents heptane: EtOAc 0-100%. The product fractions where combined and concentrated under vacuum to give 4-(2-(((tetrahydrofuran-2-yl)methyl)sulfonyl)phenoxy)-3-(trifluoromethyl)benzonitrile. LCMS Method 3: Rt.=1.05 mins; m/z 429.4 [M+H]+.

Step 2: Hydroxylamine (3.18 mL, 58.3 mmol) was added to 4-(2-(((tetrahydrofuran-2-yl)methyl)sulfonyl)phenoxy)-3-(trifluoromethyl)benzonitrile (2.4 g, 5.83 mmol) in ethanol (29.2 mL) then and the reaction mixture was stirred at 45° C. for 2 hrs. The reaction mixture was then concentrated under vacuum to provide N'-hydroxy-4-(2-(((tetrahydrofuran-2-yl)methyl)sulfonyl)phenoxy)-3-(trifluoromethyl)benzimidamide which was taken forward without purification. LCMS Method 3: Rt.=0.85 mins; m/z 445.5 [M+H]+.

Step 3: Chloroacetyl chloride (0.703 mL, 8.78 mmol) was added to a solution of N'-hydroxy-4-(2-(((tetrahydrofuran-2-yl)methyl)sulfonyl)phenoxy)-3-(trifluoromethyl)benzimidamide (2.6 g, 5.85 mmol) in toluene (11.70 mL) and the reaction mixture was then stirred at 110° C. overnight. The reaction mixture was then concentrated under vacuum. And purified on an ISCO using eluents heptane: EtOAc 0-100%. The fractions were combined and concentrated under vacuum to give 5-(chloromethyl)-3-(4-(2-(((tetrahydrofuran-2-yl)methyl)sulfonyl)phenoxy)-3-(trifluoromethyl)phenyl)-1,2,4-oxadiazole (int-C9). LCMS Method 3: Rt.=1.21 mins; m/z 520.5 [M+H]+.

D) Type 4:

Synthesis of 2-(4-hydroxytetrahydro-2H-pyran-4-yl)ethyl 4-methylbenzenesulfonate (int-D1)

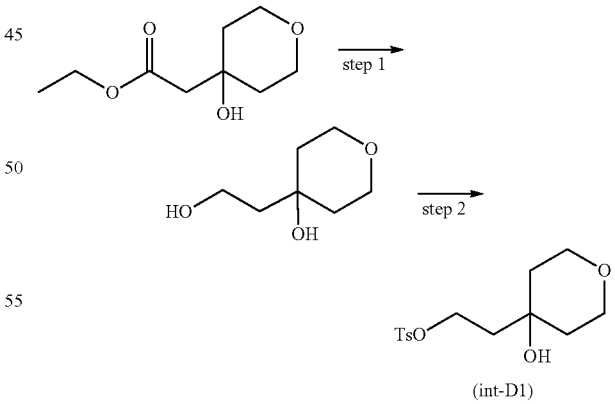

Step 1: Lithium aluminum hydride (1.250 g, 32.9 mmol) was suspended in dry tetrahydrofuran (100 mL) and cooled to 0° C. A solution of ethyl 2-(4-hydroxytetrahydro-2H-pyran-4-yl)acetate (6.2 g, 32.9 mmol) in tetrahydrofuran (100 mL) was added and the mixture was allowed to warm to room temperature overnight. 50% aqueous NaOH (12 mL) was added and the mixture was sonicated then filtered.

The organic layer was collected and the solids washed with DCM. A further 20 mL of 50% aqueous NaOH was added to the solid residue and the resulting aqueous layer was extracted with DCM (twice). The combined organic layers were dried over magnesium sulfate, filtered and evaporated to dryness to provide 4-(2-hydroxyethyl)tetrahydro-2H-pyran-4-ol.

Step 2: A solution of 4-(2-hydroxyethyl)tetrahydro-2H-pyran-4-ol (1.7 g, 11.63 mmol) in pyridine (15 mL) was treated with p-toluenesulfonyl chloride (2.439 g, 12.79 mmol) and the tot reaction mixture stirred at room temperature overnight. The mixture was then evaporated to dryness, and the residue purified by flash column chromatography, eluting with 0-100% EtOAc in heptanes, to provide 2-(4-hydroxytetrahydro-2H-pyran-4-yl)ethyl 4-methylbenzenesulfonate (int-D1). $^1$H NMR (400 MHz, CDCl$_3$) δ 7.81-7.74 (m, 2H), 7.39-7.31 (m, 2H), 4.24 (t, J=6.6 Hz, 2H), 3.77-3.62 (m, 4H), 2.44 (s, 3H), 1.85 (t, J=6.6 Hz, 2H), 1.64 (ddd, J=13.6, 10.5, 5.5 Hz, 2H), 1.52-1.42 (m, 2H).

E) Type 5:

Synthesis of 5,5-dimethyl-1-(2-morpholinoethyl) imidazolidine-2,4-dione (int-E1)

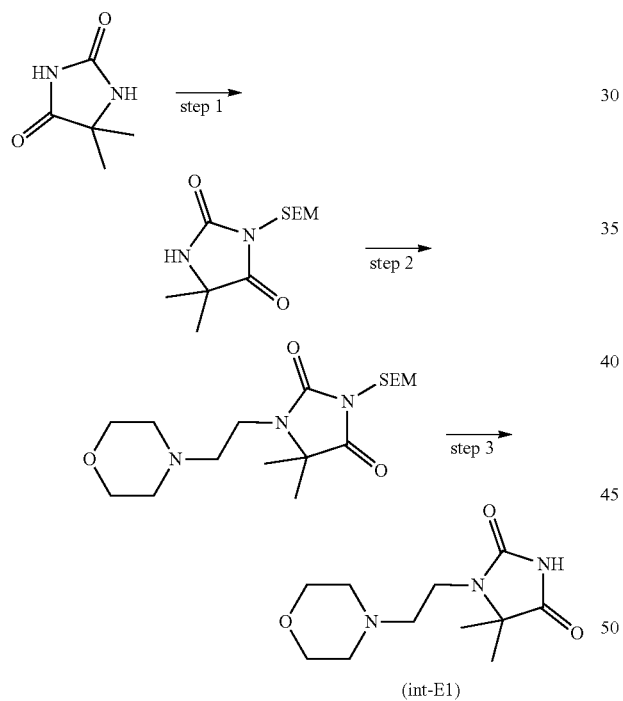

(int-E1)

Step 1: 2-(Trimethylsilyl)ethoxymethyl chloride (1.83 mL, 10.30 mmol) was added to a solution of dimethyl hydantoin (1.1 g, 8.58 mmol) and N,N-Diisopropylethylamine (4.50 mL, 25.8 mmol) in DCM (8 mL) at 0° C. portion wise over 1 h. The reaction was allowed to warm to room temperature and stirred overnight. The reaction was quenched with saturated aqueous ammonium chloride solution (20 mL) and the layers were separated. The aqueous layer was extracted with dichloromethane (2×20 mL) and the combined organic layers were washed with 1M HCl (2×10 mL) and brine (10 mL), dried over sodium sulfate, and concentrated under reduced pressure. The crude material was purified via flash column chromatography, eluting with 0-100% EtOAc in heptane to provide 5,5-dimethyl-3-((2-(trimethylsilyl)ethoxy)methyl)imidazolidine-2,4-dione. 1H NMR (400 MHz, CDCl$_3$) δ 4.93 (s, 2H), 3.67-3.58 (m, 2H), 1.46 (s, 6H), 0.99-0.90 (m, 2H), 0.00 (s, 9H).

Step 2: Cesium carbonate (3.58 g, 10.97 mmol) was added to a solution of 5,5-dimethyl-3-((2-(trimethylsilyl)ethoxy)methyl)imidazolidine-2,4-dione (0.95 g, 3.66 mmol) and 4-(2-bromoethyl)morpholine (1.21 g, 4.39 mmol) in DMF (10 mL) and the reaction stirred at room temperature overnight. The reaction was poured into water (30 mL) and extracted with ethyl acetate (3×50 mL). The combined organic layers were washed sequentially with water and brine, then dried over sodium sulfate and concentrated under reduced pressure. The material was azeotroped with heptane several times and placed under high vacuum overnight to provide 5,5-dimethyl-1-(2-morpholinoethyl)-3-((2-(trimethylsilyl)ethoxy)methyl)imidazolidine-2,4-dione. 1H NMR (400 MHz, CDCl$_3$) δ 4.92 (s, 2H), 3.71 (s, 4H), 3.66-3.57 (m, 2H), 3.43 (s, 2H), 2.67-2.44 (m, 6H), 1.43 (s, 6H), 0.99-0.90 (m, 2H), 0.00 (s, 9H).

Step 3: Trifluoroacetic acid (5.18 mL, 67.3 mmol) was added to a solution of 5,5-dimethyl-1-(2-morpholinoethyl)-3-((2-(trimethylsilyl)ethoxy)methyl)imidazolidine-2,4-dione (1.25 g, 3.36 mmol) in DCM (10 mL) and the reaction stirred at room temperature. After 4 hours, the reaction was concentrated under reduced pressure and azeotroped with toluene (3×). The crude residue was left to dry under high vacuum for 48 hours. The residue was then taken up in dichloromethane (50 mL) and washed with saturated sodium carbonate solution. The layers were separated and the aqueous layer was extracted with dichloromethane (2×50 mL). The combined organic layers were dried over sodium sulfate, filtered, and concentrated under reduced pressure. The material was dissolved in acetonitrile (10 mL), N1,N2-dimethylethane-1,2-diamine (0.362 mL, 3.36 mmol) was added, and the reaction mixture stirred at room temperature. After 30 mins, a solid precipitated out of solution. The reaction was filtered and the solid was collected to provide 5,5-dimethyl-1-(2-morpholinoethyl)imidazolidine-2,4-dione (int-E1). 1H NMR (400 MHz, (CD$_3$)$_2$SO) δ 10.76 (s, 1H), 3.58-3.53 (m, 4H), 3.30-3.25 (m, 2H), 2.47-2.38 (m, 6H), 1.29 (s, 6H).

Synthesis of 5-(hydroxymethyl)-5-methylimidazolidine-2,4-dione (int-E2)

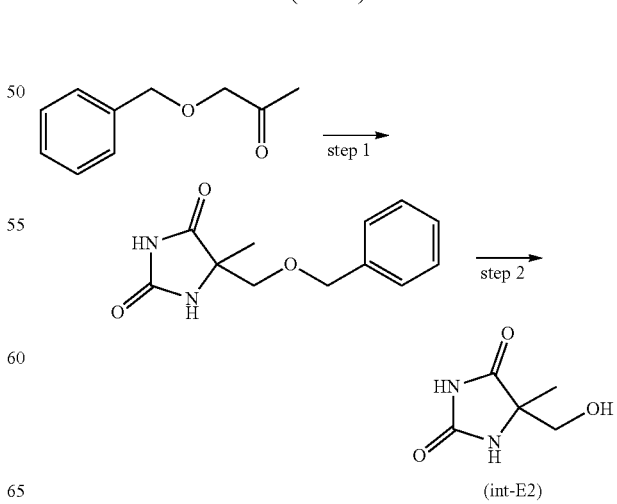

(int-E2)

Step 1: Ammonium carbonate (21.91 g, 228 mmol) was dissolved in ethanol (45.0 mL) and water (45.0 mL) and then 1-(benzyloxy)propan-2-one (9 mL, 57.0 mmol) was added. Potassium cyanide (7.42 g, 114 mmol) was then added and the reaction mixture was heated to 60° C. for 2 hr. The reaction mixture was then concentrated under vacuum to remove the ethanol and then filtered. The filtrate was then slurred with MeOH (100 mL) at 40° C. and filtered. The filtrate was then concentrated under vacuum, dissolved in DCM and then purified by an ISCO using DCM: MeOH (0-30%) with 0.1% TEA as a modifier. The product fractions where then combined and concentrated under vacuum to give 5-((benzyloxy)methyl)-5-methylimidazolidine-2,4-dione. LCMS Method 3: Rt.=0.57 mins; m/z 235.4 [M+H]+.

Step 2: 5-((benzyloxy)methyl)-5-methylimidazolidine-2,4-dione (6.5 g, 27.7 mmol) in ethanol (40 mL) was degassed N2 then 10% palladium (2.95 g, 2.77 mmol) on carbon was added, and the mixture was hydrogenated using a Parr hydrogenator (H2: 50 psi) for 72 hours. Partial conversion obtained. Addition palladium was added ((2.95 g, 2.77 mmol)) and the reaction was repeated using a Parr hydrogenator (H2: 50 psi) for 4 days. The reaction mixture was then filtered and washed with methanol to give 5-(hydroxymethyl)-5-methylimidazolidine-2,4-dione (int-E2). LCMS Method 3: Rt.=0.53 mins; m/z 252.3 [M+H]+.

Synthesis of 2-((4-methyl-2,5-dioxoimidazolidin-4-yl)methyl)isoindoline-1,3-dione (int-E3)

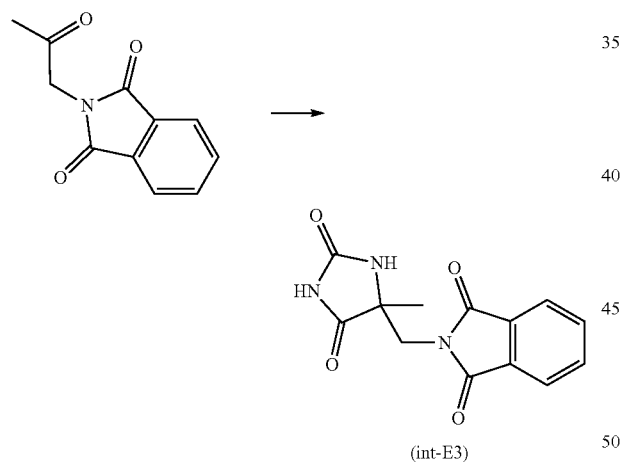

(int-E3)

2-(2-oxopropyl)isoindoline-1,3-dione (14.2 g, 69.9 mmol), ammonium carbonate (23.50 g, 245 mmol), potassium cyanide (6.83 g, 105 mmol) in ethanol (70 mL) and water (70.0 mL) were heated at 75° C. for 18 h. The reaction mixture was cooled to room temperature and the volatiles were evaporated in vacuo. The reaction mixture was partitioned between ethyl acetate (150 mL) and H$_2$O (100 mL). The aqueous phase was adjusted to pH 7 and extracted with more ethyl acetate (2×150 mL). Organic layers were combined, dried (MgSO$_4$) and concentrated in vacuo to yield the crude product 2-((4-methyl-2,5-dioxoimidazolidin-4-yl)methyl)isoindoline-1,3-dione (int-E3). $^1$H NMR (400 MHz, CD$_3$OD) δ 8.01-7.88 (m, 1H), 7.64-7.46 (m, 2H), 7.44-7.37 (m, 1H), 3.75-3.65 (m, 1H), 3.62-3.52 (m, 1H), 1.44 (s, 3H).

F) Type 6:

Synthesis of tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1)

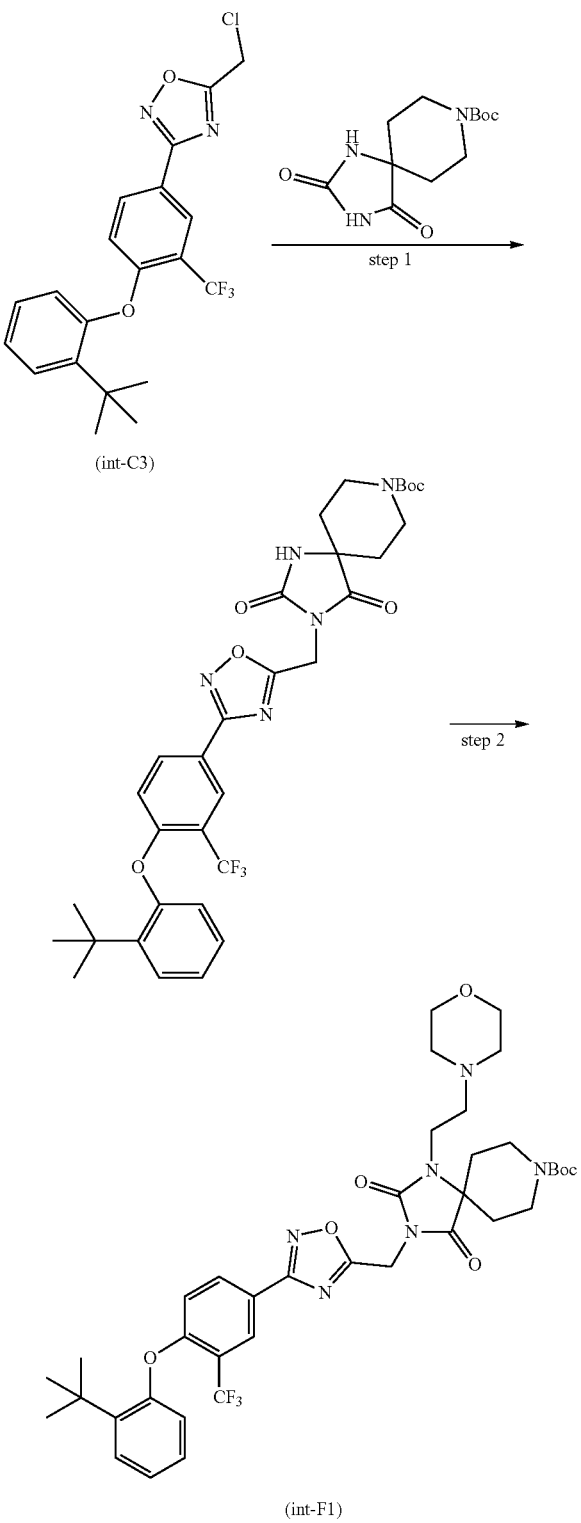

(int-F1)

Step 1: To a solution of 3-(4-(2-(tert-butyl)phenoxy)-3-(trifluoromethyl)phenyl)-5-(chloromethyl)-1,2,4-oxadiazole (int-C3) (1.0 g, 2.43 mmol) dissolved in DMF (6 mL) was added potassium carbonate (0.504 g, 3.65 mmol), followed by tert-butyl 2,4-dioxo-1,3,8-triazaspiro[4.5]decane-8-carboxylate (0.656 g, 2.43 mmol). The reaction mixture was stirred at 70° C. for 2 hours, then allowed to cool to room temperature and poured onto crushed ice. Precipitated product was collected by filtration, and the aqueous mixture was extracted with ethyl acetate (3×50 mL). The combined organic layers were washed with cold water (3×50 mL), dried over sodium sulfate, and concentrated. The resulting solid product was combined with the filtered solid product to provide tert-butyl 3-((3-(4-(2-(tert-butyl)phenoxy)-3-(trifluoromethyl)phenyl)-1,2,4-oxadiazol-5-yl)methyl)-2,4-dioxo-1,3,8-triazaspiro[4.5]decane-8-carboxylate) (0.5 g, 0.77 mmol). 1H NMR (400 MHz, CDCl$_3$) δ 8.36 (s, 1H), 8.06-8.09 (d, J=8.4 Hz, 1H), 7.46-7.48 (d, J=6.4 Hz, 1H), 7.16-7.27 (m, 2H), 6.99 (s, 1H), 6.85-6.90 (m, 2H), 5.00 (s, 1H), 3.99 (bs, 2H), 3.25-3.31 (m, 2H), 2.06-2.12 (m, 2H), 1.65-1.7 (m, 2H), 1.53 (s, 9H), 1.48 (s, 9H).

Step 2: To a solution of tert-butyl 3-((3-(4-(2-(tert-butyl)phenoxy)-3-(trifluoromethyl)phenyl)-1,2,4-oxadiazol-5-yl)methyl)-2,4-dioxo-1,3,8-triazaspiro[4.5]decane-8-carboxylate) (0.6 g, 0.93 mmol) in DMF (6 mL) was added cesium carbonate (1.093 g, 3.35 mmol) and 4-(2-bromoethyl)morpholine hydrobromide (0.308 g, 1.11 mmol). The reaction mixture was stirred at room temperature for 16 hours, and then poured onto crushed ice. Precipitated product was collected by filtration, and the aqueous mixture was extracted with ethyl acetate (3×50 mL). The combined organic layers were washed with cold water (50 mL×3), dried over sodium sulfate, and concentrated. The resulting solid product was combined with the filtered solid product to provide tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1). LCMS Method 11: Rt.=2.25 min.; m/z 758.7 [M+H], $^1$H NMR (400 MHz, CDCl$_3$) δ 8.35 (s, 1H), 8.06-8.09 (d, J=8.4 Hz, 1H), 7.47-7.49 (d, J=7.6 Hz, 1H), 7.17-7.25 (m, 2H), 6.85-6.91 (m, 2H), 4.99 (s, 2H), 4.11-4.17 (m, 2H), 3.71 (m, 4H), 3.42 (m, 4H), 2.54-2.62 (m, 6H), 1.94-1.96 (m, 2H), 1.80-1.83 (m, 2H), 1.51 (s, 9H), 1.35 (s, 9H).

Synthesis of tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2)

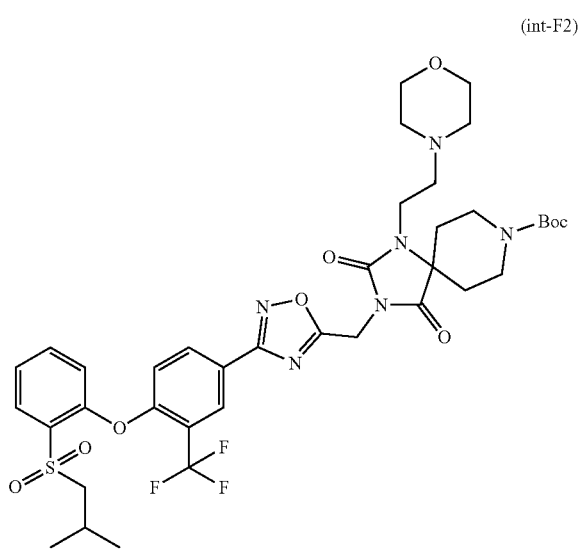 [SMILES: CC(C)CS(=O)(=O)c1ccccc1Oc1ccc(-c2noc(CN3C(=O)N(CCN4CCOCC4)C4(CCN(C(=O)OC(C)(C)C)CC4)C3=O)n2)cc1C(F)(F)F]

(int-F2)

tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1), except 3-(4-(2-(tert-butyl)phenoxy)-3-(trifluoromethyl)phenyl)-5-(chloromethyl)-1,2,4-oxadiazole (int-C3) was replaced with 5-(chloromethyl)-3-(4-(2-(isobutylsulfonyl)phenoxy)-3-(trifluoromethyl)phenyl)-1,2,4-oxadiazole (int-C2). LCMS Method 5: Rt.=3.16 mins; m/z 821.9 [M+H]+.

Synthesis of tert-butyl 1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F3)

(int-F3)

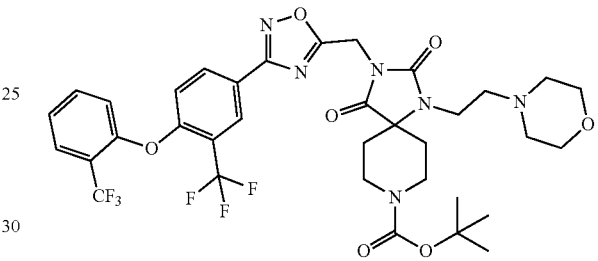

tert-butyl 1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F3) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1), except 3-(4-(2-(tert-butyl)phenoxy)-3-(trifluoromethyl)phenyl)-5-(chloromethyl)-1,2,4-oxadiazole (int-C3) was replaced with 5-(chloromethyl)-3-(3-(trifluoromethyl)-4-(2-(trifluoromethyl)phenoxy)phenyl)-1,2,4-oxadiazole (int-C5). LCMS Method 3: Rt.=1.38 mins; m/z 769.4 [M+H]+.

Synthesis of tert-butyl 3-((3-(4-(2-(N-isopropyl-N-methylsulfamoyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F4)

(int-F4)

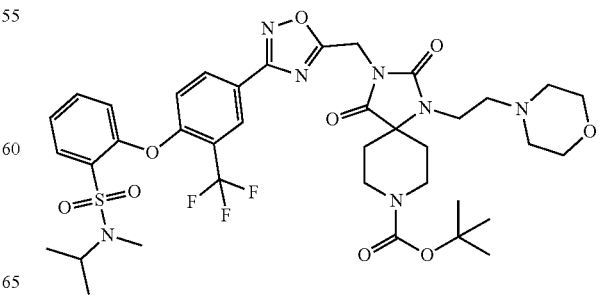

tert-butyl 3-((3-(4-(2-(N-isopropyl-N-methylsulfamoyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F4) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1), except 3-(4-(2-(tert-butyl)phenoxy)-3-(trifluoromethyl)phenyl)-5-(chloromethyl)-1,2,4-oxadiazole (int-C3) was replaced with 2-(4-(5-(chloromethyl)-1,2,4-oxadiazol-3-yl)-2-(trifluoromethyl)phenoxy)-N-isopropyl-N-methylbenzenesulfonamide (int-C4). LCMS Method 5: Rt.=3.20 mins; m/z 836.4 [M+H]+.

Synthesis of tert-butyl 1-(2-morpholinoethyl)-2,4-dioxo-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F5)

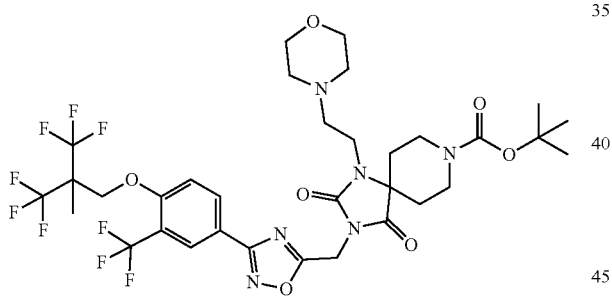

(int-F5)

tert-butyl 1-(2-morpholinoethyl)-2,4-dioxo-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F5) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1), except 3-(4-(2-(tert-butyl)phenoxy)-3-(trifluoromethyl)phenyl)-5-(chloromethyl)-1,2,4-oxadiazole (int-C3) was replaced with 5-(chloromethyl)-3-(4-(3,3,3-trifluoro-2-methyl-2-(trifluoromethyl)propoxy)-3-(trifluoromethyl)phenyl)-1,2,4-oxadiazole (int-C6). LCMS Method 3: Rt.=1.36 min, m/z 803.6 [M+H]+.

Synthesis of tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6)

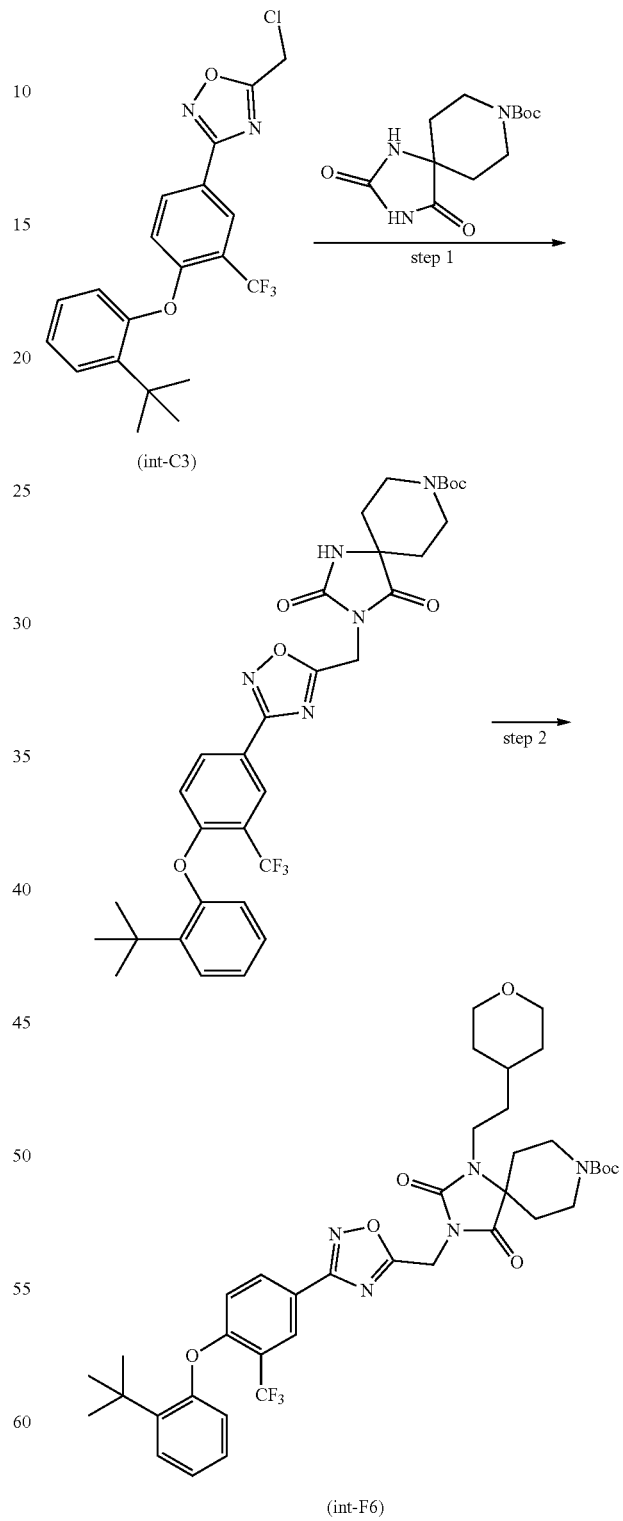

Step 1: To a solution of 3-(4-(2-(tert-butyl)phenoxy)-3-(trifluoromethyl)phenyl)-5-(chloromethyl)-1,2,4-oxadiazole (int-C3) (1.0 g, 2.43 mmol) dissolved in DMF (6 mL) was added potassium carbonate (0.504 g, 3.65 mmol), followed by tert-butyl 2,4-dioxo-1,3,8-triazaspiro[4.5]decane-8-carboxylate (0.656 g, 2.43 mmol). The reaction mixture was stirred at 70° C. for 2 hours, then allowed to cool to room temperature and poured onto crushed ice. Precipitated product was collected by filtration, and the aqueous mixture was extracted with ethyl acetate (3×50 mL). The combined organic layers were washed with cold water (3×50 mL), dried over sodium sulfate, and concentrated. The resulting solid product was combined with the filtered solid product to provide tert-butyl 3-((3-(4-(2-(tert-butyl)phenoxy)-3-(trifluoromethyl)phenyl)-1,2,4-oxadiazol-5-yl)methyl)-2,4-dioxo-1,3,8-triazaspiro[4.5]decane-8-carboxylate) (0.5 g, 0.77 mmol). 1H NMR (400 MHz, CDCl$_3$) δ 8.36 (s, 1H), 8.06-8.09 (d, J=8.4 Hz, 1H), 7.46-7.48 (d, J=6.4 Hz, 1H), 7.16-7.27 (m, 2H), 6.99 (s, 1H), 6.85-6.90 (m, 2H), 5.00 (s, 1H), 3.99 (bs, 2H), 3.25-3.31 (m, 2H), 2.06-2.12 (m, 2H), 1.65-1.7 (m, 2H), 1.53 (s, 9H), 1.48 (s, 9H).

Step 2: To a solution of (tert-butyl 3-((3-(4-(2-(tert-butyl)phenoxy)-3-(trifluoromethyl)phenyl)-1,2,4-oxadiazol-5-yl)methyl)-2,4-dioxo-1,3,8-triazaspiro[4.5]decane-8-carboxylate) (0.5 g, 0.77 mmol) in DMF (5 mL) was added cesium carbonate (0.886 g, 2.71 mmol), followed by 4-(2-bromoethyl)tetrahydro2H-pyran (0.18 g, 0.93 mmol). The reaction mixture was stirred at room temperature for 16 hours, and then poured onto crushed ice. Precipitated product was collected by filtration, and the aqueous mixture was extracted with ethyl acetate (3×50 mL). The combined organic layers were washed with cold water (3×50 mL), dried over sodium sulfate, and concentrated. The resulting solid product was combined with the filtered solid product to provide tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6). LCMS Method 11: Rt.=2.49 min.; m/z 700.6 [M+H−56]+.

Synthesis of tert-butyl 2,4-dioxo-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F7)

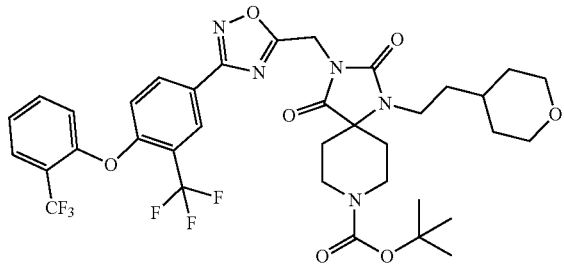

(int-F7)

tert-butyl 2,4-dioxo-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F7) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6), except 3-(4-(2-(tert-butyl)phenoxy)-3-(trifluoromethyl)phenyl)-5-(chloromethyl)-1,2,4-oxadiazole (int-C3) was replaced with 5-(chloromethyl)-3-(3-(trifluoromethyl)-4-(2-(trifluoromethyl)phenoxy)phenyl)-1,2,4-oxadiazole (int-C5). LCMS Method 3: Rt.=1.41 mins; m/z 768.1 [M+H]+.

Synthesis of tert-butyl 3-((3-(4-(2-(isobutylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F8)

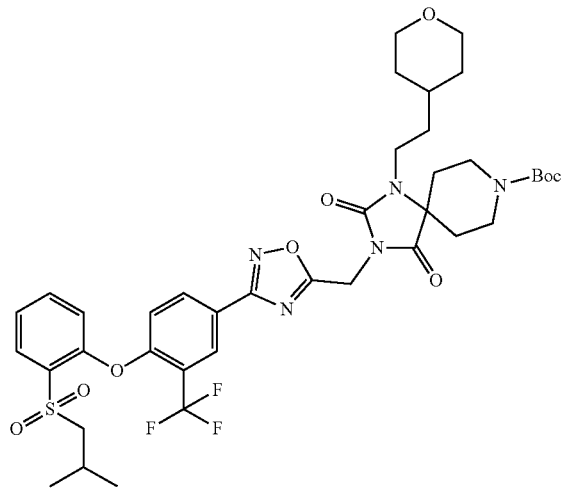

(int-F8)

tert-butyl 3-((3-(4-(2-(isobutylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F8) was obtained using a procedure similar to the procedure described for the synthesis of tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6), except 3-(4-(2-(tert-butyl)phenoxy)-3-(trifluoromethyl)phenyl)-5-(chloromethyl)-1,2,4-oxadiazole (int-C3) was replaced with 5-(chloromethyl)-3-(4-(2-(isobutylsulfonyl)phenoxy)-3-(trifluoromethyl)phenyl)-1,2,4-oxadiazole (int-C2). LCMS Method 3: Rt.=1.38 mins; m/z 820.4 [M+H]+.

Synthesis of tert-butyl 2,4-dioxo-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F9)

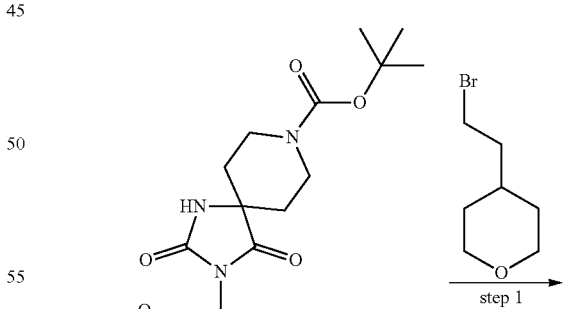

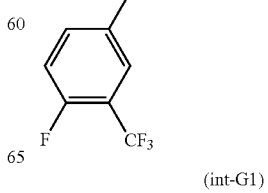

(int-G1)

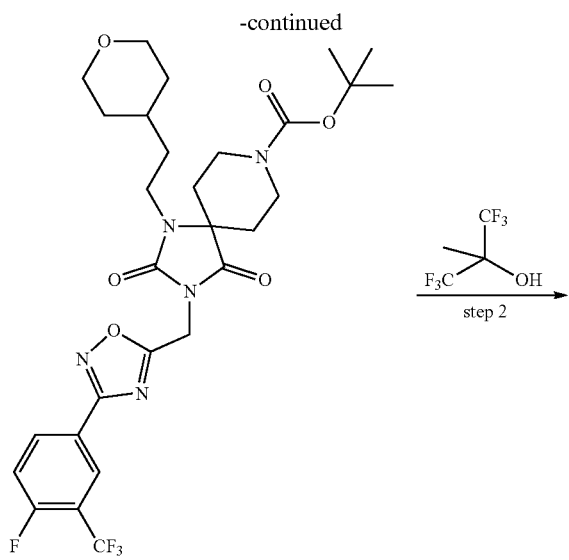

mmol) in THF (10 mL) at 0° C. After 5 mins, tert-butyl 3-((3-(4-fluoro-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (1.2 g, 1.918 mmol) in tetrahydrofuran (30 mL) was added and the reaction mixture was stirred at room temperature overnight. The mixture was then poured into a saturated ammonium chloride solution and extracted with EtOAc. The organic layer was dried over brine, anhydrous sodium sulfate, filtered and then concentrated to dryness. The residue was purified with flash column chromatography (0-100% EtOAc/hept) to provide tert-butyl 2,4-dioxo-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F9). ESI-MS m/z [M+H]$^+$: 802.3.

G) Type 7:

Synthesis of tert-butyl 3-((3-(4-fluoro-3-(trifluoromethyl)phenyl)-1,2,4-oxadiazol-5-yl)methyl)-2,4-dioxo-1,3,8-triazaspiro[4.5]decane-8-carboxylate (int-G1)

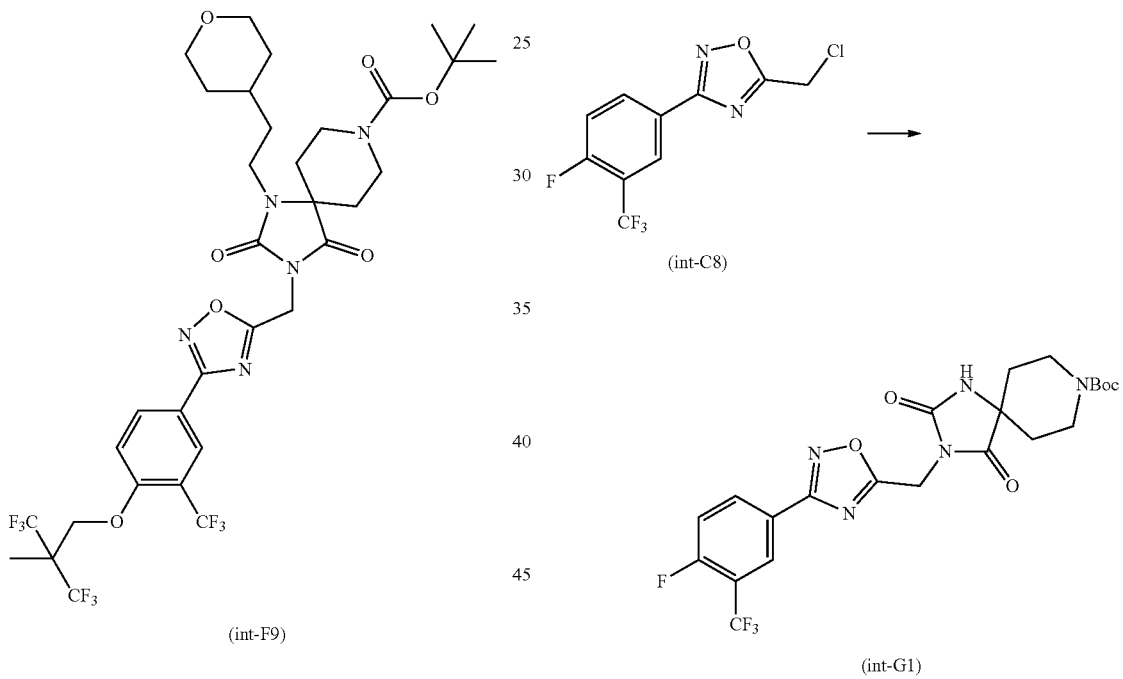

Step 1: Cesium carbonate (4315 mg, 13.24 mmol) was added to the mixture of tert-butyl 3-((3-(4-fluoro-3-(trifluoromethyl)phenyl)-1,2,4-oxadiazol-5-yl)methyl)-2,4-dioxo-1,3,8-triazaspiro[4.5]decane-8-carboxylate (int-G1) (1700 mg, 3.31 mmol), and 4-(2-bromoethyl)tetrahydro-2H-pyran (767 mg, 3.97 mmol) in DMF (15 mL). The reaction mixture was stirred at room temperature overnight, then the mixture was poured into a saturated ammonium chloride solution and extracted with EtOAc. The organic layer was washed with brine, dried over anhydrous sodium sulfate, filtered and then concentrated to dryness. The residue was purified with flash column chromatography (0-100% EtOAc/hept) to provide tert-butyl 3-((3-(4-fluoro-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate. ESI-MS m/z [M+H]$^+$: 626.2.

Step 2: Potassium 2-methylpropan-2-olate (1M in THF) (2.494 mL, 2.494 mmol) was added to 3,3,3-trifluoro-2-methyl-2-(trifluoromethyl)propan-1-ol (0.414 g, 2.110

In a 250 mL 3 neck flask, to a solution of 5-(chloromethyl)-3-(4-fluoro-3-(trifluoromethyl)phenyl)-1,2,4-oxadiazole (int-C8) (5.0 g, 17.81 mmol) and tert-butyl 2,4-dioxo-1,3,8-triazaspiro[4.5]decane-8-carboxylate (4.79 g, 17.81 mmol) in dry DMF (50 mL) was added potassium carbonate (3.69 g, 26.72 mmol). The reaction mixture was stirred at 60° C. for 4 hours, then allowed to cool to room temperature and poured onto crushed ice, stirring for 15 minutes. The formed solid precipitate was isolated by vacuum filtration, washed with cold water, and dried under vacuum to provide tert-butyl 3-((3-(4-fluoro-3-(trifluoromethyl)phenyl)-1,2,4-oxadiazol-5-yl)methyl)-2,4-dioxo-1,3,8-triazaspiro[4.5]decane-8-carboxylate (int-G1). LCMS Method 7: Rt.=1.90 min.; m/z 512.4 [M−H]−; $^1$H NMR (400 MHz, (CD$_3$)$_2$SO) δ 9.15 (s, 1H), 8.34 (m, 1H), 8.22-8.23 (m, 1H), 7.72-7.77 (m, 1H), 5.03 (s, 2H), 3.81-3.85 (m, 2H), 3.18 (m, 2H), 1.76-1.81 (m, 2H), 1.61-1.65 (m, 2H), 1.40 (s, 9H).

123

Synthesis of 3-((3-(4-fluoro-3-(trifluoromethyl)phenyl)-1,2,4-oxadiazol-5-yl)methyl)-5,5-dimethylimidazolidine-2,4-dione (int-G2)

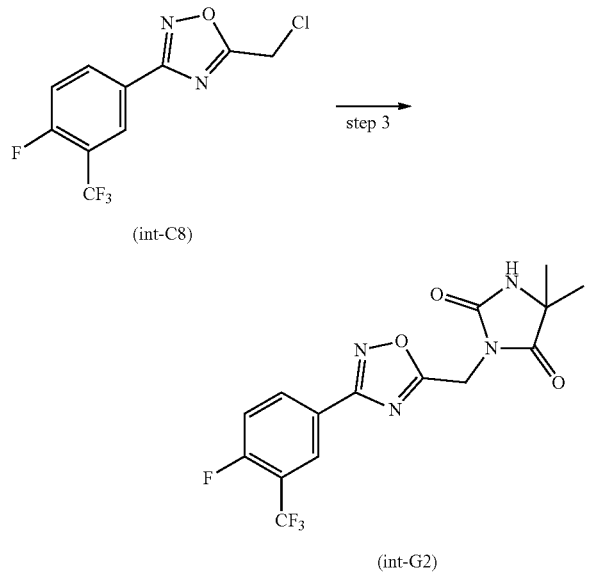

A solution of 5-(chloromethyl)-3-(4-fluoro-3-(trifluoromethyl)phenyl)-1,2,4-oxadiazole (int-C8) (4.35 g, 15.50 mmol) in DMF (25 mL) was treated with 5,5-dimethylimidazolidine-2,4-dione (2.98 g, 23.25 mmol) and potassium carbonate (4.28 g, 31.0 mmol). The reaction mixture was stirred at 60° C. for 2 hours and then poured into ice water (100 mL) and refrigerated overnight. The precipitate was collected and washed with ice-water to give 3-((3-(4-fluoro-3-(trifluoromethyl)phenyl)-1,2,4-oxadiazol-5-yl)methyl)-5,5-dimethylimidazolidine-2,4-dione (int-G2). LCMS Method 2: m/z 373.2 [M+H]+; 1H NMR (400 MHz, CDCl$_3$) δ 8.29 (dd, J=6.7, 1.9 Hz, 1H), 8.23 (ddd, J=8.4, 4.6, 2.1 Hz, 1H), 7.35-7.27 (m, 1H), 5.00 (s, 2H), 1.52 (s, 6H).

H) Type 8:

Synthesis of 3-((3-(4-fluoro-3-(trifluoromethyl)phenyl)-1,2,4-oxadiazol-5-yl)methyl)-5,5-dimethyl-1-(2-morpholinoethyl)imidazolidine-2,4-dione (int-H1)

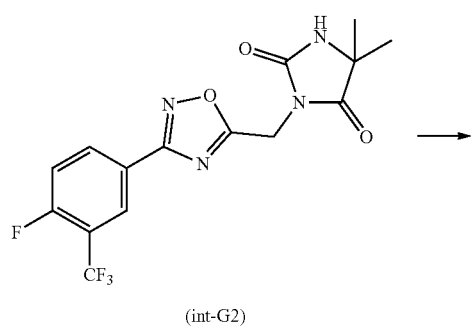

124

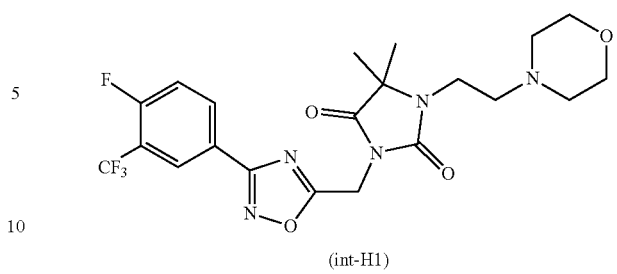

3-((3-(4-fluoro-3-(trifluoromethyl)phenyl)-1,2,4-oxadiazol-5-yl)methyl)-5,5-dimethylimidazolidine-2,4-dione (int-G2) (2 g, 5.37 mmol) and 4-(2-bromoethyl)morpholine.HBr (1.625 g, 5.91 mmol) were combined in DMF (15 mL) and treated with cesium carbonate (7.00 g, 21.49 mmol) at room temperature overnight. Water was then added, the resulting precipitate was collected, and the aqueous filtrate was then extracted with ethyl acetate (twice). The combined organics and precipitate were washed with 0.5M LiCl and then the combined organic layers were dried over MgSO4, filtered and evaporated to dryness. The residue was purified by chromatography on a ISCO 120 g cartridge, eluting with 0-10% MeOH in EtOAc. to give 3-((3-(4-fluoro-3-(trifluoromethyl)phenyl)-1,2,4-oxadiazol-5-yl)methyl)-5,5-dimethyl-1-(2-morpholinoethyl)imidazolidine-2,4-dione (int-H1). LCMS Method 5: Rt.=2.34 min m/z [M+H]+ 486.5.

I) Type 9:

Synthesis of tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1)

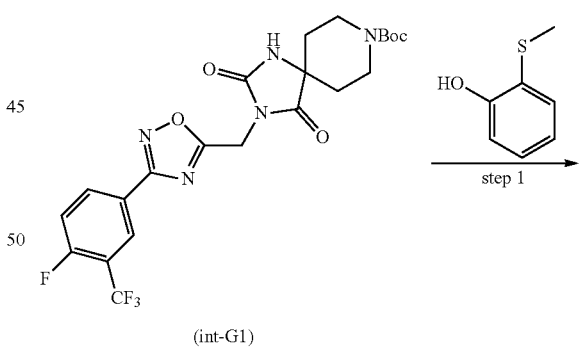

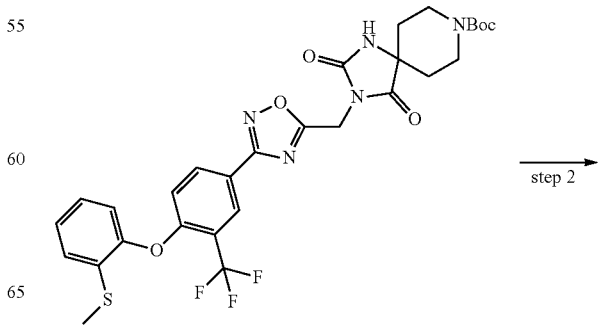

-continued

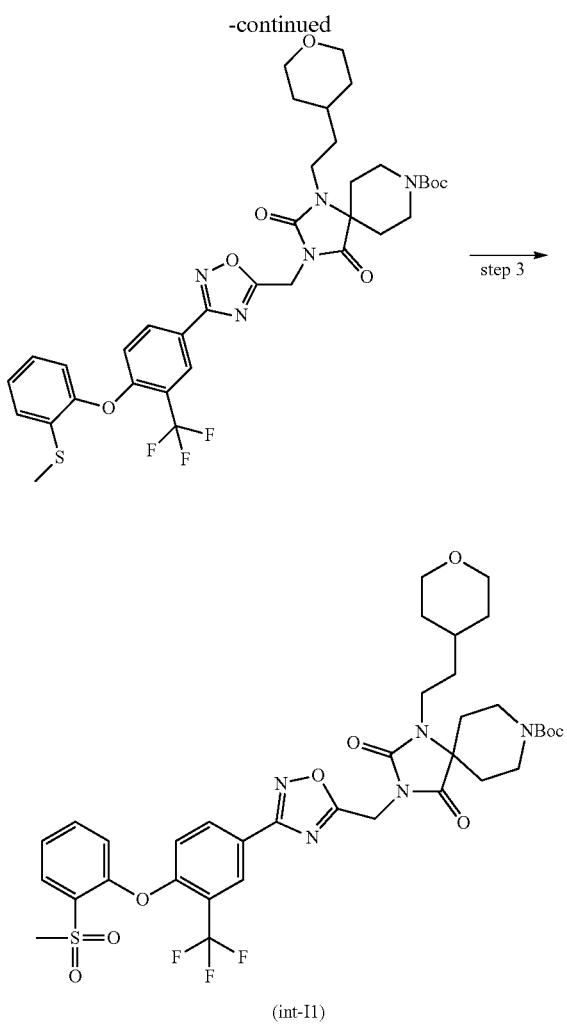

(int-I1)

Step 1: To a solution of 2-(methylthio)phenol (0.3 g, 2.14 mmol) in DMF (10 mL) was added cesium carbonate (2.09 g, 6.42 mmol), followed by tert-butyl 3-((3-(4-fluoro-3-(trifluoromethyl)phenyl)-1,2,4-oxadiazol-5-yl)methyl)-2,4-dioxo-1,3,8-triazaspiro[4.5]decane-8-carboxylate (int-G1) (1.0 g, 1.94 mmol). The reaction mixture was stirred at room temperature for 16 hours, and then poured onto crushed ice with continuous stirring. The formed solid precipitates were isolated by vacuum filtration and dried under vacuum. The crude product was purified using flash column chromatography, with the product eluted in 35-55% ethyl acetate in hexane. The product fractions were combined and concentrated to provide tert-butyl 3-((3-(4-(2-(methylthio)phenoxy)-3-(trifluoromethyl)phenyl)-1,2,4-oxadiazol-5-yl)methyl)-2,4-dioxo-1,3,8-triazaspiro[4.5]decane-8-carboxylate. LCMS Method 11: Rt.=2.14 min.; m/z 632.5 [M−H]−; 1H NMR (400 MHz, (CD$_3$)$_2$SO) δ 9.14 (s, 1H), 8.23 (s, 1H), 8.16-8.18 (d, J=8.4 Hz, 1H), 7.44-7.46 (d, J=8.0 Hz, 1H), 7.36-7.40 (t, J=7.2 Hz, 1H), 7.28-7.31 (t, J=7.2 Hz, 1H), 7.17-7.19 (d, J=7.2 Hz, 1H), 6.87-6.89 (d, J=8.8 Hz, 1H), 5.02 (s, 2H), 3.81-3.85 (m, 2H), 3.19-3.28 (m, 2H), 2.43 (s, 3H), 1.76-1.81 (m, 2H), 1.61-1.65 (m, 2H), 1.41 (s, 9H).

Step 2: To a solution of (tert-butyl 3-((3-(4-(2-(methylthio)phenoxy)-3-(trifluoromethyl)phenyl)-1,2,4-oxadiazol-5-yl)methyl)-2,4-dioxo-1,3,8-triazaspiro[4.5]decane-8-carboxylate) (0.55 g, 0.86 mmol) in DMF (5.5 mL) was added cesium carbonate (0.848 g, 2.60 mmol), followed by 4-(2-bromoethyl)tetrahydro2H-pyran (0.201 g, 1.04 mmol). The reaction mixture was stirred at room temperature for 16 hours, and then poured on crushed ice. The aqueous mixture was extracted with ethyl acetate (3×50 mL). The combined organic layers were washed with cold water (3×50 mL), dried over sodium sulfate, filtered, and concentrated to provide tert-butyl 3-((3-(4-(2-(methylthio)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate. LCMS Method 11: Rt.=2.33 min.; m/z 690.5 [M+H−56].

Step 3: To as solution of (tert-butyl 3-((3-(4-(2-(methylthio)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate) (0.62 g, 0.83 mmol) in dichloromethane (18.6 mL) was added m-chloroperoxybenzoic acid (0.43 g, 2.49 mmol) portion wise at 0° C. After the addition was complete, the reaction mixture was stirred at room temperature for 16 hours. The mixture was then diluted with dichloromethane (25 mL) and washed with saturated sodium bicarbonate solution (2×20 mL). The organic layer was dried over sodium sulfate, filtered, and concentrated. The resulting residue was purified by column chromatography, with the product eluted in 80-100% ethyl acetate in hexane. The product fractions were combined and concentrated to afford tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1). LCMS Method 8: Rt.=3.83 min.; m/z 722.2 [M+H−56].

Synthesis of tert-butyl 3-((3-(4-(2-(methylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-I2)

(int-I2)

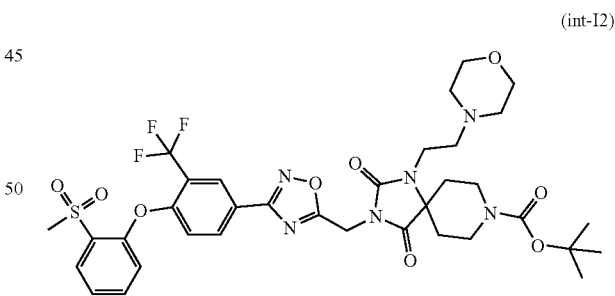

tert-butyl 3-((3-(4-(2-(methylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-I2) was obtained using a procedure similar to the procedure described for the synthesis of tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1), except 4-(2-bromoethyl)tetrahydro2H-pyran was replaced with 4-(2-bromoethyl)morpholine. LC/MS Method 8: Rt.=3.59 mins; m/z 779.3 [M+H]+.

Synthesis of tert-butyl 1-(2-morpholinoethyl)-2,4-dioxo-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-8-carboxylate (int-I3)

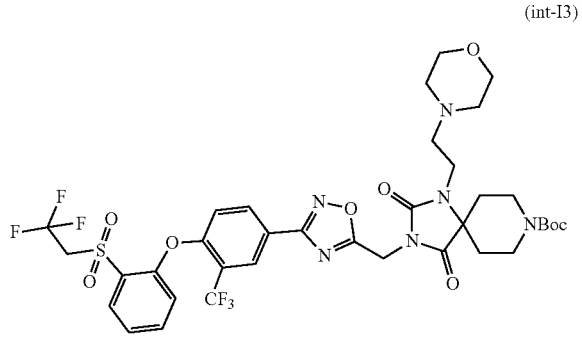 [SMILES: CC(C)(C)OC(=O)N1CCC2(CC1)C(=O)N(Cc1nc(-c3ccc(Oc4ccccc4S(=O)(=O)CC(F)(F)F)c(C(F)(F)F)c3)no1)C(=O)N2CCN1CCOCC1]

(int-I3)

tert-butyl 1-(2-morpholinoethyl)-2,4-dioxo-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-8-carboxylate (int-I3) was obtained using a procedure similar to the procedure described for the synthesis of tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1), except 2-(methylthio)phenol was replaced with 2-((2,2,2-trifluoroethyl)thio)phenol (int-A6) and 4-(2-bromoethyl)tetrahydro2H-pyran was replaced with 4-(2-bromoethyl)morpholine. LC/MS Method 7: Rt.=1.95 mins; m/z 815.5 [M+H]+.

Synthesis of tert-butyl 2,4-dioxo-1-(2-(tetrahydro-2H-pyran-4-yl)ethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-8-carboxylate (int-I4)

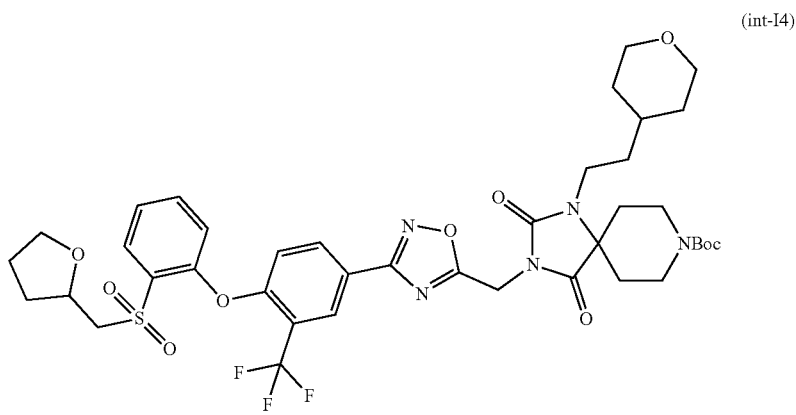 [SMILES: CC(C)(C)OC(=O)N1CCC2(CC1)C(=O)N(Cc1nc(-c3ccc(Oc4ccccc4S(=O)(=O)CC4CCCO4)c(C(F)(F)F)c3)no1)C(=O)N2CCC1CCOCC1]

(int-I4)

tert-butyl 2,4-dioxo-1-(2-(tetrahydro-2H-pyran-4-yl)ethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-8-carboxylate (int-I4) was obtained using a procedure similar to the procedure described for the synthesis of tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1), except 2-(methylthio)phenol was replaced with 2-(((tetrahydrofuran-2-yl)methyl)sulfonyl)phenol (int-B6). LCMS Method 7: Rt.=1.96 mins; m/z 792.8 [M+H−56].

Synthesis of tert-butyl 1-(2-morpholinoethyl)-2,4-dioxo-3-((3-(4-(2-(((tetrahydrofuran-2-yl)methyl) sulfonyl) phenoxy)-3-(trifluoromethyl)phenyl)-1,2,4-oxadiazol-5-yl)methyl)-1,3,8-triazaspiro[4.5]decane-8-carboxylate (int-I5)

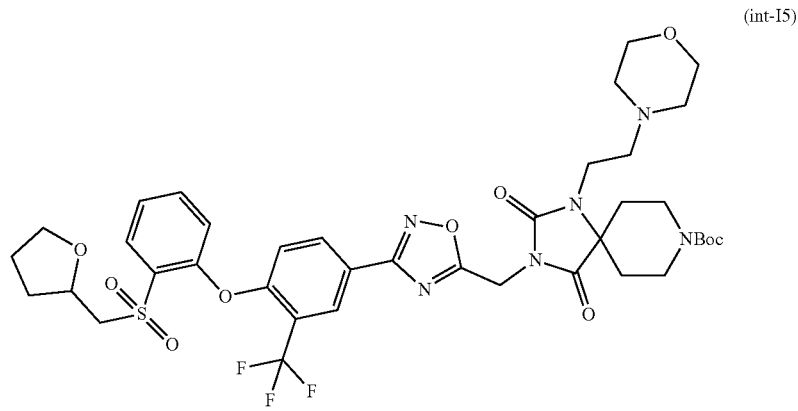 [SMILES: CC(C)(C)OC(=O)N1CCC2(CC1)C(=O)N(Cc1nc(-c3ccc(Oc4ccccc4S(=O)(=O)CC4CCCO4)c(C(F)(F)F)c3)no1)C(=O)N2CCN1CCOCC1]

tert-butyl 1-(2-morpholinoethyl)-2,4-dioxo-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-8-carboxylate (int-I5) was obtained using a procedure similar to the procedure described for the synthesis of tert-butyl 3-((3-(4-(2-(methylsulfonyl)phenoxy)-3-(trifluoromethyl)phenyl)-1,2,4-oxadiazol-5-yl) methyl)-2,4-dioxo-1-(2-(tetrahydro-2H-pyran-4-yl)ethyl)-1,3,8-triazaspiro[4.5]decane-8-carboxylate (int-I1), except 2-(methylthio)phenol was replaced with 2-(((tetrahydrofuran-2-yl)methyl)sulfonyl)phenol (int-B6) and 4-(2-bromoethyl)tetrahydro2H-pyran was replaced with 4-(2-bromoethyl)morpholine. LCMS Method 7: Rt.=1.64 mins; m/z 849.8 [M+H].

J) Type 10:

Synthesis of tert-butyl 3-((3-(4-(2-(methylsulfonyl) phenoxy)-3-(trifluoromethyl)phenyl)-1,2,4-oxadiazo
Synthesis of 2-((2-(4-(5-((4,4-dimethyl-3-(2-morpholinoethyl)-2,5-dioxoimidazolidin-1-yl)methyl)-1,2,4-oxadiazol-3-yl)-2-(trifluoromethyl)phenoxy) phenyl)thio)acetaldehyde (int-J1)

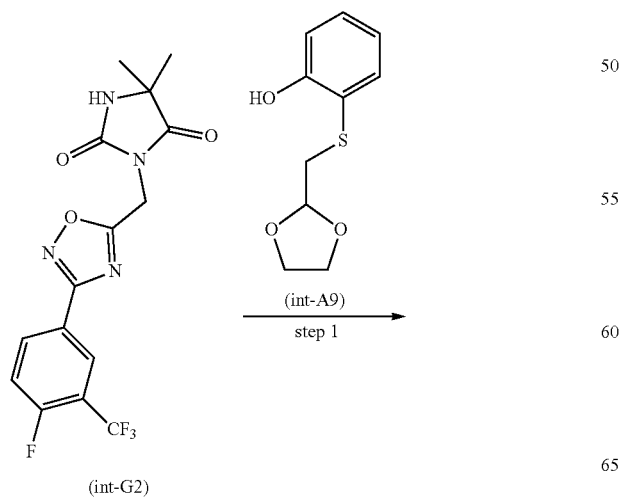

131

-continued

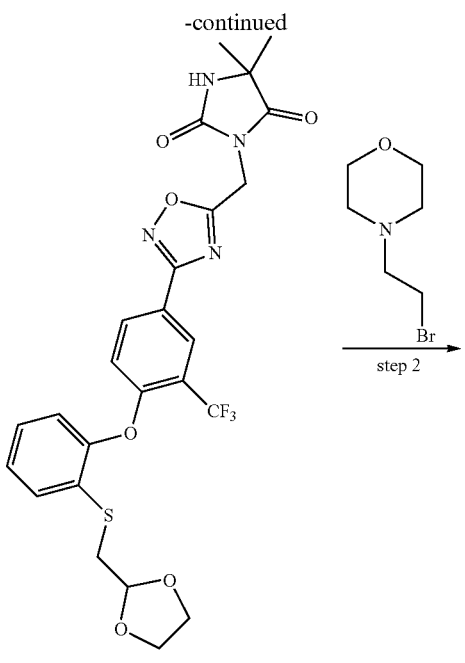

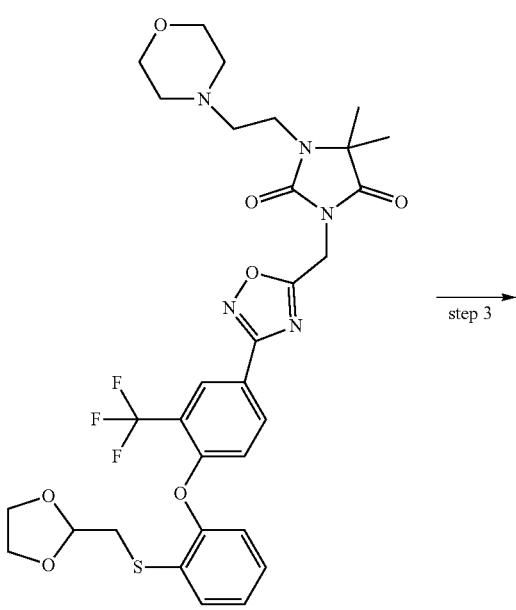

132

-continued

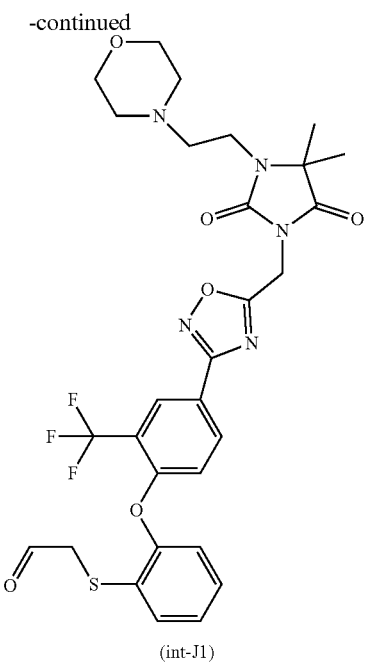

(int-J1)

Step 1: 2-(((1,3-dioxolan-2-yl)methyl)thio)phenol (int-A9) (1.3791 g, 6.50 mmol) was dissolved in DMF (13 mL) and then cesium carbonate (4.23 g, 12.99 mmol) was added. 3-((3-(4-fluoro-3-(trifluoromethyl)phenyl)-1,2,4-oxadiazol-5-yl)methyl)-5,5-dimethylimidazolidine-2,4-dione (int-G2) (2.419 g, 6.50 mmol) was added and the mixture was then stirred at 90° C. overnight. The reaction mixture was added to water (100 mL), then extracted with EtOAc (3×100 mL). The organics where then combined and dried over MgSO₄ then purified using an ISCO with eluants heptane:EtOAc 0-100%. The product fractions where combined and concentrated under vacuum to provide 3-((3-(4-(2-(((1,3-dioxolan-2-yl)methyl)thio)phenoxy)-3-(trifluoromethyl)phenyl)-1,2,4-oxadiazol-5-yl)methyl)-5,5-dimethylimidazolidine-2,4-dione. LCMS Method 3: Rt.=1.14 mins; m/z 563.3 [M−H]−; ¹H NMR (400 MHz, CDCl₃) δ 8.32 (d, 1H), 8.03 (dd, J=8.8, 2.2 Hz, 1H), 7.53 (dd, J=7.6, 1.9 Hz, 1H), 7.30-7.13 (m, 2H), 7.08 (s, 1H), 6.99 (dd, J=7.8, 1.7 Hz, 1H), 6.75 (d, J=8.7 Hz, 1H), 5.10-5.02 (m, 1H), 4.95 (d, J=4.8 Hz, 2H), 4.13-4.01 (m, 1H), 4.00-3.87 (m, 2H), 3.87-3.76 (m, 2H), 3.10 (d, J=3.4 Hz, 2H), 2.01 (s, 1H), 1.47 (s, 6H), 1.31-1.15 (m, 3H), 0.84 (td, J=7.0, 2.3 Hz, 1H).)

Step 2: 3-((3-(4-(2-(((1,3-dioxolan-2-yl)methyl)thio)phenoxy)-3-(trifluoromethyl)phenyl)-1,2,4-oxadiazol-5-yl)methyl)-5,5-dimethylimidazolidine-2,4-dione (1 g, 1.771 mmol) and 4-(2-bromoethyl)morpholine (0.585 g, 2.126 mmol) were dissolved in DMF (10 mL), and cesium carbonate (1.731 g, 5.31 mmol) was then added. The reaction mixture was then stirred at 90° C. overnight. The reaction mixture was then purified using ISCO with eluents DCM:MeOH (0-30%). The product fractions were then combined and concentrated under vacuum to give 3-((3-(4-(2-(((1,3-dioxolan-2-yl)methyl)thio)phenoxy)-3-(trifluoromethyl)phenyl)-1,2,4-oxadiazol-5-yl)methyl)-5,5-dimethyl-1-(2-morpholinoethyl)imidazolidine-2,4-dione. LCMS Method 3: Rt.=1.18 mins; m/z 678.6 [M−H]−.

Step 3: 3-((3-(4-(2-(((1,3-dioxolan-2-yl)methyl)thio)phenoxy)-3-(trifluoromethyl)phenyl)-1,2,4-oxadiazol-5-yl)methyl)-5,5-dimethyl-1-(2-morpholinoethyl)imidazolidine-2,4-dione (900 mg, 1.328 mmol) was dissolved in THF (5 mL) and then acetic acid (0.304 mL, 5.31 mmol) and HCl (0.221 mL, 1.328 mmol) were added. The reaction mixture was then stirred at room temperature for 48 hrs. Additional HCl (0.221 mL, 1.328 mmol) was added and the reaction mixture was then stirred at rt for 48 hours. The reaction mixture was then concentrated under vacuum and purified by ISCO with eluents DCM:MeOH (0-30%). The product fractions were then combined and concentrated under vacuum to provide 2-((2-(4-(5-((4,4-dimethyl-3-(2-morpholinoethyl)-2,5-dioxoimidazolidin-1-yl)methyl)-1,2,4-oxadiazol-3-yl)-2-(trifluoromethyl)phenoxy)phenyl)thio)acetaldehyde (int-J1). LCMS Method 3: Rt.=1.15 mins; m/z 632.3 [M–H]–.

K) Type 11:

Synthesis of 5,5-dimethyl-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione (int-K1)

Synthesis of 3-((3-(4-(2-(isobutylsulfonyl)phenoxy)-3-(trifluoromethyl)phenyl)-1,2,4-oxadiazol-5-yl)methyl)imidazolidine-2,4-dione (int-K2)

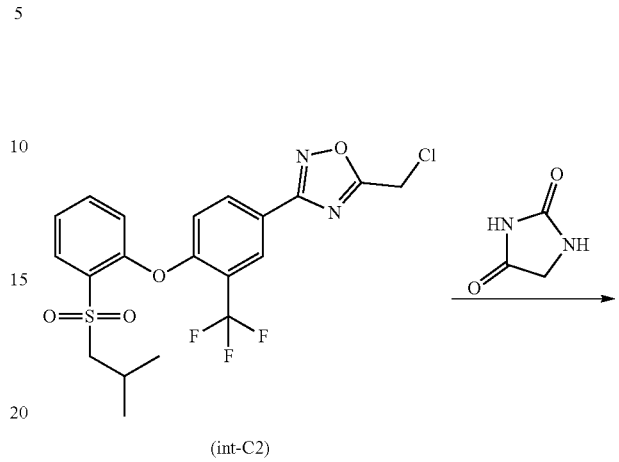

(int-C2)

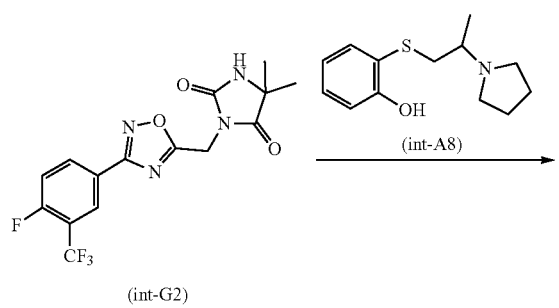

(int-K1)

To a solution of 3-((3-(4-fluoro-3-(trifluoromethyl)phenyl)-1,2,4-oxadiazol-5-yl)methyl)-5,5-dimethylimidazolidine-2,4-dione (int-G2) (1.39 g, 3.72 mmol) and 2-((2-(pyrrolidin-1-yl)propyl)thio)phenol (int-A8) (0.883 g, 3.72 mmol) in DMF (30 mL) was added potassium carbonate (771 mg, 5.58 mmol), and the resulting mixture heated to 90° C. overnight. The reaction mixture cooled to room temperature and then water was added. The mixture was extracted twice with ethyl acetate and the combined organic layers were dried over magnesium sulfate, filtered, concentrated and then purified by flash column chromatography, eluting with 0-20% MeOH in EtOAc, to provide 5,5-dimethyl-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione (int-K1). LCMS Method 3: Rt.=1.27 mins; m/z 590.3 [M–H]–.

Potassium carbonate (94 mg, 0.677 mmol) was added to a solution of imidazolidine-2,4-dione (27.1 mg, 0.271 mmol) in DMF (2 mL) and the mixture was stirred at room temperature for 30 mins. 5-(chloromethyl)-3-(4-(2-(isobutylsulfonyl)phenoxy)-3-(trifluoromethyl)phenyl)-1,2,4-oxadiazole (int-C2) (100 mg, 0.226 mmol) was then added and the reaction mixture was stirred at room temperature overnight. The reaction mixture was then purified using an ISCO with DCM:MeOH (0-30%) to obtain 3-((3-(4-(2-(isobutylsulfonyl)phenoxy)-3-(trifluoromethyl)phenyl)-1,2,4-oxadiazol-5-yl)methyl)imidazolidine-2,4-dione (int-K2). LCMS Method 3: Rt.=1.26 mins; m/z 505.4 [M–H]–.

Synthesis of 2-((1-((3-(4-(2-(isobutylthio)phenoxy)-3-(trifluoromethyl)phenyl)-1,2,4-oxadiazol-5-yl)methyl)-4-methyl-2,5-dioxoimidazolidin-4-yl)methyl)isoindoline-1,3-dione (int-K3)
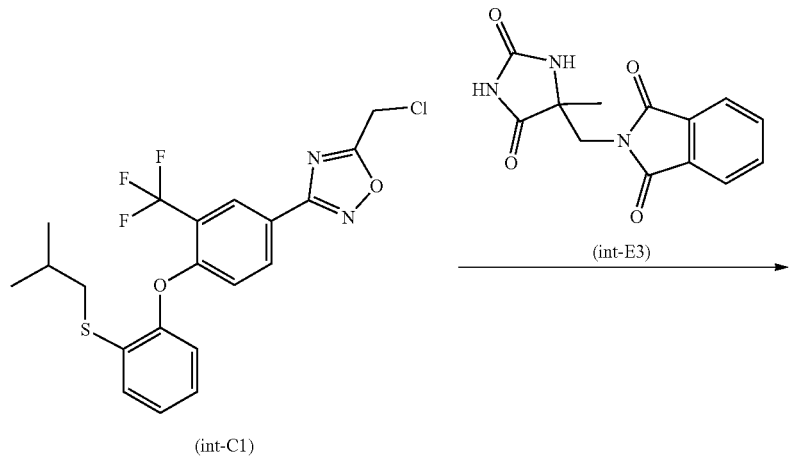
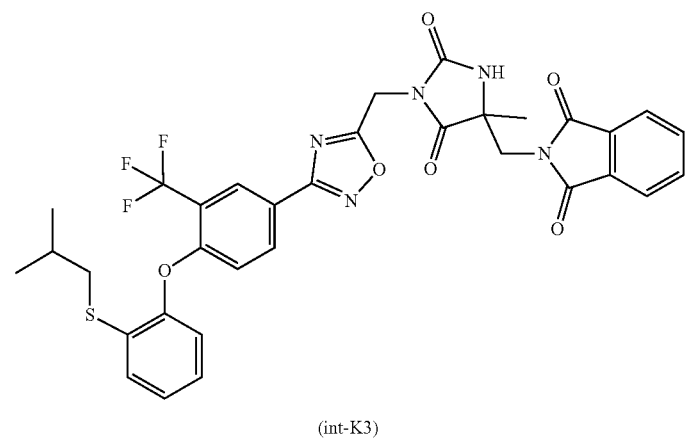

2-((1-((3-(4-(2-(isobutylthio)phenoxy)-3-(trifluoromethyl)phenyl)-1,2,4-oxadiazol-5-yl)methyl)-4-methyl-2,5-dioxoimidazolidin-4-yl)methyl)isoindoline-1,3-dione (int-K3) was obtained using a procedure similar to the procedure described for the synthesis of 3-((3-(4-(2-(isobutylsulfonyl)phenoxy)-3-(trifluoromethyl)phenyl)-1,2,4-oxadiazol-5-yl)methyl)imidazolidine-2,4-dione (int-K2), except imidazolidine-2,4-dione was replaced with 2-((4-methyl-2,5-dioxoimidazolidin-4-yl)methyl)isoindoline-1,3-dione (int-E3). LCMS Method 3: Rt.=1.35 mins; m/z 680.7 [M+H]+.

Synthesis of Exemplary Compounds

Example 1: Synthesis of 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1)

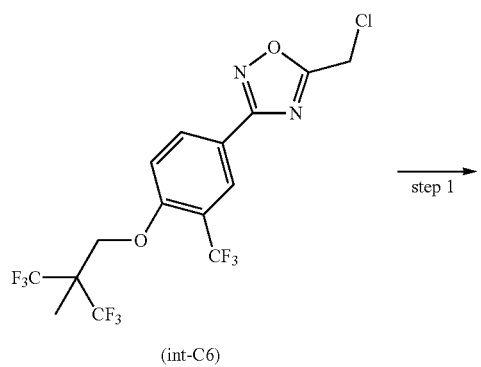

(int-C6)

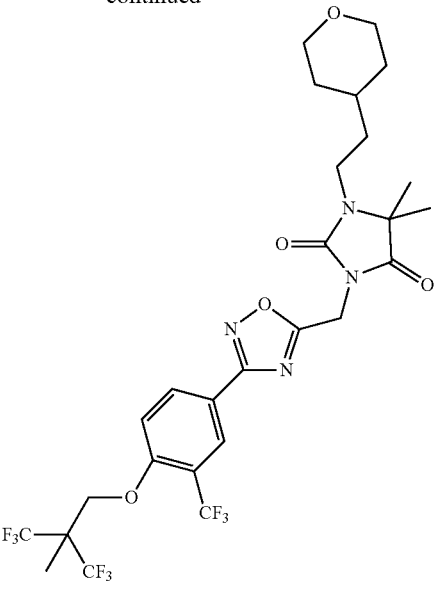

(1)

Step 1: 5-(chloromethyl)-3-(4-(3,3,3-trifluoro-2-methyl-2-(trifluoromethyl)propoxy)-3-(trifluoromethyl)phenyl)-1,2,4-oxadiazole (int-C6) (210 mg, 0.460 mmol) was dissolved in DMF (2 mL) and treated with 5,5-dimethylimidazolidine-2,4-dione (88 mg, 0.690 mmol) and potassium carbonate (127 mg, 0.920 mmol). The reaction mixture was then heated to 60° C. for 2 h, then allowed to cool to room temperature and poured into ice water (100 mL). The mixture was kept in refrigerator overnight. The precipitate was collected and washed with ice-water, and the crude product 5,5-dimethyl-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione was used in the next step without purification. LCMS Method 3: Rt.=1.21 min m/z 549.3 [M+H]+

Step 2: 4-(2-bromoethyl)tetrahydro-2H-pyran (70.4 mg, 0.365 mmol) was added to a mixture of 5,5-dimethyl-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (100 mg, 0.182 mmol), and cesium carbonate (178 mg, 0.547 mmol) in DMF (1 mL). The reaction mixture was stirred overnight, then diluted with EtOAc, washed sequentially with water and brine, then dried over sodium sulfate, filtered and concentrated. The residue was purified by flash column chromatography (0-100% EtOAc/heptane, then 0-5% MeOH/DCM) to provide 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1). LCMS Method 2 Rt.=1.35 min m/z 661.3 [M+H]+, $^1$H NMR (CD$_3$CN, 400 MHz) δ 8.21-8.50 (m, 2H), 7.36 (d, 1H, J=8.8 Hz), 4.94 (s, 2H), 4.53 (s, 2H), 3.80-4.02 (m, 2H), 3.21-3.52 (m, 4H), 2.11-2.32 (m, 1H), 1.61-1.71 (m, 2H), 1.55-1.59 (m, 5H), 1.46 (s, 6H), 1.20-1.40 (m, 2H).

Example 2; 3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)-5-propylimidazolidine-2,4-dione (2)

Example 3; 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione (3)

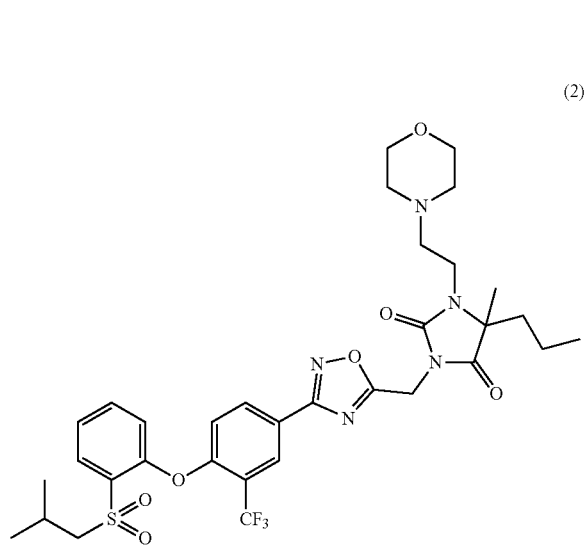 [SMILES: CCCC1(C)C(=O)N(Cc2nc(-c3ccc(Oc4ccccc4S(=O)(=O)CC(C)C)c(C(F)(F)F)c3)no2)C(=O)N1CCN1CCOCC1]

(2)

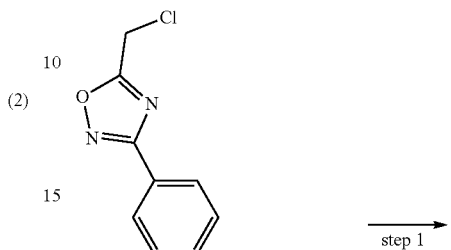

(int-C1)

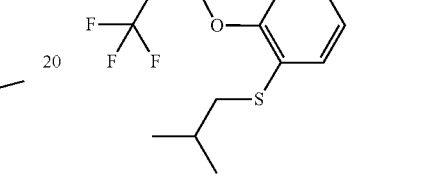

step 1

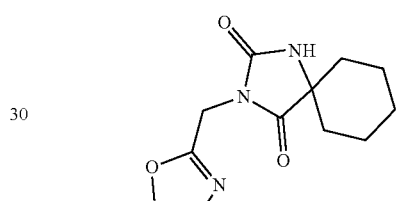

step 2

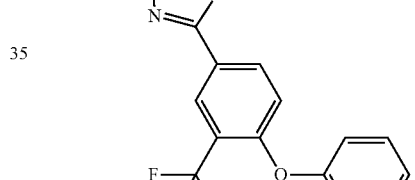

step 3

3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)-5-propylimidazolidine-2,4-dione (2) was obtained using a procedure similar to the procedure described in Example 1 for the synthesis of 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1), except 5-(chloromethyl)-3-(4-(3,3,3-trifluoro-2-methyl-2-(trifluoromethyl)propoxy)-3-(trifluoromethyl)phenyl)-1,2,4-oxadiazole (int-C6) was replaced with 5-(chloromethyl)-3-(4-(2-(isobutylsulfonyl)phenoxy)-3-(trifluoromethyl)phenyl)-1,2,4-oxadiazole (int-C2), 5,5-dimethylimidazolidine-2,4-dione was replaced with 5-methyl-5-propylimidazolidine-2,4-dione and 4-(2-bromoethyl)tetrahydro-2H-pyran was replaced with 4-(2-bromoethyl)morpholine. 1H NMR (400 MHz, CDCl$_3$) δ 8.40 (s, 1H), 8.17-8.19 (d, J=9.2 Hz, 1H), 8.14-8.16 (d, J=8.0 Hz, 1H), 7.66-7.69 (t, J=7.6 Hz, 1H), 7.42-7.46 (t, J=7.2 Hz, 1H), 7.04-7.06 (d, J=8.4 Hz, 2H), 5.02 (s, 2H), 3.73-3.75 (t, J=4.0 Hz, 4H), 3.53-3.60 (m, 1H), 3.26-3.40 (m, 3H), 2.63-2.67 (t, J=6.8 Hz, 2H), 2.57 (bs, 4H), 2.26-2.32 (m, 1H), 1.92-1.97 (m, 1H), 1.69-1.76 (m, 1H), 1.53 (s, 3H), 1.32-1.38 (m, 2H), 1.09-1.11 (d, J=6.4 Hz, 6H), 0.95-0.99 (t, J=7.2 Hz, 3H); LCMS Method 7: Rt.=4.63 min., m/z 708.4 [M+H].

-continued

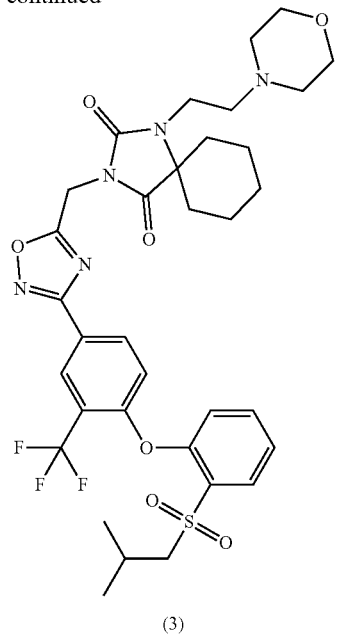

(3)

Step 1: 5-(chloromethyl)-3-(4-(2-(isobutylthio)phenoxy)-3-(trifluoromethyl)phenyl)-1,2,4-oxadiazole (int-C1) (0.25 g, 0.56 mmol) was dissolved in DMF (2.5 mL), and cesium carbonate (0.551 g, 1.69 mmol) and 1,3-diazaspiro[4.5]decane-2,4-dione (0.076 g, 0.45 mmol) were added to the reaction mixture. The mixture was stirred at room temperature for 16 hours, then poured onto crushed ice and stirred for 15 minutes. The formed precipitate was filtered and collected, then washed with water. The product was dried under vacuum to obtain 3-((3-(4-(2-(isobutylthio)phenoxy)-3-(trifluoromethyl)phenyl)-1,2,4-oxadiazol-5-yl)methyl)-1,3-diazaspiro[4.5]decane-2,4-dione. LCMS Method 11: Rt.=2.24 min.; m/z 575.5 [M+H]+; $^1$H NMR (400 MHz, (CD$_3$)$_2$SO) δ 9.02 (s, 1H), 8.11-8.22 (m, 2H), 7.53-7.55 (d, J=6.8 Hz, 1H), 7.31-7.33 (m, 2H), 7.17-7.18 (m, 1H), 6.82 (m, 1H), 5.00 (s, 2H), 2.76-2.78 (m, 2H), 1.69 (m, 4H), 1.57 (m, 4H), 1.31 (m, 1H), 0.99 (m, 2H), 0.91 (d, 6H).

Step 2: To a solution of 3-((3-(4-(2-(isobutylthio)phenoxy)-3-(trifluoromethyl)phenyl)-1,2,4-oxadiazol-5-yl)methyl)-1,3-diazaspiro[4.5]decane-2,4-dione (0.31 g, 0.54 mmol) in dichloromethane (9.3 mL) was added m-chloroperoxybenzoic acid (0.278 g, 1.62 mmol) portion-wise at 0° C. The reaction mixture was stirred at room temperature for 1 hour, and the reaction was then quenched with saturated aqueous sodium bicarbonate solution (25 mL). The organic layer was washed with saturated aqueous sodium thiosulphate solution (20 mL×5), then dried over sodium sulfate and concentrated to provide 3-((3-(4-(2-(isobutylsulfonyl)phenoxy)-3-(trifluoromethyl)phenyl)-1,2,4-oxadiazol-5-yl)methyl)-1,3-diazaspiro[4.5]decane-2,4-dione (0.325 g, 99.3% yield). LCMS Method 11: Rt.=2.30 min.; m/z 605 [M−H]−; 1H NMR (400 MHz, (CD$_3$)$_2$SO) δ 9.02 (s, 1H), 8.22-8.26 (m, 2H), 8.00-8.02 (m, 1H), 7.80-7.84 (m, 1H), 7.54-7.58 (m, 1H), 7.33-7.35 (m, 1H), 7.10-7.15 (m, 1H), 5.01 (s, 2H), 3.31 (d, 2H), 1.98-2.06 (m, 1H), 1.56-1.75 (m, 8H), 1.32 (m, 2H), 1.00 (d, 6H).

Step 3: To a solution of 3-((3-(4-(2-(isobutylsulfonyl)phenoxy)-3-(trifluoromethyl)phenyl)-1,2,4-oxadiazol-5-yl)methyl)-1,3-diazaspiro[4.5]decane-2,4-dione (0.325 g, 0.53 mmol) dissolved in DMF (3.2 mL) was added cesium carbonate (0.348 g, 1.07 mmol) and 4-(2-bromoethyl) morpholine.HBr (0.162 g, 0.58 mmol) The reaction mixture was stirred at room temperature for 2 hours, then poured onto crushed ice and stirred for 15 minutes. The formed precipitate was filtered and collected, then washed with water. The crude product was purified by preparative HPLC, and product fractions were combined and lyophilized to provide 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione (3). LCMS Method 7: Rt.=4.69 min.; m/z 720.4 [M+H], LCMS Method 8: Rt.=5.25 min.; m/z 720.3 [M+H]+; $^1$H NMR (400 MHz, CDCl$_3$) δ 8.41 (s, 1H), 8.14-8.19 (m, 2H), 7.66-7.70 (t, d, J=8.0 Hz, 1H), 7.42-7.46 (t, d, J=7.6 Hz, 1H), 7.03-7.07 (m, 2H), 5.00 (s, 2H), 3.74 (bs, 4H), 3.44-3.48 (t, J=7.6 Hz, 2H), 3.38-3.39 (d, J=6.4 Hz, 2H), 2.63-2.67 (t, J=5.6 Hz, 2H), 2.58 (bs, 4H), 2.26-2.32 (m, 1H), 2.08-2.15 (m, 2H), 1.66-1.91 (m, 7H), 1.21-1.32 (m, 1H), 1.09-1.11 (d, J=6.4 Hz, 6H).

Example 4: 3-((3-(4-(2-(isobutylsulfonyl)phenoxy)-3-(trifluoromethyl)phenyl)-1,2,4-oxadiazol-5-yl)methyl)-5,5-dimethyl-1-(2-(tetrahydro-2H-pyran-4-yl)ethyl)imidazolidine-2,4-dione (4)

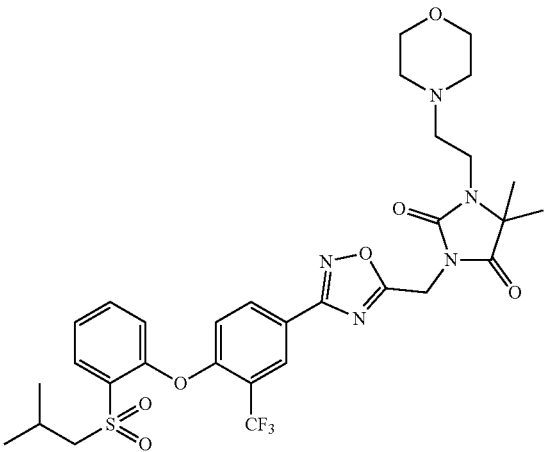

(4)

3-((3-(4-(2-(isobutylsulfonyl)phenoxy)-3-(trifluoromethyl)phenyl)-1,2,4-oxadiazol-5-yl)methyl)-5,5-dimethyl-1-(2-(tetrahydro-2H-pyran-4-yl)ethyl)imidazolidine-2,4-dione (4) was obtained using a procedure similar to the procedure described in Example 1 for the synthesis of 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1), except 5-(chloromethyl)-3-(4-(3,3,3-trifluoro-2-methyl-2-(trifluoromethyl)propoxy)-3-(trifluoromethyl)phenyl)-1,2,4-oxadiazole (int-C6) was replaced with 5-(chloromethyl)-3-(4-(2-(isobutylsulfonyl)phenoxy)-3-(trifluoromethyl)phenyl)-1,2,4-oxadiazole (int-C2), and 4-(2-bromoethyl)morpholine was replaced with 4-(2-bromoethyl)tetrahydro-2H-pyran. $^1$H NMR (400 MHz, CDCl$_3$) δ 8.39 (d, J=2.1 Hz, 1H), 8.18-8.10 (m, 2H), 7.68-7.61 (m, 1H), 7.42 (td, J=7.6, 1.1 Hz, 1H), 7.06-7.00 (m, 2H), 5.00 (s, 1H), 4.02-3.89 (m, 3H), 3.46-3.27 (m, 7H), 2.97 (s, 1H), 2.90 (d, J=0.6 Hz, 1H), 2.34-2.19 (m, 1H), 1.72-1.68 (m, 1H), 1.68-1.63 (m, 3H), 1.51 (s, 4H), 1.40 (s, 2H), 1.08 (d, J=6.7 Hz, 6H); LCMS Method 5: Rt.=3.01 min., m/z 679.7 [M+H].

Example 5; 2-(4-(5-((4,4-dimethyl-2,5-dioxo-3-(2-(tetrahydro-2H-pyran-4-yl)ethyl)imidazolidin-1-yl)methyl)-1,2,4-oxadiazol-3-yl)-2-(trifluoromethyl)phenoxy)-N-isopropyl-N-methylbenzenesulfonamide (5)

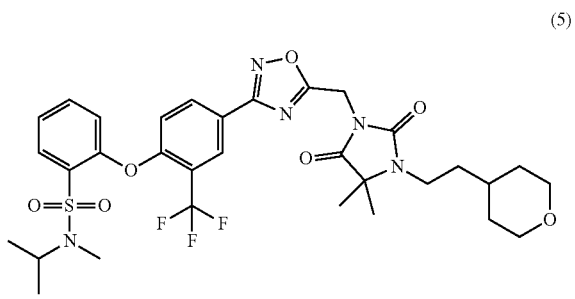 [SMILES: CC(C)N(C)S(=O)(=O)c1ccccc1Oc1ccc(-c2noc(CN3C(=O)N(CCC4CCOCC4)C(C)(C)C3=O)n2)cc1C(F)(F)F]

(5)

2-(4-(5-((4,4-dimethyl-2,5-dioxo-3-(2-(tetrahydro-2H-pyran-4-yl)ethyl)imidazolidin-1-yl)methyl)-1,2,4-oxadiazol-3-yl)-2-(trifluoromethyl)phenoxy)-N-isopropyl-N-methylbenzenesulfonamide (5) was obtained using a procedure similar to the procedure described in Example 1 for the synthesis of 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1), except 5-(chloromethyl)-3-(4-(3,3,3-trifluoro-2-methyl-2-(trifluoromethyl)propoxy)-3-(trifluoromethyl)phenyl)-1,2,4-oxadiazole (int-C6) was replaced with 2-(4-(5-(chloromethyl)-1,2,4-oxadiazol-3-yl)-2-(trifluoromethyl)phenoxy)-N-isopropyl-N-methylbenzenesulfonamide (int-C4). $^1$H NMR (400 MHz, CDCl$_3$) δ 8.28 (d, J=2.1 Hz, 1H), 8.04 (dd, J=8.6, 2.1 Hz, 1H), 7.99 (dd, J=7.9, 1.7 Hz, 1H), 7.46 (ddd, J=8.2, 7.4, 1.7 Hz, 1H), 7.25 (td, J=7.6, 1.1 Hz, 1H), 6.94-6.82 (m, 2H), 4.91 (s, 2H), 4.19-4.02 (m, 1H), 3.88 (ddt, J=11.5, 4.8, 2.3 Hz, 3H), 3.36-3.19 (m, 3H), 2.74 (s, 3H), 1.64-1.45 (m, 7H), 1.43 (s, 6H), 0.99 (brs, 6H); LCMS Method 5: Rt.=3.15 min., m/z 694.4 [M+H].

Example 6: 1-(2-(4-hydroxytetrahydro-2H-pyran-4-yl)ethyl)-3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (6)

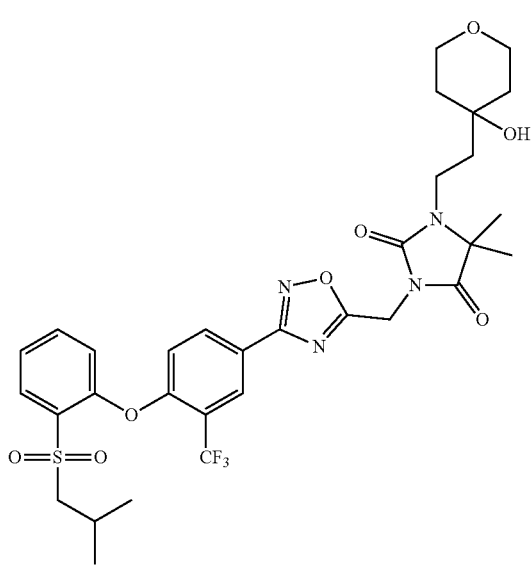

(6)

1-(2-(4-hydroxytetrahydro-2H-pyran-4-yl)ethyl)-3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (6) was obtained using a procedure similar to the procedure described in Example 1 for the synthesis of 5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (1), except 5-(chloromethyl)-3-(4-(3,3,3-trifluoro-2-methyl-2-(trifluoromethyl)propoxy)-3-(trifluoromethyl)phenyl)-1,2,4-oxadiazole (int-C6) was replaced with 5-(chloromethyl)-3-(4-(2-(isobutylsulfonyl)phenoxy)-3-(trifluoromethyl)phenyl)-1,2,4-oxadiazole (int-C2), and 4-(2-bromoethyl)tetrahydro-2H-pyran was replaced with 2-(4-hydroxytetrahydro-2H-pyran-4-yl)ethyl 4-methylbenzenesulfonate (int-D1). $^1$H NMR (400 MHz, CDCl$_3$) δ 8.39 (d, J=2.1 Hz, 1H), 8.15 (ddd, J=11.7, 8.3, 1.9 Hz, 2H), 7.66 (ddd, J=8.2, 7.4, 1.7 Hz, 1H), 7.42 (td, J=7.6, 1.1 Hz, 1H), 7.08-6.99 (m, 2H), 5.00 (s, 2H), 3.84-3.70 (m, 4H), 3.59-3.51 (m, 2H), 3.37 (d, J=6.5 Hz, 2H), 2.27 (dp, J=13.3, 6.7 Hz, 1H), 1.91-1.83 (m, 2H), 1.73 (ddd, J=13.5, 10.4, 5.5 Hz, 2H), 1.64-1.54 (m, 8H), 1.08 (d, J=6.7 Hz, 6H); LCMS Method 4: Rt.=4.69 min., m/z 695.5 [M+H].

Example 1; 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7)

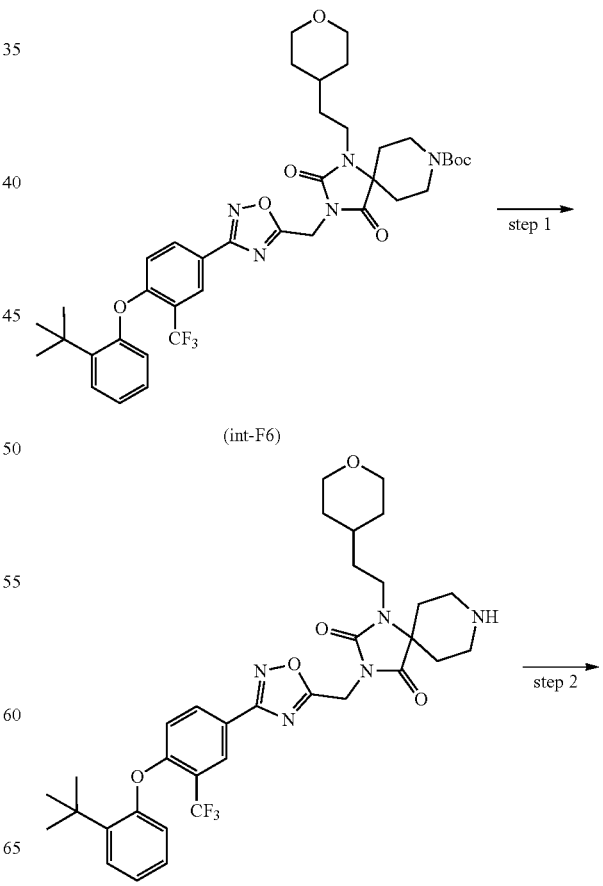

-continued

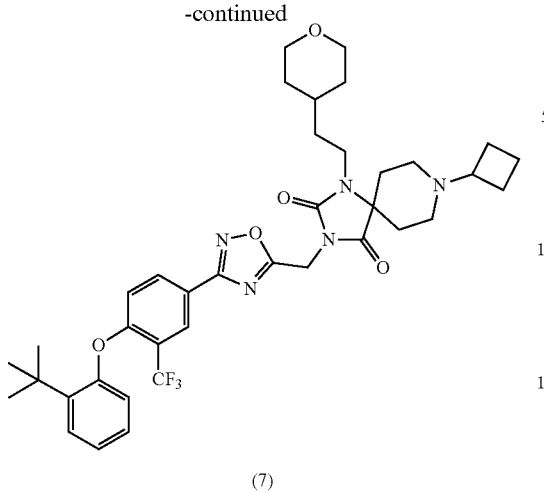

(7)

Step 1: To a solution of tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) (0.6 g, 0.79 mmol) in dichloromethane (6 mL) was added 4M HCl in dioxane (3.0 mL) dropwise. The reaction mixture was stirred at room temperature for 2 hours, then concentrated in vacuo to remove HCl. The mixture was diluted with ethyl acetate (30 mL) and washed with saturated sodium bicarbonate (3×15 mL). The aqueous layer was extracted with ethyl acetate (20 mL), and the combined organic layers were dried over sodium sulfate, filtered, and concentrated in vacuo to provide 3-((3-(4-(2-(tert-butyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione. LCMS Method 11: Rt.=1.87 min.; m/z 656.6 [M+H]+.

Step 2: To a solution of (3-((3-(4-(2-(tert-butyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione) (0.4 g, 0.61 mmol) in dichloromethane (5.6 mL) was added acetic acid (0.4 mL) dropwise, followed by cyclobutanone (0.128 g, 1.83 mmol) and sodium triacetoxyborohydride (0.388 g, 1.83 mmol). The reaction mixture was stirred at room temperature for 16 hours, and the reaction then quenched with saturated sodium bicarbonate (20 mL). The aqueous layer was extracted with dichloromethane (3×25 mL), and the combined organic layers were dried over sodium sulfate, filtered, and concentrated in vacuo. The crude product was purified by preparative HPLC, and pure fractions lyophilized to obtain 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7). LCMS Method 7: Rt.=5.33 min; m/z 710.4 [M+H], LCMS Method 8: Rt.=5.33 min.; m/z 710.4 [M+H]; $^1$H NMR (400 MHz, CD$_3$OD) δ 8.35 (s, 1H), 8.17-8.19 (d, J=8.8 Hz, 1H), 7.52-7.55 (d, J=6.4 Hz, 1H), 7.22-7.29 (m, 2H), 6.97-6.99 (d, J=8.8 Hz, 1H), 6.87-6.89 (d, J=8.0 Hz, 1H), 5.07 (s, 2H), 3.92-3.94 (d, J=8.4 Hz, 2H), 3.64 (m, 1H), 3.40 (m, 5H), 3.32 (m, 3H), 2.33 (m, 4H), 2.13-2.20 (m, 2H), 1.84-1.91 (m, 2H), 1.65-1.74 (m, 5H), 1.40 (s, 9H), 1.25-1.30 (m, 4H).

Example 8: 8-cyclobutyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (8)

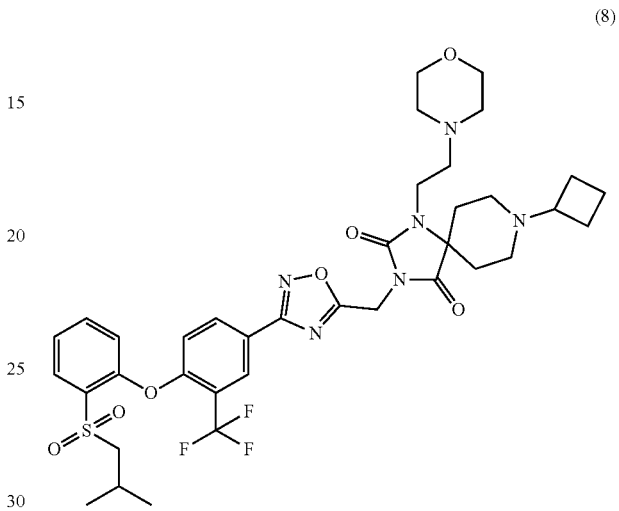

(8)

8-cyclobutyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (8) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2). $^1$H NMR (400 MHz, CD$_3$OD) δ 8.37 (d, J=2.1 Hz, 1H), 8.22 (dd, J=8.7, 2.2 Hz, 1H), 8.08 (dd, J=7.9, 1.7 Hz, 1H), 7.77 (ddd, J=8.3, 7.5, 1.7 Hz, 1H), 7.51 (ddd, J=7.7, 7.7, 1.0 Hz, 1H), 7.20 (dd, J=8.2, 1.0 Hz, 1H), 7.08 (d, J=8.7 Hz, 1H), 5.02 (s, 2H), 3.71-3.63 (m, 4H), 3.46 (dd, J=7.8, 6.6 Hz, 2H), 3.37 (d, J=6.5 Hz, 2H), 2.97-2.81 (m, 3H), 2.67-2.48 (m, 8H), 2.24-2.04 (m, 5H), 1.99-1.81 (m, 4H), 1.81-1.67 (m, 2H), 1.05 (d, J=6.7 Hz, 6H); LCMS Method 5: Rt.=3.07 min., m/z 775.5 [M+H]$^+$.

Example 9. 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione 9)

Example 10. 3-((3-(4-(2-(isobutylsulfonyl)phenoxy)-3-(trifluoromethyl)phenyl)-1,2,4-oxadiazol-5-yl)methyl)-8-methyl-1-(2-morpholinoethyl)-1,3,8-triazaspiro[4.5]decane-2,4-dione (10)

(9)

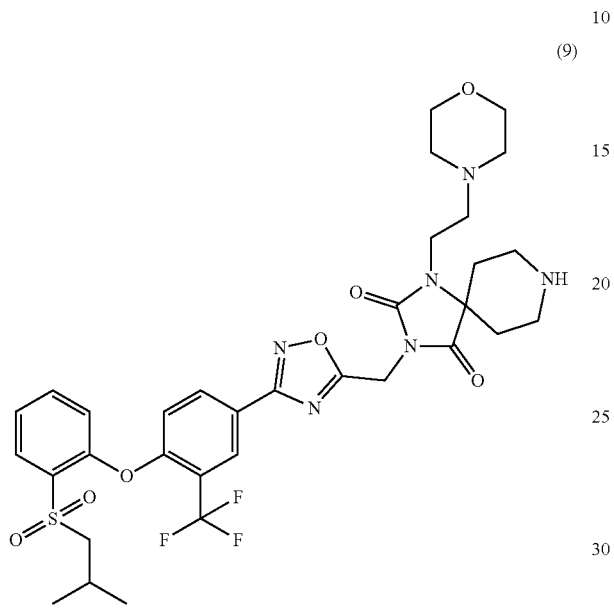

(10)

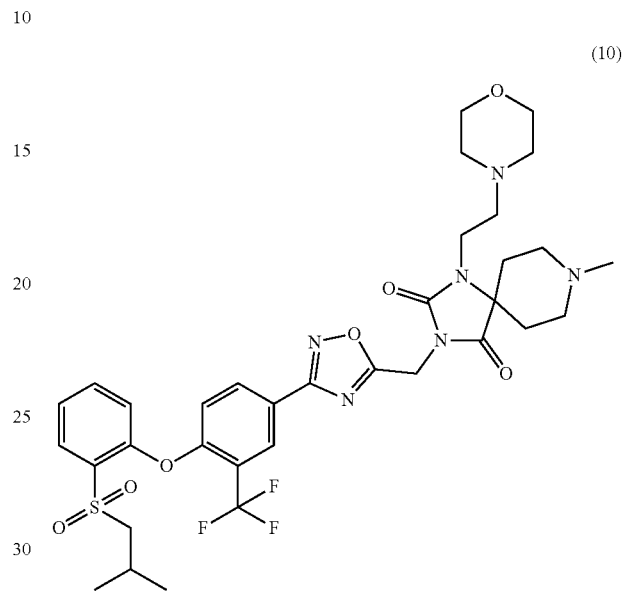

3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (9) was obtained using the procedure described in step 1 of Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2). $^1$H NMR (400 MHz, (CD$_3$)$_2$SO) δ 8.29-8.19 (m, 2H), 8.04-8.00 (m, 1H), 7.85-7.80 (m, 1H), 7.59-7.55 (m, 1H), 7.36-7.33 (m, 1H), 7.29-7.10 (m, 2H), 5.04 (s, 2H), 3.55 (t, J=4.6 Hz, 4H), 3.37-3.35 (m, 4H), 3.09 (t, J=12.5 Hz, 2H), 2.98 (d, J=13.7 Hz, 2H), 2.49-2.39 (m, 6H), 2.05 (tq, J=13.3, 6.4 Hz, 1H), 1.98-1.96 (2H, m), 1.70 (d, J=13.3 Hz, 2H), 0.96 (d, J=6.7 Hz, 6H); LCMS Method 5: Rt.=2.64 min., m/z 721.8 [M+H]$^+$.

3-((3-(4-(2-(isobutylsulfonyl)phenoxy)-3-(trifluoromethyl)phenyl)-1,2,4-oxadiazol-5-yl)methyl)-8-methyl-1-(2-morpholinoethyl)-1,3,8-triazaspiro[4.5]decane-2,4-dione (10) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with formaldehyde with sodium cyanoborohydride used as the reducing agent. $^1$H NMR (400 MHz, CDCl$_3$) δ 8.29 (d, J=2.1 Hz, 1H), 8.05 (ddd, J=8.0, 4.4, 2.0 Hz, 2H), 7.58 (tt, J=7.7, 2.0 Hz, 1H), 7.41-7.30 (m, 1H), 7.01-6.88 (m, 2H), 4.91 (s, 2H), 3.67-3.57 (m, 4H), 3.39 (m, 2H), 3.27 (d, J=6.6 Hz, 2H), 2.97 (m, 4H), 2.56 (m, 3H), 2.46 (d, J=6.2 Hz, 6H), 2.21 (m, 3H), 1.86-1.78 (m, 2H), 0.99 (d, J=6.7 Hz, 6H); LCMS Method 5: Rt.=2.75 min., m/z 735.8 [M+H]$^+$.

Example 11; 2-(4-(5-((8-cyclobutyl-1-(2-morpholinoethyl)-2,4-dioxo-1,3,8-triazaspiro[4.5]decan-3-yl)methyl)-1,2,4-oxadiazol-3-yl)-2-(trifluoromethyl)phenoxy)-N-isopropyl-N-methylbenzenesulfonamide (11)

Example 12: 8-cyclobutyl-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione (12)

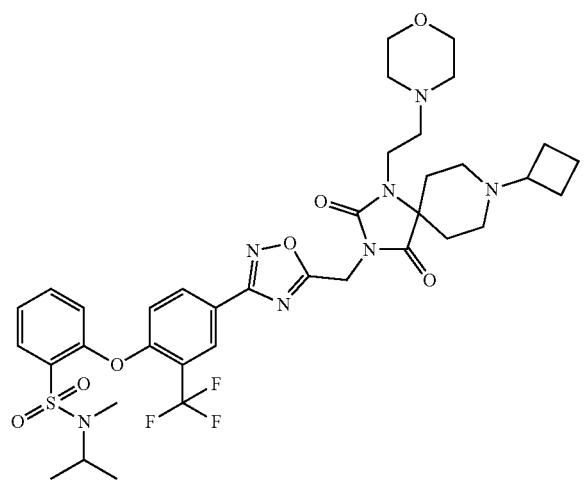
(11)

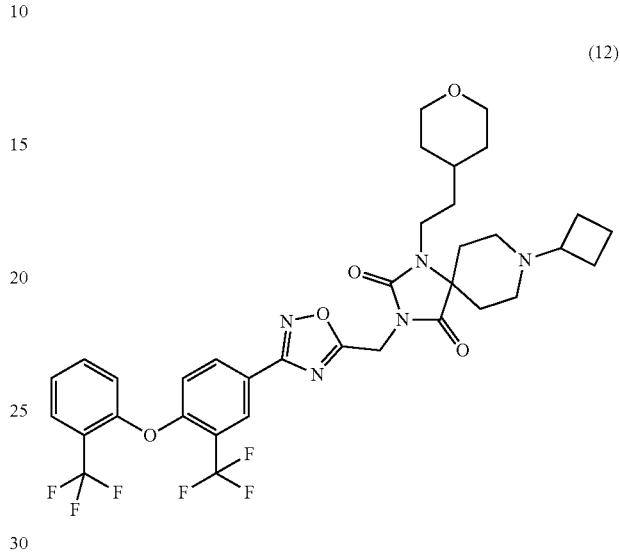
(12)

2-(4-(5-((8-cyclobutyl-1-(2-morpholinoethyl)-2,4-dioxo-1,3,8-triazaspiro[4.5]decan-3-yl)methyl)-1,2,4-oxadiazol-3-yl)-2-(trifluoromethyl)phenoxy)-N-isopropyl-N-methylbenzenesulfonamide (11) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(N-isopropyl-N-methylsulfamoyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F4). $^1$H NMR (400 MHz, (CD3)$_2$SO) δ 8.27-8.17 (m, 2H), 7.98 (dd, J=7.9, 1.7 Hz, 1H), 7.72 (td, J=7.8, 1.7 Hz, 1H), 7.48 (td, J=7.7, 1.1 Hz, 1H), 7.20 (dd, J=8.3, 1.1 Hz, 1H), 7.04 (d, J=8.7 Hz, 1H), 5.02 (d, J=4.8 Hz, 2H), 4.08 (p, J=6.7 Hz, 1H), 3.54 (t, J=4.6 Hz, 4H), 3.36 (d, J=14.7 Hz, 2H), 2.69 (m, 6H), 2.43 (m, 8H), 2.05-1.98 (m, 4H), 1.82-1.68 (m, 4H), 1.61 (t, J=8.7 Hz, 2H), 0.96 (d, J=6.7 Hz, 6H); LCMS Method 5: Rt.=3.07 min., m/z 790.4 [M+H]$^+$.

8-cyclobutyl-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione (12) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 2,4-dioxo-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F7). $^1$H NMR (400 MHz, (CD$_3$)$_2$SO) δ 8.28-8.18 (m, 2H), 7.90 (dd, J=7.9, 1.6 Hz, 1H), 7.82-7.73 (m, 1H), 7.54-7.46 (m, 1H), 7.33 (d, J=8.3 Hz, 1H), 7.18 (d, J=8.7 Hz, 1H), 5.02 (s, 2H), 3.84-3.76 (m, 2H), 3.28-3.14 (m, 4H), 2.79 (q, J=7.7 Hz, 1H), 2.71 (d, J=11.5 Hz, 2H), 2.44-2.34 (m, 2H), 2.04-1.93 (m, 4H), 1.79 (d, J=9.5 Hz, 2H), 1.72 (d, J=13.2 Hz, 2H), 1.61 (d, J=13.8 Hz, 4H), 1.50 (t, J=7.1 Hz, 3H), 1.26-1.12 (m, 2H); LCMS Method 5: Rt.=3.40 min., m/z 722.5 [M+H]$^+$.

Example 13: 8-cyclobutyl-1-(2-morpholinoethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione (13)

Example 14: 8-cyclobutyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (14)

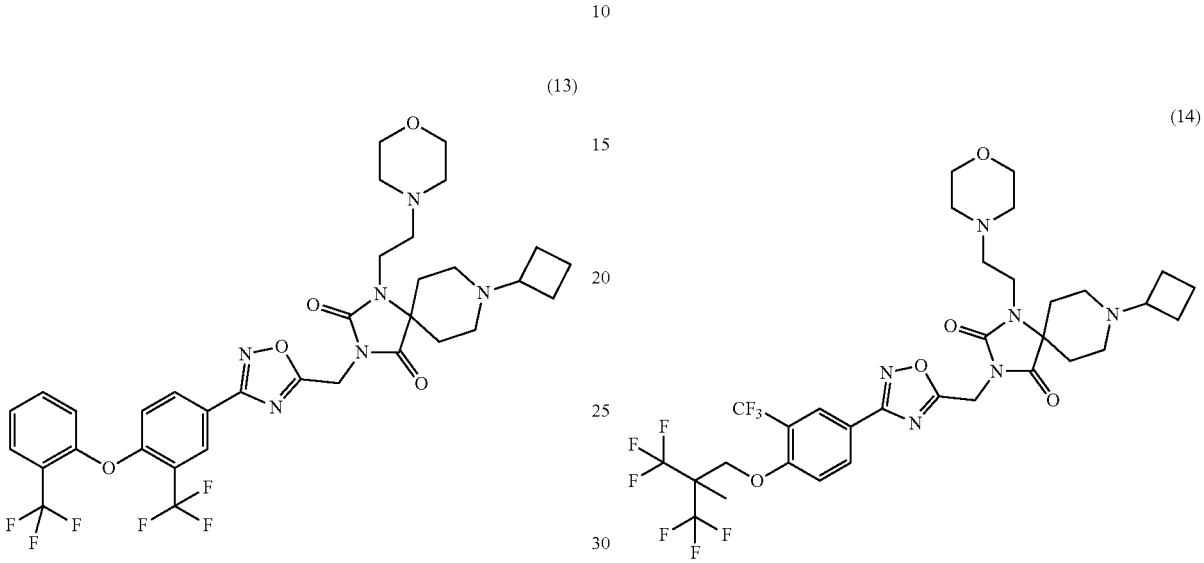

8-cyclobutyl-1-(2-morpholinoethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione (13) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F3). $^1$H NMR (400 MHz, (CD3)$_2$SO) δ 8.28-8.18 (m, 2H), 7.93-7.86 (m, 1H), 7.78 (t, J=7.9 Hz, 1H), 7.50 (t, J=7.6 Hz, 1H), 7.34 (d, J=8.3 Hz, 1H), 7.18 (d, J=8.7 Hz, 1H), 5.02 (s, 2H), 3.54 (t, J=4.6 Hz, 4H), 3.16 (d, J=5.0 Hz, 1H), 2.80 (q, J=7.8 Hz, 1H), 2.71 (d, J=11.4 Hz, 2H), 2.46 (d, J=7.6 Hz, 9H), 2.00 (d, J=4.2 Hz, 2H), 1.97 (s, 2H), 1.74 (dd, J=19.6, 11.1 Hz, 4H), 1.66-1.59 (m, 2H); LCMS Method 5: Rt.=3.18 min., m/z 723.5 [M+H]$^+$.

8-cyclobutyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (14) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 1-(2-morpholinoethyl)-2,4-dioxo-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F5). $^1$H NMR (CD$_3$CN, 400 MHz) δ 7.90-8.41 (m, 2H), 7.22-7.45 (m, 1H), 4.87 (s, 2H), 4.47 (s, 2H), 3.51-3.65 (m, 4H), 3.33 (t, 2H, J=7.3 Hz), 2.68-2.91 (m, 3H), 2.50 (t, 2H, J=7.3 Hz), 2.35-2.51 (m, 6H), 1.98-2.09 (m, 3H), 1.65-1.82 (m, 4H), 1.55-1.60 (m, 2H), 1.47-1.52 (m, 4H); LCMS Method 6: Rt.=3.22 min., m/z 757.8 [M+H]$^+$.

Example 15; 8-cyclobutyl-3-((3-(4-(2-(methylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (15)

Example 16; 3-((3-(4-(2-(tert-butyl)phenoxy)-3-(trifluoromethyl)phenyl)-1,2,4-oxadiazol-5-yl)methyl)-8-cyclobutyl-1-(2-morpholinoethyl)-1,3,8-triazaspiro[4.5]decane-2,4-dione (16)

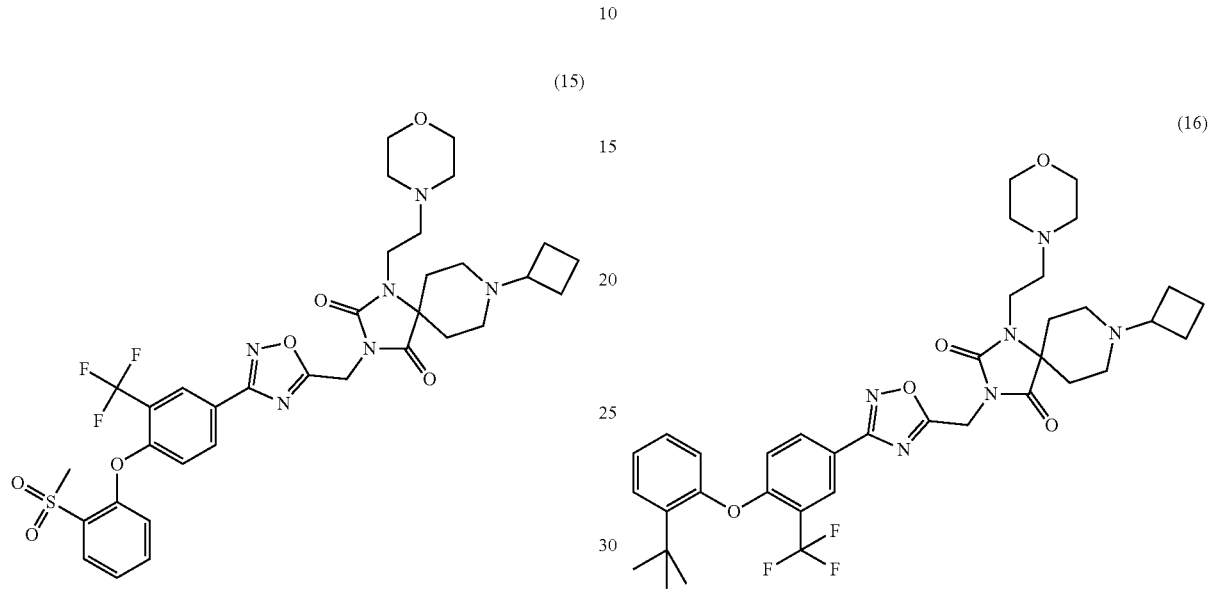

8-cyclobutyl-3-((3-(4-(2-(methylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (15) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(methylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-I2). 1H NMR (400 MHz, MeOD) δ 8.38 (s, 1H), 8.23-8.25 (d, J=7.6 Hz, 1H), 8.10-8.11 (d, J=6.8 Hz, 1H), 7.77-7.80 (t, J=6.8 Hz, 1H), 7.50-7.54 (t, J=7.6 Hz, 1H), 7.21-7.23 (d, J=8.0 Hz, 1H), 7.09-7.11 (d, J=8.4 Hz, 1H), 5.04 (s, 2H), 3.68-3.70 (t, J=4.4 Hz, 4H), 3.46-3.49 (t, J=6.8 Hz, 2H), 3.269 (m, 3H), 2.91-2.99 (m, 3H), 2.62-2.68 (m, 4H), 2.56 (bs, 4H), 2.12-2.14 (m, 4H), 1.87-1.96 (m, 4H), 1.76 (m, 2H); LCMS Method 7: Rt.=3.75 min., m/z 733.3 [M+H]$^+$.

3-((3-(4-(2-(tert-butyl)phenoxy)-3-(trifluoromethyl)phenyl)-1,2,4-oxadiazol-5-yl)methyl)-8-cyclobutyl-1-(2-morpholinoethyl)-1,3,8-triazaspiro[4.5]decane-2,4-dione (16) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(tert-butyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F1). $^1$H NMR (400 MHz, CD$_3$OD) δ 8.35 (s, 1H), 8.16-8.18 (d, J=8.8 Hz, 1H), 7.51-7.53 (d, J=6.0 Hz, 1H), 7.19-7.24 (m, 2H), 6.96-6.98 (d, J=8.8 Hz, 1H), 6.87-6.89 (d, J=8.0 Hz, 1H), 5.03 (s, 2H), 3.68-3.70 (m, 4H), 3.46-3.49 (t, J=6.8 Hz, 2H), 2.86-2.94 (m, 3H), 2.56-2.67 (m, 8H), 2.16 (m, 4H), 1.9 (m, 4H), 1.75 (m, 2H), 1.40 (s, 9H); LCMS Method 7: Rt.=4.49 min., m/z 711.4 [M+H]$^+$.

Example 17; 8-cyclobutyl-3-((3-(4-(2-(methylsulfonyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione (17)

Example 18: 8-cyclobutyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione (18)

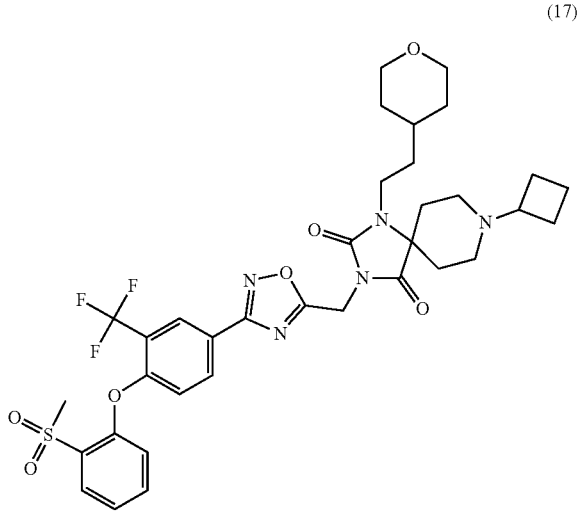 [SMILES: CS(=O)(=O)c1ccccc1Oc1ccc(-c2noc(CN3C(=O)N(CCC4CCOCC4)C4(CCN(C5CCC5)CC4)C3=O)n2)cc1C(F)(F)F]

(17)

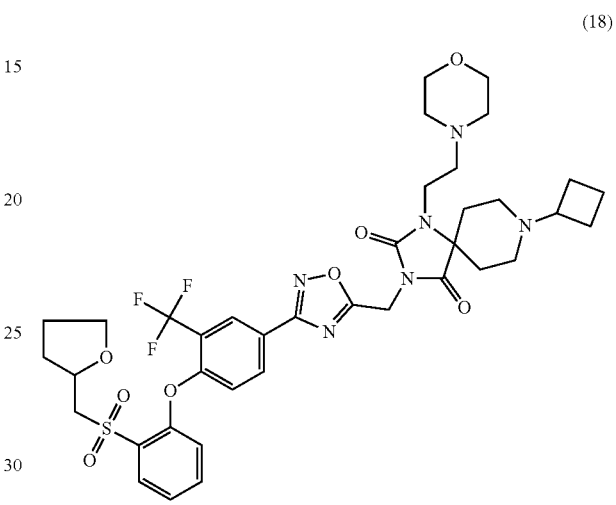

(18)

8-cyclobutyl-3-((3-(4-(2-(methylsulfonyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione (17) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(methylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-I1). $^1$H NMR (400 MHz, (CD$_3$)$_2$SO) δ 8.26 (s, 1H), 8.22-8.24 (d, J=8.8 Hz, 1H), 8.01-8.03 (d, J=7.6 Hz, 1H), 7.80-7.84 (t, J=7.2 Hz, 1H), 7.54-7.58 (t, J=7.6 Hz, 1H), 7.33-7.35 (d, J=8.0 Hz, 1H), 7.14-7.16 (d, J=8.8 Hz, 1H), 5.03 (s, 2H), 3.80-3.82 (d, J=8.0 Hz, 2H), 3.21-3.33 (m, 4H), 2.77-2.80 (m, 1H), 2.69-2.72 (m, 4H), 2.33-2.42 (m, 4H), 1.96-1.98 (m, 4H), 1.71-1.80 (m, 4H), 1.60-1.63 (m, 4H), 1.50 (m, 2H), 1.15-120 (m, 2H); LCMS Method 8: Rt.=3.68 min., m/z 732.3 [M+H]$^+$.

8-cyclobutyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione (18) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 1-(2-morpholinoethyl)-2,4-dioxo-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-8-carboxylate (int-I5). $^1$H NMR (400 MHz, CD$_3$OD) δ 8.38 (s, 1H), 8.22-8.25 (d, J=12 Hz, 1H), 8.06-8.08 (d, J=8 Hz, 1H), 7.75-7.79 (t, J=16 Hz, 1H), 7.49-7.53 (t, J=16 Hz, 1H), 7.18-7.20 (d, J=8 Hz, 1H), 7.09-7.11 (d, J=8 Hz, 1H), 5.04 (s, 2H), 4.31 (br, 1H), 3.80 (m, 2H), 3.60 (m, 4H), 3.50 (m, 2H), 3.48 (m, 2H), 2.90 (m, 3H), 2.64 (m, 8H), 2.11-2.13 (m, 5H), 1.86-1.95 (m, 6H), 1.68-1.76 (m, 3H); LCMS Method 7: Rt.=3.88 min., m/z 803.4 [M+H]$^+$.

Example 19: 8-cyclobutyl-1-(2-(tetrahydro-2H-pyran-4-yl)ethyl)-3-((3-(4-(2-((((tetrahydrofuran-2-yl)methyl) sulfonyl) phenoxy)-3-(trifluoromethyl) phenyl)-1,2,4-oxadiazol-5-yl)methyl)-1,3,8-triazaspiro[4.5]decane-2,4-dione (19)

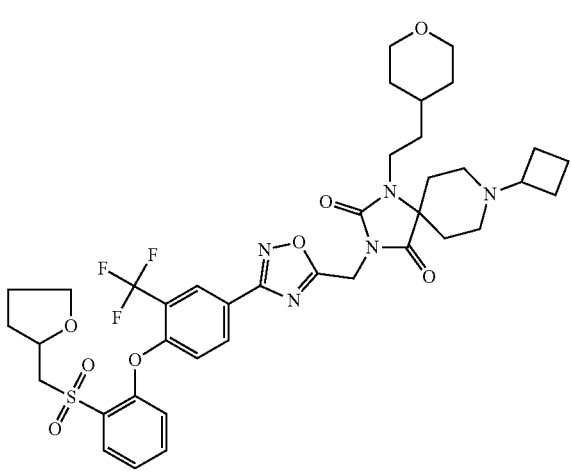

(20)

8-cyclobutyl-1-(2-(tetrahydro-2H-pyran-4-yl)ethyl)-3-((3-(4-(2-((((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione (20) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 2,4-dioxo-1-(2-(tetrahydro-2H-pyran-4-yl)ethyl)-3-((3-(4-(2-((((tetrahydrofuran-2-yl)methyl)sulfonyl)phenoxy)-3-(trifluoromethyl) phenyl)-1,2,4-oxadiazol-5-yl)methyl)-1,3,8-triazaspiro[4.5]decane-8-carboxylate (int-I4). 1H NMR (400 MHz, CD$_3$OD) δ 8.39 (s, 1H), 8.23-8.25 (d, J=8.0 Hz, 1H), 8.06-8.08 (d, J=7.6 Hz, 1H), 7.75-7.79 (t, J=8.0 Hz, 1H), 7.49-7.53 (t, J=7.6 Hz, 1H), 7.18-7.20 (d, J=8.0 Hz, 1H), 7.10-7.12 (d, J=8.4 Hz, 1H), 5.04 (s, 2H), 4.31 (m, 1H), 3.92-3.95 (d, J=12 Hz, 2H), 3.71-3.80 (m, 2H), 3.55-3.64 (m, 2H), 3.33-3.44 (m, 5H), 2.87-2.94 (m, 3H), 2.57-2.63 (t, J=11.6 Hz, 2H), 2.11-2.13 (m, 5H), 1.86-1.95 (m, 6H), 1.64-1.76 (m, 8H), 1.31-1.34 (m, 3H); LCMS Method 8: Rt.=4.10 min., m/z 802.4 [M+H]$^+$.

Example 20: 8-(4-hydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (20)

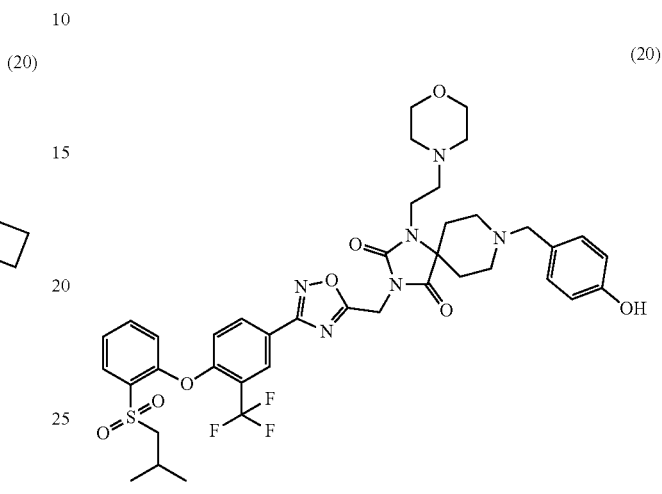

(20)

8-(4-hydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (20) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with 4-hydroxybenzaldehyde. 1H NMR (400 MHz, CD$_3$OD) δ 8.40 (d, J=2.1 Hz, 1H), 8.25 (dd, J=8.7, 2.2 Hz, 1H), 8.11 (dd, J=7.9, 1.7 Hz, 1H), 7.80 (ddd, J=8.2, 7.4, 1.7 Hz, 1H), 7.54 (td, J=7.7, 1.0 Hz, 1H), 7.27-7.15 (m, 3H), 7.11 (d, J=8.7 Hz, 1H), 6.83-6.73 (m, 2H), 5.06 (s, 2H), 3.73-3.65 (m, 4H), 3.55 (s, 2H), 3.52-3.45 (m, 2H), 3.40 (d, J=6.5 Hz, 2H), 2.96-2.88 (m, 2H), 2.88-2.76 (m, 2H), 2.71-2.60 (m, 2H), 2.60-2.51 (m, 4H), 2.25-2.11 (m, 3H), 1.91-1.82 (m, 2H), 1.08 (d, J=6.7 Hz, 6H); LCMS Method 5: Rt.=2.79 min., m/z 827.9 [M+H]+.

Example 21; 8-(3,5-dihydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (21)

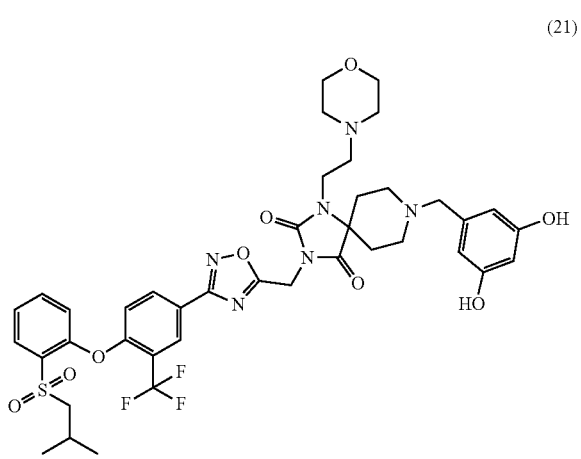 [SMILES: CC(C)CS(=O)(=O)c1ccccc1Oc1ccc(-c2noc(CN3C(=O)N(CCN4CCOCC4)C4(CCN(Cc5cc(O)cc(O)c5)CC4)C3=O)n2)cc1C(F)(F)F]

(21)

8-(3,5-dihydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (21) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with 3,5-dihydroxybenzaldehyde. $^1$H NMR (400 MHz, CD$_3$OD) δ 8.40 (d, J=2.1 Hz, 1H), 8.25 (dd, J=8.7, 2.2 Hz, 1H), 8.10 (dd, J=7.9, 1.7 Hz, 1H), 7.80 (ddd, J=8.3, 7.5, 1.7 Hz, 1H), 7.54 (td, J=7.7, 1.1 Hz, 1H), 7.22 (dd, J=8.3, 1.0 Hz, 1H), 7.10 (d, J=8.7 Hz, 1H), 6.32 (d, J=2.2 Hz, 2H), 6.21 (t, J=2.2 Hz, 1H), 5.05 (s, 2H), 3.74-3.65 (m, 4H), 3.54-3.44 (m, 4H), 3.39 (d, J=6.5 Hz, 2H), 2.96-2.87 (m, 2H), 2.85-2.75 (m, 2H), 2.68-2.61 (m, 2H), 2.60-2.52 (m, 4H), 2.27-2.11 (m, 3H), 1.90-1.81 (m, 2H), 1.07 (d, J=6.7 Hz, 6H); LCMS Method 5: Rt.=2.57 min., m/z 843.7 [M+H]$^+$.

Example 22; 3-((3-(4-(2-(isobutylsulfonyl)phenoxy)-3-(trifluoromethyl)phenyl)-1,2,4-oxadiazol-5-yl)methyl)-8-(1-methylpiperidin-4-yl)-1-(2-morpholinoethyl)-1,3,8-triazaspiro[4.5]decane-2,4-dione (22)

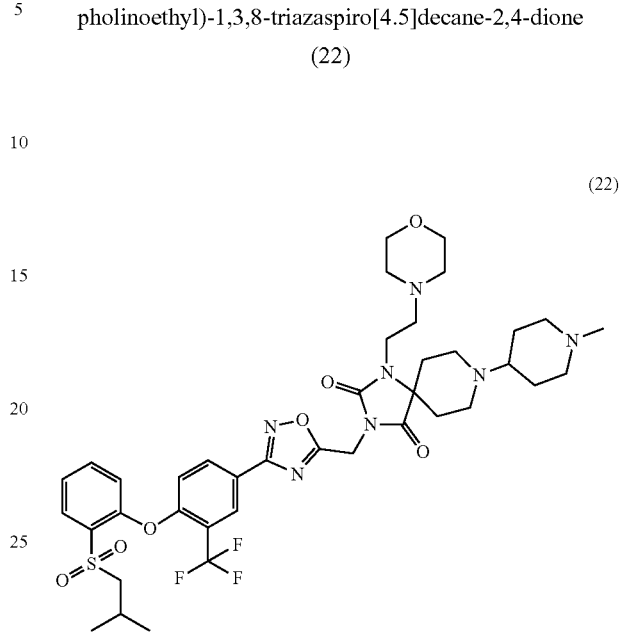

(22)

3-((3-(4-(2-(isobutylsulfonyl)phenoxy)-3-(trifluoromethyl)phenyl)-1,2,4-oxadiazol-5-yl)methyl)-8-(1-methylpiperidin-4-yl)-1-(2-morpholinoethyl)-1,3,8-triazaspiro[4.5]decane-2,4-dione (22) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with 1-methylpiperidin-4-one. $^1$H NMR (400 MHz, CD$_3$OD) δ 8.40 (d, J=2.1 Hz, 1H), 8.25 (dd, J=8.7, 2.1 Hz, 1H), 8.11 (dd, J=7.9, 1.7 Hz, 1H), 7.80 (ddd, J=8.3, 7.5, 1.7 Hz, 1H), 7.55 (td, J=7.7, 1.1 Hz, 1H), 7.23 (dd, J=8.3, 1.0 Hz, 1H), 7.11 (d, J=8.7 Hz, 1H), 5.06 (s, 2H), 3.74-3.66 (m, 4H), 3.53-3.46 (m, 2H), 3.40 (d, J=6.5 Hz, 2H), 3.08-2.92 (m, 6H), 2.70-2.61 (m, 2H), 2.62-2.53 (m, 4H), 2.51-2.39 (m, 1H), 2.30 (s, 3H), 2.27-2.02 (m, 5H), 1.98-1.85 (m, 4H), 1.71-1.57 (m, 2H), 1.08 (d, J=6.8 Hz, 6H); LCMS Method 5: Rt.=2.76 min.; m/z 818.8 [M+H]$^+$.

Example 23; 3-((3-(4-(2-(isobutylsulfonyl)phenoxy)-3-(trifluoromethyl)phenyl)-1,2,4-oxadiazol-5-yl)methyl)-8-(1-methylpyrrolidin-3-yl)-1-(2-morpholinoethyl)-1,3,8-triazaspiro[4.5]decane-2,4-dione (23)

Example 24; 8-ethyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (24)

(23)

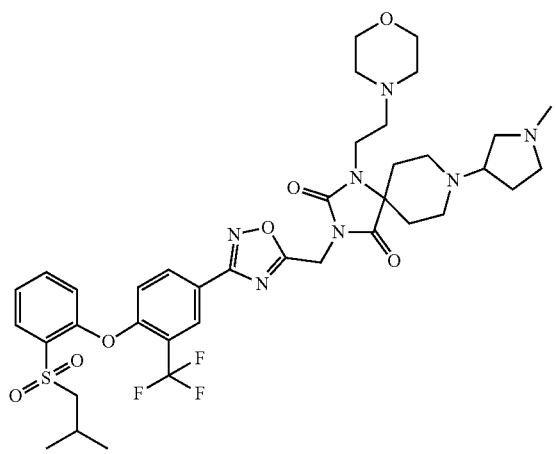

(24)

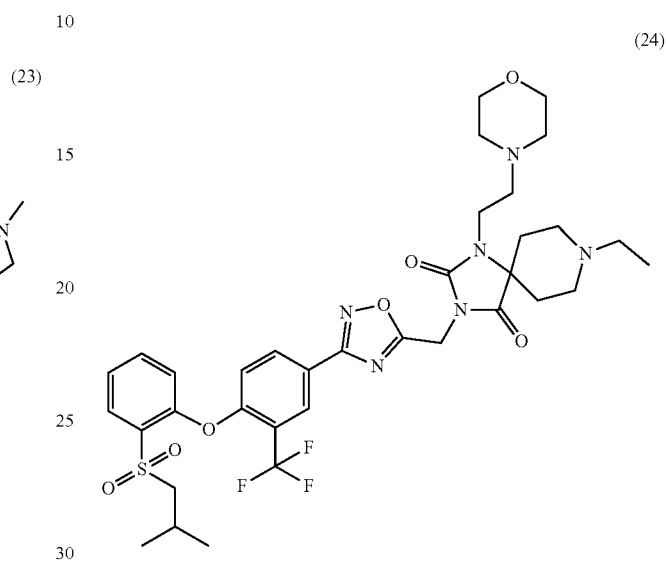

3-((3-(4-(2-(isobutylsulfonyl)phenoxy)-3-(trifluoromethyl)phenyl)-1,2,4-oxadiazol-5-yl)methyl)-8-(1-methylpyrrolidin-3-yl)-1-(2-morpholinoethyl)-1,3,8-triazaspiro[4.5]decane-2,4-dione (23) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with 1-methylpyrrolidin-3-one. $^1$H NMR (400 MHz, CD$_3$OD) δ 8.41 (d, J=2.1 Hz, 1H), 8.26 (dd, J=8.7, 2.2 Hz, 1H), 8.12 (dd, J=7.9, 1.7 Hz, 1H), 7.81 (ddd, J=8.2, 7.5, 1.7 Hz, 1H), 7.56 (td, J=7.7, 1.1 Hz, 1H), 7.24 (dd, J=8.3, 1.0 Hz, 1H), 7.12 (d, J=8.7 Hz, 1H), 5.07 (s, 2H), 3.75-3.67 (m, 4H), 3.54-3.46 (m, 2H), 3.41 (d, J=6.5 Hz, 2H), 3.18-3.05 (m, 1H), 3.05-2.92 (m, 2H), 2.92-2.76 (m, 4H), 2.71-2.62 (m, 2H), 2.62-2.48 (m, 5H), 2.47-2.39 (m, 1H), 2.40 (s, 3H), 2.28-2.04 (m, 4H), 1.96-1.77 (m, 3H), 1.09 (d, J=6.7 Hz, 6H); LCMS Method 5: Rt.=2.72 min., m/z 804.6 [M+H]$^+$.

8-ethyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (24) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with acetaldehyde. $^1$H NMR (400 MHz, CD$_3$OD) δ 8.37 (d, J=2.1 Hz, 1H), 8.22 (dd, J=8.8, 2.1 Hz, 1H), 8.13-8.04 (m, 1H), 7.84-7.73 (m, 1H), 7.52 (td, J=7.6, 1.0 Hz, 1H), 7.20 (dd, J=8.3, 1.1 Hz, 1H), 7.07 (d, J=8.8 Hz, 1H), 5.07 (s, 2H), 3.71-3.63 (m, 4H), 3.56-3.43 (m, 6H), 3.36 (d, J=6.5 Hz, 2H), 3.20-3.11 (m, 2H), 2.68-2.62 (m, 2H), 2.60-2.52 (m, 4H), 2.48-2.37 (m, 2H), 2.24-2.09 (m, 3H), 1.41-1.26 (m, 3H), 1.05 (d, J=6.7 Hz, 6H); LCMS Method 5: Rt.=2.88 min., m/z 749.4 [M+H]$^+$.

Example 25; 3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyridazin-3-ylmethyl)-1,3,8-triazaspiro[4.5]decane-2,4-dione (25)

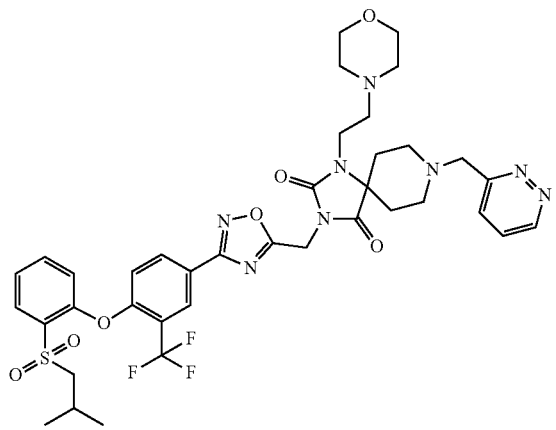

(25)

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyridazin-3-ylmethyl)-1,3,8-triazaspiro[4.5]decane-2,4-dione (25) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with pyridazine-3-carbaldehyde. $^1$H NMR (400 MHz, CD$_3$OD) δ 9.10 (dd, J=4.9, 1.7 Hz, 1H), 8.34 (d, J=2.1 Hz, 1H), 8.20 (dd, J=8.8, 2.1 Hz, 1H), 8.06 (dd, J=7.9, 1.7 Hz, 1H), 7.87 (dd, J=8.5, 1.7 Hz, 1H), 7.81-7.68 (m, 2H), 7.50 (td, J=7.6, 1.1 Hz, 1H), 7.19 (dd, J=8.3, 1.0 Hz, 1H), 7.06 (d, J=8.7 Hz, 1H), 5.03 (s, 2H), 3.94 (s, 2H), 3.70-3.62 (m, 4H), 3.52-3.43 (m, 2H), 3.36 (d, J=6.5 Hz, 2H), 3.01-2.91 (m, 2H), 2.90-2.80 (m, 2H), 2.66-2.57 (m, 2H), 2.57-2.49 (m, 4H), 2.25-2.09 (m, 3H), 1.88-1.79 (m, 2H), 1.04 (d, J=6.7 Hz, 6H); LCMS Method 5: Rt.=2.62 min., m/z 813.6 [M+H]$^+$.

Example 26; 3-((3-(4-(2-(isobutylsulfonyl)phenoxy)-3-(trifluoromethyl)phenyl)-1,2,4-oxadiazol-5-yl)methyl)-1-(2-morpholinoethyl)-8-((tetrahydro-2H-pyran-4-yl)methyl)-1,3,8-triazaspiro[4.5]decane-2,4-dione (26)

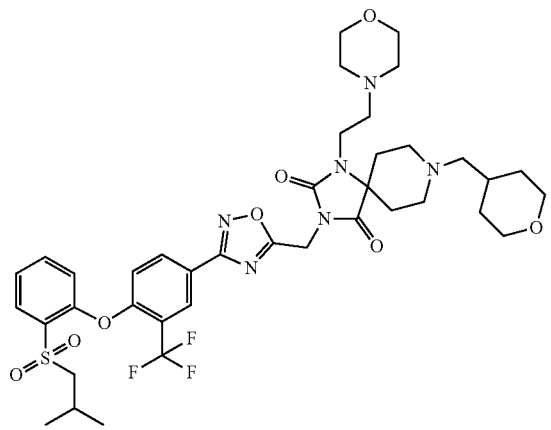

(26)

3-((3-(4-(2-(isobutylsulfonyl)phenoxy)-3-(trifluoromethyl)phenyl)-1,2,4-oxadiazol-5-yl)methyl)-1-(2-morpholinoethyl)-8-((tetrahydro-2H-pyran-4-yl)methyl)-1,3,8-triazaspiro[4.5]decane-2,4-dione (26) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with tetrahydro-2H-pyran-4-carbaldehyde. $^1$H NMR (400 MHz, CD$_3$OD) δ 8.38-8.34 (m, 1H), 8.21 (dd, J=8.7, 2.1 Hz, 1H), 8.07 (dd, J=7.9, 1.7 Hz, 1H), 7.77 (td, J=7.8, 1.7 Hz, 1H), 7.51 (td, J=7.7, 1.1 Hz, 1H), 7.20 (dd, J=8.3, 1.1 Hz, 1H), 7.07 (d, J=8.7 Hz, 1H), 5.02 (s, 2H), 3.97-3.89 (m, 2H), 3.70-3.63 (m, 4H), 3.51-3.33 (m, 6H), 2.86 (d, J=11.6 Hz, 2H), 2.74 (td, J=12.2, 2.6 Hz, 2H), 2.66-2.50 (m, 6H), 2.31 (d, J=7.0 Hz, 2H), 2.22-2.10 (m, 3H), 1.90-1.77 (m, 3H), 1.76-1.60 (m, 2H), 1.37-1.18 (m, 2H), 1.04 (d, J=6.7 Hz, 6H); LCMS Method 5: Rt.=2.97 min., m/z 819.6 [M+H]$^+$.

Example 27: 8-(cyclopropylmethyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (27)

Example 28; 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28)

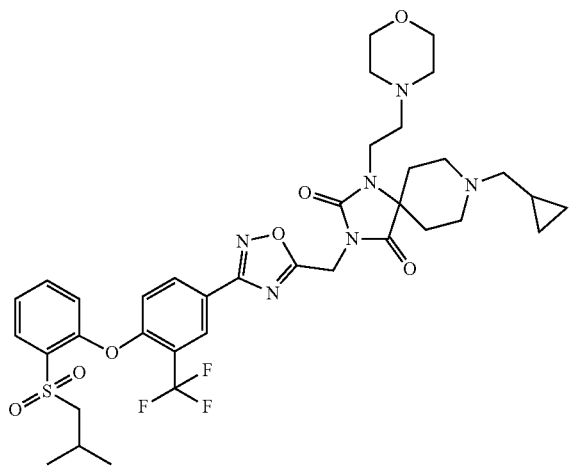

(27)

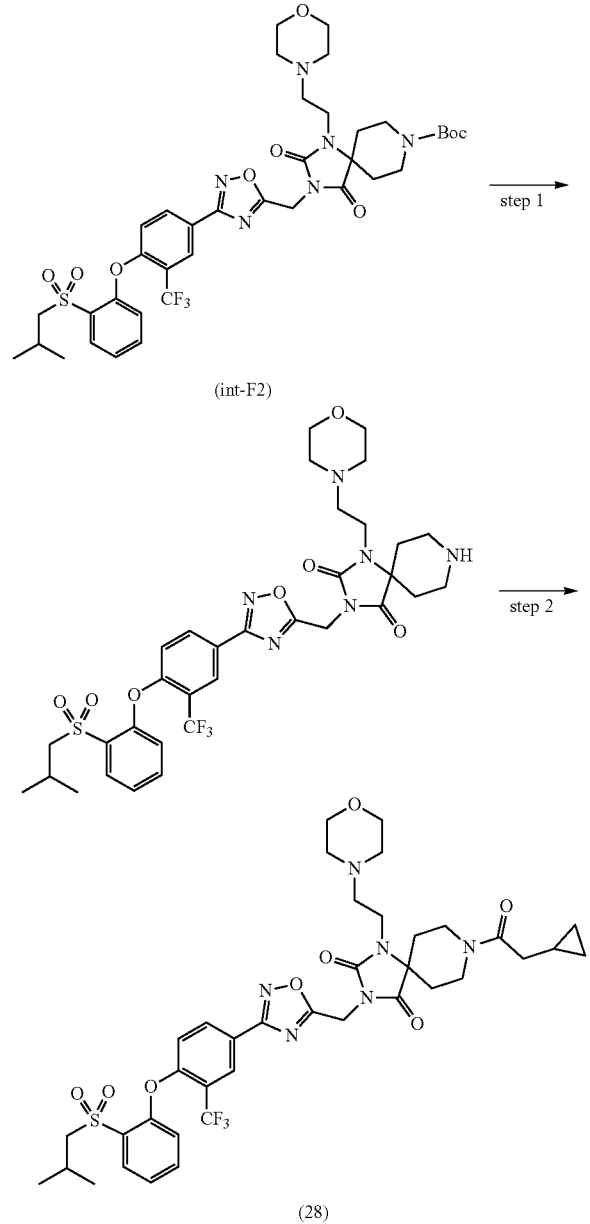

8-(cyclopropylmethyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (27) was obtained using a procedure similar to the procedure described in Example 7 for the synthesis of 3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione (7), except tert-butyl 3-((3-(4-(2-(tert-butyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F6) was replaced with tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) and cyclobutanone was replaced with cyclopropanecarbaldehyde. $^1$H NMR (400 MHz, CD$_3$OD) δ 8.35 (d, J=2.0 Hz, 1H), 8.20 (dd, J=8.7, 2.1 Hz, 1H), 8.07 (dd, J=7.9, 1.7 Hz, 1H), 7.76 (td, J=7.8, 1.7 Hz, 1H), 7.50 (td, J=7.7, 1.1 Hz, 1H), 7.19 (dd, J=8.2, 1.0 Hz, 1H), 7.07 (d, J=8.7 Hz, 1H), 5.02 (s, 2H), 3.71-3.62 (m, 4H), 3.49-3.42 (m, 2H), 3.36 (d, J=6.5 Hz, 2H), 3.09-3.01 (m, 2H), 2.84-2.74 (m, 2H), 2.67-2.58 (m, 2H), 2.58-2.50 (m, 4H), 2.36 (d, J=6.6 Hz, 2H), 2.22-2.09 (m, 3H), 1.91-1.81 (m, 2H), 1.04 (d, J=6.7 Hz, 6H), 0.96-0.86 (m, 1H), 0.62-0.49 (m, 2H), 0.23-0.11 (m, 2H); LCMS Method 5: Rt.=3.07 min., m/z 775.3 [M+H]$^+$.

Step 1: To a flask containing tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) (1.78 g, 2.168 mmol) was added DCM (21.7 mL), followed by TFA (8.35 mL, 108 mmol). The reaction was allowed to stir at room temperature under nitrogen. After 45 minutes, the reaction mixture was concentrated in vacuo to remove TFA. The mixture was diluted with ethyl acetate (60 mL) and washed with saturated sodium bicarbonate (4×5 mL). The aqueous layer was extracted with ethyl acetate (20 mL), and the combined organics were washed with brine, dried over sodium sulfate, filtered, and concentrated in vacuo to give 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione. The product was used directly in the next step without purification.

Step 2: To a vial containing 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (50 mg, 0.069 mmol), 2-cyclopropylacetic acid (10.4 mg, 0.104 mmol), and (1-[Bis(dimethylamino)methylene]-1H-1,2,3-triazolo[4,5-b]pyridinium 3-oxide hexafluorophosphate (47.5 mg, 0.125 mmol) was added DCM (0.7 mL) followed by N,N-diisopropylethylamine (36 iL, 0.208 mmol). The reaction was allowed to stir at room temperature overnight, then concentrated in vacuo and the residue purified on reverse phase ISCO, 10-100% acetonitrile in water with 0.1% ammonium hydroxide. Pure fractions were combined and lyophilized to provide 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28). LCMS Method 1: Rt. 2.86 min., m/z 803.3. [M+H]$^+$; $^1$H NMR (400 MHz, CD$_3$OD) δ 8.36 (d, J=2.1 Hz, 1H), 8.21 (dd, J=8.7, 2.1 Hz, 1H), 8.07 (dd, J=7.9, 1.7 Hz, 1H), 7.77 (ddd, J=8.2, 7.4, 1.7 Hz, 1H), 7.51 (td, J=7.6, 1.0 Hz, 1H), 7.20 (dd, J=8.3, 1.0 Hz, 1H), 7.07 (d, J=8.7 Hz, 1H), 5.05 (s, 2H), 4.64-4.55 (m, 1H), 4.03-3.94 (m, 1H), 3.83-3.73 (m, 1H), 3.69-3.60 (m, 4H), 3.49-3.39 (m, 2H), 3.36 (d, J=6.5 Hz, 2H), 3.34-3.25 (m, 1H), 2.63-2.54 (m, 2H), 2.54-2.47 (m, 4H), 2.45-2.29 (m, 2H), 2.24-1.96 (m, 3H), 1.96-1.82 (m, 2H), 1.04 (d, J=6.7 Hz, 6H), 1.03-0.96 (m, 1H), 0.62-0.47 (m, 2H), 0.27-0.13 (m, 2H).

Example 29; 3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-5-carbonyl)-1,3,8-triazaspiro[4.5]decane-2,4-dione (29)

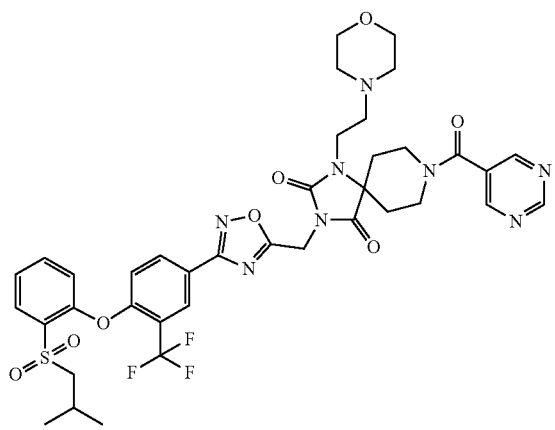

(29)

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-5-carbonyl)-1,3,8-triazaspiro[4.5]decane-2,4-dione (29) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with pyrimidine-5-carboxylic acid. 1H NMR (400 MHz, CD$_3$OD) δ 9.24 (s, 1H), 8.94 (s, 2H), 8.36 (d, J=2.1 Hz, 1H), 8.21 (dd, J=8.7, 2.2 Hz, 1H), 8.07 (dd, J=7.9, 1.7 Hz, 1H), 7.77 (ddd, J=8.3, 7.5, 1.7 Hz, 1H), 7.51 (td, J=7.7, 1.0 Hz, 1H), 7.19 (dd, J=8.2, 1.0 Hz, 1H), 7.06 (d, J=8.7 Hz, 1H), 5.07 (s, 2H), 4.77-4.64 (m, 1H), 4.02-3.87 (m, 1H), 3.80-3.70 (m, 1H), 3.70-3.55 (m, 5H), 3.55-3.46 (m, 2H), 3.36 (d, J=6.5 Hz, 2H), 2.65-2.58 (m, 2H), 2.58-2.48 (m, 4H), 2.26-2.08 (m, 3H), 2.07-1.97 (m, 1H), 1.93-1.80 (m, 1H), 1.04 (d, J=6.7 Hz, 6H); LCMS Method 5: Rt.=2.59 min., m/z 827.6 [M+H]$^+$.

Example 30; 1-(2-morpholinoethyl)-8-(pyrimidine-5-carbonyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (30)

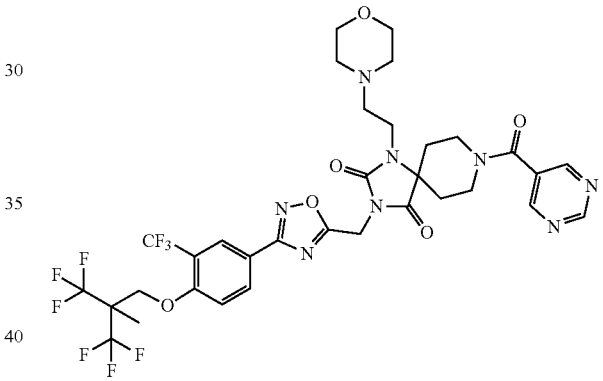

(30)

1-(2-morpholinoethyl)-8-(pyrimidine-5-carbonyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (30) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) was replaced with tert-butyl 1-(2-morpholinoethyl)-2,4-dioxo-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F5) and 2-cyclopropylacetic acid was replaced with pyrimidine-5-carboxylic acid. $^1$H NMR (CD$_3$CN, 400 MHz) δ 9.23 (s, 1H), 8.86 (s, 2H), 8.19-8.35 (m, 2H), 7.19-7.45 (m, 1H), 4.96 (s, 2H), 4.53 (s, 2H), 3.75-3.96 (m, 2H), 3.60-3.64 (m, 4H), 3.41 (t, 3H, J=7.1 Hz), 2.35-2.65 (m, 7H), 2.20-2.41 (m, 2H), 2.06-2.25 (m, 2H), 1.60 (s, 3H); LCMS Method 1: Rt.=2.73 min., m/z 809.4 [M+H]$^+$.

Example 31: 8-(pyrimidine-5-carbonyl)-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (31)

Example 32; 8-(3-(dimethylamino)propanoyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (32)

(31)

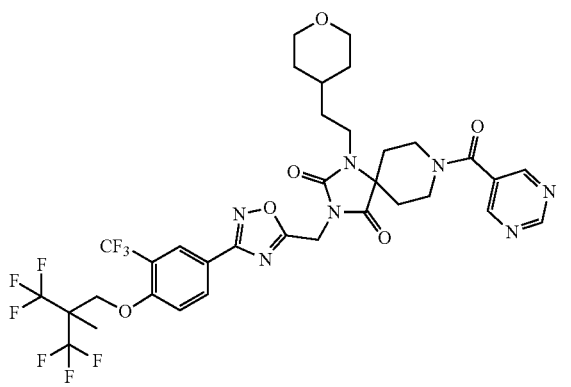

(32)

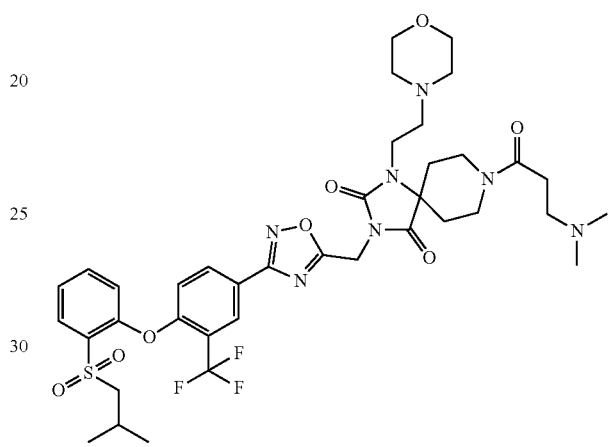

8-(pyrimidine-5-carbonyl)-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (31) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) was replaced with tert-butyl 2,4-dioxo-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F9) and 2-cyclopropylacetic acid was replaced with pyrimidine-5-carboxylic acid. $^1$H NMR (CD$_3$CN, 400 MHz) δ 9.18 (s, 1H), 8.81 (s, 2H), 8.11-8.42 (m, 2H), 7.20-7.51 (m, 1H), 4.90 (s, 2H), 4.52-4.71 (m, 1H), 4.47 (s, 2H), 3.71-3.92 (m, 3H), 3.61-3.72 (m, 1H), 3.41-3.53 (m, 1H), 3.21-3.30 (m, 4H), 1.51-1.63 (m, 8H, J=13.2 Hz), 1.19-1.22 (m, 4H), 0.71-0.89 (m, 2H); LCMS Method 1: Rt.=2.88 min., m/z 808.3 [M+H]$^+$.

8-(3-(dimethylamino)propanoyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (32) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28) except 2-cyclopropylacetic acid was replaced with 3-(dimethylamino)propanoic acid. $^1$H NMR (400 MHz, CD$_3$OD) δ 8.41 (d, J=2.1 Hz, 1H), 8.27 (dd, J=8.7, 2.2 Hz, 1H), 8.11 (dd, J=7.9, 1.7 Hz, 1H), 7.81 (ddd, J=8.2, 7.5, 1.7 Hz, 1H), 7.55 (td, J=7.7, 1.1 Hz, 1H), 7.24 (dd, J=8.2, 1.1 Hz, 1H), 7.11 (d, J=8.7 Hz, 1H), 5.10 (s, 2H), 4.67-4.58 (m, 1H), 4.10-4.01 (m, 1H), 3.74-3.61 (m, 4H), 3.55-3.45 (m, 2H), 3.40 (d, J=6.5 Hz, 2H), 2.79-2.48 (m, 9H), 2.35 (s, 6H), 2.28-1.87 (m, 5H), 1.77-1.62 (m, 1H), 1.53-1.34 (m, 2H), 1.07 (d, J=7.0 Hz, 6H); LCMS Method 5: Rt.=2.81 min., m/z 820.6 [M+H]$^+$.

Example 33; 3-((3-(4-(2-(isobutylsulfonyl)phenoxy)-3-(trifluoromethyl)phenyl)-1,2,4-oxadiazol-5-yl)methyl)-8-(1-methylpiperidine-4-carbonyl)-1-(2-morpholinoethyl)-1,3,8-triazaspiro[4.5]decane-2,4-dione (33)

Example 34; 3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-4-carbonyl)-1,3,8-triazaspiro[4.5]decane-2,4-dione (34)

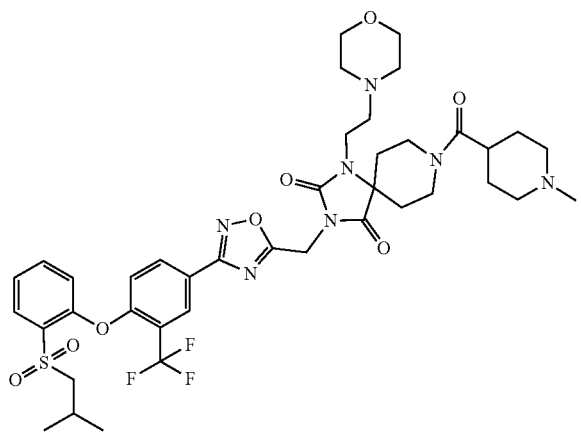

(33)

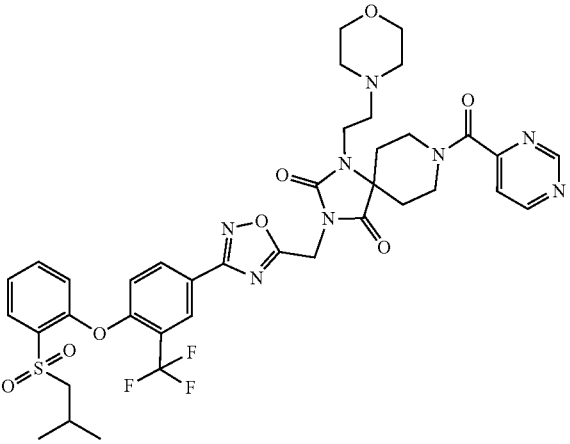

(34)

3-((3-(4-(2-(isobutylsulfonyl)phenoxy)-3-(trifluoromethyl)phenyl)-1,2,4-oxadiazol-5-yl)methyl)-8-(1-methylpiperidine-4-carbonyl)-1-(2-morpholinoethyl)-1,3,8-triazaspiro[4.5]decane-2,4-dione (33) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with 1-methylpiperidine-4-carboxylic acid. $^1$H NMR (400 MHz, CD$_3$OD) δ 8.36 (d, J=2.1 Hz, 1H), 8.22 (dd, J=8.7, 2.2 Hz, 1H), 8.07 (dd, J=7.9, 1.7 Hz, 1H), 7.77 (ddd, J=8.3, 7.5, 1.7 Hz, 1H), 7.52 (td, J=7.6, 1.0 Hz, 1H), 7.20 (dd, J=8.3, 1.0 Hz, 1H), 7.07 (d, J=8.7 Hz, 1H), 5.06 (s, 2H), 4.63-4.53 (m, 1H), 4.17-4.01 (m, 1H), 3.87-3.74 (m, 1H), 3.69-3.61 (m, 4H), 3.49-3.40 (m, 2H), 3.37 (d, J=6.5 Hz, 2H), 3.34-3.26 (m, 1H), 2.97-2.85 (m, 2H), 2.75-2.64 (m, 1H), 2.58 (t, J=7.1 Hz, 2H), 2.55-2.47 (m, 4H), 2.26 (s, 3H), 2.22-2.04 (m, 4H), 2.04-1.80 (m, 4H), 1.80-1.69 (m, 3H), 1.05 (d, J=6.7 Hz, 6H); LCMS Method 5: Rt.=2.82 min., m/z 846.6 [M+H]$^+$.

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-4-carbonyl)-1,3,8-triazaspiro[4.5]decane-2,4-dione (34) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with pyrimidine-4-carboxylic acid. $^1$H NMR (400 MHz, CD$_3$OD) δ 9.23 (d, J=1.4 Hz, 1H), 8.96 (d, J=5.1 Hz, 1H), 8.35 (d, J=2.1 Hz, 1H), 8.21 (dd, J=8.7, 2.2 Hz, 1H), 8.07 (dd, J=7.9, 1.7 Hz, 1H), 7.77 (ddd, J=8.2, 7.4, 1.7 Hz, 1H), 7.71 (dd, J=5.1, 1.5 Hz, 1H), 7.51 (td, J=7.7, 1.1 Hz, 1H), 7.19 (dd, J=8.2, 1.0 Hz, 1H), 7.06 (d, J=8.7 Hz, 1H), 5.06 (s, 2H), 4.74-4.66 (m, 1H), 3.90-3.76 (m, 2H), 3.71-3.63 (m, 4H), 3.57 (td, J=13.2, 3.1 Hz, 1H), 3.50 (t, J=7.0 Hz, 2H), 3.36 (d, J=6.5 Hz, 2H), 2.67-2.57 (m, 2H), 2.56-2.50 (m, 4H), 2.35-2.08 (m, 3H), 2.06-1.98 (m, 1H), 1.90-1.82 (m, 1H), 1.04 (d, J=6.7 Hz, 6H); LCMS Method 5: Rt.=2.60 min., m/z 827.6 [M+H]$^+$.

Example 35; 8-butyryl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (35)

Example 36; 3-((3-(4-(2-(isobutylsulfonyl)phenoxy)-3-(trifluoromethyl)phenyl)-1,2,4-oxadiazol-5-yl)methyl)-8-(pyrazine-2-carbonyl)-1-(2-(tetrahydro-2H-pyran-4-yl)ethyl)-1,3,8-triazaspiro[4.5]decane-2,4-dione (36)

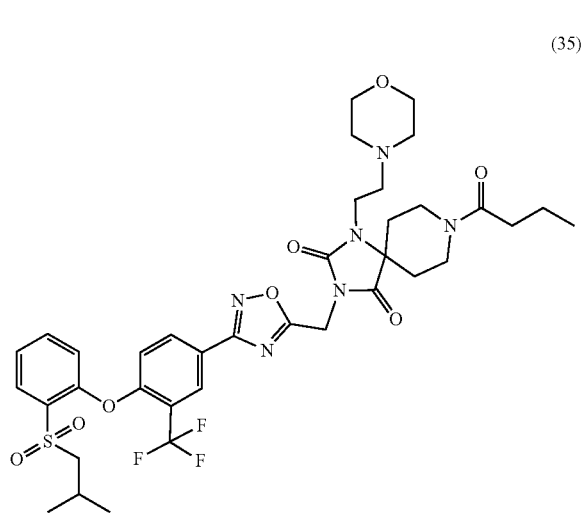 [SMILES: CCCC(=O)N1CCC2(CC1)C(=O)N(Cc1nc(-c3ccc(Oc4ccccc4S(=O)(=O)CC(C)C)c(C(F)(F)F)c3)no1)C(=O)N2CCN1CCOCC1]

(35)

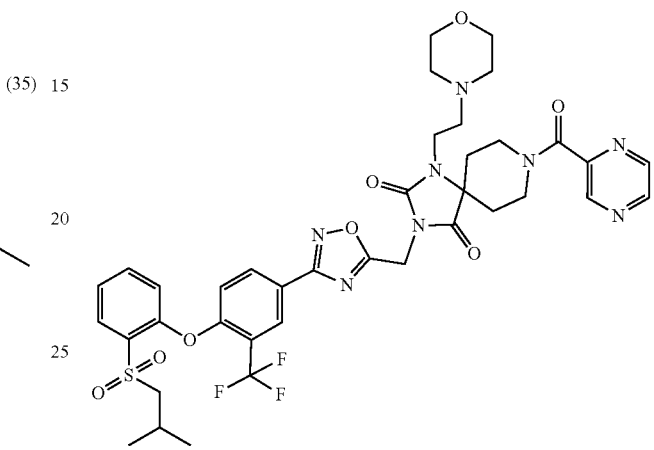

(36)

8-butyryl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (35) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with butyric acid. $^1$H NMR (400 MHz, CD$_3$OD) δ 8.37 (d, J=2.1 Hz, 1H), 8.23 (dd, J=8.8, 2.1 Hz, 1H), 8.08 (dd, J=7.9, 1.7 Hz, 1H), 7.77 (ddd, J=8.3, 7.5, 1.7 Hz, 1H), 7.52 (td, J=7.7, 1.1 Hz, 1H), 7.20 (dd, J=8.3, 1.0 Hz, 1H), 7.08 (d, J=8.7 Hz, 1H), 5.06 (s, 2H), 4.63-4.55 (m, 1H), 4.07-3.97 (m, 1H), 3.84-3.73 (m, 1H), 3.70-3.61 (m, 4H), 3.50-3.41 (m, 2H), 3.37 (d, J=6.5 Hz, 2H), 3.32-3.24 (m, 1H), 2.59 (t, J=7.1 Hz, 2H), 2.55-2.47 (m, 4H), 2.47-2.37 (m, 2H), 2.25-2.05 (m, 2H), 2.05-1.84 (m, 3H), 1.65 (h, J=7.5 Hz, 2H), 1.05 (d, 6.6 Hz, 6H), 0.99 (t, 7.5 Hz, 3H); LCMS Method 5: Rt.=2.85 min., m/z 791.5 [M+H]$^+$.

3-((3-(4-(2-(isobutylsulfonyl)phenoxy)-3-(trifluoromethyl)phenyl)-1,2,4-oxadiazol-5-yl)methyl)-8-(pyrazine-2-carbonyl)-1-(2-(tetrahydro-2H-pyran-4-yl)ethyl)-1,3,8-triazaspiro[4.5]decane-2,4-dione (36) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) was replaced with tert-butyl 3-((3-(4-(2-(isobutylsulfonyl)phenoxy)-3-(trifluoromethyl)phenyl)-1,2,4-oxadiazol-5-yl)methyl)-2,4-dioxo-1-(2-(tetrahydro-2H-pyran-4-yl)ethyl)-1,3,8-triazaspiro[4.5]decane-8-carboxylate (int-F8) and 2-cyclopropylacetic acid was replaced with pyrazine-2-carboxylic acid. $^1$H NMR (400 MHz, CD$_3$OD) δ 8.89 (d, J=1.5 Hz, 1H), 8.71 (d, J=2.6 Hz, 1H), 8.64 (dd, J=2.6, 1.5 Hz, 1H), 8.35 (d, J=2.1 Hz, 1H), 8.21 (dd, J=8.7, 2.1 Hz, 1H), 8.07 (dd, J=7.9, 1.7 Hz, 1H), 7.77 (ddd, J=8.2, 7.5, 1.7 Hz, 1H), 7.51 (td, J=7.6, 1.1 Hz, 1H), 7.20 (dd, J=8.3, 1.0 Hz, 1H), 7.06 (d, J=8.7 Hz, 1H), 5.06 (s, 2H), 4.77-4.68 (m, 1H), 4.01-3.79 (m, 4H), 3.63-3.53 (m, 1H), 3.44-3.33 (m, 6H), 2.32-2.08 (m, 3H), 2.08-1.97 (m, 1H), 1.91-1.81 (m, 1H), 1.74-1.65 (m, 2H), 1.65-1.55 (m, 3H), 1.42-1.21 (m, 2H), 1.04 (d, J=6.7 Hz, 6H); LCMS Method 1: Rt.=2.87 min., m/z 826.2 [M+H]$^+$.

Example 37; 3-((3-(4-(2-(isobutylsulfonyl)phenoxy)-3-(trifluoromethyl)phenyl)-1,2,4-oxadiazol-5-yl)methyl)-8-(pyrimidine-5-carbonyl)-1-(2-(tetrahydro-2H-pyran-4-yl)ethyl)-1,3,8-triazaspiro[4.5]decane-2,4-dione (37)

Example 38: 5,5-dimethyl-1-(2-morpholinoethyl)-3-((3-(4-(2-(((tetrahydrofuran-3-yl)methyl) sulfonyl) phenoxy)-3-(trifluoromethyl)phenyl)-1,2,4-oxadiazol-5-yl)methyl) imidazolidine-2,4-dione (38)

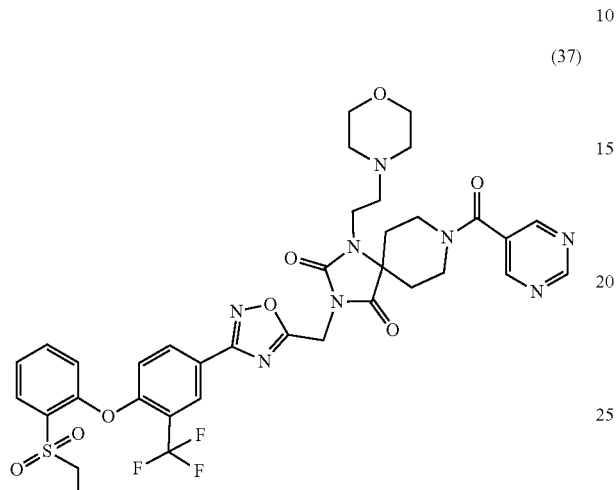

(37)

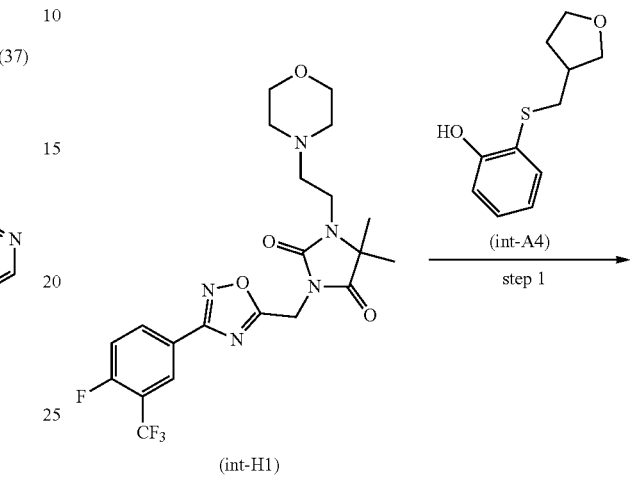

(int-H1)

3-((3-(4-(2-(isobutylsulfonyl)phenoxy)-3-(trifluoromethyl)phenyl)-1,2,4-oxadiazol-5-yl)methyl)-8-(pyrimidine-5-carbonyl)-1-(2-(tetrahydro-2H-pyran-4-yl)ethyl)-1,3,8-triazaspiro[4.5]decane-2,4-dione (37) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except tert-butyl 3-((3-(4-(2-(isobutylsulfonyl)phenoxy)-3-(trifluoromethyl)phenyl)-1,2,4-oxadiazol-5-yl)methyl)-1-(2-morpholino ethyl)-2,4-dioxo-1,3,8-triazaspiro[4.5]decane-8-carboxylate (int-F2) was replaced with tert-butyl 3-((3-(4-(2-(isobutylsulfonyl)phenoxy)-3-(trifluoromethyl)phenyl)-1,2,4-oxadiazol-5-yl)methyl)-2,4-dioxo-1-(2-(tetrahydro-2H-pyran-4-yl) ethyl)-1,3,8-triazaspiro[4.5]decane-8-carboxylate (int-F8) and 2-cyclopropylacetic acid was replaced with pyrimidine-5-carboxylic acid. $^1$H NMR (400 MHz, CD$_3$OD) δ 9.23 (s, 1H), 8.94 (s, 2H), 8.34 (d, J=2.1 Hz, 1H), 8.19 (dd, J=8.7, 2.1 Hz, 1H), 8.06 (dd, J=7.9, 1.7 Hz, 1H), 7.76 (ddd, J=8.2, 7.4, 1.7 Hz, 1H), 7.51 (td, J=7.6, 1.0 Hz, 1H), 7.19 (dd, J=8.3, 1.0 Hz, 1H), 7.05 (d, J=8.7 Hz, 1H), 5.06 (s, 2H), 3.93 (d, J=12.2 Hz, 1H), 3.99-3.84 (m, 3H), 3.78-3.69 (m, 1H), 3.65-3.53 (m, 1H), 3.44-3.32 (m, 6H), 2.25-2.07 (m, 3H), 2.06-1.96 (m, 1H), 1.89-1.80 (m, 1H), 1.68 (d, J=13.4 Hz, 2H), 1.64-1.54 (m, 3H), 1.36-1.20 (m, 2H), 1.04 (d, J=6.7 Hz, 6H); LCMS Method 5: Rt.=2.76 min, m/z 826.4 [M+H]$^+$.

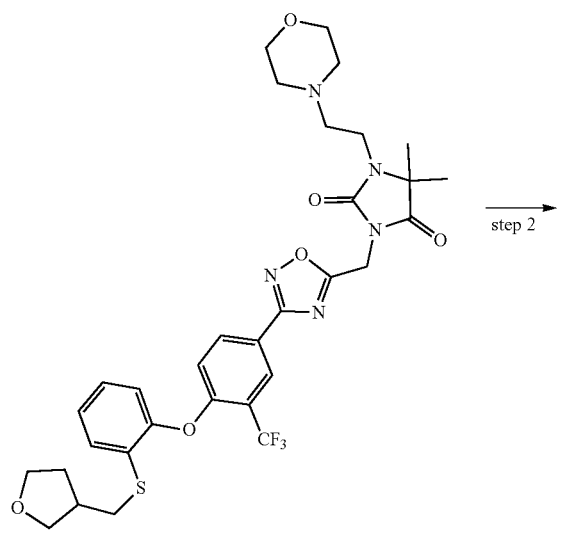

-continued

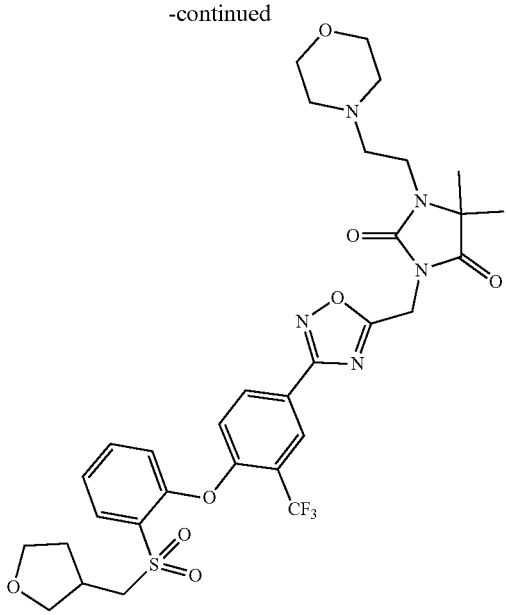

(38)

Step 1: To a solution of 2-(((tetrahydrofuran-3-yl)methyl)thio)phenol (int-A4) (120 mg, 0.6 mmol) in DMF (5 mL) was added potassium carbonate (157 mg, 1.1 mmol), followed by 3-((3-(4-fluoro-3-(trifluoromethyl)phenyl)-1,2,4-oxadiazol-5-yl)methyl)-5,5-dimethyl-1-(2-morpholinoethyl)imidazolidine-2,4-dione (int-H1) (305 mg, 0.6 mmol). The reaction mixture was stirred at 90° C. for 16 hours. The crude reaction mixture was quenched with water and then extracted with dichloromethane. The organic layer was separated and washed with brine, dried over anhydrous sodium sulfate, filtered, and concentrated in vacuo to obtain 5,5-dimethyl-1-(2-morpholinoethyl)-3-((3-(4-(2-(((tetrahydrofuran-3-yl)methyl)thio)phenoxy)-3-(trifluoromethyl)phenyl)-1,2,4-oxadiazol-5-yl)methyl)imidazolidine-2,4-dione, which was carried onto next step without purification. LCMS Method 10: Rt.=1.396 min.; m/z 676.15 [M+H]+.

Step 2: To a solution of 5,5-dimethyl-1-(2-morpholinoethyl)-3-((3-(4-(2-(((tetrahydrofuran-3-yl)methyl)thio)phenoxy)-3-(trifluoromethyl)phenyl)-1,2,4-oxadiazol-5-yl)methyl)imidazolidine-2,4-dione (400 mg, 0.6 mmol) in neat trifluroacetic acid (8.0 mL), cooled to 0° C. with an ice-water bath, was added hydrogen peroxide (21 µL, 0.9 mmol). The reaction mixture was stirred at room temperature for 16 hours. The crude reaction mixture was concentrated in vacuo and was quenched with saturated aqueous sodium bicarbonate solution and extracted with dichloromethane. The organic layer was isolated, washed with brine, dried over anhydrous sodium sulfate, filtered and concentrated in vacuo. The crude residue was purified by preparative reverse-phase HPLC; Mobile Phase: 0.1% HCOOH in water and acetonitrile to afford 5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione (38). LCMS Method 9: Rt.=0.55 min.; m/z 708.3 [M+H]+; $^1$H NMR (400 MHz, (CD$_3$)$_2$SO) δ 8.27 (d, J=2.1 Hz, 1H), 8.24 (dd, J=8.6, 2.2 Hz, 1H), 8.03 (dd, J=7.9, 1.7 Hz, 1H), 7.84 (ddd, J=8.3, 7.4, 1.7 Hz, 1H), 7.58 (td, J=7.7, 1.1 Hz, 1H), 7.35 (dd, J=8.3, 1.0 Hz, 1H), 7.17 (d, J=8.7 Hz, 1H), 5.07 (s, 2H), 3.82-3.48 (m, 10H), 3.41 (s, 2H), 2.48-2.35 (m, 3H), 1.98 (dq, J=10.5, 3.8, 2.8 Hz, 1H), 1.66-1.53 (m, 1H), 1.42 (s, 6H).

Example 39; 3-((3-(4-(2-((3-hydroxycyclobutyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (39)

(39)

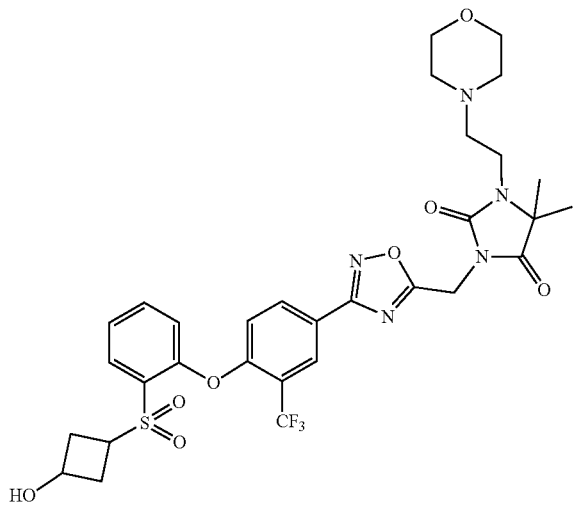

3-((3-(4-(2-((3-hydroxycyclobutyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (39) was obtained using a procedure similar to the procedure described in Example 38 for the synthesis of 5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione (38), except 2-(((tetrahydrofuran-3-yl)methyl)thio)phenol (int-A4) was replaced with 2-((3-hydroxycyclobutyl)thio)phenol (int-A7). $^1$H NMR (400 MHz, CD$_2$Cl$_2$) δ 8.46-8.41 (m, 1H), 8.25-8.18 (m, 1H), 8.14-8.07 (m, 1H), 7.69 (t, J=7.7 Hz, 1H), 7.45 (t, J=7.6 Hz, 1H), 7.05 (dd, J=11.8, 8.4 Hz, 2H), 5.00 (s, 2H), 4.25 (t, J=7.2 Hz, 1H), 3.91 (p, J=8.3 Hz, 1H), 3.67 (t, J=4.7 Hz, 4H), 3.47 (t, J=7.0 Hz, 2H), 2.66-2.58 (m, 4H), 2.52 (t, J=4.8 Hz, 4H), 2.41-2.35 (m, 2H), 1.52 (s, 6H); LCMS Method 5: Rt.=1.59 mins.; m/z 694.5 [M+H]$^+$.

Example 40: 5,5-dimethyl-1-(2-morpholinoethyl)-3-((3-(4-(2-(((tetrahydro-2H-pyran-3-yl)methyl) sulfonyl) phenoxy)-3-(trifluoromethyl)phenyl)-1,2,4-oxadiazol-5-yl)methyl) imidazolidine-2,4-dione (40)

Example 41: 5,5-dimethyl-1-(2-morpholinoethyl)-3-((3-(3-(trifluoromethyl)-4-(2-(trifluoromethyl)phenoxy)phenyl)-1,2,4-oxadiazol-5-yl)methyl)imidazolidine-2,4-dione (41)

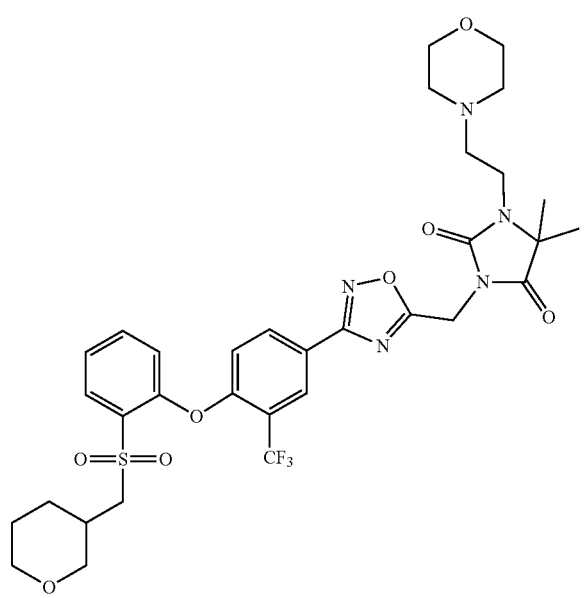

(40)

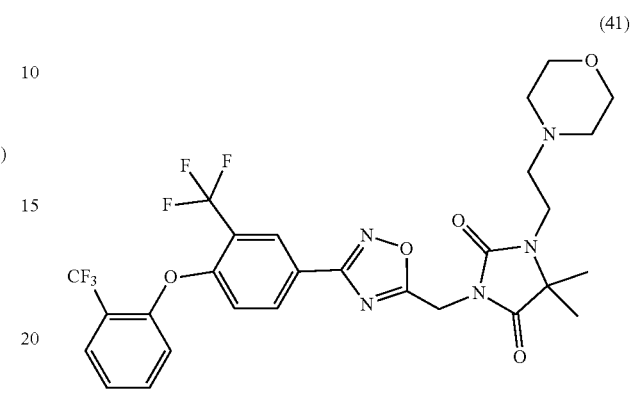

(41)

5,5-dimethyl-1-(2-morpholinoethyl)-3-((3-(3-(trifluoromethyl)-4-(2-(trifluoromethyl)phenoxy)phenyl)-1,2,4-oxadiazol-5-yl)methyl)imidazolidine-2,4-dione (41) was obtained using a procedure similar to the procedure described in step 1 of Example 38 for the synthesis of 5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione (38), except 2-(((tetrahydrofuran-3-yl)methyl)thio)phenol (int-A4) was replaced with 2-(trifluoromethyl)phenol. $^1$H NMR (400 MHz, CDCl$_3$) δ 8.32 (d, J=2.1 Hz, 1H), 8.08 (dd, J=8.7, 2.1 Hz, 1H), 7.69 (dd, J=7.9, 1.7 Hz, 1H), 7.58-7.48 (m, 1H), 7.33-7.23 (m, 1H), 7.01 (d, J=8.3 Hz, 1H), 6.88 (d, J=8.7 Hz, 1H), 4.96 (s, 2H), 3.67-3.60 (m, 4H), 3.43 (dd, J=8.3, 6.0 Hz, 2H), 2.58 (t, J=7.1 Hz, 2H), 2.52-2.45 (m, 4H), 1.47 (s, 6H); LCMS Method 5: Rt.=2.91 mins.; m/z 628.4 [M+H]$^+$.

5,5-dimethyl-1-(2-morpholinoethyl)-3-((3-(4-(2-(((tetrahydro-2H-pyran-3-yl)methyl)sulfonyl)phenoxy)-3-(trifluoromethyl)phenyl)-1,2,4-oxadiazol-5-yl)methyl)imidazolidine-2,4-dione (40) was obtained using a procedure similar to the procedure described in Example 38 for the synthesis of 5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione (38), except 2-(((tetrahydrofuran-3-yl)methyl)thio)phenol (int-A4) was replaced with 2-(((tetrahydro-2H-pyran-3-yl)methyl)thio)phenol (int-A5). $^1$H NMR (400 MHz, (CD$_3$)$_2$SO) δ 8.27 (d, J=2.1 Hz, 1H), 8.23 (dd, J=8.7, 2.2 Hz, 1H), 8.03 (dd, J=7.9, 1.7 Hz, 1H), 7.84 (ddd, J=8.2, 7.4, 1.7 Hz, 1H), 7.58 (td, J=7.6, 1.1 Hz, 1H), 7.35 (dd, J=8.3, 1.1 Hz, 1H), 7.15 (d, J=8.7 Hz, 1H), 5.08 (s, 2H), 4.00 (s, 1H), 3.85-3.38 (m, 10H), 3.16 (dd, J=11.2, 8.9 Hz, 2H), 2.43 (s, 2H), 2.09-1.91 (m, 1H), 1.86-1.70 (m, 1H), 1.60-1.20 (m, 10H); LCMS Method 9: Rt.=0.60 mins.; m/z 722.3 [M+H]$^+$.

Example 42: 5,5-dimethyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (42)

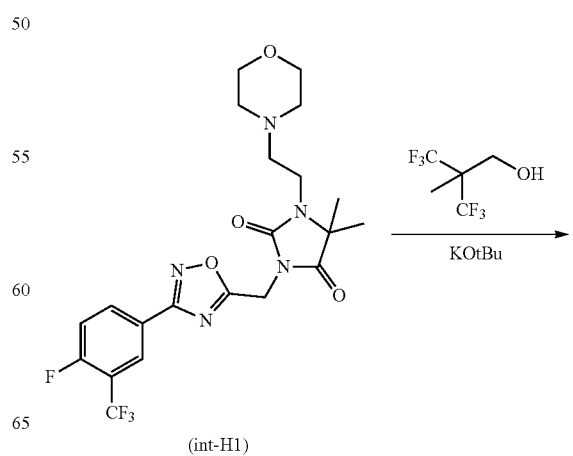

(int-H1)

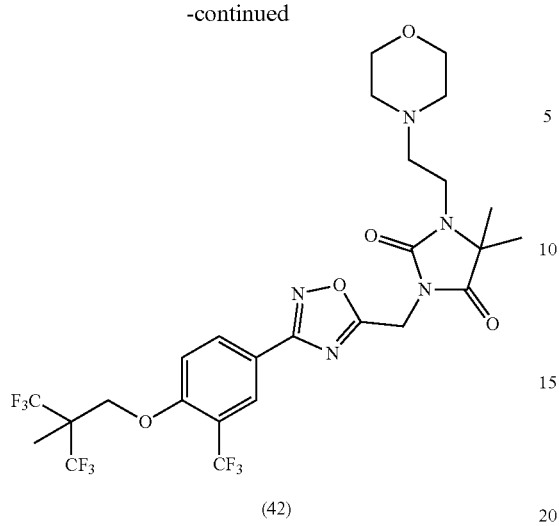

(42)

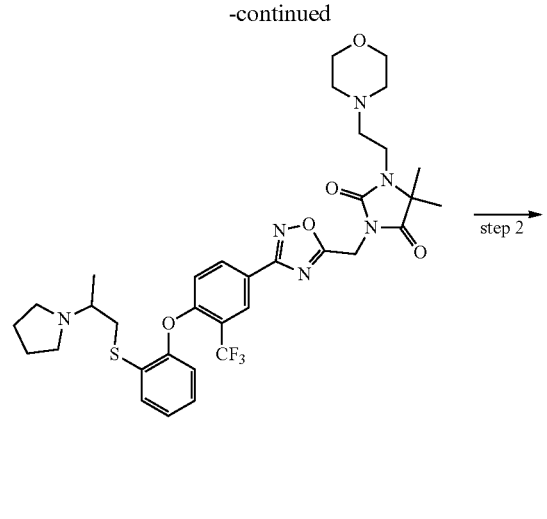

3,3,3-trifluoro-2-methyl-2-(trifluoromethyl)propan-1-ol (404 mg, 2.060 mmol) was treated with KOtBu (1M in THF) (0.618 mL, 0.618 mmol) and then with 3-((3-(4-fluoro-3-(trifluoromethyl)phenyl)-1,2,4-oxadiazol-5-yl)methyl)-5,5-dimethyl-1-(2-morpholinoethyl)imidazolidine-2,4-dione (int-H1) (100 mg, 0.206 mmol) in THF (1 mL). The mixture was stirred for 72 hours, then water (5 mL) and ethyl acetate (5 mL) were added. The layers were separated and the aqueous layer was extracted with ethyl acetate. The combined organic layers were dried over magnesium sulfate, filtered and evaporated to dryness. The residue was purified using reverse phase flash chromatography, eluting with 0-100% MeCN in water to provide 5,5-dimethyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (42). LCMS Method 4: Rt.=2.96 mins.; m/z 662.6 [M+H]+; $^1$H NMR (400 MHz, CDCl$_3$) δ 8.16 (d, J=2.1 Hz, 1H), 8.08 (dd, J=8.7, 2.2 Hz, 1H), 6.95 (d, J=8.7 Hz, 1H), 4.86 (s, 2H), 4.23 (s, 2H), 3.59 (t, J=4.6 Hz, 4H), 3.37 (t, J=7.1 Hz, 2H), 2.53 (t, J=7.2 Hz, 2H), 2.48-2.41 (m, 4H), 1.49 (s, 3H), 1.40 (s, 6H).

Example 43: 5,5-dimethyl-1-(2-morpholinoethyl)-3-((3-(4-(2-((2-(pyrrolidin-1-yl) propyl) sulfonyl) phenoxy)-3-(trifluoromethyl)phenyl)-1,2,4-oxadiazol-5-yl)methyl)imidazolidine-2,4-dione (43)

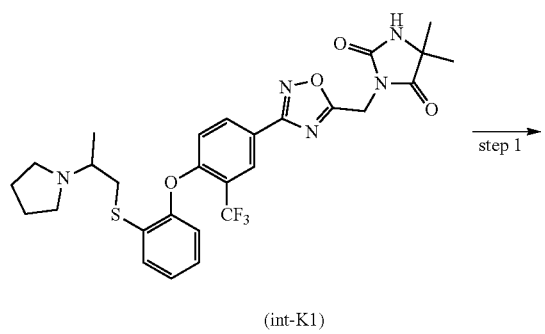

(int-K1)

(43)

Step 1: A solution of 5,5-dimethyl-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione (int-K1) (100 mg, 0.170 mmol) in DMF (3 mL) was treated with cesium carbonate (138 mg, 0.424 mmol) and 4-(2-bromoethyl)morpholine (51.3 mg, 0.187 mmol) and stirred at room temperature for 5 days. Water was added, and the mixture then extracted with ethyl acetate (twice). The combined organic layers were washed with 0.5 M LiCl, then dried over magnesium sulfate, filtered and concentrated. The residue was purified by flash column chromatography, eluting with 0-20% methanol in DCM, to provide a solution of 5,5-dimethyl-1-(2-morpholinoethyl)-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione. LCMS Method 3: Rt.=1.31 m/z 703.6 [M+H]+

Step 2: A solution of 5,5-dimethyl-1-(2-morpholinoethyl)-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione (24 mg, 0.034 mmol) in TFA (2 mL) was cooled to 0° C., treated dropwise with hydrogen peroxide (5.23 µl, 0.051 mmol), and allowed to warm to room temperature over 2 hrs. The reaction mixture was concentrated in vacuo to remove TFA, and to the residue was added saturated aqueous sodium bicarbonate (1 mL). The aqueous mixture was extracted twice with ethyl acetate, and the combined organic layers were dried over sodium sulfate, filtered, and concentrated. The residue was purified by flash column chromatography, eluting with 0-30% MeOH in DCM. Product fractions were collected, combined, and concentrated to provide 5,5-dimethyl-1-(2-morpholinoethyl)-3-((3-(4-(2-((2-(pyrrolidin-1-yl)propyl)sulfonyl)phenoxy)-3-(trifluoromethyl)phenyl)-1,2,4-oxadiazol-5-yl)methyl)imidazolidine-2,4-dione (43). LCMS Method 5: Rt. 2.73 mins.; m/z 735.5 [M+H]+; $^1$H NMR (400 MHz, CDCl$_3$) δ 8.30 (d, J=2.1 Hz, 1H), 8.03 (ddd, J=21.0, 8.3, 1.9 Hz, 2H), 7.56 (ddd, J=8.2, 7.4, 1.7 Hz, 1H), 7.32 (td, J=7.7, 1.1 Hz, 1H), 6.99-6.88 (m, 2H), 4.91 (s, 2H), 3.80-3.71 (m, 1H), 3.66-3.59 (m, 4H), 3.39 (dd, J=7.6, 6.7 Hz, 2H), 3.26 (dd, J=12.7, 6.6 Hz, 2H), 2.55 (s, 4H), 2.49-2.42 (m, 5H), 2.41-2.32 (m, 3H), 1.56-1.46 (m, 2H), 1.44 (s, 6H), 1.14 (d, J=6.1 Hz, 3H).

Example 44; 3-((3-(4-(2-(isobutylsulfonyl)phenoxy)-3-(trifluoromethyl)phenyl)-1,2,4-oxadiazol-5-yl)methyl)-1-(2-morpholinoethyl)imidazolidine-2,4-dione (44)

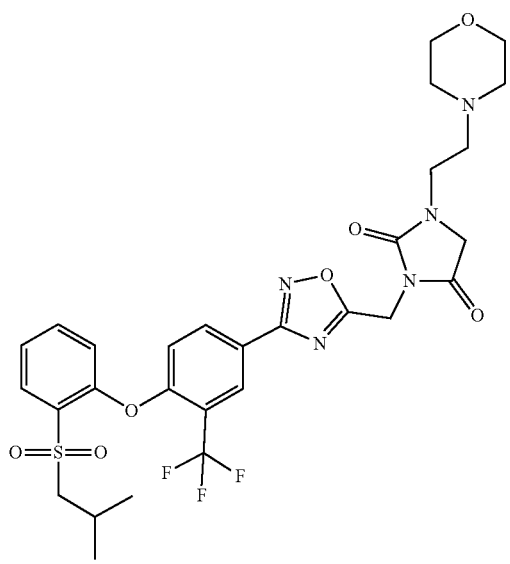

(44)

3-((3-(4-(2-(isobutylsulfonyl)phenoxy)-3-(trifluoromethyl)phenyl)-1,2,4-oxadiazol-5-yl)methyl)-1-(2-morpholinoethyl)imidazolidine-2,4-dione (44) was obtained using a procedure similar to the procedure described in Example 43 for the synthesis of 5,5-dimethyl-1-(2-morpholinoethyl)-3-((3-(4-(2-((2-(pyrrolidin-1-yl)propyl)sulfonyl)phenoxy)-3-(trifluoromethyl)phenyl)-1,2,4-oxadiazol-5-yl)methyl)imidazolidine-2,4-dione (43), except 5,5-dimethyl-3-((3-(4-(2-((2-(pyrrolidin-1-yl)propyl)thio)phenoxy)-3-(trifluoromethyl)phenyl)-1,2,4-oxadiazol-5-yl)methyl)imidazolidine-2,4-dione (int-K1) was replaced with 3-((3-(4-(2-(isobutylsulfonyl)phenoxy)-3-(trifluoromethyl)phenyl)-1,2,4-oxadiazol-5-yl)methyl)imidazolidine-2,4-dione (int-K2). $^1$H NMR (400 MHz, CDCl$_3$) δ 8.40 (d, J=2.1 Hz, 1H), 8.19 (dd, J=8.7, 2.1 Hz, 1H), 8.12 (dd, J=7.9, 1.7 Hz, 1H), 7.69-7.60 (m, 1H), 7.46-7.37 (m, 1H), 7.03 (d, J=8.3, 1.0 Hz, 2H), 5.31 (s, 1H), 5.01 (s, 2H), 4.19 (s, 2H), 3.74-3.67 (m, 4H), 3.61 (t, J=5.9 Hz, 2H), 3.36 (d, J=6.5 Hz, 2H), 2.61 (t, J=5.7 Hz, 2H), 2.52 (s, 3H), 2.27 (dq, J=13.4, 6.7 Hz, 1H), 1.07 (d, J=6.7 Hz, 6H); LCMS Method 3: Rt.=1.13 mins.; m/z 652.7 [M+H]+.

Example 45; 7-((3-(4-(2-(isobutylsulfonyl)phenoxy)-3-(trifluoromethyl)phenyl)-1,2,4-oxadiazol-5-yl)methyl)-5-(2-morpholinoethyl)-5,7-diazaspiro[3.4]octane-6,8-dione (45)

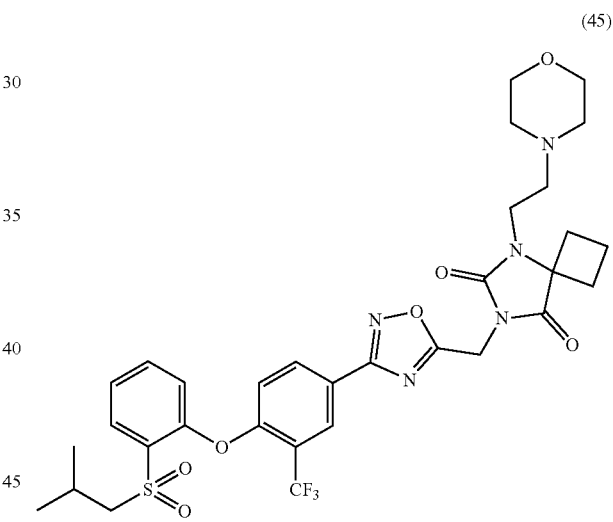

(45)

7-((3-(4-(2-(isobutylsulfonyl)phenoxy)-3-(trifluoromethyl)phenyl)-1,2,4-oxadiazol-5-yl)methyl)-5-(2-morpholinoethyl)-5,7-diazaspiro[3.4]octane-6,8-dione (44) was obtained using a procedure similar to the procedure described in Example 3 for the synthesis of 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione (3), except 1,3-diazaspiro[4.5]decane-2,4-dione was replaced with 5,7-diazaspiro[3.4]octane-6,8-dione. 1H NMR (400 MHz, CDCl$_3$) δ 8.42 (s, 1H), 8.14-8.20 (m, 2H), 7.66-7.69 (t, d, J=6.8 Hz, 1H), 7.42-7.46 (t, d, J=7.6 Hz, 1H), 7.04-7.07 (m, 2H), 5.01 (s, 2H), 3.74-3.76 (m, 4H), 3.61-3.64 (t, J=6.8 Hz, 2H), 3.38-3.40 (d, J=6.8 Hz, 2H), 2.59-2.71 (m, 9H), 2.27-2.34 (m, 2H), 1.92-1.94 (m, 1H), 1.26-1.32 (m, 1H), 1.09-1.11 (d, J=6.4 Hz, 6H); LCMS Method 7: Rt.=4.48 mins.; m/z 692.3 [M+H]+.

Example 46; 5-(hydroxymethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione (46)

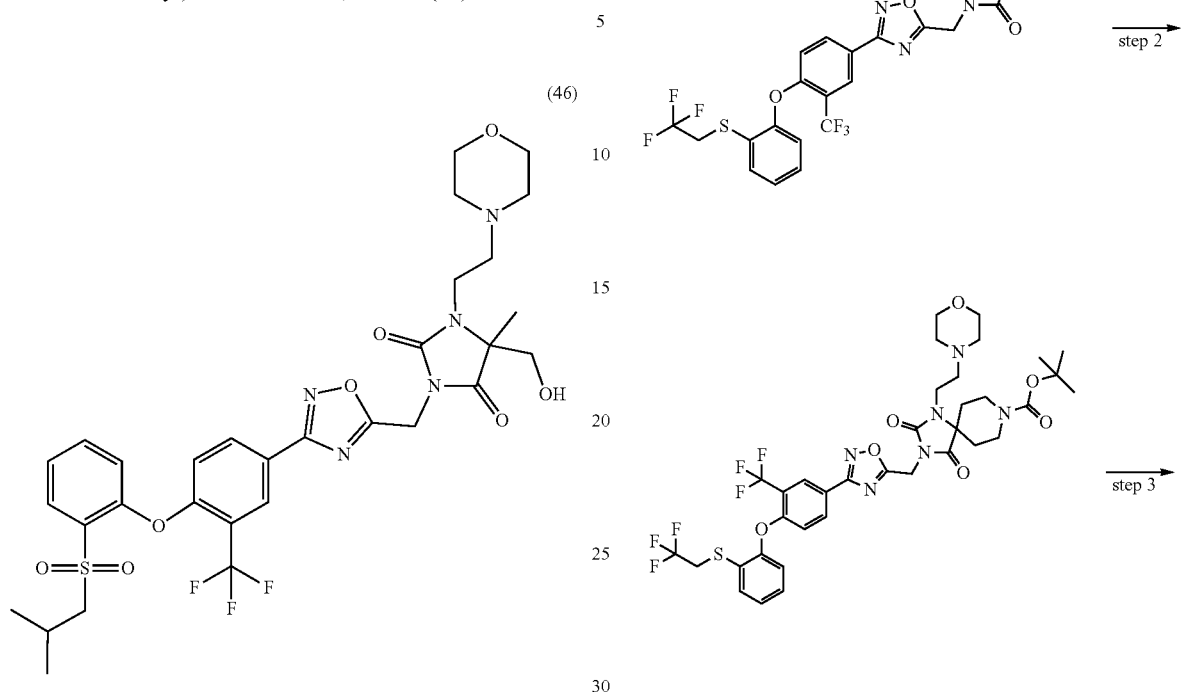

5-(hydroxymethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione (46) was obtained using a procedure similar to the procedure described in Example 3 for the synthesis of 3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione (3), except 1,3-diazaspiro[4.5]decane-2,4-dione was replaced with 5-(hydroxymethyl)-5-methylimidazolidine-2,4-dione (int-E2). $^1$H NMR (400 MHz, CDCl$_3$) δ 8.33-8.28 (m, 1H), 8.09-8.01 (m, 2H), 7.61-7.53 (m, 1H), 7.38-7.30 (m, 1H), 7.00-6.89 (m, 2H), 5.01-4.87 (m, 2H), 4.05 (q, J=7.2 Hz, 3H), 3.27 (d, J=6.5 Hz, 2H), 2.25-2.11 (m, 1H), 1.97 (s, 4H), 1.52 (s, 6H), 1.35 (s, 2H), 1.19 (t, J=7.1 Hz, 4H), 0.99 (d, J=6.7 Hz, 5H); LCMS Method 5: Rt.=2.64 mins.; m/z 696.8 [M+H]$^+$.

Example 47: 8-cyclobutyl-1-(2-morpholinoethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione (47)

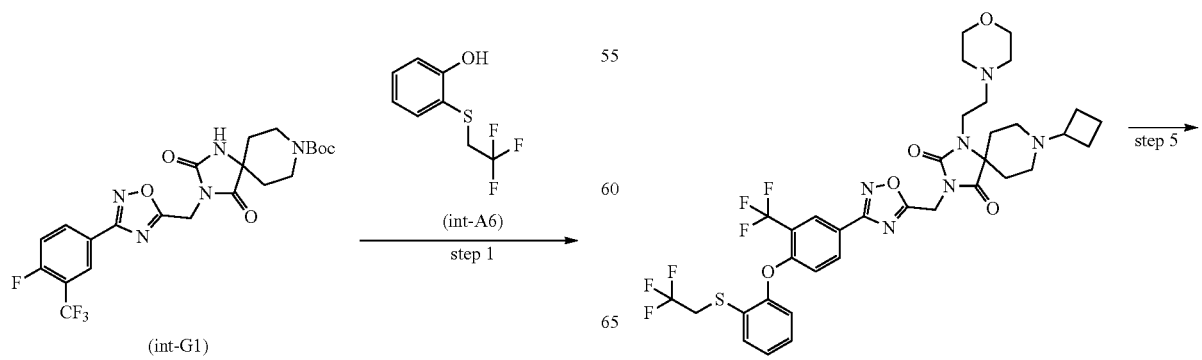

-continued

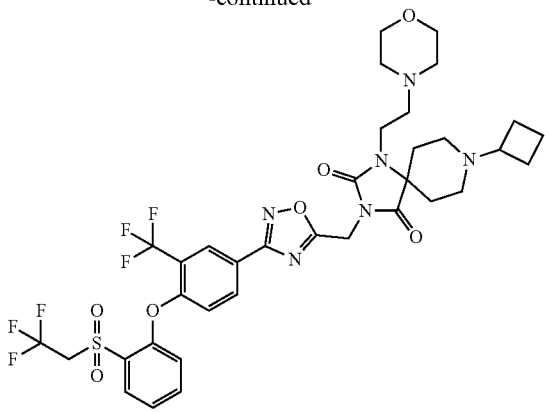

(47)

Step 1: To a solution of tert-butyl 3-((3-(4-fluoro-3-(trifluoromethyl)phenyl)-1,2,4-oxadiazol-5-yl)methyl)-2,4-dioxo-1,3,8-triazaspiro[4.5]decane-8-carboxylate (int-G1) (1.5 g, 2.92 mmol) in DMF (15 mL) was added potassium carbonate (1.08 g, 7.30 mmol). After stirring for 15 minutes at room temperature 2-((2,2,2-trifluoroethyl)thio)phenol (int-A6) (0.73 g, 3.50 mmol) was added. The reaction mixture was stirred at 60° C. for 16 hours, then diluted with water (100 mL) and extracted with ethyl acetate (3×50 mL). The combined organic layers were washed with cold water (3×50 mL), then dried over sodium sulfate and concentrated to obtain tert-butyl 2,4-dioxo-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-8-carboxylate. LCMS Method 11: Rt.=2.11 min; m/z 700.3 [M−H]−, 1H NMR (400 MHz, (CD$_3$)$_2$SO) δ 9.14 (s, 1H), 8.25 (s, 1H), 8.18-8.20 (d, J=8.4 Hz, 1H), 7.75-7.77 (d, J=7.6 Hz, 1H), 7.35-7.44 (m, 2H), 7.21-7.22 (d, J=7.6 Hz, 1H), 6.91-6.93 (d, J=8.8 Hz, 1H), 5.02 (s, 2H), 3.97-4.04 (m, 2H), 3.81-3.84 (m, 2H), 3.17 (m, 2H), 1.75-1.78 (m, 2H), 1.56-1.64 (m, 2H), 1.40 (s, 9H).

Step 2: To a solution of tert-butyl 2,4-dioxo-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-8-carboxylate (1.2 g, 71 mmol) dissolved in DMF (12 mL) was added cesium carbonate (1.67 g, 5.13 mmol), followed by 4-(2-bromoethyl)morpholine (0.396 g, 2.05 mmol). The reaction mixture was stirred at room temperature for 16 hours. The mixture was then diluted with cold water (50 mL) and extracted with ethyl acetate (3×50 mL). The combined organic layers were washed with cold water (5×50 mL), then dried over sodium sulfate and concentrated to provide tert-butyl 1-(2-morpholinoethyl)-2,4-dioxo-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-8-carboxylate. LCMS Method 11: Rt.=2.21 min; m/z 814.6 [M+H].

Step 3: To a solution of tert-butyl 1-(2-morpholinoethyl)-2,4-dioxo-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-8-carboxylate (1.1 g, 1.35 mmol) in dichloromethane (11 mL) was added 4M HCl in dioxane (11 mL) dropwise at 0° C. The reaction mixture was stirred at room temperature for 1 hour, then concentrated in vacuo and triturated with n-pentane. The resulting solid material was dissolved in dichloromethane (50 mL) and the organic layer was washed with saturated sodium bicarbonate solution (3×25 mL), water, and brine, then dried over sodium sulfate, filtered, and concentrated to provide 1-(2-morpholinoethyl)-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-2,4-dione. LCMS Method 11: Rt.=1.76 min.; m/z 714.5 [M+H].

Step 4: To a solution of 1-(2-morpholinoethyl)-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-2,4-dione (0.85 g, 1.19 mmol) dissolved in 1-2-dichloroethane (8.5 mL) was added cyclobutanone (0.25 g, 3.57 mmol) and the reaction mixture stirred for 20 minutes. Sodium triacetoxyborohydride (0.757 g, 3.57 mmol) was then added, and the reaction mixture was stirred at room temperature for 16 hours, then diluted with water (50 mL). The mixture was extracted with dichloromethane (3×25 mL), and the combined organic layers were washed with brine, then dried over sodium sulfate, filtered, and concentrated to provide 8-cyclobutyl-1-(2-morpholinoethyl)-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-2,4-dione. LCMS Method 8: Rt.=4.33 min.; m/z 768.3 [M+H].

Step 5: To a solution of 8-cyclobutyl-1-(2-morpholinoethyl)-3-((3-(4-(2-((2,2,2-trifluoroethyl)thio)phenoxy)-3-(trifluoromethyl)phenyl)-1,2,4-oxadiazol-5-yl)methyl)-1,3,8-triazaspiro[4.5]decane-2,4-dione (0.72 g, 0.93 mmol) in dichloromethane (8.5 mL) was added m-chloroperoxybenzoic acid (0.486 g, 2.81 mmol) portion wise, and the reaction mixture stirred at room temperature for 4 hours. The mixture was then diluted with dichloromethane (25 mL) and water (25 mL). The organic layer was separated and with saturated sodium bicarbonate solution (2×20 mL), then dried over sodium sulfate and concentrated. The crude product was purified by preparative HPLC, and product fractions were combined and lyophilized to provide 8-cyclobutyl-1-(2-morpholinoethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione (47). LCMS Method 7: Rt.=4.01 min.; m/z 800.7 [M+H], LCMS (Method 8): Rt.=3.97 mins.; m/z 800.3 [M+H], Rt.=3.07 min. $^1$H NMR (400 MHz, (CD$_3$)$_2$SO) δ 8.27 (s, 2H), 7.94-7.96 (d, J=6.8 Hz, 1H), 7.68 (m, 1H), 7.59-7.61 (d, J=7.2 Hz, 1H), 7.43-7.45 (d, J=8.8 Hz, 1H), 7.19-7.20 (d, J=7.2 Hz, 1H), 5.04 (s, 2H), 4.01-4.20 (m, 4H), 3.86 (m, 2H), 3.62-3.64 (d, J=8.8 Hz, 2H), 2.84-2.86 (d, J=8.8 Hz, 2H), 2.76 (m, 3H), 2.36 (m, 4H), 1.97-2.09 (m, 4H), 1.89 (m, 2H), 1.64 (m, 2H), 1.23 (m, 2H).

Example 48; 8-cyclobutyl-1-(2-(tetrahydro-2H-pyran-4-yl)ethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione (48)

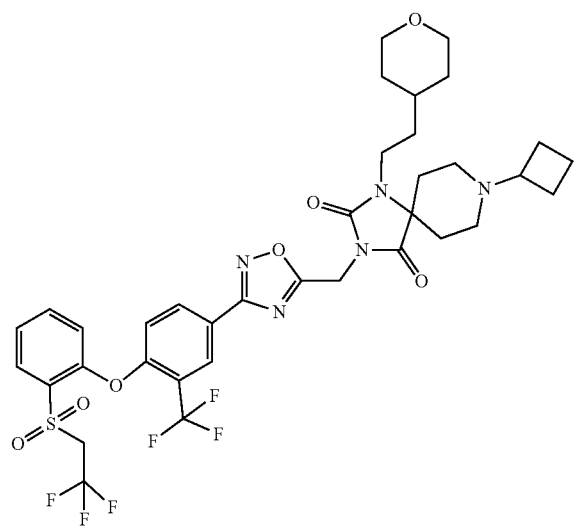

(48)

8-cyclobutyl-1-(2-(tetrahydro-2H-pyran-4-yl)ethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione (48) was obtained using a procedure similar to the procedure described in Example 47 for the synthesis of 8-cyclobutyl-1-(2-morpholinoethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione (47), except 4-(2-bromoethyl)morpholine was replaced with 4-(2-bromoethyl)tetrahydro2H-pyran. 1H NMR (400 MHz, MeOD) δ 8.42 (s, 1H), 8.31-8.33 (d, J=8.4 Hz, 1H), 8.00-8.02 (d, J=8.0 Hz, 1H), 7.68-7.71 (t, J=7.6 Hz, 1H), 7.57-7.61 (t, J=7.6 Hz, 1H), 7.35-7.37 (d, J=8.4 Hz, 1H), 7.12-7.14 (d, J=8.0 Hz, 1H), 5.08 (s, 2H), 3.92-4.05 (m, 5H), 3.75-3.80 (t, J=10.4 Hz, 2H), 3.41-3.49 (m, 4H), 3.12-3.15 (m, 2H), 2.84-2.89 (t, J=10.0 Hz, 2H), 2.59-2.64 (t, J=10.4 Hz, 2H), 2.10 (m, 2H), 1.88-1.91 (d, J=14.0 Hz, 2H), 1.68-1.82 (m, 7H), 1.31 (m, 2H); LCMS Method 8: Rt.=4.01 mins.; m/z 800.7 [M+H]+.

Example 49; 3-((3-(3-chloro-4-(2-(isobutylsulfonyl)phenoxy)phenyl)-1,2,4-oxadiazol-5-yl)methyl)-5,5-dimethyl-1-(2-morpholinoethyl)imidazolidine-2,4-dione (49)

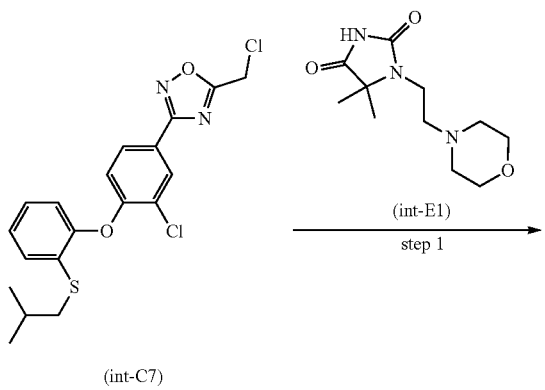

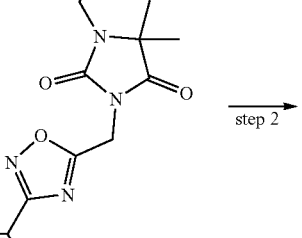

step 2

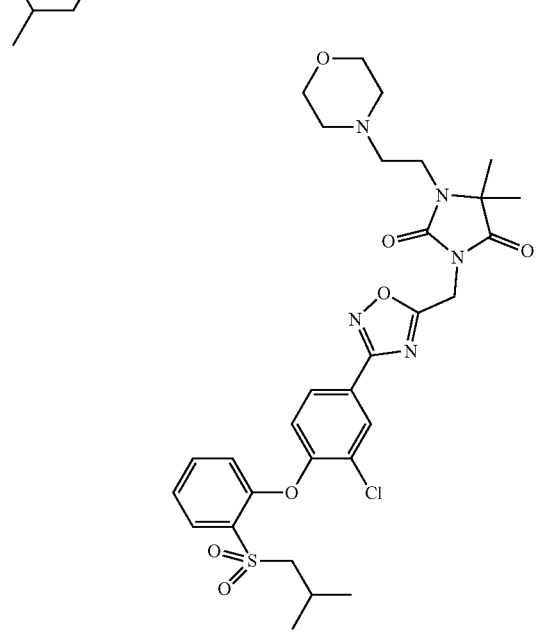

(49)

Step 1: Cesium carbonate (119 mg, 0.366 mmol) was added to a solution 3-(3-chloro-4-(2-(isobutylthio)phenoxy)phenyl)-5-(chloromethyl)-1,2,4-oxadiazole (int-C7) (50 mg, 0.122 mmol) and 5,5-dimethyl-1-(2-morpholinoethyl)imidazolidine-2,4-dione (int-E1) (29.5 mg, 0.122 mmol) in DMF (1 mL) and the reaction stirred at room temperature overnight. The reaction was filtered and azeotroped with toluene (3×), and the crude material was purified via flash column chromatography, eluting 0-10% MeOH in DCM. Product fractions were collected, combined, and concentrated to provide 3-((3-(3-chloro-4-(2-(isobutylthio)phenoxy)phenyl)-1,2,4-oxadiazol-5-yl)methyl)-5,5-dimethyl-1-(2-morpholinoethyl)imidazolidine-2,4-dione. LCMS Method 5: Rt.=3.30 min.; m/z 614.3 [M+H]; 1H NMR (400 MHz, (CD3)2SO) δ 8.06 (d, J=2.1 Hz, 1H), 7.86 (dd, J=8.6, 2.1 Hz, 1H), 7.54-7.48 (m, 1H), 7.32-7.26 (m, 2H), 7.13-7.08 (m, 1H), 6.84 (d, J=8.6 Hz, 1H), 5.03 (s, 2H), 3.54 (t, J=4.6 Hz, 4H), 3.41 (t, J=7.0 Hz, 2H), 2.83 (d, J=6.8 Hz, 2H), 2.44 (s, 4H), 1.77-1.68 (m, 1H), 1.41 (s, 6H), 0.92 (d, J=6.7 Hz, 6H).

Step 2: Hydrogen peroxide (7.32 μl, 0.072 mmol) was added to a solution of 3-((3-(3-chloro-4-(2-(isobutylthio) phenoxy)phenyl)-1,2,4-oxadiazol-5-yl)methyl)-5,5-dimethyl-1-(2-morpholinoethyl)imidazolidine-2,4-dione (20 mg, 0.033 mmol) in TFA (1 mL) at 0° C. The reaction was allowed to warm to room temperature and stirred at room temperature overnight. The reaction was concentrated under reduced pressure and the crude residue was taken up in EtOAc and poured into saturated aqueous sodium bicarbonate solution. The layers were separated and the organic layer was washed sequentially with saturated aqueous sodium bicarbonate solution, water, brine, then dried over sodium sulfate, filtered, and concentrated under reduced pressure to provide 3-((3-(3-chloro-4-(2-(isobutylsulfonyl)phenoxy) phenyl)-1,2,4-oxadiazol-5-yl)methyl)-5,5-dimethyl-1-(2-morpholinoethyl)imidazolidine-2,4-dione (49). LCMS Method 5: Rt.=2.71 mins.; m/z 646.3 [M+H], Rt.=2.71 min. $^1$H NMR (400 MHz, (CD$_3$)$_2$SO) δ 8.13 (d, J=2.1 Hz, 1H), 7.99 (dd, J=7.9, 1.7 Hz, 1H), 7.95 (dd, J=8.6, 2.1 Hz, 1H), 7.81-7.75 (m, 1H), 7.53-7.48 (m, 1H), 7.24 (dd, J=8.3, 1.0 Hz, 1H), 7.19 (d, J=8.6 Hz, 1H), 5.05 (s, 2H), 3.55 (s, 4H), 3.46 (d, J=6.5 Hz, 2H), 3.43 (d, J=7.2 Hz, 2H), 2.43 (s, 4H), 2.14-2.03 (m, 1H), 1.41 (s, 6H), 0.99 (d, J=6.7 Hz, 6H).

Example 50; 3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (50a), and 3-((3-(4-(2-(isobutylsulfonyl)phenoxy)-3-(trifluoromethyl)phenyl)-1,2,4-oxadiazol-5-yl) methyl)-5,5-dimethyl-1-(3-(pyrrolidin-1-yl)propyl) imidazolidine-2,4-dione (50b)

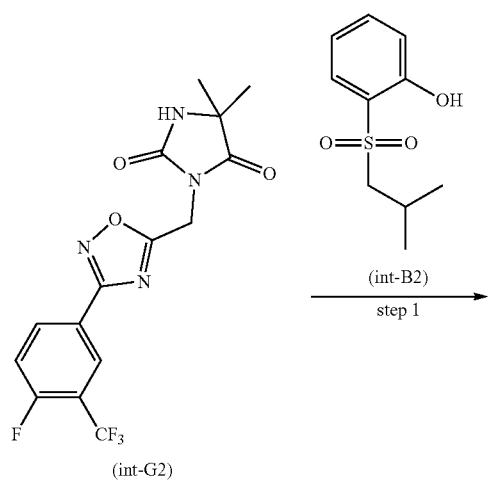

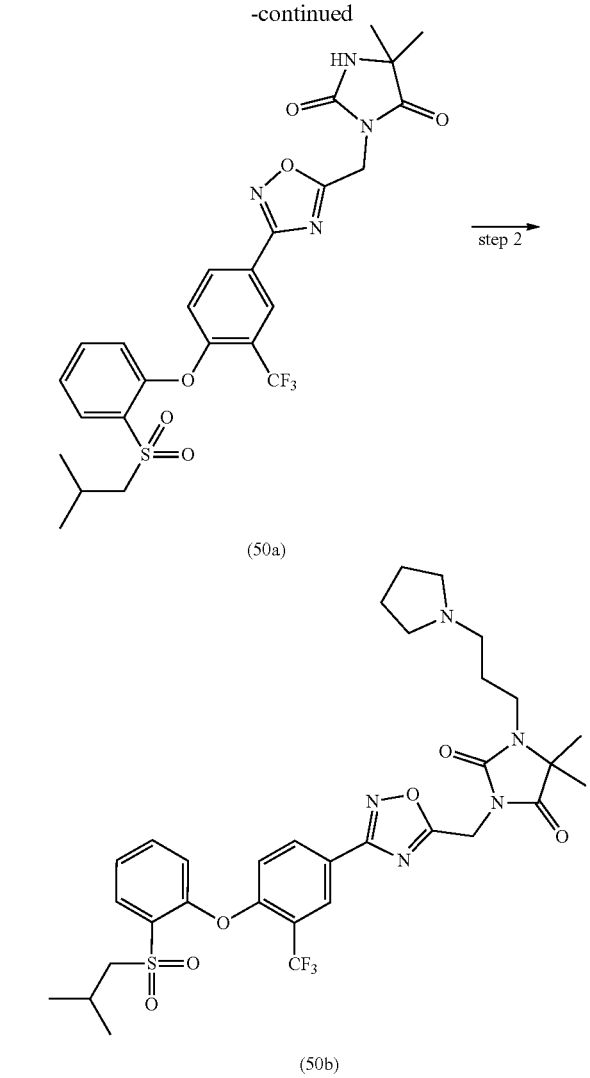

Step 1: To a solution of 2-(isobutylsulfonyl)phenol (int-B2) (1.75 g, 8.17 mmol) and 3-((3-(4-fluoro-3-(trifluoromethyl)phenyl)-1,2,4-oxadiazol-5-yl)methyl)-5,5-dimethylimidazolidine-2,4-dione (int-G2) (3.04 g, 8.17 mmol) in DMF (30 mL) was added potassium carbonate (2.257 g, 16.33 mmol), and the resulting mixture heated to 100° C. for 16 hours. The reaction mixture cooled to room temperature and then water was added. The mixture was extracted twice with ethyl acetate and the combined organic layers were washed with 0.5 M LiCl (100 mL) and brine, then dried over magnesium sulfate, filtered, concentrated and then purified by flash column chromatography, eluting with 0-100% EtOAc in heptane, to provide 3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (50a). LCMS Method 4: Rt. 2.67 mins, m/z 566.0 [M+H]$^+$, $^1$H NMR (400 MHz, DMSO-d6) δ 8.55 (s, 1H), 8.28 (d, J=2.1 Hz, 1H), 8.25 (dd, J=8.7, 2.2 Hz, 1H), 8.03 (dd, J=7.9, 1.7 Hz, 1H), 7.82 (ddd, J=8.3, 7.5, 1.7 Hz, 1H), 7.57 (td, J=7.6, 1.0 Hz, 1H), 7.33 (dd, J=8.2, 1.0 Hz, 1H), 7.15 (d, J=8.7 Hz, 1H), 5.02 (s, 2H), 3.36 (d, J=6.5 Hz, 2H), 2.07 (hept, J=6.6 Hz, 1H), 1.38 (s, 6H), 0.98 (d, J=6.7 Hz, 6H).

Step 2: A solution of 3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (50a) (100 mg, 0.177 mmol) in DMF (2 mL) was treated with 1-(3-bromopropyl)pyrrolidine (161 mg, 0.706 mmol) and cesium carbonate (345 mg, 1.059 mmol) at room temperature, and the reaction mixture then heated to 60° C. for 8 hours. The reaction mixture cooled to room temperature, and the product was isolated without work up by HPLC 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione (50b). LCMS Method 4: Rt.=2.04 mins.; m/z 677.9 MH+; $^1$H NMR (400 MHz, CD$_3$OD) δ 8.40 (d, J=2.1 Hz, 1H), 8.25 (dd, J=8.7, 2.1 Hz, 1H), 8.10 (dd, J=7.9, 1.7 Hz, 1H), 7.80 (ddd, J=8.3, 7.5, 1.7 Hz, 1H), 7.54 (td, J=7.7, 1.0 Hz, 1H), 7.23 (dd, J=8.3, 1.1 Hz, 1H), 7.09 (d, J=8.7 Hz, 1H), 5.08 (s, 2H), 3.54-3.43 (m, 4H), 3.38 (d, J=6.6 Hz, 2H), 3.08-2.95 (m, 4H), 2.88 (d, J=2.2 Hz, 1H), 2.26-2.12 (m, 2H), 2.12-1.82 (m, 4H), 1.53 (s, 6H), 1.07 (d, J=6.8 Hz, 6H).

Example 51; 3-((3-(4-(2-(isobutylsulfonyl)phenoxy)-3-(trifluoromethyl)phenyl)-1,2,4-oxadiazol-5-yl)methyl)-5,5-dimethyl-1-(pyridin-2-ylmethyl)imidazolidine-2,4-dione (51)

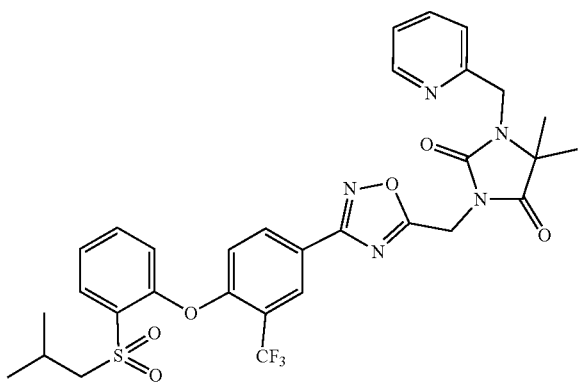

(51)

3-((3-(4-(2-(isobutylsulfonyl)phenoxy)-3-(trifluoromethyl)phenyl)-1,2,4-oxadiazol-5-yl)methyl)-5,5-dimethyl-1-(pyridin-2-ylmethyl)imidazolidine-2,4-dione (51) was obtained using a procedure similar to the procedure described in Example 50 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione (50b), except 1-(3-bromopropyl)pyrrolidine was replaced with 2-(bromomethyl)pyridine and step 2 was carried out at room temperature. LCMS Method 5: Rt.=3.10 mins.; m/z 657.9 [M+H]+; $^1$H NMR (400 MHz, CDCl$_3$) δ 8.59-8.53 (m, 1H), 8.40 (d, J=2.1 Hz, 1H), 8.20-8.10 (m, 1H), 7.74-7.62 (m, 1H), 7.48-7.38 (m, 1H), 7.25 (ddd, J=7.6, 4.9, 1.2 Hz, 1H), 7.08-7.00 (m, 2H), 5.07 (s, 2H), 4.76 (s, 2H), 3.37 (d, J=6.5 Hz, 2H), 2.35-2.20 (m, 1H), 1.43 (s, 6H), 1.22 (d, J=6.1 Hz, 3H), 1.09 (d, J=6.7 Hz, 6H).

Example 52; 3-((3-(4-(2-((2-hydroxypropyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (52)

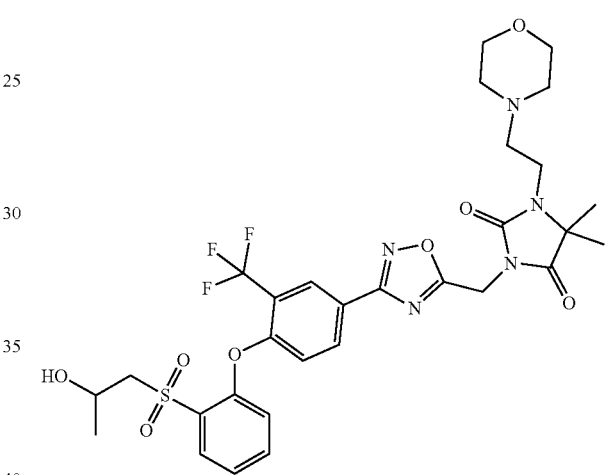

(52)

3-((3-(4-(2-((2-hydroxypropyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (52) was obtained using a procedure similar to the procedure described in Example 50 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione (50b), except 2-(isobutylsulfonyl)phenol (int-B2) was replaced with 2-((2-hydroxypropyl)sulfonyl)phenol (int-B3), 1-(3-bromopropyl)pyrrolidine was replaced with 4-(2-bromoethyl)morpholine and step 2 was carried out at room temperature. LCMS Method 2: Rt.=0.81 mins.; m/z 682.2 [M+H]+; $^1$H NMR (400 MHz, CDCl$_3$) δ 8.31 (d, J=2.0 Hz, 1H), 8.09 (dd, J=8.7, 2.1 Hz, 1H), 8.04 (dd, J=7.9, 1.7 Hz, 1H), 7.61-7.54 (m, 1H), 7.34 (td, J=7.7, 1.1 Hz, 1H), 6.99-6.90 (m, 2H), 4.91 (s, 2H), 3.65-3.58 (m, 4H), 3.57 (d, J=1.8 Hz, 1H), 3.43-3.32 (m, 4H), 2.54 (t, J=7.2 Hz, 2H), 2.45 (t, J=4.3 Hz, 4H), 1.43 (s, 6H), 1.20 (d, J=6.4 Hz, 3H).

Example 53: 5,5-dimethyl-1-(2-morpholinoethyl)-3-((3-(4-(2-(((tetrahydro-2H-pyran-2-yl)methyl) sulfonyl) phenoxy)-3-(trifluoromethyl)phenyl)-1,2,4-oxadiazol-5-yl)methyl) imidazolidine-2,4-dione (53)

Example 54; 1-(cyclopropylmethyl)-3-((3-(4-(2-((2-methoxyethyl)sulfonyl)phenoxy)-3-(trifluoromethyl) phenyl)-1,2,4-oxadiazol-5-yl)methyl)-5,5-dimethyl-imidazolidine-2,4-dione (54)

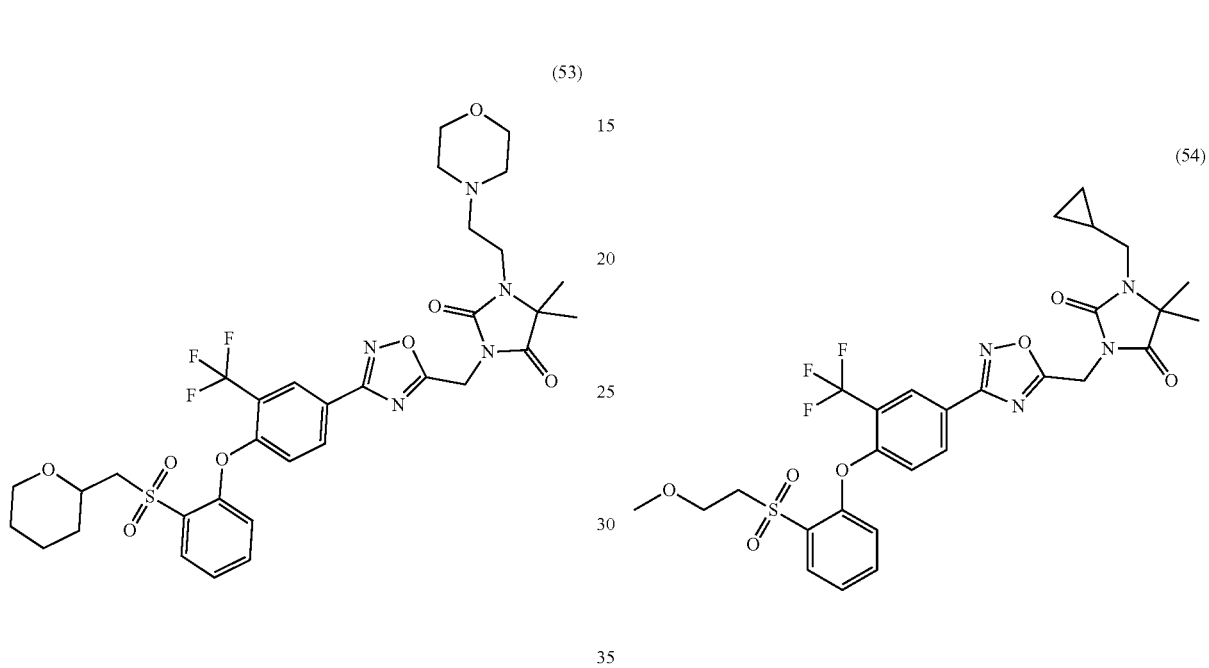

5,5-dimethyl-1-(2-morpholinoethyl)-3-((3-(4-(2-(((tetrahydro-2H-pyran-2-yl)methyl)sulfonyl)phenoxy)-3-(trifluoromethyl)phenyl)-1,2,4-oxadiazol-5-yl)methyl)imidazolidine-2,4-dione (53) was obtained using a procedure similar to the procedure described in Example 50 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione (50b), except 2-(isobutylsulfonyl)phenol (int-B2) was replaced with 2-(((tetrahydro-2H-pyran-2-yl)methyl)sulfonyl)phenol (int-B4), 1-(3-bromopropyl)pyrrolidine was replaced with 4-(2-bromoethyl)morpholine and step 2 was carried out at room temperature. LCMS Method 2: Rt.=0.95 mins.; m/z 722.5 [M+H]+; $^1$H NMR (400 MHz, CDCl$_3$) δ 8.29 (d, J=2.1 Hz, 1H), 8.05 (dd, J=8.7, 2.2 Hz, 1H), 8.00 (dd, J=7.9, 1.7 Hz, 1H), 7.59-7.49 (m, 1H), 7.34-7.25 (m, 1H), 6.99-6.89 (m, 2H), 4.90 (s, 2H), 3.86-3.76 (m, 1H), 3.73-3.66 (m, 1H), 3.66-3.56 (m, 5H), 3.38 (t, J=7.2 Hz, 2H), 3.31 (dd, J=14.4, 3.5 Hz, 1H), 3.22 (td, J=11.3, 3.1 Hz, 1H), 2.54 (t, J=7.1 Hz, 2H), 2.45 (t, J=4.7 Hz, 3H), 1.74 (q, J=4.4, 4.0 Hz, 1H), 1.60-1.51 (m, 1H), 1.47-1.22 (m, 11H).

1-(cyclopropylmethyl)-3-((3-(4-(2-((2-methoxyethyl) sulfonyl)phenoxy)-3-(trifluoromethyl)phenyl)-1,2,4-oxadiazol-5-yl)methyl)-5,5-dimethylimidazolidine-2,4-dione (54) was obtained using a procedure similar to the procedure described in Example 50 for the synthesis of 3-((3-(4-(2-(isobutylsulfonyl)phenoxy)-3-(trifluoromethyl)phenyl)-1,2, 4-oxadiazol-5-yl)methyl)-5,5-dimethyl-1-(3-(pyrrolidin-1-yl)propyl)imidazolidine-2,4-dione (50b), except 2-(isobutylsulfonyl)phenol (int-B2) was replaced with 2-((2-methoxyethyl)sulfonyl)phenol (int-B5), 1-(3-bromopropyl) pyrrolidine was replaced with (bromomethyl)cyclopropane and step 2 was carried out at room temperature. LCMS Method 3: Rt.=1.19 mins.; m/z 623.6 [M+H]+; $^1$H NMR (400 MHz, CDCl$_3$) δ 8.31 (d, J=2.1 Hz, 1H), 8.08 (dd, J=8.7, 2.1 Hz, 1H), 8.02 (dd, J=7.9, 1.7 Hz, 1H), 7.61-7.53 (m, 1H), 7.37-7.28 (m, 1H), 6.99-6.91 (m, 2H), 4.93 (s, 2H), 3.73 (t, J=6.1 Hz, 2H), 3.66-3.58 (m, 2H), 3.18 (d, J=7.0 Hz, 2H), 3.15 (s, 3H), 1.47 (s, 6H), 1.07-0.93 (m, 1H), 0.58-0.47 (m, 2H), 0.32-0.24 (m, 2H).

197

Example 55; 5,5-dimethyl-3-((3-(4-(2-(methylsulfonyl)phenoxy)-3-(trifluoromethyl)phenyl)-1,2,4-oxadiazol-5-yl)methyl)-1-(2-morpholinoethyl)imidazolidine-2,4-dione (55)

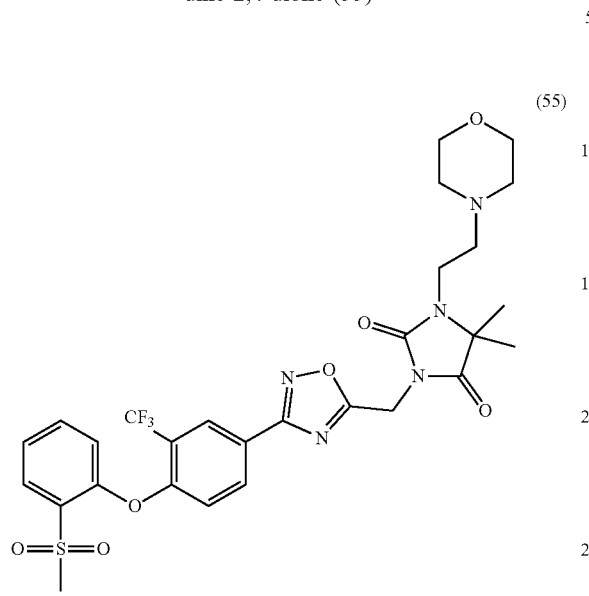

5,5-dimethyl-3-((3-(4-(2-(methylsulfonyl)phenoxy)-3-(trifluoromethyl)phenyl)-1,2,4-oxadiazol-5-yl)methyl)-1-(2-morpholinoethyl)imidazolidine-2,4-dione (55) was obtained using a procedure similar to the procedure described in Example 50 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl) imidazolidine-2,4-dione (50b), except 2-(isobutylsulfonyl) phenol (int-B2) was replaced with 2-(methylsulfonyl) phenol, 1-(3-bromopropyl)pyrrolidine was replaced with 4-(2-bromoethyl)morpholine and step 2 was carried out at room temperature. LCMS Method 4: Rt.=1.60 mins.; m/z 638.5 [M+H]+; $^1$H NMR (400 MHz, CDCl$_3$) δ 8.31 (d, J=2.1 Hz, 1H), 8.11-8.03 (m, 2H), 7.58 (ddd, J=8.2, 7.5, 1.7 Hz, 1H), 7.34 (td, J=7.6, 1.0 Hz, 1H), 7.00-6.91 (m, 2H), 4.92 (s, 2H), 4.20-3.30 (m, 6H), 2.60-2.40 (m, 6H), 1.47 (d, J=6.7 Hz, 9H).

Example 56; 1-(2-morpholinoethyl)-3-((3-(4-(2-((((tetrahydrofuran-2-yl)methyl)sulfonyl)phenoxy)-3-(trifluoromethyl)phenyl)-1,2,4-oxadiazol-5-yl) methyl)-8-oxa-1,3-diazaspiro[4.5]decane-2,4-dione (56)

198

-continued

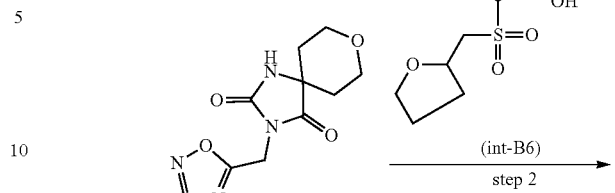

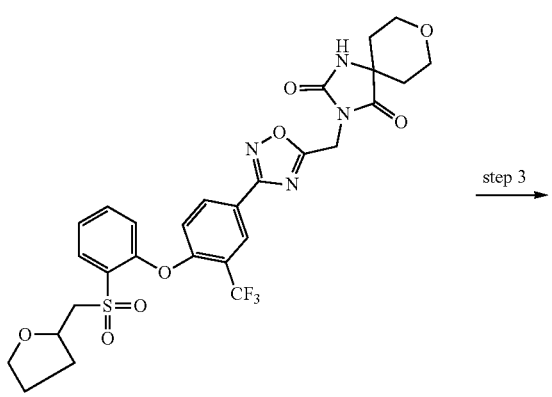

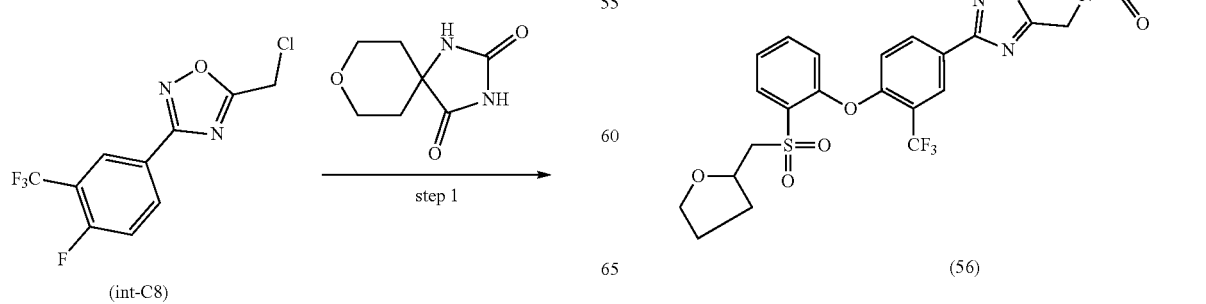

Step 1: To a solution of 5-(chloromethyl)-3-(4-fluoro-3-(trifluoromethyl)phenyl)-1,2,4-oxadiazole (int-C8) (181 mg, 0.646 mmol) and 8-oxa-1,3-diazaspiro[4.5]decane-2,4-dione (100 mg, 0.588 mmol) in DMF (1.5 mL) was added potassium carbonate (203 mg, 1.469 mmol) and the resulting mixture stirred at room temperature for 16 hours. Water (10 mL) and ethyl acetate (20 mL) were added, the layers separated, and the aqueous layer extracted with ethyl acetate (20 mL). The combined organic layers were washed with 0.5M LiCl (15 mL) and brine, then dried over sodium sulfate, filtered, and concentrated. The residue was purified by flash column chromatography, eluting with 0-100% ethyl acetate in heptane to provide 3-((3-(4-fluoro-3-(trifluoromethyl)phenyl)-1,2,4-oxadiazol-5-yl)methyl)-8-oxa-1,3-diazaspiro[4.5]decane-2,4-dione. 1H NMR (400 MHz, CDCl$_3$) δ 8.30 (dd, J=6.8, 2.2 Hz, 1H), 8.24 (ddd, J=8.7, 4.6, 2.2 Hz, 1H), 7.98 (s, 1H), 7.32 (t, J=9.2 Hz, 1H), 5.02 (s, 2H), 4.05 (dt, J=12.2, 4.5 Hz, 2H), 3.70 (ddd, J=12.4, 9.7, 2.9 Hz, 2H), 2.21 (ddd, J=13.9, 9.7, 4.3 Hz, 2H), 1.74 (dddd, J=13.7, 4.8, 3.0, 1.3 Hz, 2H).

Step 2: A solution of 2-((((tetrahydrofuran-2-yl)methyl)sulfonyl)phenol (int-B6) (105 mg, 0.434 mmol) in DMF (3 mL) was treated with cesium carbonate (189 mg, 0.579 mmol) and stirred for 30 mins. Then 3-((3-(4-fluoro-3-(trifluoromethyl)phenyl)-1,2,4-oxadiazol-5-yl)methyl)-8-oxa-1,3-diazaspiro[4.5]decane-2,4-dione (120 mg, 0.290 mmol) was added and the mixture heated at 90° C. for 72 hours. The reaction mixture was then allowed to cool to room temperature, and water and ethyl acetate were added. The aqueous layer was extracted with ethyl acetate, and the combined organic layers were washed with 0.5 M LiCl and brine, then dried over magnesium sulfate, filtered and evaporated to dryness to obtain 3-((3-(4-(2-(((tetrahydrofuran-2-yl)methyl)sulfonyl)phenoxy)-3-(trifluoromethyl)phenyl)-1,2,4-oxadiazol-5-yl)methyl)-8-oxa-1,3-diazaspiro[4.5]decane-2,4-dione. The crude material was used directly in the next step.

Step 3: A solution of 3-((3-(4-(2-(((tetrahydrofuran-2-yl)methyl)sulfonyl)phenoxy)-3-(trifluoromethyl)phenyl)-1,2,4-oxadiazol-5-yl)methyl)-8-oxa-1,3-diazaspiro[4.5]decane-2,4-dione (59 mg, 0.093 mmol) in DMF (2 mL) was treated with 4-(2-bromoethyl)morpholine HBr salt (38.2 mg, 0.139 mmol) and then cesium carbonate (91 mg, 0.278 mmol). The resulting mixture was then stirred at room temperature overnight. Water was then added, and the mixture was extracted twice with ethyl acetate. The combined organic layers were washed with 0.5M LiCl solution and brine, and then the combined organic layers were dried over magnesium sulfate, filtered and evaporated to dryness. The residue was purified by flash column chromatography, eluting with 0-20% MeOH (with 2 M NH3 additive) in EtOAc, to provide product, which was further purified using HPLC to provide 1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-8-oxa-1,3-diazaspiro[4.5]decane-2,4-dione (56). $^1$H NMR (400 MHz, CDCl$_3$) δ 8.38 (d, J=2.1 Hz, 1H), 8.13 (dtt, J=8.3, 6.4, 4.2 Hz, 2H), 7.66 (ddd, J=8.3, 7.5, 1.7 Hz, 1H), 7.43 (td, J=7.6, 1.1 Hz, 1H), 7.07-6.93 (m, 2H), 5.00 (s, 2H), 4.42-4.30 (m, 1H), 4.17 (m, 2H), 3.99 (dd, J=11.9, 5.2 Hz, 2H), 3.84-3.62 (m, 6H), 3.56-3.42 (m, 2H), 2.66-2.56 (m, 6H), 2.12 (td, J=12.9, 5.4 Hz, 2H), 1.99-1.61 (m, 8H); LCMS Method 4: Rt.=1.76 mins.; m/z 750.7 [M+H]+.

Example 57; 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (57)

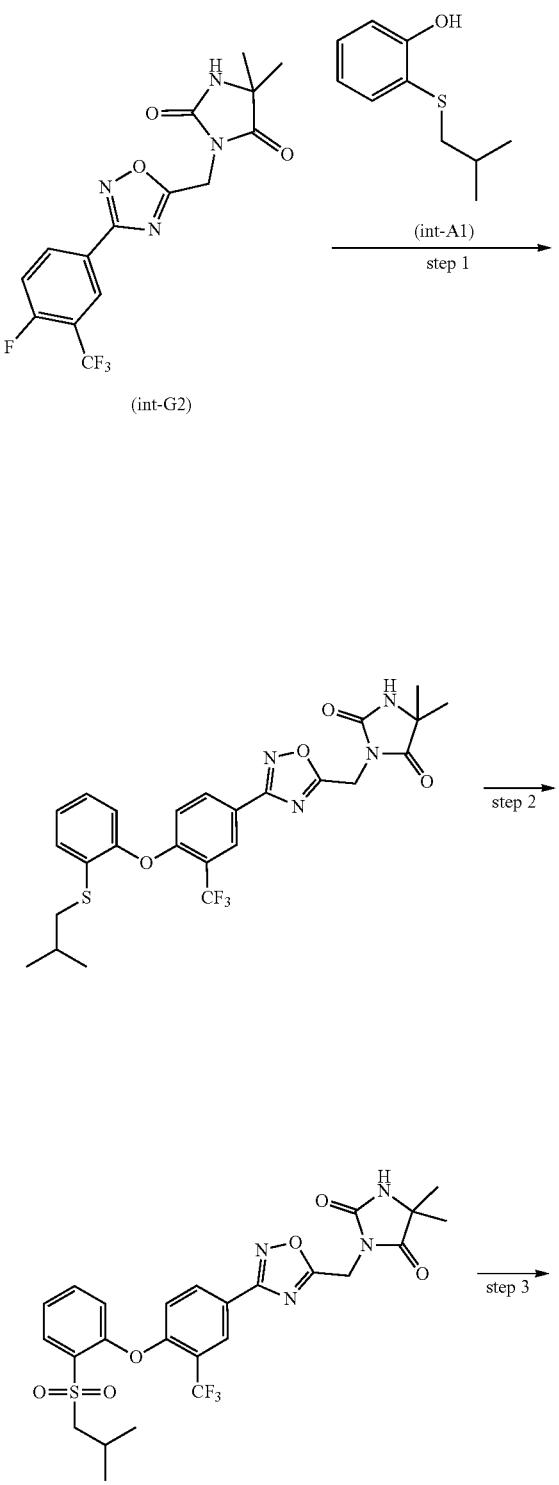

-continued

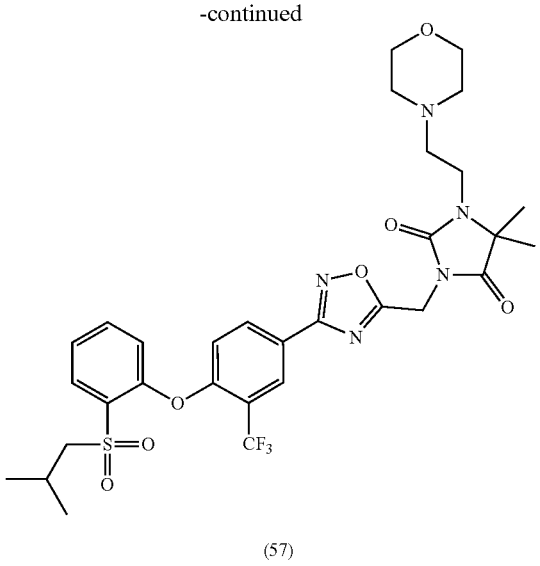

(57)

Step 1: To a solution of 3-((3-(4-fluoro-3-(trifluoromethyl)phenyl)-1,2,4-oxadiazol-5-yl)methyl)-5,5-dimethylimidazolidine-2,4-dione (int-G2) (7.26 g, 39.8 mmol) in DMF (100 mL) was added 2-(isobutylthio)phenol (int-A1) (4.94 g, 13.27 mmol) and potassium carbonate (5.50 g, 39.8 mmol). The mixture was heated at 90° C. overnight, then left to cool to room temperature, and then diluted with saturated ammonium chloride solution. The mixture was extracted with EtOAc, and the organic layer washed with brine, dried over sodium sulfate, filtered, and concentrated. The residue was purified by flash column chromatography (0-60% EtOAc/Heptanes) to provide: 3-((3-(4-(2-(isobutylthio)phenoxy)-3-(trifluoromethyl)phenyl)-1,2,4-oxadiazol-5-yl)methyl)-5,5-dimethylimidazolidine-2,4-dione. LCMS Method 5: m/z [M+]=535.4. 1H NMR (400 MHz, CD$_2$Cl$_2$) δ 8.39 (d, J=2.0 Hz, 1H), 8.11 (dd, J=8.7, 2.1 Hz, 1H), 7.49 (dd, J=5.8, 3.5 Hz, 1H), 7.34-7.19 (m, 2H), 7.13-6.95 (m, 1H), 6.80 (d, J=8.8 Hz, 1H), 5.77 (s, 1H), 4.99 (s, 2H), 2.82 (d, J=6.9 Hz, 2H), 1.84 (dh, J=13.3, 6.8 Hz, 1H), 1.55 (s, 6H), 1.01 (d, J=6.8 Hz, 6H).

Step 2: mCPBA (8.43 g, 37.6 mmol) was added to a mixture of 3-((3-(4-(2-(isobutylthio)phenoxy)-3-(trifluoromethyl)phenyl)-1,2,4-oxadiazol-5-yl)methyl)-5,5-dimethylimidazolidine-2,4-dione (6.7 g, 12.53 mmol) in dichloromethane (200 mL). After stirring for 1 hour, saturated sodium bicarbonate solution was added. The organic layer was washed with brine, dried over sodium sulfate, filtered, and concentrated. The residue was purified by flash column chromatography (0-100% EtOAc/heptanes) to provide 3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione (50a). LCMS Method 5: m/z [M+H]+ 567.2; 1H NMR (400 MHz, (CD$_3$)$_2$SO) δ 8.55 (s, 1H), 8.28 (d, J=2.1 Hz, 1H), 8.25 (dd, J=8.7, 2.2 Hz, 1H), 8.03 (dd, J=7.9, 1.7 Hz, 1H), 7.82 (ddd, J=8.3, 7.5, 1.7 Hz, 1H), 7.57 (td, J=7.6, 1.0 Hz, 1H), 7.33 (dd, J=8.2, 1.0 Hz, 1H), 7.15 (d, J=8.7 Hz, 1H), 5.02 (s, 2H), 3.36 (d, J=6.5 Hz, 2H), 2.07 (hept, J=6.6 Hz, 1H), 1.38 (s, 6H), 0.98 (d, J=6.7 Hz, 6H).

Step 3: 4-(2-bromoethyl)morpholine (7.09 g, 25.8 mmol) was added to a mixture of 3-((3-(4-(2-(isobutylsulfonyl) phenoxy)-3-(trifluoromethyl)phenyl)-1,2,4-oxadiazol-5-yl) methyl)-5,5-dimethylimidazolidine-2,4-dione (50a) (7.3 g, 12.88 mmol) and cesium carbonate (14.69 g, 45.1 mmol) in DMF (100 mL). The mixture was stirred overnight. The mixture was then diluted with ethyl acetate, then washed sequentially with water and brine, dried over sodium sulfate, filtered and concentrated. The residue was purified by flash column chromatography (0-100% EtOAc/Heptane, then 1% triethylamine in EtOAc) to provide 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl) imidazolidine-2,4-dione (57). LCMS Method 5: Rt.=2.81 mins.; m/z [M+H]+ 680.5. $^1$H NMR (400 MHz, CDCl$_3$) δ 8.38 (d, J=2.1 Hz, 1H), 8.20-8.10 (m, 2H), 7.64 (ddd, J=8.2, 7.4, 1.7 Hz, 1H), 7.41 (td, J=7.6, 1.1 Hz, 1H), 7.04-6.97 (m, 2H), 4.99 (s, 2H), 3.71 (br s, 4H), 3.48 (s, 2H), 3.35 (d, J=6.6 Hz, 2H), 2.65 (s, 2H), 2.56 (s, 4H), 2.26 (hept, J=6.7 Hz, 1H), 1.52 (s, 6H), 1.07 (d, J=6.7 Hz, 6H).

Example 58; 3-((3-(4-(2-((2-methoxyethyl)sulfonyl)
phenoxy)-3-(trifluoromethyl)phenyl)-1,2,4-oxadi-
azol-5-yl)methyl)-5,5-dimethyl-1-(2-morpholino-
ethyl)imidazolidine-2,4-dione (58)

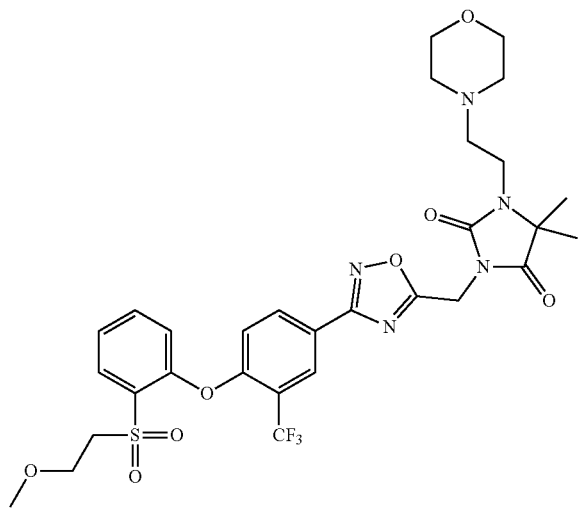

(58)

3-((3-(4-(2-((2-methoxyethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (58) was obtained using a procedure similar to the procedure described in Example 57 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (57), except 2-(isobutylthio) phenol (int-A1) was replaced with 2-((2-methoxyethyl)thio) phenol (int-A2). $^1$H NMR (400 MHz, (CD$_3$)$_2$SO) δ 8.26 (d, J=2.1 Hz, 1H), 8.23 (dd, J=8.7, 2.2 Hz, 1H), 7.98 (dd, J=7.9, 1.7 Hz, 1H), 7.81 (m, J=8.2-1.7 Hz, 1H), 7.55 (td, J=7.6, 1.1 Hz, 1H), 7.32 (dd, J=8.3, 1.1 Hz, 1H), 7.12 (d, J=8.7 Hz, 1H), 5.06 (s, 2H), 3.74-3.62 (m, 4H), 3.53 (t, J=4.6 Hz, 4H), 3.41 (t, J=7.0 Hz, 2H), 3.06 (s, 3H), 2.45-2.39 (m, 6H), 1.41 (s, 6H); LCMS Method 4: Rt.=1.64 mins.; m/z 682.5 [M+H]+.

Example 59: 5,5-dimethyl-1-(2-(tetrahydro-2H-pyran-4-yl)ethyl)-3-((3-(4-(2-((tetrahydrofuran-3-yl)sulfonyl)phenoxy)-3-(trifluoromethyl)phenyl)-1,2,4-oxadiazol-5-yl)methyl)imidazolidine-2,4-dione (59)

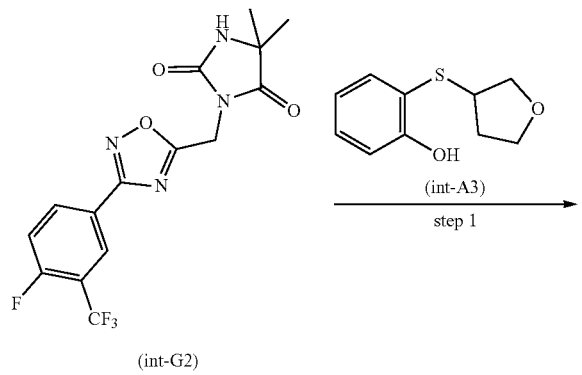

(int-G2)

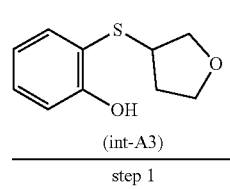

(int-A3)

step 1

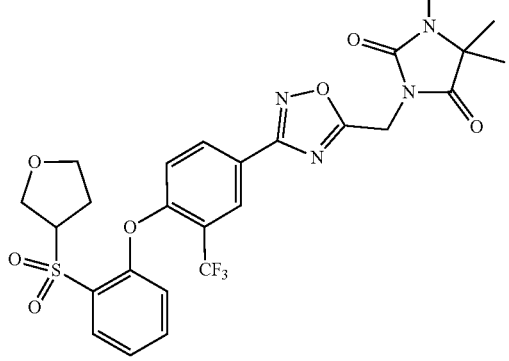

(59)

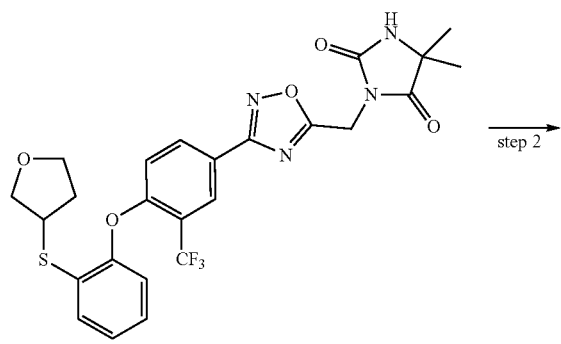

step 2

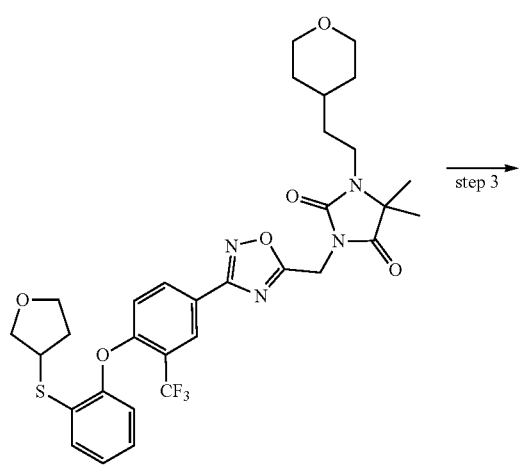

step 3

Step 1: To a solution of 2-((tetrahydrofuran-3-yl)thio)phenol (int-A3) (1.05 g, 5.35 mmol) and 3-((3-(4-fluoro-3-(trifluoromethyl)phenyl)-1,2,4-oxadiazol-5-yl)methyl)-5,5-dimethylimidazolidine-2,4-dione (int-G2) (1.992 g, 5.35 mmol) in DMF (20 mL) was added potassium carbonate (1.109 g, 8.02 mmol) and the mixture was heated to 90° C. overnight. The reaction mixture was allowed to cool to room temperature, and water was added. The resulting mixture was extracted twice with ethyl acetate, and the combined organic layers were dried over magnesium sulfate, filtered, and evaporated to dryness. The residue was purified by flash column chromatography, eluting with 0-100% EtOAc in MeOH, to provide 5,5-dimethyl-3-((3-(4-(2-((tetrahydrofuran-3-yl)thio)phenoxy)-3-(trifluoromethyl)phenyl)-1,2,4-oxadiazol-5-yl)methyl)imidazolidine-2,4-dione. LCMS Method 3: Rt.=1.15 mins.; [M+H]+ 549.3.

Step 2: To a solution of 5,5-dimethyl-3-((3-(4-(2-((tetrahydrofuran-3-yl)thio)phenoxy)-3-(trifluoromethyl)phenyl)-1,2,4-oxadiazol-5-yl)methyl)imidazolidine-2,4-dione (100 mg, 0.182 mmol) in DMF (3 mL) was added cesium carbonate (119 mg, 0.365 mmol) and 4-(2-bromoethyl)tetrahydro-2H-pyran (38.7 mg, 0.201 mmol), and the resulting mixture stirred at room temperature for 16 hours. Water was added, and the mixture was extracted twice with ethyl acetate. The combined organic layers were washed with 0.5 M LiCl solution, then dried over magnesium sulfate, filtered, and evaporated to dryness. The residue was purified by flash column chromatography, eluting with 0-100% EtOAc in heptanes to provide 5,5-dimethyl-1-(2-(tetrahydro-2H-pyran-4-yl)ethyl)-3-((3-(4-(2-((tetrahydrofuran-3-yl)thio)phenoxy)-3-(trifluoromethyl)phenyl)-1,2,4-oxadiazol-5-yl)methyl)imidazolidine-2,4-dione.

Step 3: A solution of 5,5-dimethyl-1-(2-(tetrahydro-2H-pyran-4-yl)ethyl)-3-((3-(4-(2-((tetrahydrofuran-3-yl)thio)phenoxy)-3-(trifluoromethyl)phenyl)-1,2,4-oxadiazol-5-yl)methyl)imidazolidine-2,4-dione (121 mg, 0.183 mmol) in dichloromethane (5 mL) was treated with mCPBA (181 mg, 0.733 mmol) and the reaction mixture stirred at room temperature for 2 hours. Saturated aqueous sodium bicarbonate solution was added, and the aqueous layer extracted twice with dichloromethane. The combined organic layers were dried over magnesium sulfate, filtered and evaporated to dryness. The residue was purified by flash column chromatography, eluting with 0-100% EtOAc in heptanes, to provide 5,5-dimethyl-1-(2-(tetrahydro-2H-pyran-4-yl)ethyl)-3-((3-(4-(2-((tetrahydrofuran-3-yl)sulfonyl)phenoxy)-3-(trifluoromethyl)phenyl)-1,2,4-oxadiazol-5-yl)methyl)imidazolidine-2,4-dione (59). $^1$H NMR (400 MHz, CDCl$_3$) δ 8.40 (d, J=2.1 Hz, 1H), 8.16 (ddd, J=13.4, 8.3, 1.9 Hz, 2H), 7.68 (ddd, J=8.3, 7.5, 1.7 Hz, 1H), 7.43 (td, J=7.6, 1.1 Hz, 1H), 7.08-7.00 (m, 2H), 5.00 (s, 2H), 4.39 (ddt, J=9.8, 8.0, 5.1 Hz, 1H), 4.07-3.92 (m, 4H), 3.87 (ddd, J=8.5, 7.2, 5.9 Hz, 1H), 3.43-3.33 (m, 4H), 2.23 (s, 1H), 1.73-1.59 (m, 5H), 1.52 (s, 6H), 1.43-1.22 (m, 4H); LCMS Method 5: Rt.=2.59 mins; m/z 693.5 [M+H]+.

Example 60; 5-((dimethylamino)methyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione (60)

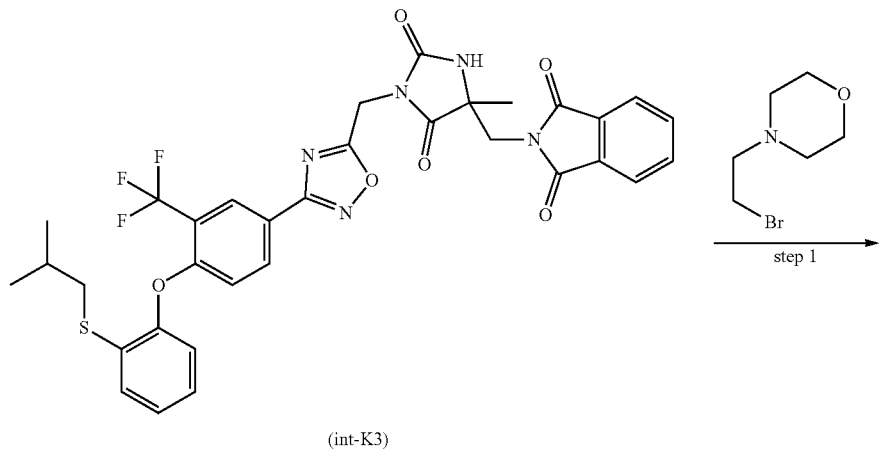

(int-K3)

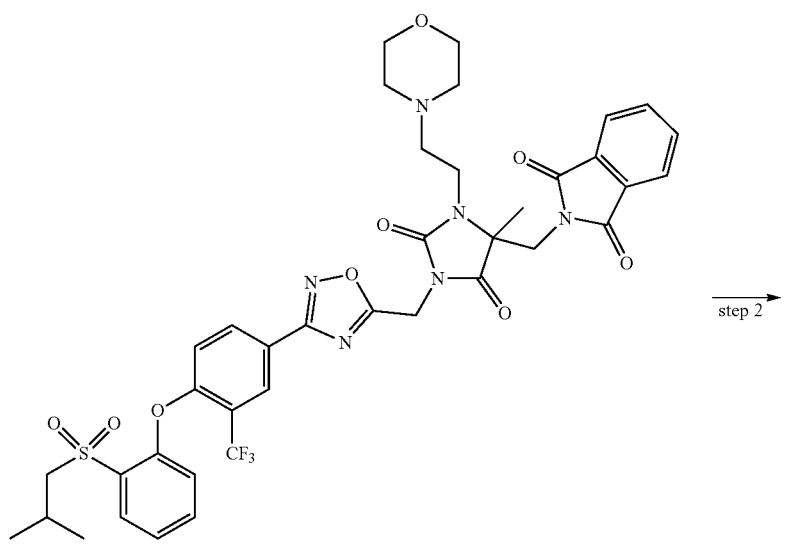

-continued

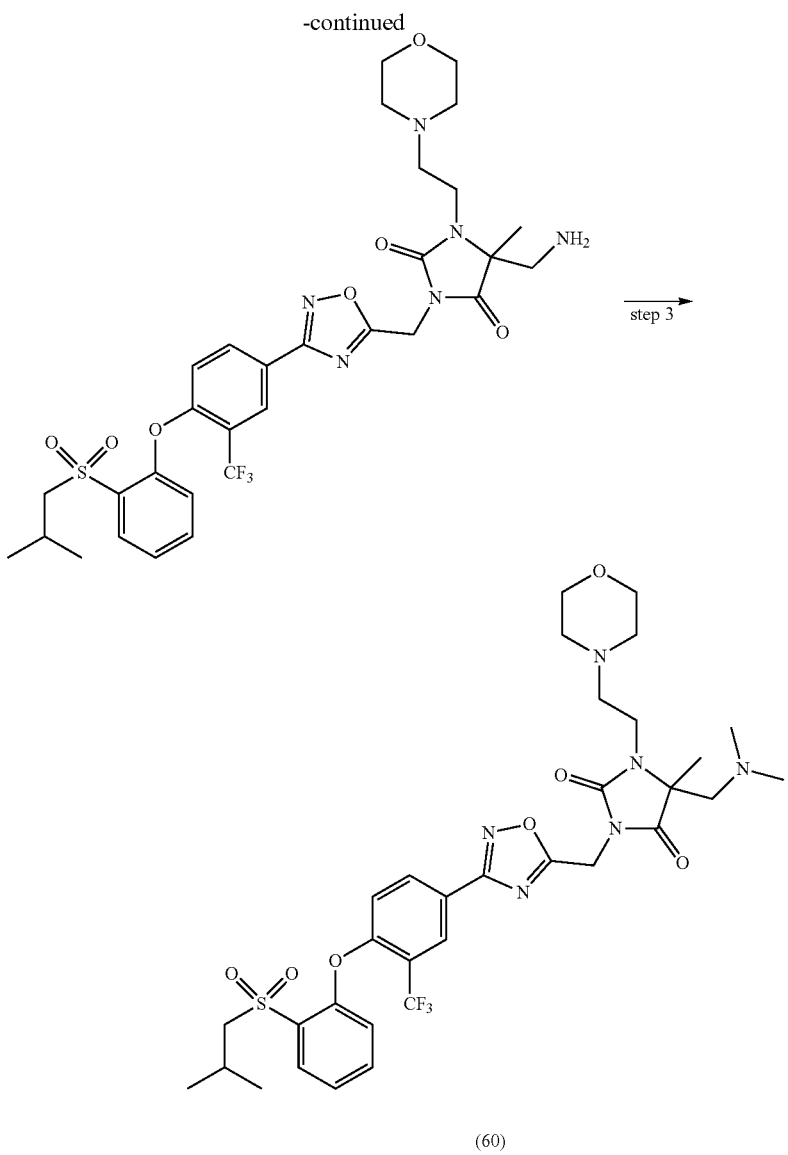

(60)

Step 1: Cesium carbonate (72.9 mg, 0.224 mmo) was added to a solution of 2-((1-((3-(4-(2-(isobutylthio)phenoxy)-3-(trifluoromethyl)phenyl)-1,2,4-oxadiazol-5-yl)methyl)-4-methyl-2,5-dioxoimidazolidin-4-yl)methyl)isoindoline-1,3-dione (int-K3) (76 mg, 0.112 mmol) and 4-(2-bromoethyl)morpholine (46.1 mg, 0.168 mmol) in DMF (2 mL) and the reaction stirred at room temperature overnight. The reaction was poured into water (30 mL) and extracted with ethyl acetate (3×50 mL). The combined organic layers were washed with 0.5 M LiCl, then dried over magnesium sulfate, filtered and concentrated. The residue was purified by flash column chromatography, eluting with 50-100% EtOAc in heptane to provide 2-((1-((3-(4-(2-(isobutylsulfonyl)phenoxy)-3-(trifluoromethyl)phenyl)-1,2,4-oxadiazol-5-yl)methyl)-4-methyl-3-(2-morpholinoethyl)-2,5-dioxoimidazolidin-4-yl)methyl)isoindoline-1,3-dione. LCMS Method 1: Rt.=3.36 min., m/z 793.6 [M+H]+.

Step 2: A solution of 2-((1-((3-(4-(2-(isobutylsulfonyl)phenoxy)-3-(trifluoromethyl)phenyl)-1,2,4-oxadiazol-5-yl)methyl)-4-methyl-3-(2-morpholinoethyl)-2,5-dioxoimidazolidin-4-yl)methyl)isoindoline-1,3-dione (210 mg, 0.255 mmol) in ethanol (3 mL) was treated with hydrazine hydrate (0.037 mL, 0.764 mmol) at room temperature, and the reaction mixture heated to 60° C. for 1 hour. The mixture was then allowed to cool to room temperature overnight. The mixture was evaporated to dryness, and the residue purified by reverse phase flash column chromatography, eluting with 0-100% acetonitrile in water to provide 5-(aminomethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione.

Step 3: A solution of 5-(aminomethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione (50 mg, 0.072 mmol) in methanol (2 mL) was treated with sodium cyanoborohydride (9.95 mg, 0.158 mmol) and acetic acid (0.021 mL, 0.360 mmol), then cooled to 0° C. After 10 minutes, a solution of formalin (0.064 mL, 0.864 mmol) in methanol (1 mL) was added dropwise. The reaction mixture was allowed to warm to room temperature and stirred for 2 hours, then quenched by the addition of saturated aqueous sodium carbonate solution. The mixture was evaporated to dryness, the residue partitioned between water and DCM, and the aqueous layer extracted with DCM. The combined organic layers were dried over magnesium sulfate, filtered and concentrated to provide 5-((dimethylamino)methyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione (60). $^1$H NMR (400 MHz, CDCl$_3$) δ 8.32 (d, J=2.1 Hz, 1H), 8.09 (dd, J=8.7, 2.1 Hz, 1H), 8.04 (dd, J=7.9, 1.7 Hz, 1H), 7.57 (ddd, J=8.3, 7.4, 1.7 Hz, 1H), 7.33 (td, J=7.6, 1.1 Hz, 1H), 6.95 (dt, J=8.6, 1.4 Hz, 2H), 4.99-4.86 (m, 2H), 3.73-3.60 (m, 6H), 3.35-3.25 (m, 2H), 3.10 (ddd, J=14.4, 8.7, 5.9 Hz, 1H), 2.72 (d, J=14.3 Hz, 1H), 2.64 (ddd, J=12.4, 8.7, 5.7 Hz, 1H), 2.59-2.44 (m, 6H), 2.17 (s, 6H), 1.33 (s, 3H), 0.99 (d, J=6.8 Hz, 6H). LCMS Method 1: Rt.=2.80 mins; m/z 723.3 [M−H]−.

Example 61; 3-((3-(4-(2-((2-(bis(2-methoxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (61)

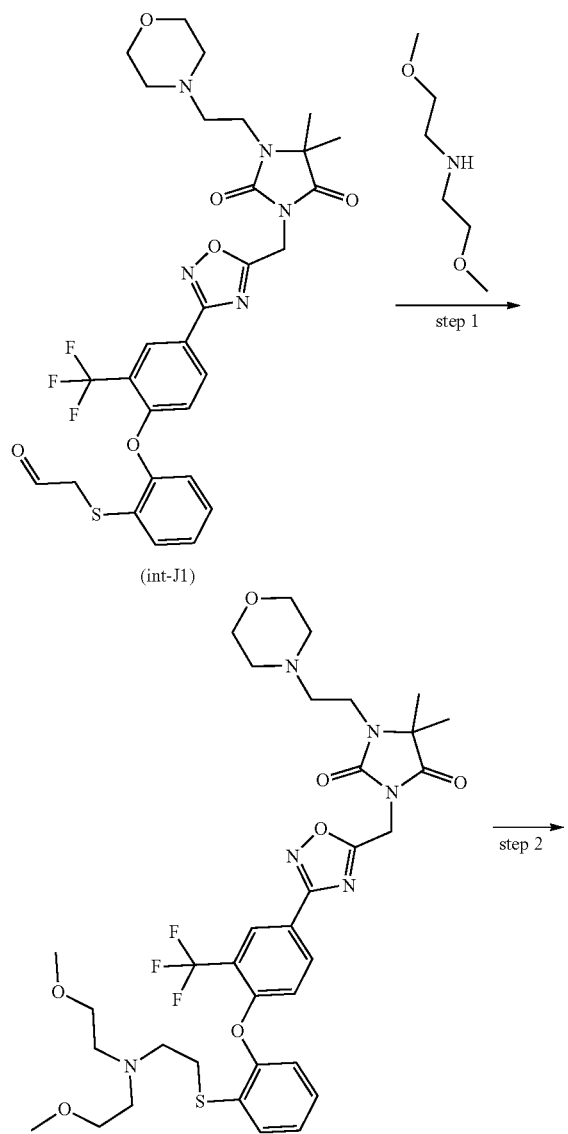

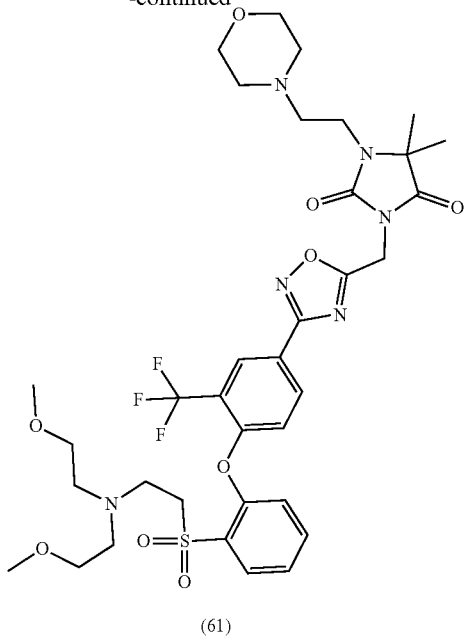

Step 1: To a solution of 2-((2-(4-(5-((4,4-dimethyl-3-(2-morpholinoethyl)-2,5-dioxoimidazolidin-1-yl)methyl)-1,2,4-oxadiazol-3-yl)-2-(trifluoromethyl)phenoxy)phenyl)thio)acetaldehyde (int-J1) (50 mg, 0.079 mmol) in 1,2-dichloroethane (2 mL) was added bis(2-methoxyethyl)amine (12.61 mg, 0.095 mmol). Sodium triacetoxyborohydride (26.8 mg, 0.126 mmol) and acetic acid (9.03 μl, 0.158 mmol) were then added and the reaction mixture was stirred overnight at room temperature. The reaction mixture was then quenched with water (5 mL), the aqueous solution was then extracted with DCM (3×20 mL). The organics were then combined and dried over magnesium sulfate to provide 3-((3-(4-(2-((2-(bis(2-methoxyethyl)amino)ethyl)thio)phenoxy)-3-(trifluoromethyl)phenyl)-1,2,4-oxadiazol-5-yl)methyl)-5,5-dimethyl-1-(2-morpholinoethyl)imidazolidine-2,4-dione. LCMS Method 3: Rt.=1.22 mins; m/z 751.5 [M+H]+.

Step 2: 3-((3-(4-(2-((2-(bis(2-methoxyethyl)amino)ethyl)thio)phenoxy)-3-(trifluoromethyl)phenyl)-1,2,4-oxadiazol-5-yl)methyl)-5,5-dimethyl-1-(2-morpholinoethyl)imidazolidine-2,4-dione (60 mg, 0.080 mmol) in TFA (1 mL) was cooled to 0° C. and treated with H$_2$O$_2$ (30% aq) (12 μl, 0.117 mmol) and then allowed to warm to room temperature over 2 hrs. TFA was removed in vacuum and the residue partitioned between ethyl acetate and sat aq NaHCO3. The combined organic layers were dried over magnesium sulfate, filtered and evaporated to dryness, the organics were purified using SFC mass directed prep. The fractions were combined and concentrated under vacuum to give 3-((3-(4-(2-((2-(bis(2-methoxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (61). LCMS Method 5: Rt.=2.46 mins; m/z 783.7 [M+H]+; $^1$H NMR (400 MHz, CDCl$_3$) δ 8.43-8.37 (m, 1H), 8.20-8.07 (m, 2H), 7.74-7.61 (m, 1H), 7.48-7.37 (m, 1H), 7.10-6.98 (m, 2H), 5.01 (d, J=1.1 Hz, 2H), 3.75-3.70 (m, 4H), 3.64 (s, 1H), 3.52-3.47 (m, 2H), 3.42-3.23 (m, 8H), 3.10 (s, 1H), 2.73-2.59 (m, 5H), 2.56 (s, 3H), 2.11 (s, 1H), 1.66 (s, 3H), 1.54 (s, 6H).

211

Example 62: 3-((3-(4-(2-((2-(bis(2-hydroxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (62)

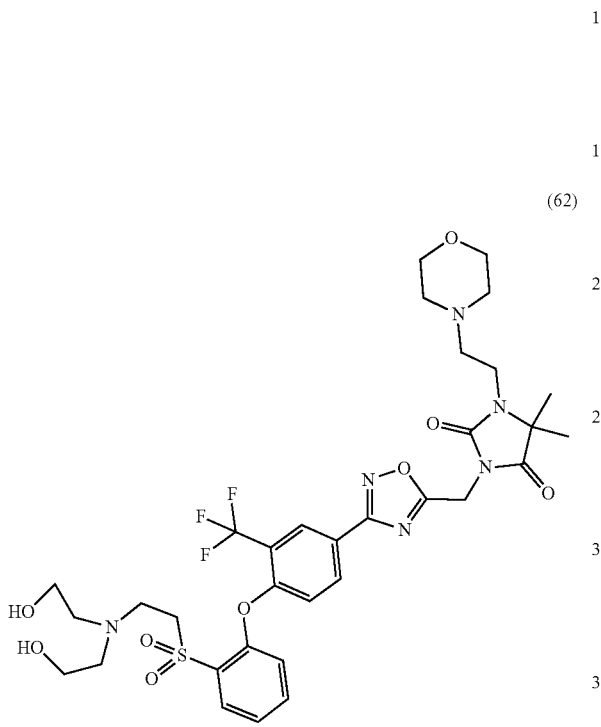

(62)

3-((3-(4-(2-((2-(bis(2-hydroxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (62) was obtained using a procedure similar to the procedure described in Example 61 for the synthesis of 3-((3-(4-(2-((2-(bis(2-methoxyethyl)amino)ethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (61), except bis(2-methoxyethyl)amine was replaced with 2,2'-azanediylbis(ethan-1-ol). $^1$H NMR (400 MHz, CDCl$_3$) δ 8.41 (dd, J=6.2, 2.1 Hz, 1H), 8.20 (dd, J=8.6, 2.1 Hz, 1H), 8.12 (dd, J=8.0, 1.7 Hz, 1H), 7.75-7.64 (m, 1H), 7.49-7.39 (m, 1H), 7.13-6.99 (m, 2H), 5.01 (s, 3H), 4.34 (s, 2H), 3.72 (t, J=4.6 Hz, 4H), 3.62 (t, J=4.9 Hz, 1H), 3.50 (t, J=7.2 Hz, 3H), 2.70-2.61 (m, 5H), 2.60-2.53 (m, 6H), 2.10 (s, 4H), 1.53 (s, 6H); LCMS Method 5: Rt.=1.96 mins.; m/z 755.7 [M+H]+.

212

Example 63: 8-cyclobutyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (63)

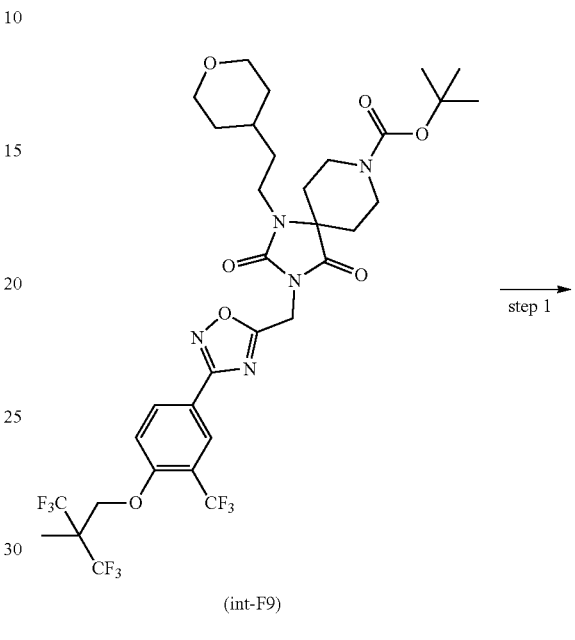

(int-F9)

→ step 1

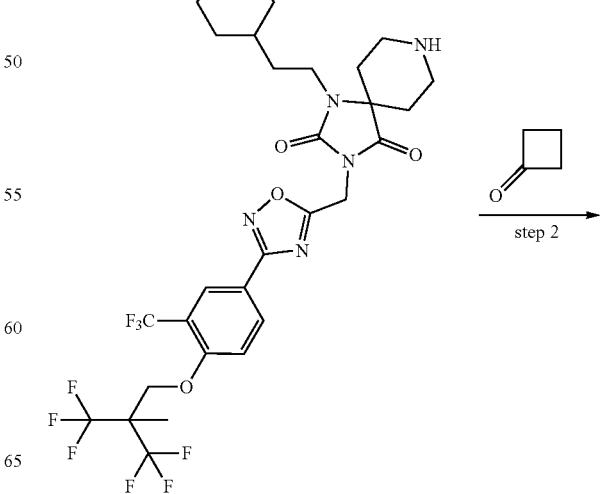

→ step 2

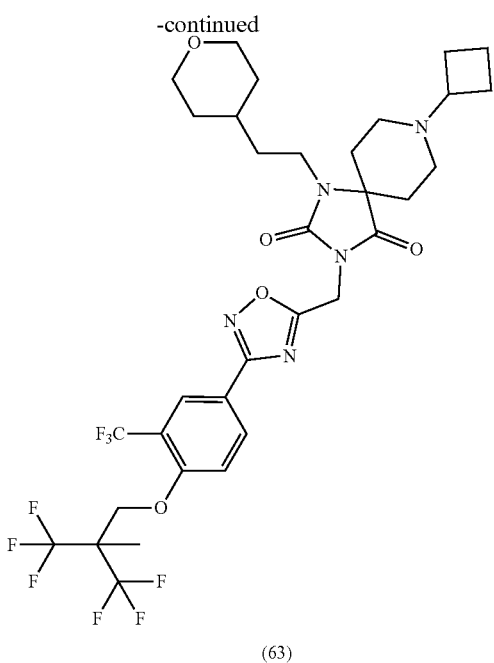

(63)

Step 1: 4 M HCl in dioxane (3.18 mL, 12.72 mmol) was added to the tert-butyl 2,4-dioxo-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-8-carboxylate (int-F9) (1.7 g, 2.120 mmol) in DCM (30 mL). The reaction mixture was stirred overnight and then concentrated to provide crude 1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione as a hydrogen chloride salt, which was carried to next step without purification. ESI-MS m/z [M+H]⁺: 702.9 Step 2: Sodium triacetoxyborohydride (2.029 g, 9.57 mmol) was added to a mixture of 1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (1.57 g, 1.595 mmol) and cyclobutanone (0.477 mL, 6.38 mmol) in dichloroethane (30 mL) and the resulting mixture was stirred at room temperature overnight. The mixture was then diluted with DCM, and washed with saturated sodium bicarbonate solution. The organic layer was washed with brine, dried over anhydrous sodium sulfate, filtered and then concentrated to dryness. The residue was purified with reverse phase-C18 chromatography (10-100% 0.1% NH₄OH in ACN/water) to provide 8-cyclobutyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione (63). LCMS Method 2: Rt.=1.08; m/z [M+H]⁺ 756.4;

1H NMR (CD₃CN, 400 MHz) δ 8.15-8.26 (m, 2H), 7.30 (d, 1H, J=8.3 Hz), 4.87 (s, 2H), 4.47 (s, 2H), 3.69-3.91 (m, 2H), 3.21-3.43 (m, 4H), 2.71-3.02 (m, 3H), 2.3-2.6 (m, 2H), 1.98-2.12 (m, 4H), 1.69-1.91 (m, 4H), 1.61-1.65 (m, 4H), 1.51-1.55 (m, 5H), 1.11-1.28 (m, 3H).

Example 64: 5,5-dimethyl-1-(2-morpholinoethyl)-3-((3-(4-(2-(((tetrahydrofuran-2-yl)methyl) sulfonyl) phenoxy)-3-(trifluoromethyl)phenyl)-1,2,4-oxadiazol-5-yl)methyl) imidazolidine-2,4-dione (64)

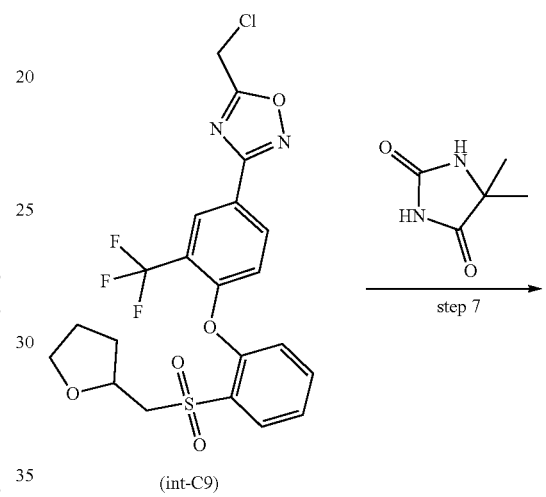

(int-C9)

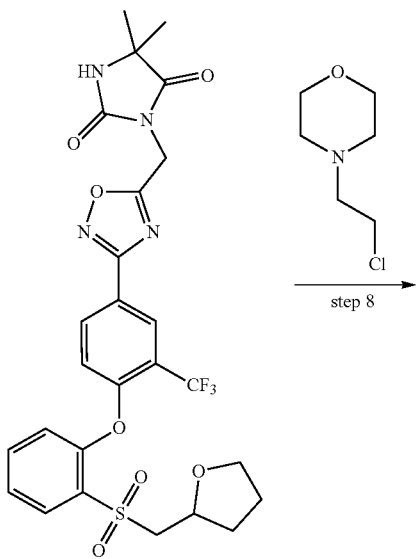

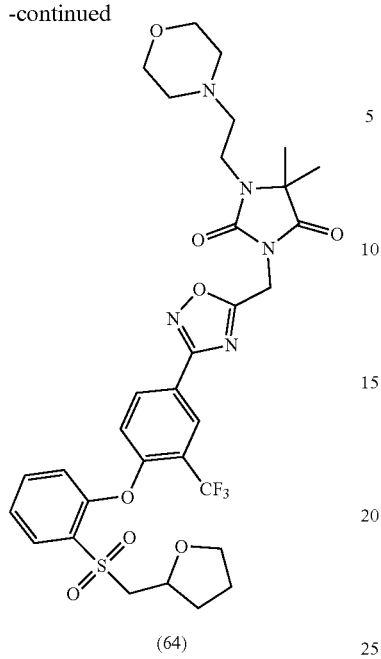

(64)

Step 1: Potassium carbonate (0.646 g, 4.68 mmol) was added to a solution of 5,5-dimethylimidazolidine-2,4-dione (0.599 g, 4.68 mmol) in DMF (7.79 mL) and the reaction mixture was stirred at room temperature for 30 mins. 5-(chloromethyl)-3-(4-(2-(((tetrahydrofuran-2-yl)methyl) sulfonyl)phenoxy)-3-(trifluoromethyl)phenyl)-1,2,4-oxadiazole (int-C9) (1.96 g, 3.90 mmol) was then added and the reaction mixture was stirred at room temperature overnight. The reaction mixture was then added to water (30 mL), then extracted with EtOAc (3×50 mL), and the organics were then combined and concentrated under vacuum and then purified using an ISCO with eluants heptane: EtOAc (0-100%). The fractions were then combined and concentrated under vacuum to give 5,5-dimethyl-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione. LCMS Method 3: Rt.=1.10 mins; m/z 595.9 [M+H]+.

Step 2: Cesium carbonate (603 mg, 1.850 mmol) was added to a solution of 5,5-dimethyl-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione (500 mg, 0.841 mmol) in DMF (3.364 mL) and the reaction mixture was stirred at room temperature for 30 mins. 4-(2-chloroethyl)morpholine (347 mg, 1.261 mmol) was then added and the reaction mixture was stirred at room temperature overnight. An addition 220 mg of cesium carbonate was added and the reaction mixture was again stirred at room temperature overnight. The reaction mixture was then purified using an ISCO column and eluted with EtOAc: MeOH (10% NH4) (0-20%). The product fractions were combined and concentrated under vacuum to give 5,5-dimethyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)imidazolidine-2,4-dione (64). LCMS Method 2: Rt.=0.90 mins; m/z 708.7 [M+H]+; $^1$H NMR (400 MHz, CDCl$_3$) δ 8.30 (d, J=2.1 Hz, 1H), 8.11-8.01 (m, 2H), 7.61-7.52 (m, 1H), 7.37-7.29 (m, 1H), 6.98-6.91 (m, 2H), 4.92 (s, 2H), 4.35-4.24 (m, 1H), 3.74-3.65 (m, 2H), 3.62 (t, J=4.6 Hz, 4H), 3.40 (d, J=4.0 Hz, 5H), 2.55 (t, J=7.2 Hz, 2H), 2.45 (t, J=4.7 Hz, 3H), 2.09-1.97 (m, 1H), 1.90-1.72 (m, 2H), 1.44 (s, 6H), 1.19 (s, 1H).

Example 65: 5,5-dimethyl-1-(2-morpholinoethyl)-3-((3-(3-(trifluoromethyl)-4-((4-(trifluoromethyl)pyridin-3-yl)oxy)phenyl)-1,2,4-oxadiazol-5-yl)methyl) imidazolidine-2,4-dione (65)

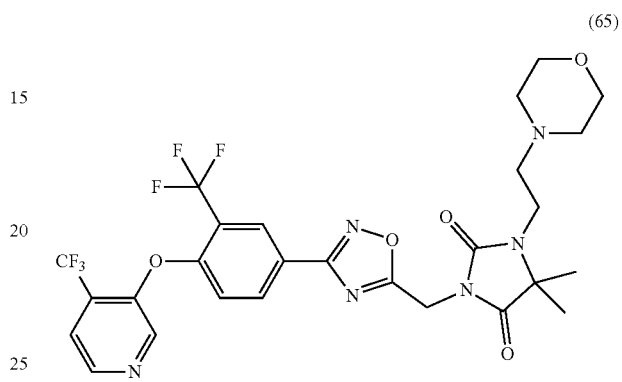

(65)

5,5-dimethyl-1-(2-morpholinoethyl)-3-((3-(3-(trifluoromethyl)-4-((4-(trifluoromethyl)pyridin-3-yl)oxy)phenyl)-1,2,4-oxadiazol-5-yl)methyl)imidazolidine-2,4-dione (65) was obtained using a procedure similar to the procedure described in Example 50 for the synthesis of 3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione (50b), except 2-(isobutylsulfonyl)phenol (int-B2) was replaced with 4-(trifluoromethyl)pyridin-3-ol and 1-(3-bromopropyl)pyrrolidine was replaced with 4-(2-bromoethyl)morpholine, and step 2 was carried out at room temperature. 1H NMR (400 MHz, METHANOL-d$_4$) δ ppm 8.55 (dd, J=4.40, 1.10 Hz, 1H) 8.40 (d, J=2.08 Hz, 1H) 8.28 (dd, J=8.68, 1.83 Hz, 1H) 7.63-7.74 (m, 2H) 7.18 (d, J=8.68 Hz, 1H) 5.05 (s, 2H) 3.64-3.69 (m, 4H) 3.52 (t, J=7.15 Hz, 2H) 2.62 (t, J=7.15 Hz, 2H) 2.51-2.56 (m, 4H) 1.50 (s, 6H). LCMS Method 2: Rt.=0.89 mins.; m/z 629.4 [M+H]$^+$.

Example 66. 5,5-dimethyl-1-(2-morpholinoethyl)-3-((3-(3-(trifluoromethyl)-4-(3,3,3-trifluoropropoxy) phenyl)-1,2,4-oxadiazol-5-yl)methyl)imidazolidine-2,4-dione (66)

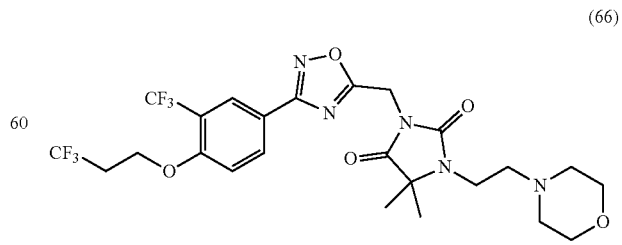

(66)

5,5-dimethyl-1-(2-morpholinoethyl)-3-((3-(3-(trifluoromethyl)-4-(3,3,3-trifluoropropoxy)phenyl)-1,2,4-oxadiazol-5-yl)methyl)imidazolidine-2,4-dione (66) was obtained using a procedure similar to the procedure described in Example 42 for the synthesis of 5,5-dimethyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione (42), except that 3,3,3-trifluoro-2-methyl-2-(trifluoromethyl)propan-1-ol was replaced by 3,3,3-trifluoropropan-1-ol. 1H NMR (400 MHz, Chloroform-d) δ 8.14 (d, J=2.2 Hz, 1H), 8.06 (dd, J=8.7, 2.2 Hz, 1H), 6.94 (d, J=8.7 Hz, 1H), 4.86 (s, 2H), 4.22 (t, J=6.5 Hz, 2H), 3.60 (t, J=4.6 Hz, 4H), 3.37 (t, J=7.1 Hz, 2H), 2.67-2.49 (m, 5H), 2.44 (s, 3H), 1.40 (s, 6H). m/z 580.5 [M+H]+.

Example 67. 6-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-6-oxohexanoic acid (67)

Example 68. 4-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-4-oxobutanoic acid (68)

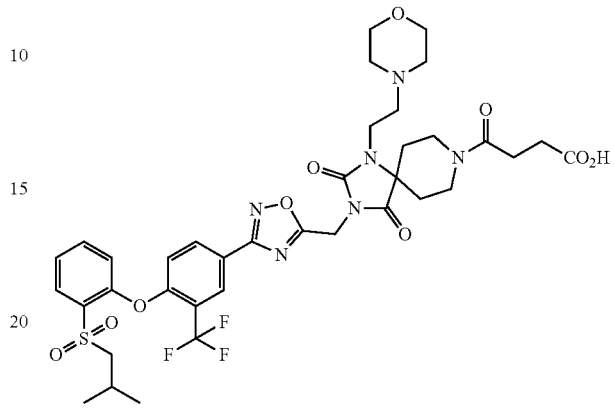

(68)

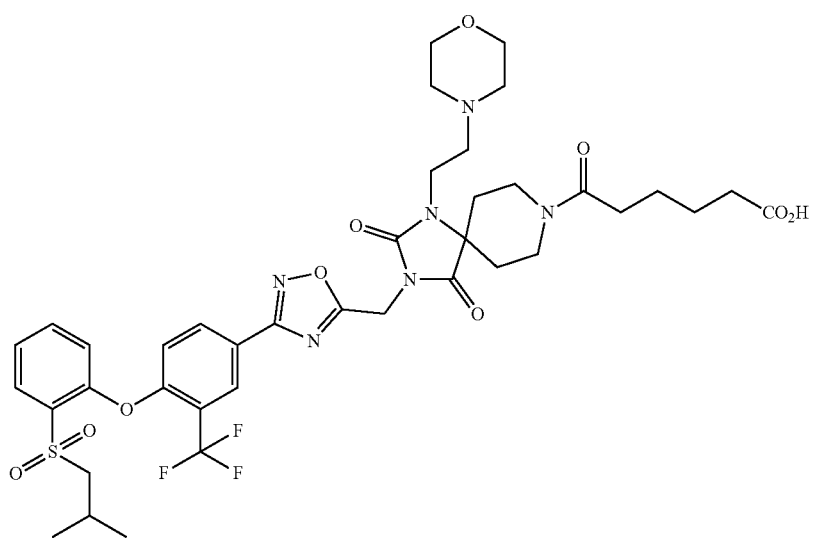

(67)

6-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-6-oxohexanoic acid (67) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with adipic acid. 1H NMR (400 MHz, Methanol-d4) δ 8.36 (d, J=2.1 Hz, 1H), 8.21 (dd, J=8.7, 2.2 Hz, 1H), 8.07 (dd, J=7.9, 1.7 Hz, 1H), 7.77 (td, J=7.8, 1.7 Hz, 1H), 7.60-7.43 (m, 1H), 7.20 (d, J=8.2 Hz, 1H), 7.07 (d, J=8.7 Hz, 1H), 5.06 (s, 2H), 4.65-4.53 (m, 1H), 4.07-3.95 (m, 1H), 3.72-3.61 (m, 4H), 3.59-3.44 (m, 2H), 3.36 (d, J=6.5 Hz, 2H), 2.78-2.49 (m, 7H), 2.46-2.23 (m, 3H), 2.23-1.83 (m, 5H), 1.68 (m, 4H), 1.40-1.34 (m, 2H), 1.04 (d, J=6.8 Hz, 6H). m/z 849.5 [M+H]+.

4-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decan-8-yl)-4-oxobutanoic acid (68) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except 2-cyclopropylacetic acid was replaced with succinic acid. 1H NMR (400 MHz, Methanol-d4) δ 8.37 (d, J=2.1 Hz, 1H), 8.22 (dd, J=8.7, 2.2 Hz, 1H), 8.07 (dd, J=7.9, 1.7 Hz, 1H), 7.77 (ddd, J=8.2, 7.5, 1.7 Hz, 1H), 7.51 (td, J=7.7, 1.0 Hz, 1H), 7.20 (dd, J=8.3, 1.0 Hz, 1H), 7.08 (d, J=8.7 Hz, 1H), 5.06 (s, 2H), 4.62-4.50 (m, 1H), 4.11-4.01 (m, 1H), 3.89-3.74 (m, 1H), 3.69-3.61 (m, 4H), 3.47 (t, J=7.1 Hz, 2H), 3.37 (d, J=6.5 Hz, 2H), 2.88-2.71 (m, 1H), 2.70-2.47 (m, 9H), 2.30-2.09 (m, 2H), 2.08-1.95 (m, 1H), 1.95-1.81 (m, 2H), 1.37 (d, J=6.6 Hz, 1H), 1.04 (d, J=6.7 Hz, 6H). m/z 821.4 [M+H]+.

Example 69. 6-(1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decan-8-yl)-6-oxohexanoic acid (69)

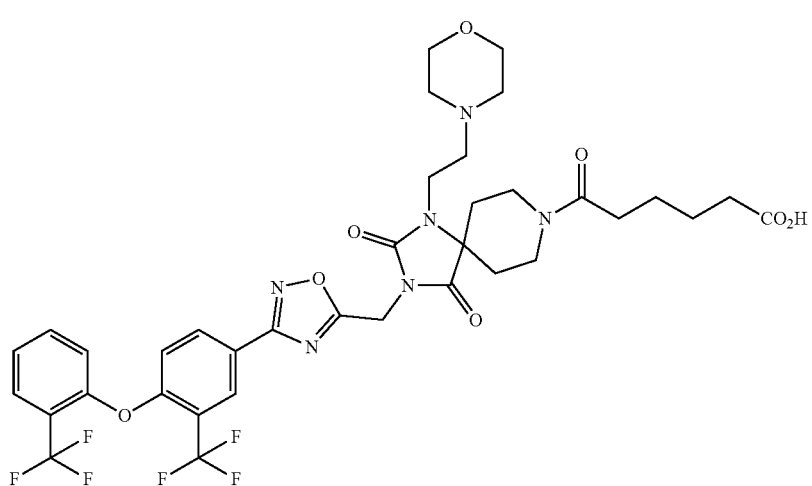

(69)

6-(1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decan-8-yl)-6-oxohexanoic acid (69) was obtained using a procedure similar to the procedure described in Example 28 for the synthesis of 8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione (28), except tert-butyl 3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-dioxo-1,3,8-triazaspiro[4.5]decane-8-carboxylate (int-F2) was replaced with tert-butyl 3-((3 tert-butyl 1-(2-morpholinoethyl)-2,4-dioxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-8-carboxylate (int-F3) and 2-cyclopropylacetic acid was replaced with adipic acid. 1H NMR (400 MHz, DMSO-d6) δ 12.01 (s, 1H), 8.29-8.19 (m, 2H), 7.90 (dd, J=8.1, 1.6 Hz, 1H), 7.83-7.74 (m, 1H), 7.55-7.46 (m, 1H), 7.34 (d, J=8.3 Hz, 1H), 7.19 (d, J=8.7 Hz, 1H), 5.06 (s, 2H), 4.47 (d, J=12.9 Hz, 1H), 3.92 (d, J=13.6 Hz, 1H), 3.63-3.47 (m, 5H), 3.18-3.02 (m, 2H), 2.41-2.36 (m, 6H), 2.22 (d, J=6.7 Hz, 2H), 2.04 (d, J=13.4 Hz, 1H), 1.89 (dt, J=12.8, 6.6 Hz, 1H), 1.78 (s, 2H), 1.56-1.48 (m, 3H), 1.30-1.20 (m, 4H). m/z 795.5 [M+H]+.

Example 70. 5,5-dimethyl-3-((3-(3-(trifluoromethyl)-4-(2-((trifluoromethyl)thio)phenoxy)phenyl)-1,2,4-oxadiazol-5-yl)methyl)imidazolidine-2,4-dione (70)

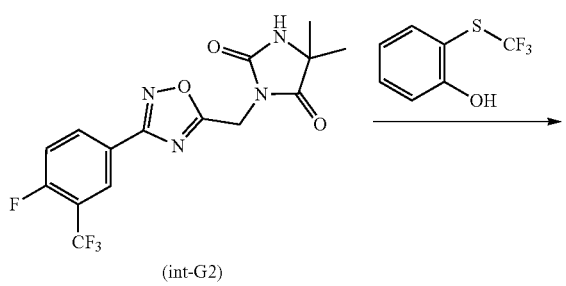

(int-G2)

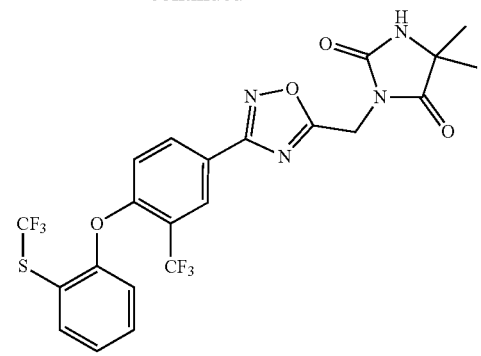

(70)

To a solution of 3-((3-(4-fluoro-3-(trifluoromethyl)phenyl)-1,2,4-oxadiazol-5-yl)methyl)-5,5-dimethylimidazolidine-2,4-dione (int-G2) (0.107 mmol) and 2-((trifluoromethyl)thio)phenol (0.215 mmol) in DMF (3 mL) was added potassium carbonate (0.215 mmol), and the resulting mixture was heated at 95° C. for 16 h. The reaction mixture was then diluted with ethyl acetate, washed sequentially with aqueous HCl solution (1.0 M) and brine, dried over sodium sulfate, and concentrated. The residue was subjected to flash chromatography (0-100% 0-100% EtOAc/hexanes) to afford 5,5-dimethyl-3-((3-(3-(trifluoromethyl)-4-(2-((trifluoromethyl)thio)phenoxy)phenyl)-1,2,4-oxadiazol-5-yl)methyl)imidazolidine-2,4-dione (70). 1H NMR (400 MHz, CDCl3) δ 8.32 (d, J=2.1 Hz, 1H), 8.04 (dd, J=8.7, 2.2 Hz, 1H), 7.72-7.74 (m, 1H), 7.43-7.48 (m, 1H), 7.21-7.26 (m, 1H), 7.01 (dd, J=8.2, 1.3 Hz, 1H), 6.76 (d, J=8.7 Hz, 1H), 5.78 (s, NH 1H), 4.92 (s, 2H), 1.48 (s, 6H). m/z 590.2 [M+H]+.

Example 71. 5,5-dimethyl-3-((3-(3-(trifluoromethyl)-4-(2-(trifluoromethyl)phenoxy)phenyl)-1,2,4-oxadiazol-5-yl)methyl)imidazolidine-2,4-dione (71a)) and 1,5,5-trimethyl-3-((3-(3-(trifluoromethyl)-4-(2-(trifluoromethyl)phenoxy)phenyl)-1,2,4-oxadiazol-5-yl)methyl)imidazolidine-2,4-dione (71b))

luoromethyl)phenoxy)phenyl)-1,2,4-oxadiazol-5-yl)methyl)imidazolidine-2,4-dione (71a). $^1$H NMR (400 MHz, CD$_3$OD) δ 8.35 (d, J=2.1 Hz, 1H), 8.17 (dd, J=8.7, 2.1 Hz, 1H), 7.77 (dd, J=7.8, 1.6 Hz, 1H), 7.61-7.64 (m, 1H), 7.36-7.40 (m, 1H), 7.10 (d, J=8.2 Hz, 1H), 6.97 (d, J=8.7 Hz, 1H), 5.00 (s, 2H), 1.48 (s, 6H). m/z 515 [M+H]$^+$.

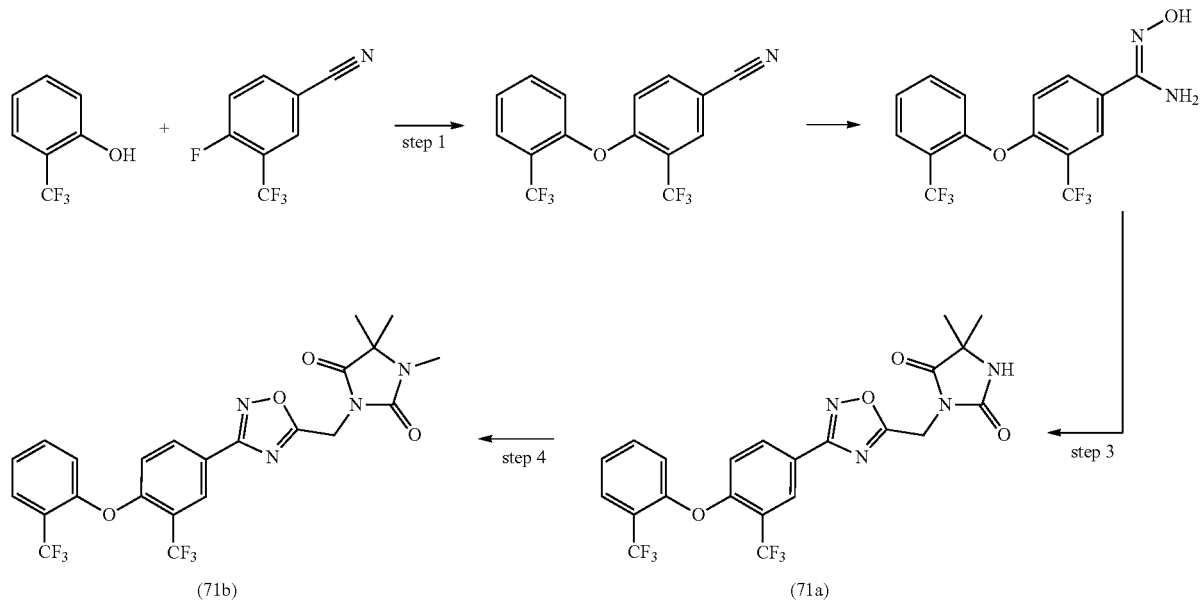

Step 1: To a solution of 2-(trifluoromethyl)phenol (71.5 mmol) and 4-fluoro-3-(trifluoromethyl)benzonitrile (47.6 mmol) in DMF (200 mL) was added potassium carbonate (119 mmol), and the resulting a mixture was heated at 95° C. for 15 h. The mixture was allowed to cool to room temperature, then poured over ice with stirring and filtered cold to afford 3-(trifluoromethyl)-4-(2-(trifluoromethyl)phenoxy)benzonitrile. $^1$H NMR (400 MHz, (CD$_3$)$_2$SO) δ 8.42 (s, 1H), 8.12 (d, J=8 Hz, 1H), 7.90 (d, J=8 Hz, 1H), 7.78-7.80 (m, 1H), 7.51-7.54 (m, 1H), 7.39 (d, J=8 Hz, 1H), 7.12 (d, J=8 Hz, 1H), m/z 332 [M+H]$^+$.

Step 2: To a solution of 3-(trifluoromethyl)-4-(2-(trifluoromethyl)phenoxy)benzonitrile (31.8 mmol) in ethanol (200 mML) was added an aqueous solution of hydroxylamine (34.9 mmol, 50% w/w), and the resulting mixture was stirred at 25° C. for 15 h, then concentrated. The residue was dissolved in minimal amount of ethanol, poured into ice-water with stirring, and filtered cold to afford (Z)—N'-hydroxy-3-(trifluoromethyl)-4-(2-(trifluoromethyl)phenoxy)benzimidamide. $^1$H NMR (400 MHz, (CDs)$_2$SO) δ 9.83 (s, OH, 1H), 8.08 (s, 1H), 7.96 (d, J=8 Hz, 1H), 7.86 (d, J=8 Hz, 1H), 7.70-7.73 (m, 1H), 7.40-7.42 (m, 1H), 7.16 (d, J=9 Hz, 1H), 7.06 (d, J=9 Hz, 1H), 6.03 (s, NH, 2H). m/z 365 [M+H]$^+$.

Step 3: To a solution of (Z)—N'-hydroxy-3-(trifluoromethyl)-4-(2-(trifluoromethyl)phenoxy)benzimidamide (0.4 mmol), 2-(4,4-dimethyl-2,5-dioxoimidazolidin-1-yl)acetic acid (0.4 mmol), HATU (0.48 mmol) in DMF (4 mL) was added N,N-diisopropylethylamine (DIEA) (0.084 mL) and the resulting mixture was stirred at 25° C. for 1 h, heated at 90° C. for 15 h, and subjected directly to HPLC purification (0.035% (v/v) TFA in acetonitrile/0.05% (v/v) TFA in water) to afford 5,5-dimethyl-3-((3-(3-(trifluoromethyl)-4-(2-(trif- Step 4: To a solution 5,5-dimethyl-3-((3-(3-(trifluoromethyl)-4-(2-(trifluoromethyl)phenoxy)phenyl)-1,2,4-oxadiazol-5-yl)methyl)imidazolidine-2,4-dione (71a) (0.039 mmol) and iodomethane (0.058 mmol) in DMF (1 mL) was added cesium carbonate (0.078 mmol) and the resulting mixture was stirred at 25° C. for 2 h, then subjected directly to HPLC purification (0.035% (v/v) TFA in acetonitrile/ 0.05% (v/v) TFA in water) to afford 1,5,5-trimethyl-3-((3-(3-(trifluoromethyl)-4-(2-(trifluoromethyl)phenoxy)phenyl)-1,2,4-oxadiazol-5-yl)methyl)imidazolidine-2,4-dione (71b). $^1$H NMR (400 MHz, CD$_3$OD) δ 8.34 (d, J=2.1 Hz, 1H), 8.16 (dd, J=8.7, 2.2 Hz, 1H), 7.77 (dd, J=7.8, 1.6 Hz, 1H), 7.61-7.64 (m, 1H), 7.36-7.40 (m, 1H), 7.10 (d, J=8.2 Hz, 1H), 6.97 (d, J=8.7 Hz, 1H), 5.02 (s, 2H), 2.89 (s, 3H), 1.47 (s, 6H). m/z 529 [M+H]$^+$.

Characterization of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione Form A Preparation of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (57)

A 100 mg/mL solution of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione (57) was prepared in ethanol solution at 50° C. The clear solution was then slowly cooled to room temperature. Upon completion of precipitate formation, the resulting solids were collected using a filter and dried to provide Form A. The characterization of Form A was conducted using X-ray powder diffraction (XRPD), differential scanning calorimetry (DCA), and thermogravimetry analysis (TGA) techniques.

X-Ray Powder Diffraction

The X-ray powder diffraction (XRPD) data was collected on a D8 Advance diffractometer using CuKα1 radiation (1.54056 Å) with germanium monochromator at room temperature. The data were collected from 3 to 45° 2θ. Detector scan on solid state LynxEye detector was performed using 0.02° per step with 19.2 s/step scan speed. The sample was measured on a zero background silicon wafer. FIG. 1 illustrates the XRPD of Form A.

TABLE 1

X-ray powder diffraction data for Form A.
Angle/°2theta 7.2
7.8
8.2
10.7
11.6
12.5
13.8
14.5
15.0
15.8
17.7
18.9
20.7
21.3
21.8
22.1
23.1

Differential Scanning Calorimetry

Melting properties of Form A were obtained from differential scanning calorimetry (DCA) thermograms, recorded with a TA Discovery Q5000 (ThermoAnalytical). Samples were sealed in standard 40 µl aluminum pans, pin-holed and heated in the DSC from 30° C. to 300° C., at a heating rate of 10 K/min. Dry $N_2$ gas, at a flow rate of 50 mL/min was used to purge the DSC equipment during the measurement. FIG. 2 illustrates the DSC profile of Form A.

The DSC curve of Form A (FIG. 2) shows a single endothermic peak with an onset temperature of about 118.6° C. and a peak temperature of about 121.5° C., which is due to the melting of the sample.

Thermogravimetric Analysis

Figure 3:
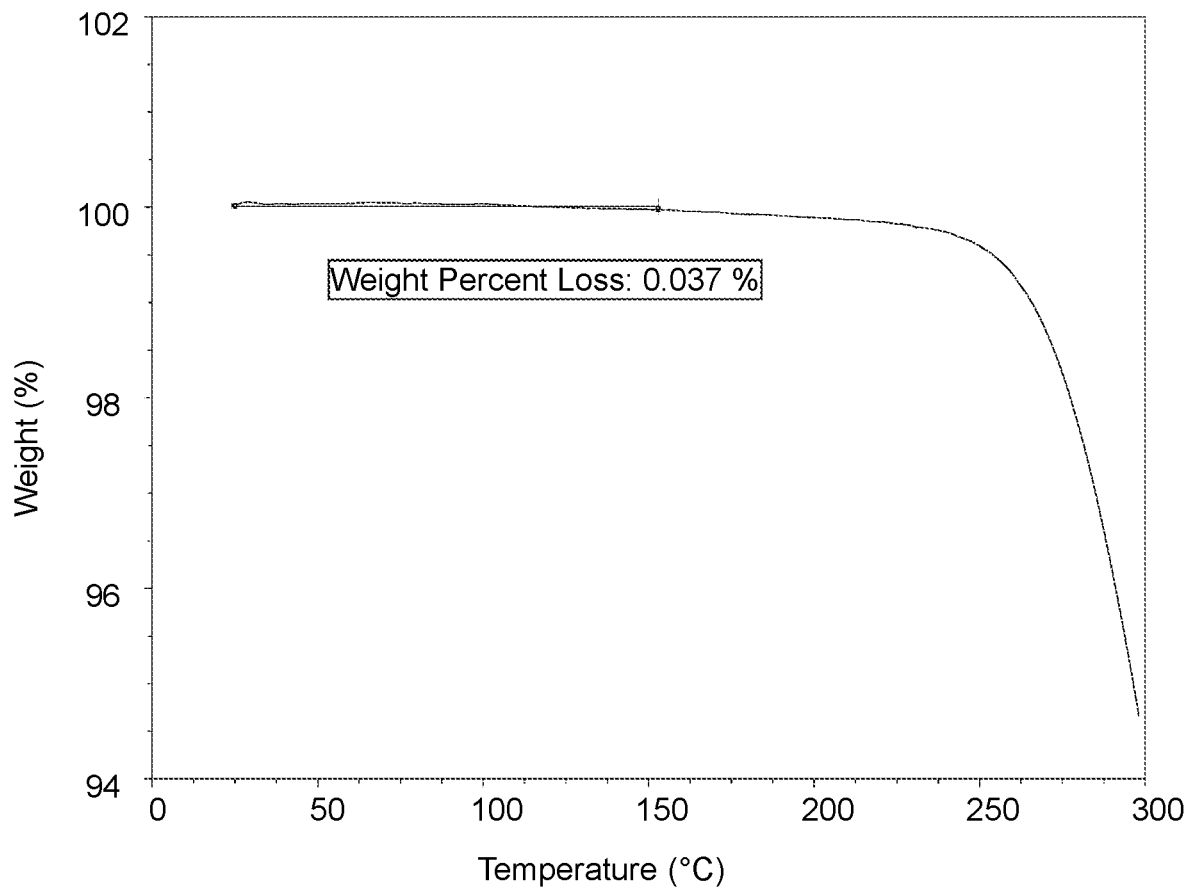
FIG. 3 provides an illustrative thermogravimetric analysis (TGA) profile of the crystalline form of 3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)

Form A was analyzed using thermogravimetry analysis (TGA). Loss on drying was determined by TGA using a TA Discovery Q2000 (ThermoAnalytical), resulting in a weight vs. temperature curve. Samples were weighed into 100 µL aluminum crucibles and sealed. The seals were pin-holed and the crucibles heated in the TGA from 30° C. to 300° C. at a heating rate of 10 K/min. Dry $N_2$ gas was used for purging. FIG. 3 illustrates the TGA profile of Form A.

The TGA curve (FIG. 3) shows no significant mass loss until the sample melts. For example mass losses of only about 0.04 weight % up to a temperature of about 150° C. was observed.

Biological Activity

The LXR agonist compounds provided herein were shown to induce stearoyl-CoA desaturase-1 (SCD1) expression thereby increasing lipid desaturation of meibum and reducing meibum melting temperature which can lead to reduced tear film evaporation and ameliorating the symptoms of Meibomian gland dysfunction and evaporative dry eye disease. To investigate the effect of the compounds provided herein, SCD1 expression following treatment with the LXR agonist compounds provided herein was evaluated. Changes in the global desaturation index in SZ95 sebocytes upon administration of the LXR agonist compounds provided herein was also investigated. Finally, in vivo measurement of meibum melting temperature was investigated for certain exemplary LXR agonist compounds provided herein.

Measurement of SCD1 Expression in SZ95-SCD1-HiBit Cells

SCD1 expression levels in SZ95 cells were quantitated using the HiBiT system (Promega) in which a small peptide sequence (SmBiT) with a larger protein (LgBiT) reconstitutes luciferase activity and can generate a luminescent signal used for quantitation. SZ95-SCD1-HiBit cells were generated by editing the SCD1 gene of SZ95 cells resulting in the addition of an 8 amino acid linker sequence (gssggssg, SEQ ID NO:1) followed by an 11-amino acid SmBiT sequence (vsgwrlfkkis, SEQ ID NO:2) at the carboxy-terminus of the SCD1 protein. The gRNA targeting sequence used was actacaagagtggctgagtt (SEQ ID NO: 3) and the SCD1 insertion oligonucleotide encoding the SmBiT sequence was:

(SEQ ID NO: 4)
1:5'gaagaaagtctccaaggccgccatcttggccaggattaaaagaac cggagatggaaactacaagagtggcggtagtagtggtggtagtagtggt gtgagcggctggcggctgttcaagaagattagctgagtttggggtccct caggttccttttcaaaaaccagccaggcactactattttaatatctat ttattaacta-3'.

The DNA sequence encoding the SCD1 with the linker and SmBiT tag at the carboxy-terminal tail of the protein is:

(SEQ ID NO: 5)
Atgccggcccacttgctgcaggacgatatctctagctcctataccacca ccaccaccattacagcgcctccctccagggtcctgcagaatggaggaga taagttggagacgatgccctctacttggaagacgacattcgccctgat ataaaagatgatatatatgaccccacctacaaggataaggaaggcccaa gccccaaggttgaatatgtctggagaaacatcatccttatgtctctgct acacttgggagccctgtatgggatcactttgattcctacctgcaagttc tacacctggctttgggggtattctactattttgtcagtgccctgggca taacagcaggagctcatcgtctgtggagccaccgctcttacaaagctcg gctgcccctacggctctttctgatcattgccaacacaatggcattccag aatgatgtctatgaatgggctcgtgaccaccgtgcccaccacaagtttt cagaaacacatgctgatcctcataattcccgacgtggcttttcttctc tcacgtgggttggctgcttgtgcgcaaacacccagctgtcaaagagaag gggagtacgctagacttgtctgacctagaagctgagaaactggtgatgt tccagaggaggtactacaaacctggcttgctgatgatgtgcttcatcct gcccacgcttgtgccctggtatttctggggtgaaacttttcaaaacagt gtgttcgttgccactttcttgcgatatgctgtggtgcttaatgccacct ggctggtgaacagtgctgcccacctcttcggatatcgtccttatgacaa -continued

```
gaacattagccccgggagaatatcctggtttcacttggagctgtgggt gagggcttccacaactaccaccactcctttccctatgactactctgcca gtgagtaccgctggcacatcaacttcaccacattcttcattgattgcat ggccgccctcggtctggcctatgaccggaagaaagtctccaaggccgcc atcttggccaggattaaaagaaccggagatggaaactacaagagtggcg gtagtagtggtggtagtagtggtgtgagcggctggcggctgttcaagaa gattagctga.
```

SZ95-SCD1-HiBit cells were seeded in 384-well cell culture white plates at a density of 3000 cells/30 μl. Water was added to edge wells to avoid evaporation. Cells were incubated in a humidified incubator with 5% $CO_2$ at 37° C. overnight. Tested compounds were diluted at a ratio of 1:3 in DMSO using an Agilent BRAVO Automated Liquid Handling Platform and, after further serial dilutions, added to cells at final concentrations starting from 18 μM. 2-(3-(3-((2-chloro-3-(trifluoromethyl)benzyl)(2,2-diphenylethyl)amino)propoxy)phenyl)acetic acid was used as a reference compound in each plate. Cells in the assay plate were incubated in a humidified incubator with 5% $CO_2$ at 37° C. for 48 h.

The assay plates were removed from the incubator and allowed to equilibrate to room temperature. Nano-Glo® HiBiT Detection Reagent (Promega; a mixture of Nano-Glo HiBiT Detection Buffer, Nano-Glo HiBiT Detection Substrate, and LgBiT protein, according to the manufacturer's instructions) was added into assay plates, at a volume equal to cell culture medium in each well. Plates were placed on an orbital shaker at a speed of 300-600 rpm for 10 min at room temperature, and read on an EnVision Plate Reader using luminescence detection with a 1 second read time.

The assay measures the increase in SCD1 protein production in vitro. Results are shown in Table 2 below. $A_{max}$ refers to the percent $EC_{50}$ of the tested compound compared to a reference compound, 2-(3-(3-((2-chloro-3-(trifluoromethyl)benzyl)(2,2-diphenylethyl)amino)propoxy)phenyl) acetic acid.

Sentinel Lipid Assay (SLA)

The sentinel lipid assay was used quantify the change in the global desaturation index in SZ95 sebocytes upon administration of certain LXR agonist compounds provided herein. The assay measures a smaller subset of lipid analytes in meibum (termed "sentinel lipids") which would model the global changes the population of both saturated and desaturated lipids in the cells. In order to define this smaller subset of lipids, a complete lipid profile was recorded on dose response curves (eight levels from 4 nM to 10 uM) of Compounds 1-72. An elastic net regression model was applied separately to both the saturated and desaturated lipids to determine the minimum combination of coefficients and analytes, which could be used to adequately model the total population of lipids. The elastic net model was able to reduce the behavior of 425 lipids to 11 lipids and the correlation between the desaturation indices observed using the complete set of lipids with from the 11 sentinel lipids was 0.96.

A medium throughput assay was created using this reduced set of sentinel lipids. A single batch is defined as triplicate examples of three unique plates (i.e., a single batch of cells is used to create nine plates for LC-MSMS analysis). Lipids were extracted from the cells using a 1:1 mixture of methylene chloride/methanol containing 10 nM of deuterated standards of triglycerides, which are used as internal standards for quantitating the lipid abundance. The lipids were separated prior to mass spectrometric analysis using a five minute HPLC gradient. The abundance of the sentinel lipids and the internal standards are measured using multiple reaction monitor mode (MRM) on a triple quadrupole mass spectrometer. The data was transformed from total ion current to nmoles/$10^6$ cells, which are multiplied by the coefficients from the elastic net model to determine the effective desaturated and saturated content, and therein the desaturation index of the dosed cells. In order to compare compounds from multiple batches with one another, the measure raw desaturation index was normalized by dividing it by the desaturation index of the DMSO dosed cells, and all data was assessed as the fraction by which the compound increases the desaturation index above 1.

SZ95 (immortalized human sebaceous gland cells) cells were seeded in Greiner bio-one 96-well polypropylene plates that were pre-treated with 50 μg/mL Human Plasma Fibronectin (Thermo Fisher Scientific) at a density of $10^4$ cells/135 μl. Cells were incubated in a humidified incubator with 5% $CO_2$ at 37° C. overnight. Test compounds were diluted at a ratio of 1:3 and added to cells at final concentrations starting from 10 μM. 2-(3-(3-((2-chloro-3-(trifluoromethyl)benzyl)(2,2-diphenylethyl)amino)propoxy)phenyl)acetic acid was used as a positive control reference compound in each plate. Cells in the assay plate were incubated in a humidified incubator with 5% $CO_2$ at 37° C. for 72 h.

Culture medium was removed from the cells and cells in culture plates were washed with ice cold phosphate buffered saline three times. Plates were heat sealed and stored in a −80° C. freezer prior to Sentinel lipid assay. Results from the sentinel lipid assay are shown in Table 2. The $A_{max}$ value refers to the percent $EC_{50}$ of the tested compound compared to a reference compound, 2-(3-(3-((2-chloro-3-(trifluoromethyl)benzyl)(2,2-diphenylethyl)amino)propoxy)phenyl) acetic acid.

TABLE 2

Results from HiBiT assay and Sentinal Lipid Assay (SLA)

| Compound No. | HiBit $EC_{50}$ (nM) | HiBit Amax | HiBit Normalized Amax[b] | SLA $EC_{50}$ (nM) | SLA Amax | SLA Normalized Amax[b] |
|---|---|---|---|---|---|---|
| 1 | 0.496 | 87.2 | 91.7 | 4.6 | 83.6 | 87.1 |
| 2 | 1.505 | 90.5 | 95.2 | 4.6 | 182.2 | 189.8 |
| 3 | 1.238 | 74.7 | 78.5 | 4.6 | 111.9 | 116.6 |
| 4 | n.d. | n.d. | n.d. | 4.6 | 145.5 | 151.6 |
| 5 | 0.056 | 83.4 | 87.7 | 4.6 | 145.8 | 151.9 |
| 6 | 43.633 | 66.4 | 69.8 | 37.5 | 96.7 | 100.7 |
| 7 | 0.128 | 85.6 | 90.0 | 4.6 | 105.3 | 109.7 |

TABLE 2-continued

Results from HiBiT assay and Sentinal Lipid Assay (SLA)

| Compound No. | HiBit EC$_{50}$ (nM) | HiBit Amax | HiBit Normalized Amax[b] | SLA EC$_{50}$ (nM) | SLA Amax | SLA Normalized Amax[b] |
|---|---|---|---|---|---|---|
| 8 | 0.111 | 114.0 | 119.9 | 4.6 | 220.8 | 230.0 |
| 9 | 3.304 | 93.3 | 98.1 | 4.6 | 141.5 | 147.4 |
| 10 | 0.079 | 105.7 | 111.1 | 4.6 | 124.0 | 129.2 |
| 11 | 0.058 | 91.2 | 95.9 | 4.6 | 134.3 | 139.9 |
| 12 | 0.081 | 77.9 | 81.9 | 4.6 | 124.8 | 130.0 |
| 13 | 0.102 | 78.2 | 82.2 | 4.6 | 90.7 | 94.5 |
| 14 | 0.241 | 86.5 | 91.0 | 4.6 | 125.2 | 130.4 |
| 15 | 0.101 | 84.0 | 88.3 | 4.6 | 116.2 | 121.0 |
| 16 | 0.116 | 90.2 | 94.8 | 4.6 | 139.9 | 145.7 |
| 17 | 0.041 | 190.5 | 200.3 | 4.6 | 97.4 | 101.5 |
| 18 | 0.133 | 132.5 | 139.3 | 4.6 | 135.2 | 140.8 |
| 19 | 0.042 | 184.2 | 193.7 | 4.6 | 140.3 | 146.1 |
| 20 | 0.078 | 89.1 | 93.7 | 4.6 | 149.0 | 155.2 |
| 21 | 0.241 | 79.6 | 83.7 | 4.6 | 97.5 | 101.6 |
| 22 | 1.827 | 128.6 | 135.2 | 4.6 | 153.8 | 160.2 |
| 23 | 3.482 | 80.9 | 85.1 | 4.6 | 168.9 | 175.9 |
| 24 | 0.050 | 111.0 | 116.7 | 4.6 | 157.9 | 164.5 |
| 25 | 1.619 | 93.4 | 98.2 | 4.6 | 182.1 | 189.7 |
| 26 | 0.796 | 91.6 | 96.3 | 4.6 | 108.1 | 112.6 |
| 27 | 0.254 | 84.7 | 89.1 | 4.6 | 109.1 | 113.6 |
| 28 | 0.697 | 71.1 | 74.8 | 4.6 | 138.9 | 144.7 |
| 29 | 0.796 | 83.4 | 87.7 | 4.6 | 129.3 | 134.7 |
| 30 | 1.044 | 84.9 | 89.3 | 34.4 | 82.1 | 85.5 |
| 31 | 0.440 | 78.3 | 82.3 | 4.6 | 96.3 | 100.3 |
| 32 | 2.420 | 80.7 | 84.9 | 4.6 | 96.2 | 100.2 |
| 33 | 8.531 | 107.2 | 112.7 | 4.6 | 116.5 | 121.4 |
| 34 | 0.380 | 81.5 | 85.7 | 4.6 | 164.0 | 170.8 |
| 35 | 0.616 | 69.5 | 73.1 | 17.2 | 116.6 | 121.5 |
| 36 | 0.119 | 77.5 | 81.5 | 4.6 | 125.7 | 130.9 |
| 37 | 0.066 | 87.3 | 91.8 | 4.6 | 139.6 | 145.4 |
| 38 | 5.264 | 72.1 | 75.8 | 4.6 | 154.1 | 160.5 |
| 39 | 1.401 | 89.3 | 93.9 | 4.6 | 163.7 | 170.5 |
| 40 | 7.083 | 71.0 | 74.7 | 4.6 | 161.1 | 167.8 |
| 41 | 0.167 | 88.4 | 93.0 | 4.6 | 88.5 | 92.2 |
| 42 | 1.524 | 81.9 | 86.1 | 4.6 | 150.4 | 156.7 |
| 43 | 1.145 | 80.0 | 84.1 | 4.6 | 140.8 | 146.7 |
| 44 | 6.646 | 73.2 | 77.0 | 4.6 | 82.9 | 86.4 |
| 45 | 2.523 | 89.6 | 94.2 | 4.6 | 155.1 | 161.6 |
| 46 | 6.062 | 93.2 | 98.0 | 4.6 | 163.3 | 170.1 |
| 47 | 0.728 | 76.6 | 80.5 | 4.6 | 141.5 | 147.4 |
| 48 | 0.053 | 88.9 | 93.5 | 4.6 | 119.8 | 124.8 |
| 49 | 11.914 | 70.9 | 74.6 | 40.6 | 109.5 | 114.1 |
| 50a | 254.800 [a] | 67.0 | 70.5 | n.d. | n.d. | n.d. |
| 50b | 29.774 | 63.8 | 67.1 | 23.7 | 58.2 | 60.6 |
| 51 | 12.245 | 84.4 | 88.7 | 4.6 | 115.7 | 120.5 |
| 52 | 2.914 | 75.6 | 79.5 | 4.6 | 114.2 | 119.0 |
| 53 | 0.264 | 96.2 | 101.2 | 4.6 | 140.0 | 145.8 |
| 54 | 3.864 | 80.7 | 84.9 | 4.6 | 150.6 | 156.9 |
| 55 | 4.430 | 87.1 | 91.6 | 4.6 | 154.5 | 160.9 |
| 56 | 1.013 | 72.8 | 76.6 | 4.6 | 179.7 | 187.2 |
| 57 | 0.217 | 84.1 | 88.4 | 4.6 | 168.6 | 175.6 |
| 58 | 0.281 | 101.6 | 106.8 | 4.6 | 160.7 | 167.4 |
| 59 | n.d. | n.d. | n.d. | 4.6 | 134.6 | 140.2 |
| 60 | n.d. | n.d. | n.d. | 4.6 | 169.8 | 176.9 |
| 61 | 9.097 | 75.0 | 78.9 | 4.6 | 171.2 | 178.3 |
| 62 | n.d. | n.d. | n.d. | 9.7 | 148.3 | 154.5 |
| 63 | 0.217 | 74.6 | 78.4 | 4.6 | 72.2 | 75.2 |
| 64 | 0.063 | 97.9 | 102.9 | 4.6 | 154.0 | 160.4 |
| 65 | 15.082 | 66.4 | 69.8 | 4.6 | 103.7 | 108.0 |
| 66 | 186.602 | 78.2 | 82.3 | 21.1 | 95.1 | 99.0 |
| 67 | 3.938 | 84.5 | 88.9 | 4.6 | 99.1 | 103.2 |
| 68 | 4.600 [a] | 79.9 | 84.0 | n.d. | n.d. | n.d. |
| 69 | 0.665 | 72.7 | 76.4 | n.d. | n.d. | n.d. |
| 70 | n.d. | n.d. | n.d. | 99.2 | 64.7 | 67.4 |
| 71 | 138.800 [a] | 65.3 | 68.7 | >10,000 | 49.8 | 51.9 |
| 72 | n.d. | n.d. | n.d. | 29.8 | 79.5 | 82.8 |
| Reference Compound | 65.400 | 95.1 | 100.0 | 87.3 | 96.0 | 100.0 |

Notes:
n.d. indicates not determined and the lowest dose used in the SLA assay was 4.6 nM.
[a] indicates that the initial dilution for the compound was 1:100 in assay medium rather than 1:3 in DMSO. The lowest dose used in the SLA assay was 4.6 nM.
[b] indicates normalized Amax values based on the reference compound Amax of 100%.

This data indicates that the compounds of the invention disclosed herein robustly upregulate SCD1 protein production in SZ95 cells and in turn increase the desaturation index of the lipids these cells produce. By increasing the desaturation index, the viscosity of meibum may be lowered leading to better meibum outflow in vivo and ameliorating the signs and symptoms of Meibomian gland dysfunction and evaporative dry eye disease. These data indicate the potential of the compounds of the invention disclosed herein to lower meibum melting temperature in vivo and thereby ameliorate symptoms of evaporative dry eye disease.

In Vivo Measurement of Lowered Meibum Melting Temperature

For compounds 8 and 57, the lowering of rat meibum melting temperature was measured in naive Sprague Dawley rats. The test animals were administered either vehicle, or a suspension of 1% of compound 8 or 1% of compound 57, as eye drops twice a day for fourteen days. The rat meibum was collected after administration of the compounds and analyzed by differential scanning calorimetry to measure the melting point. The lowering of meibum melting point in rats administered compound 8 or compound 57 was compared to the vehicle.

Melting properties of meibum were obtained using differential scanning calorimetry thermograms, recorded on a TA Discovery Q5000 (ThermoAnalytical). Samples were sealed in standard 40 µl aluminum pans and subjected to a heat-cool-heat cycle with melting temperatures being recorded on the second heating ramp. The samples were first heated to 150° C. at 30K/min then cooled −30° C. at 30K/min. Next, the sample was heated to 75° C. with an underlying heating rate of 2K/min, a period of modulation of 60 seconds and a temperature amplitude of modulation of 1° C. Dry $N_2$ gas, at a flow rate of 50 mL/min was used to purge the DSC equipment during the measurement. Onset of melting and peak temperatures were recorded with peak temperature quoted as the melting point.

Results from the assay are shown Table 3 and in FIG. 4. Results were analyzed using an unpaired t test with Welch's correction.

TABLE 3

Results from in vivo administration of compound 8 and compound 57

|  | Compound 57 | Compound 8 |
|---|---|---|
| P value | <0.0001 | <0.0001 |
| Mean ± SEM of Vehicle | 30.27 ± 0.1917 | 30.27 ± 0.1917 |
| Mean ± SEM of Compound | 28.08 ± 0.2945 | 28.29 ± 0.2920 |
| Change of Tm | −2.181 ± 0.3731 | −1.977 ± 0.3731 |

As seen in the results presented herein, the exemplary compounds of the invention provided herein lowered meibum melting temperature in vivo and increased meibum desaturation index in vitro.

The invention claimed is:

1. A compound according to Formula (I):

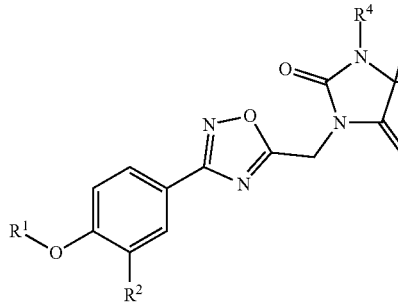

or a pharmaceutically acceptable salt, solvate, co-crystal, polymorph, or stereoisomer thereof, wherein:

$R^1$ is

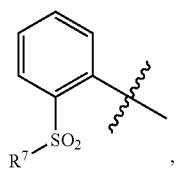

, $C_1$-$C_6$alkyl,
phenyl, or
5-6 membered heteroaryl having 1 to 3 heteroatoms independently selected from the heteroatoms N, O and S as ring members,
wherein the phenyl and heteroaryl are optionally substituted with one $R^{10}$, and the $C_1$-$C_6$alkyl is substituted with one or two —$CF_3$;

$R^2$ is —$CF_3$ or Cl;

$R^{3a}$a is
H, or
$C_1$-$C_6$alkyl optionally substituted with one, two, or three substituents independently selected from the group consisting of —OH and —$N(R^{12})_2$;

$R^{3b}$ is
H, or
$C_1$-$C_6$alkyl optionally substituted with one, two, or three substituents independently selected from the group consisting of —OH and —$N(R^{12})_2$;

or $R^{3a}$a and $R^{3b}$ together with the carbon atom they are attached to may combine to form a $C_3$-$C_8$cycloalkyl, wherein the cycloalkyl is optionally substituted with one $R^5$;

or $R^{3a}$a and $R^{3b}$ together with the carbon atom they are attached to may combine to form a 4-6 membered heterocycloalkyl having 1 to 2 ring members independently selected from N, NH, $NR^{12}$, O or S, wherein the heterocycloalkyl is optionally substituted with one $R^5$;

$R^4$ is $C_1$-$C_6$alkyl substituted with one or two groups independently selected from:
$R^6$,
4-6 membered heterocycloalkyl having 1 to 2 ring members independently selected from N, NH, $NR^{12}$, O or S,
5-6 membered heteroaryl having 1 to 3 heteroatoms independently selected from the heteroatoms N, O and S as ring members, and
$C_3$-$C_8$cycloalkyl,
wherein the heterocycloalkyl is optionally substituted with one or two substituents independently selected from —OH and $C_1$-$C_3$alkyl;

each $R^5$ is independently selected from:
—C(=O)$R^8$,
$C_1$-$C_3$alkyl,
$C_3$-$C_8$cycloalkyl, and
4-6 membered heterocycloalkyl having 1 to 2 ring members independently selected from N, NH, $NR^{12}$, O or S,
wherein the $C_1$-$C_3$alkyl is optionally substituted with one $R^9$, and the heterocycloalkyl is optionally substituted with one $C_1$-$C_3$alkyl or —C(=O)$R^8$;

each $R^6$ is independently selected from —OH and $C_1$-$C_3$alkyl;

$R^7$ is
$C_1$-$C_6$alkyl,
—$N(R^{12})_2$,
$C_3$-$C_8$cycloalkyl, or
4-6 membered heterocycloalkyl having 1 to 2 ring members independently selected from N, NH, $NR^{12}$, O or S,
wherein the $C_1$-$C_6$alkyl is optionally substituted with one or more $R^{11}$, and the $C_3$-$C_8$cycloalkyl is optionally substituted with one or more —OH;

$R^8$ is
$C_1$-$C_6$alkyl,
5-6 membered heteroaryl having 1 to 3 heteroatoms independently selected from the heteroatoms N, O and S as ring members, or
4-6 membered heterocycloalkyl having 1 to 2 ring members independently selected from N, NH, $NR^{12}$, O or S,
wherein the heterocycloalkyl is optionally substituted with one $C_1$-$C_6$alkyl, and the $C_1$-$C_6$alkyl is optionally substituted with one or more substituents selected from the group consisting of —C(=O)OH, $N(R^{12})_2$, and $C_3$-$C_8$cycloalkyl;

$R^9$ is
phenyl,
$C_3$-$C_8$cycloalkyl,
4-6 membered heterocycloalkyl having 1 to 2 ring members independently selected from N, NH, $NR^{12}$, O or S, or
5-6 membered heteroaryl having 1 to 3 heteroatoms independently selected from the heteroatoms N, O and S as ring members,
wherein the heteroaryl is optionally substituted with —OH, the heterocycloalkyl is optionally substituted with $C_1$-$C_6$alkyl, and the phenyl is optionally substituted with one or two —OH;

$R^{10}$ is $C_1$-$C_6$alkyl or $C_1$-$C_6$haloalkyl;

each $R^{11}$ is independently selected from
halogen,
$C_1$-$C_6$haloalkyl,
$C_1$-$C_6$alkoxy,
—$N(R^{13})_2$,
—OH, and
4-6 membered heterocycloalkyl having 1 to 2 ring members independently selected from N, NH, $NR^{12}$, O or S;

each $R^{12}$ is independently selected from H and $C_1$-$C_6$alkyl, and each $R^{13}$ is independently selected from
H, and
$C_1$-$C_6$alkyl,
wherein the alkyl is optionally substituted with —OH or $C_1$-$C_6$alkoxy.

2. The compound according to claim 1, wherein the compound is a compound of Formula (Ia)

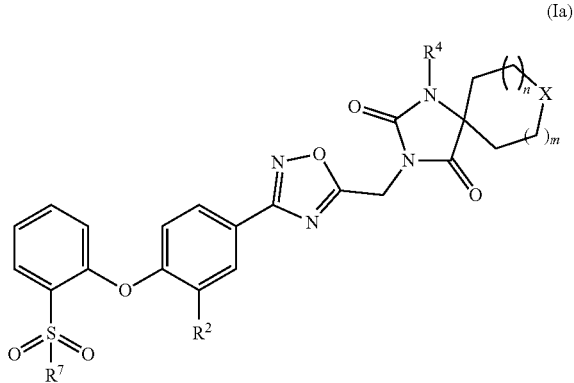

or a pharmaceutically acceptable salt, solvate, co-crystal, polymorph or stereoisomer thereof,
wherein:
X is $NR^5$, $CH_2$, or O;
n is 0 or 1, and
m is 0 or 1.

3. The compound according to claim 1, wherein the compound is a compound of Formula (Ie)

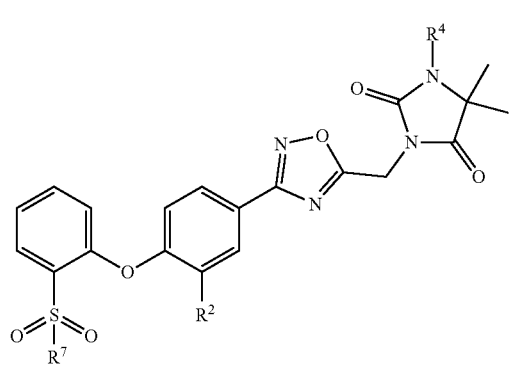

(Ie)

or a pharmaceutically acceptable salt, solvate, co-crystal, polymorph or stereoisomer thereof.

4. The compound according to claim 1, wherein the compound is selected from the group consisting of:

5,5-dimethyl-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione;

3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)-5-propylimidazolidine-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(2-(tetrahydro-2H-pyran-4-yl)ethyl)imidazolidine-2,4-dione;

2-(4-(5-((4,4-dimethyl-2,5-dioxo-3-(2-(tetrahydro-2H-pyran-4-yl)ethyl)imidazolidin-1-yl)methyl)-1,2,4-oxadiazol-3-yl)-2-(trifluoromethyl)phenoxy)-N-isopropyl-N-methylbenzenesulfonamide;

1-(2-(4-hydroxytetrahydro-2H-pyran-4-yl)ethyl)-3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione;

3-((3-(4-(2-(tert-butyl)phenoxy)-3-(trifluoromethyl)phenyl)-1,2,4-oxadiazol-5-yl)methyl)-8-cyclobutyl-1-(2-(tetrahydro-2H-pyran-4-yl)ethyl)-1,3,8-triazaspiro[4.5]decane-2,4-dione;

8-cyclobutyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-methyl-1-(2-morpholinoethyl)-1,3,8-triazaspiro[4.5]decane-2,4-dione;

2-(4-(5-((8-cyclobutyl-1-(2-morpholinoethyl)-2,4-dioxo-1,3,8-triazaspiro[4.5]decan-3-yl)methyl)-1,2,4-oxadiazol-3-yl)-2-(trifluoromethyl)phenoxy)-N-isopropyl-N-methylbenzenesulfonamide;

8-cyclobutyl-1-(2-(tetrahydro-2H-pyran-4-yl)ethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione;

8-cyclobutyl-1-(2-morpholinoethyl)-3-((3-(3-(trifluoromethyl)-4-(2-(trifluoromethyl)phenoxy)phenyl)-1,2,4-oxadiazol-5-yl)methyl)-1,3,8-triazaspiro[4.5]decane-2,4-dione;

8-cyclobutyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-cyclobutyl-3-((3-(4-(2-(methylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(tert-butyl)phenoxy)-3-(trifluoromethyl)phenyl)-1,2,4-oxadiazol-5-yl)methyl)-8-cyclobutyl-1-(2-morpholinoethyl)-1,3,8-triazaspiro[4.5]decane-2,4-dione;

8-cyclobutyl-1-(2-(tetrahydro-2H-pyran-4-yl)ethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione;

8-cyclobutyl-3-((3-(4-(2-(methylsulfonyl)phenoxy)-3-(trifluoromethyl)phenyl)-1,2,4-oxadiazol-5-yl)methyl)-1-(2-(tetrahydro-2H-pyran-4-yl)ethyl)-1,3,8-triazaspiro[4.5]decane-2,4-dione;

8-cyclobutyl-1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione;

8-cyclobutyl-1-(2-(tetrahydro-2H-pyran-4-yl)ethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-1,3,8-triazaspiro[4.5]decane-2,4-dione;

8-(4-hydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-(3,5-dihydroxybenzyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutyl sulfonyl)phenoxy)-3-(trifluoromethyl)phenyl)-1,2,4-oxadiazol-5-yl)methyl)-8-(1-methylpiperidin-4-yl)-1-(2-morpholinoethyl)-1,3,8-triazaspiro[4.5]decane-2,4-dione;

3-((3-(4-(2-(isobutyl sulfonyl)phenoxy)-3-(trifluoromethyl)phenyl)-1,2,4-oxadiazol-5-yl)methyl)-8-(1-methylpyrrolidin-3-yl)-1-(2-morpholinoethyl)-1,3,8-triazaspiro[4.5]decane-2,4-dione;

8-ethyl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutyl sulfonyl)phenoxy)-3-(trifluoromethyl)phenyl)-1,2,4-oxadiazol-5-yl)methyl)-1-(2-morpholinoethyl)-8-(pyridazin-3-ylmethyl)-1,3,8-triazaspiro[4.5]decane-2,4-dione;

3-((3-(4-(2-(isobutyl sulfonyl)phenoxy)-3-(trifluoromethyl)phenyl)-1,2,4-oxadiazol-5-yl)methyl)-1-(2-morpholinoethyl)-8-((tetrahydro-2H-pyran-4-yl)methyl)-1,3,8-triazaspiro[4.5]decane-2,4-dione;

8-(cyclopropylmethyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

8-(2-cyclopropylacetyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutyl sulfonyl)phenoxy)-3-(trifluoromethyl)phenyl)-1,2,4-oxadiazol-5-yl)methyl)-1-(2-morpholinoethyl)-8-(pyrimidine-5-carbonyl)-1,3,8-triazaspiro[4.5]decane-2,4-dione;

1-(2-morpholinoethyl)-8-(pyrimidine-5-carbonyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-(pyrimidine-5-carbonyl)-1-(2-(tetrahydro-2H-pyran-4-yl)ethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)-1,3,8-triazaspiro[4.5]decane-2,4-dione;

8-(3-(dimethylamino)propanoyl)-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(1-methylpiperidine-4-carbonyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-8-(pyrimidine-4-carbonyl)-1,3,8-triazaspiro[4.5]decane-2,4-dione;

8-butyryl-3-((3-(4-(2-(isobutylsulfonyl)phenoxy)-3-(trifluoromethyl)phenyl)-1,2,4-oxadiazol-5-yl)methyl)-1-(2-morpholinoethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(pyrazine-2-carbonyl)-1-(2-(tetrahydro-2H-pyran-4-yl)ethyl)-1,3,8-triazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-8-(pyrimidine-5-carbonyl)-1-(2-(tetrahydro-2H-pyran-4-yl)ethyl)-1,3,8-triazaspiro[4.5]decane-2,4-dione;

5,5-dimethyl-1-(2-morpholinoethyl)-3-((3-(4-(2-(((tetrahydrofuran-3-yl)methyl)sulfonyl)phenoxy)-3-(trifluoromethyl)phenyl)-1,2,4-oxadiazol-5-yl)methyl)imidazolidine-2,4-dione;

3-((3-(4-(2-((3-hydroxycyclobutyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-morpholinoethyl)-3-((3-(4-(2-(((tetrahydro-2H-pyran-3-yl)methyl)sulfonyl)phenoxy)-3-(trifluoromethyl)phenyl)-1,2,4-oxadiazol-5-yl)methyl)imidazolidine-2,4-dione;

5,5-dimethyl-1-(2-morpholinoethyl)-3-((3-(3-(trifluoromethyl)-4-(2-(trifluoromethyl)phenoxy)phenyl)-1,2,4-oxadiazol-5-yl)methyl)imidazolidine-2,4-dione;

5,5-dimethyl-1-(2-morpholinoethyl)-3-((3-(4-(3,3,3-trifluoro-2-methyl-2-(trifluoromethyl)propoxy)-3-(trifluoromethyl)phenyl)-1,2,4-oxadiazol-5-yl)methyl)imidazolidine-2,4-dione;

5,5-dimethyl-1-(2-morpholinoethyl)-3-((3-(4-(2-((2-(pyrrolidin-1-yl)propyl)sulfonyl)phenoxy)-3-(trifluoromethyl)phenyl)-1,2,4-oxadiazol-5-yl)methyl)imidazolidine-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)imidazolidine-2,4-dione;

3-((3-(4-(2-(isobutylsulfonyl)phenoxy)-3-(trifluoromethyl)phenyl)-1,2,4-oxadiazol-5-yl)methyl)-1-(2-morpholinoethyl)-1,3-diazaspiro[4.5]decane-2,4-dione;

7-((3-(4-(2-(isobutylsulfonyl)phenoxy)-3-(trifluoromethyl)phenyl)-1,2,4-oxadiazol-5-yl)methyl)-5-(2-morpholinoethyl)-5,7-diazaspiro[3.4]octane-6,8-dione;

5-(hydroxymethyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione;

8-cyclobutyl-1-(2-morpholinoethyl)-3-((3-(4-(2-((2,2,2-trifluoroethyl)sulfonyl)phenoxy)-3-(trifluoromethyl)phenyl)-1,2,4-oxadiazol-5-yl)methyl)-1,3,8-triazaspiro[4.5]decane-2,4-dione;

3-((3-(3-chloro-4-(2-(isobutylsulfonyl)phenoxy)phenyl)-1,2,4-oxadiazol-5-yl)methyl)-5,5-dimethyl-1-(2-morpholinoethyl)imidazolidine-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(3-(pyrrolidin-1-yl)propyl)imidazolidine-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(pyridin-2-ylmethyl)imidazolidine-2,4-dione;

3-((3-(4-(2-((2-hydroxypropyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-morpholinoethyl)-3-((3-(4-(2-(((tetrahydro-2H-pyran-2-yl)methyl)sulfonyl)phenoxy)-3-(trifluoromethyl)phenyl)-1,2,4-oxadiazol-5-yl)methyl)imidazolidine-2,4-dione;

1-(cyclopropylmethyl)-3-((3-(4-(2-((2-methoxyethyl)sulfonyl)phenoxy)-3-(trifluoromethyl)phenyl)-1,2,4-oxadiazol-5-yl)methyl)-5,5-dimethylimidazolidine-2,4-dione;

5,5-dimethyl-3-((3-(4-(2-(methylsulfonyl)phenoxy)-3-(trifluoromethyl)phenyl)-1,2,4-oxadiazol-5-yl)methyl)-1-(2-morpholinoethyl)imidazolidine-2,4-dione;

1-(2-morpholinoethyl)-3-((3-(4-(2-(((tetrahydrofuran-2-yl)methyl)sulfonyl)phenoxy)-3-(trifluoromethyl)phenyl)-1,2,4-oxadiazol-5-yl)methyl)-8-oxa-1,3-diazaspiro[4.5]decane-2,4-dione;

3-((3-(4-(2-(isobutylsulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

3-((3-(4-(2-((2-methoxyethyl)sulfonyl)phenoxy)-3-(trifluoromethyl)phenyl)-1,2,4-oxadiazol-5-yl)methyl)-5,5-dimethyl-1-(2-morpholinoethyl)imidazolidine-2,4-dione;

5,5-dimethyl-1-(2-(tetrahydro-2H-pyran-4-yl)ethyl)-3-((3-(4-(2-((tetrahydrofuran-3-yl)sulfonyl)phenoxy)-3-(trifluoromethyl)phenyl)-1,2,4-oxadiazol-5-yl)methyl)imidazolidine-2,4-dione;

5-((dimethylamino)methyl)-3-((3-(4-(2-(isobutylsulfonyl)phenoxy)-3-(trifluoromethyl)phenyl)-1,2,4-oxadiazol-5-yl)methyl)-5-methyl-1-(2-morpholinoethyl)imidazolidine-2,4-dione;

3-((3-(4-(2-((2-(bis(2-methoxyethyl)amino)ethyl)sulfo-
nyl)phenoxy)-3-(trifluoromethyl)phenyl)-1,2,4-oxadi-
azol-5-yl)methyl)-5,5-dimethyl-1-(2-morpholinoethyl)
imidazolidine-2,4-dione;

3-((3-(4-(2-((2-(bis(2-hydroxyethyl)amino)ethyl)sulfo-
nyl)phenoxy)-3-(trifluoromethyl)phenyl)-1,2,4-oxadi-
azol-5-yl)methyl)-5,5-dimethyl-1-(2-morpholinoethyl)
imidazolidine-2,4-dione;

5,5-dimethyl-1-(2-morpholinoethyl)-3-((3-(4-(2-(((tetra-
hydrofuran-2-yl)methyl)sulfonyl)phenoxy)-3-(trifluo-
romethyl)phenyl)-1,2,4-oxadiazol-5-yl)methyl)imida-
zolidine-2,4-dione;

(R or S) 5,5-dimethyl-1-(2-morpholinoethyl)-3-((3-(4-(2-
(((tetrahydrofuran-2-yl)methyl)sulfonyl)phenoxy)-3-
(trifluoromethyl)phenyl)-1,2,4-oxadiazol-5-yl)methyl)
imidazolidine-2,4-dione, (R or S) 5,5-dimethyl-1-(2-morpholinoethyl)-3-((3-(4-(2-
(((tetrahydrofuran-2-yl)methyl)sulfonyl)phenoxy)-3-
(trifluoromethyl)phenyl)-1,2,4-oxadiazol-5-yl)methyl)
imidazolidine-2,4-dione; and a pharmaceutically acceptable salt, solvate, co-crystal,
polymorph, or stereoisomer thereof.

5. The compound of claim 4, wherein the compound is
3-((3-(4-(2-(isobutylsulfonyl)phenoxy)-3-(trifluoromethyl)
phenyl)-1,2,4-oxadiazol-5-yl)methyl)-5,5-dimethyl-1-(2-
morpholinoethyl)imidazolidine-2,4-dione.

6. The compound of claim 4, wherein the compound is
8-cyclobutyl-1-(2-(tetrahydro-2H-pyran-4-yl)ethyl)-3-((3-
(4-(3,3,3-trifluoro-2-methyl-2-(trifluoromethyl)propoxy)-3-
(trifluoromethyl)phenyl)-1,2,4-oxadiazol-5-yl)methyl)-1,3,
8-triazaspiro[4.5]decane-2,4-dione or a pharmaceutically
acceptable salt thereof.

7. A pharmaceutical composition comprising a compound
according to claim 1, or a pharmaceutically acceptable salt,
solvate, co-crystal, polymorph, or stereoisomer thereof, and
one or more pharmaceutically acceptable carriers.

8. A method for the treatment of meibomian gland dys-
function comprising administration of a therapeutically
effective amount of a compound according to claim 1, or a
pharmaceutically acceptable salt, solvate, co-crystal, poly-
morph or stereoisomer thereof, to a patient in need of
treatment thereof.

9. A crystalline form of 3-((3-(4-(2-(isobutylsulfonyl)
phenoxy)-3-(trifluoromethyl)phenyl)-1,2,4-oxadiazol-5-yl)
methyl)-5,5-dimethyl-1-(2-morpholinoethyl)imidazolidine-
2,4-dione characterized by an X-ray powder diffraction
pattern comprising one or more peaks at 2-Theta angles
selected from 7.2±0.2, 7.8±0.2, 8.2±0.2, 10.7±0.2, 11.6±0.2,
12.5±0.2, 13.8±0.2, 14.5±0.2, 15.0±0.2, 15.8±0.2, 17.7±0.2,
18.9±0.2, 20.7±0.2, 21.3±0.2, 21.8±0.2, 22.1±0.2, and
23.1±0.2.

10. A compound according to Formula (I'):

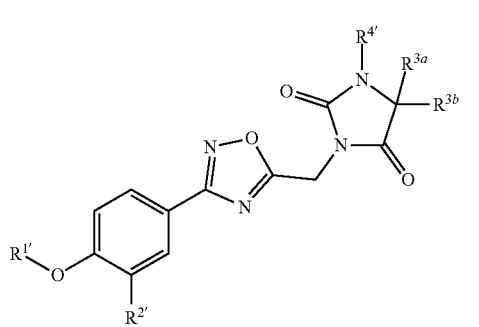

or a pharmaceutically acceptable salt, solvate, co-crystal,
polymorph, or stereoisomer thereof,
wherein:
$R^{1'}$ is

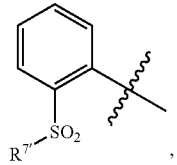

$C_1$-$C_6$alkyl,
phenyl or
5-6 membered heteroaryl having 1 to 3 heteroatoms
independently selected from the heteroatoms N, O
and S as ring members,
wherein the phenyl and heteroaryl are optionally sub-
stituted with one $R^{10'}$, and the $C_1$-$C_6$alkyl is option-
ally substituted with one or two —$CF_3$;

$R^2$ is $C_1$-$C_6$haloalkyl or halo;

$R^{3a}$ is
hydrogen or
$C_1$-$C_6$alkyl optionally substituted with one, two, or
three substituents independently selected from the
group consisting of —OH and —$N(R^{12'})_2$;

$R^{3b}$ is
hydrogen or
$C_1$-$C_6$alkyl optionally substituted with one, two, or
three substituents independently selected from the
group consisting of —OH and —$N(R^{12'})_2$;

or $R^{3a}$ and $R^{3b}$ together with the carbon atom they are
attached to may combine to form a $C_3$-$C_8$cycloalkyl,
wherein said cycloalkyl is optionally substituted with
one $R^5$;

or $R^{3a}$ and $R^{3b}$ together with the carbon atom they are
attached to may combine to form a 4-6 membered
heterocycloalkyl having 1 to 2 ring members indepen-
dently selected from N, NH, $NR^{12'}$, O and S, wherein
said heterocycloalkyl is optionally substituted with one
$R^5$;

$R^{4'}$ is
hydrogen, or
$C_1$-$C_6$alkyl optionally substituted with one or two
groups independently selected from:
$R^6$,
4-6 membered heterocycloalkyl having 1 to 2 ring
members independently selected from N, NH,
$NR^{12'}$, O and S,
5-6 membered heteroaryl having 1 to 3 heteroatoms
independently selected from the heteroatoms N, O
and S as ring members, and
$C_3$-$C_8$cycloalkyl,
wherein the heterocycloalkyl is optionally substi-
tuted with one or two substituents independently
selected from —OH and $C_1$-$C_3$alkyl;

each $R^5$ is independently selected from
—C(=O)$R^{8'}$,
$C_1$-$C_3$alkyl,
$C_3$-$C_8$cycloalkyl, and
4-6 membered heterocycloalkyl having 1 to 2 ring
members independently selected from N, NH, $NR^{12'}$,
O and S, wherein the $C_1$-$C_3$alkyl is optionally substituted with one $R^9$, and the heterocycloalkyl is optionally substituted with one $C_1$-$C_3$alkyl or —C(=O)$R^{8'}$;

each $R^6$ is independently selected from —OH and $C_1$-$C_3$alkyl;

$R^7$ is
- $C_1$-$C_6$alkyl,
- —N($R^{12'}$)$_2$,
- $C_3$-$C_8$cycloalkyl, or
- 4-6 membered heterocycloalkyl having 1 to 2 ring members independently selected from N, NH, $NR^{12'}$, O and S, wherein the $C_1$-$C_6$alkyl is optionally substituted with one or more $R^{11}$, and the $C_3$-$C_8$cycloalkyl is optionally substituted with one or more —OH;

$R^{8'}$ is
- $C_1$-$C_6$alkyl,
- $C_1$-$C_6$alkyl-COOH,
- 5-6 membered heteroaryl having 1 to 3 heteroatoms independently selected from the heteroatoms N, O and S as ring members, or
- 4-6 membered heterocycloalkyl having 1 to 2 ring members independently selected from N, NH, $NR^{12'}$, O and S, wherein the heterocycloalkyl is optionally substituted with one $C_1$-$C_6$alkyl, and the $C_1$-$C_6$alkyl is optionally substituted with one or more substituents selected from the group consisting of —C(=O)OH, N($R^{12'}$)$_2$, and $C_3$-$C_8$cycloalkyl;

$R^9$ is
- phenyl,
- $C_3$-$C_8$cycloalkyl,
- 4-6 membered heterocycloalkyl having 1 to 2 ring members independently selected from N, NH, $NR^{12'}$, O and S, or
- 5-6 membered heteroaryl having 1 to 3 heteroatoms independently selected from the heteroatoms N, O and S as ring members, wherein the heteroaryl is optionally substituted with —OH, the heterocycloalkyl is optionally substituted with $C_1$-$C_6$alkyl, and the phenyl is optionally substituted with one or two —OH;

$R^{10'}$ is $C_1$-$C_6$alkyl, $C_1$-$C_6$haloalkyl, or S—$CF_3$;

each $R^{11}$ is independently selected from
- halogen,
- $C_1$-$C_6$haloalkyl,
- $C_1$-$C_6$alkoxy,
- —N($R^{13}$)$_2$,
- —OH, and
- 4-6 membered heterocycloalkyl having 1 to 2 ring members independently selected from N, NH, $NR^{12'}$, O and S;

each $R^{12'}$ is independently selected from
- hydrogen,
- $C_1$-$C_6$alkyl, and
- —C(=O)$R^{8'}$; and each $R^{13}$ is independently selected from
- hydrogen, and
- $C_1$-$C_6$alkyl, wherein the alkyl is optionally substituted with —OH or $C_1$-$C_6$alkoxy.

11. The compound according to claim 10, wherein the compound is selected from the group consisting of:
3-((3-(4-(2-(isobutylsulfonyl)phenoxy)-3-(trifluoromethyl)phenyl)-1,2,4-oxadiazol-5-yl)methyl)-5,5-dimethylimidazolidine-2,4-dione,
5,5-dimethyl-1-(2-morpholinoethyl)-3-((3-(3-(trifluoromethyl)-4-((4-(trifluoromethyl)pyridin-3-yl)oxy)phenyl)-1,2,4-oxadiazol-5-yl)methyl)imidazolidine-2,4-dione,
5,5-dimethyl-1-(2-morpholinoethyl)-3-((3-(3-(trifluoromethyl)-4-(3,3,3-trifluoropropoxy)phenyl)-1,2,4-oxadiazol-5-yl)methyl)imidazolidine-2,4-dione,
6-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-di oxo-1,3,8-triazaspiro[4.5]decan-8-yl)-6-oxohexanoic acid,
4-(3-((3-(4-(2-(isobutylsulfonyl)phenoxy)-3-(trifluoromethyl)phenyl)-1,2,4-oxadiazol-5-yl)methyl)-1-(2-morpholinoethyl)-2,4-di oxo-1,3,8-tri azaspiro[4.5]decan-8-yl)-4-oxobutanoic acid,
6-(1-(2-morpholinoethyl)-2,4-di oxo-3-((3-(3-(trifluoromethyl)-4-(2-(trifluoromethyl)phenoxy)phenyl)-1,2,4-oxadiazol-5-yl)methyl)-1,3,8-triazaspiro[4.5]decan-8-yl)-6-oxohexanoic acid,
5,5-dimethyl-3-((3-(3-(trifluoromethyl)-4-(2-((trifluoromethyl)thio)phenoxy)phenyl)-1,2,4-oxadiazol-5-yl)methyl)imidazolidine-2,4-dione,
5,5-dimethyl-3-((3-(3-(trifluoromethyl)-4-(2-(trifluoromethyl)phenoxy)phenyl)-1,2,4-oxadiazol-5-yl)methyl)imidazolidine-2,4-dione, and
1,5,5-trimethyl-3-((3-(3-(trifluoromethyl)-4-(2-(trifluoromethyl)phenoxy)phenyl)-1,2,4-oxadiazol-5-yl)methyl)imidazolidine-2,4-dione,
or a pharmaceutically acceptable salt, solvate, co-crystal, polymorph, or stereoisomer thereof.

12. A pharmaceutical composition comprising a compound according to claim 10, or a pharmaceutically acceptable salt, solvate, co-crystal, polymorph, or stereoisomer thereof, and one or more pharmaceutically acceptable carriers.

13. A method for the treatment of meibomian gland dysfunction comprising administration of a therapeutically effective amount of a compound according to claim 10, or a pharmaceutically acceptable salt, solvate, co-crystal, polymorph or stereoisomer thereof, to a patient in need of treatment thereof.

14. A method for the treatment of evaporative dry eye disease comprising administration of a therapeutically effective amount of a compound according to claim 1, or a pharmaceutically acceptable salt, solvate, co-crystal, polymorph or stereoisomer thereof, to a patient in need of treatment thereof.

15. A method for the treatment of an ocular disease or disorder comprising administration of a therapeutically effective amount of a compound according to claim 1, or a pharmaceutically acceptable salt, solvate, co-crystal, polymorph or stereoisomer thereof, to a patient in need of treatment thereof.

16. A method for the treatment of meibomian gland dysfunction comprising administration of a therapeutically effective amount of a compound according to claim 11, or a pharmaceutically acceptable salt, solvate, co-crystal, polymorph or stereoisomer thereof, to a patient in need of treatment thereof.

17. A method for the treatment of evaporative dry eye disease comprising administration of a therapeutically effective amount of a compound according to claim 11, or a pharmaceutically acceptable salt, solvate, co-crystal, polymorph or stereoisomer thereof, to a patient in need of treatment thereof.

18. A method for the treatment of an ocular disease or disorder comprising administration of a therapeutically effective amount of a compound according to claim 11, or a pharmaceutically acceptable salt, solvate, co-crystal, polymorph or stereoisomer thereof, to a patient in need of treatment thereof.

19. A method for the treatment of meibomian gland dysfunction comprising administration of a therapeutically effective amount of a compound according to claim 4, or a pharmaceutically acceptable salt, solvate, co-crystal, polymorph or stereoisomer thereof, to a patient in need of treatment thereof.

20. A method for the treatment of evaporative dry eye disease comprising administration of a therapeutically effective amount of a compound according to claim 4, or a pharmaceutically acceptable salt, solvate, co-crystal, polymorph or stereoisomer thereof, to a patient in need of treatment thereof.

21. A method for the treatment of an ocular disease or disorder comprising administration of a therapeutically effective amount of a compound according to claim 4, or a pharmaceutically acceptable salt, solvate, co-crystal, polymorph or stereoisomer thereof, to a patient in need of treatment thereof.

\* \* \* \* \*